(12) United States Patent
Makarov et al.

(10) Patent No.: US 12,371,731 B2
(45) Date of Patent: *Jul. 29, 2025

(54) NORMALIZATION OF NGS LIBRARY CONCENTRATION

(71) Applicant: Integrated DNA Technologies, Inc., Coralville, IA (US)

(72) Inventors: Vladimir Makarov, Ann Arbor, MI (US); Sergey Chupreta, Gregory, MI (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/322,200

(22) Filed: May 23, 2023

(65) Prior Publication Data

US 2024/0068011 A1 Feb. 29, 2024

Related U.S. Application Data

(63) Continuation of application No. 17/214,251, filed on Mar. 26, 2021, now Pat. No. 11,697,836, which is a continuation of application No. 16/294,561, filed on Mar. 6, 2019, now Pat. No. 10,961,562, which is a continuation of application No. PCT/US2017/050354, filed on Sep. 6, 2017.

(60) Provisional application No. 62/384,118, filed on Sep. 6, 2016.

(51) Int. Cl.
*C12Q 1/6806* (2018.01)
*C12N 15/00* (2006.01)
*C12Q 1/686* (2018.01)
*C12Q 1/6876* (2018.01)
*C40B 40/08* (2006.01)

(52) U.S. Cl.
CPC .......... *C12Q 1/6806* (2013.01); *C12N 15/00* (2013.01); *C12Q 1/686* (2013.01); *C12Q 1/6876* (2013.01); *C40B 40/08* (2013.01)

(58) Field of Classification Search
None
See application file for complete search history.

(56) References Cited

U.S. PATENT DOCUMENTS

| | | | |
|---|---|---|---|
| 4,988,617 A | 1/1991 | Andegren et al. | |
| 6,297,010 B1 | 10/2001 | Stefano | |
| 7,718,403 B2 | 5/2010 | Kamberov et al. | |
| 8,455,197 B2 | 6/2013 | Rand | |
| 11,697,836 B2 * | 7/2023 | Makarov | C12Q 1/686 435/6.12 |
| 2010/0129874 A1 | 5/2010 | Mitra et al. | |
| 2012/0289414 A1 | 11/2012 | Mitra et al. | |
| 2014/0378317 A1 | 12/2014 | Fu et al. | |
| 2016/0046987 A1 | 2/2016 | Kim et al. | |

FOREIGN PATENT DOCUMENTS

| | | |
|---|---|---|
| CN | 104619894 A | 5/2015 |
| CN | 104830961 A | 8/2015 |
| JP | 2006519621 A5 | 4/2007 |
| JP | 2010539956 A5 | 11/2011 |
| JP | 2014057565 A | 4/2014 |
| JP | 2015510766 A5 | 5/2016 |
| WO | 2001061036 A2 | 8/2001 |
| WO | 2012044847 A1 | 4/2012 |
| WO | 2013138536 A1 | 9/2013 |
| WO | 2014047678 A1 | 4/2014 |
| WO | 2018048957 A3 | 3/2015 |
| WO | 2015134552 A1 | 9/2015 |

OTHER PUBLICATIONS

Lin et al., "Isolation, Characterization, and Kinetic Properties of Truncated Forms of T4 DNA Polymerase That Exhibit 3'-5' Exonuclease Activity," The Journal of Biological Chemistry, July, vol. 269, No. 30, pp. 19286-19294. (Year: 1994).*
Gilar et al., "Study of phosphorothioate-modified oligonucleotide resistance to 3'-exonuclease using capillary electrophoresis," Journal of Chromatography B, vol. 714, pp. 13-20. (Year: 1998).*
International Search Report and Written Opinion mailed Apr. 19, 2018 in PCT/US17/50354.
Corrected International Preliminary Report on Patentability mailed Jan. 18, 2019 in PCT/US17/50354.
European Search Report mailed Feb. 17, 2020 in EP Application No. 17849489.4.
Notice of Reasons for Rejection mailed Apr. 15, 2020 in JP Application No. 2019-512800.
Notice on the First Office Action mailed Nov. 3, 2022 in CN Application No. 201780068285.4.
International Preliminary Report on Patentability mailed Oct. 11, 2018 in PCT/US2017/050354.
Office Action mailed Jul. 16, 2020 in CA Application No. 3,035,698.
Office Action mailed Jun. 25, 2021 in CA Application No. 3,035,698.
Office Action mailed Jul. 20, 2022 in CA Application No. 3,035,698.
Examination Report mailed Feb. 24, 2021 for CA Application No. 2017324946.

* cited by examiner

*Primary Examiner* — Young J Kim
(74) *Attorney, Agent, or Firm* — Barnes & Thornburg LLP

(57) ABSTRACT

A bottleneck in the Next Generation Sequencing (NGS) workflow is the quantification of libraries for accurate pooling and loading of the sequencing instrument flow cell or chip. Disclosed herein are methods that improve performance and reduce time compared to existing methods.

20 Claims, 105 Drawing Sheets
Specification includes a Sequence Listing.

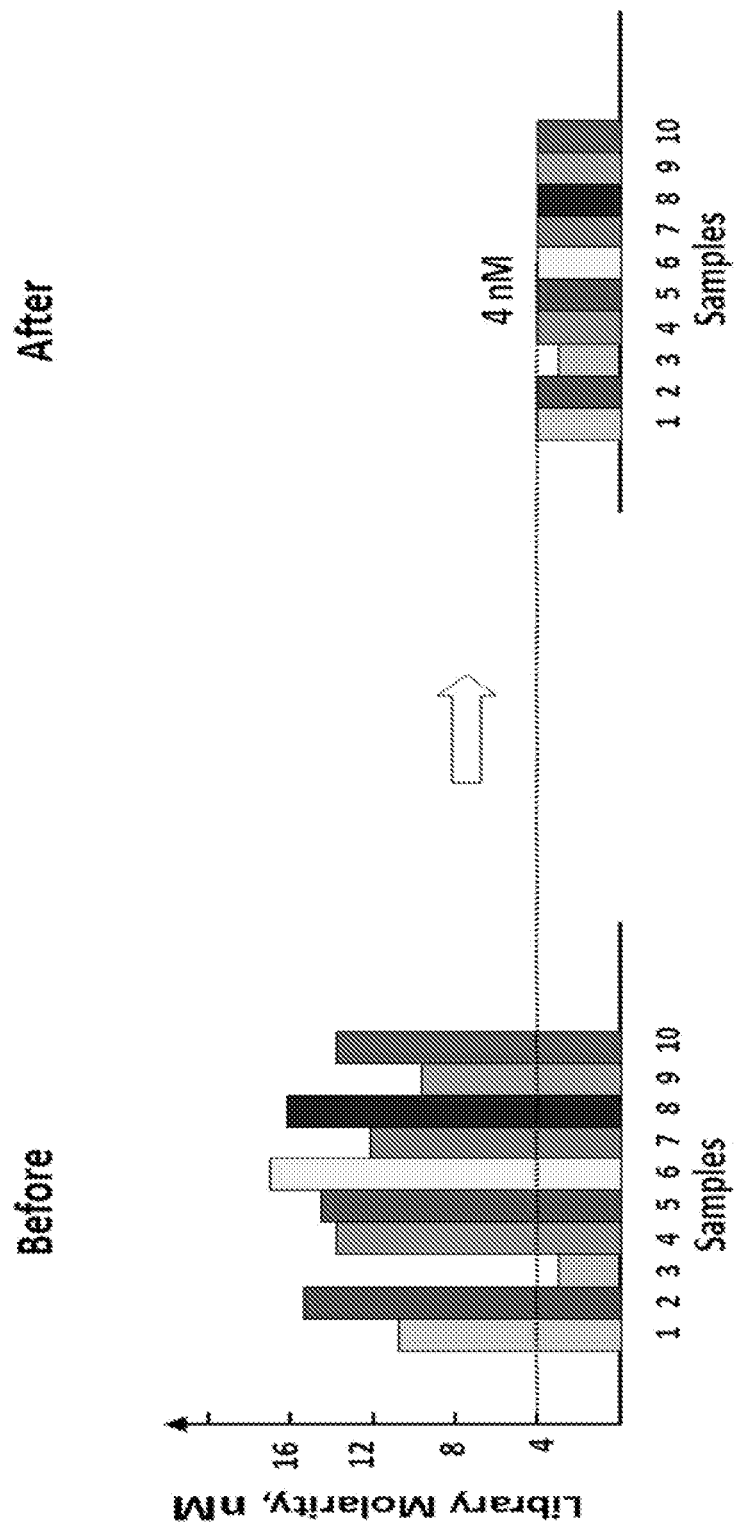

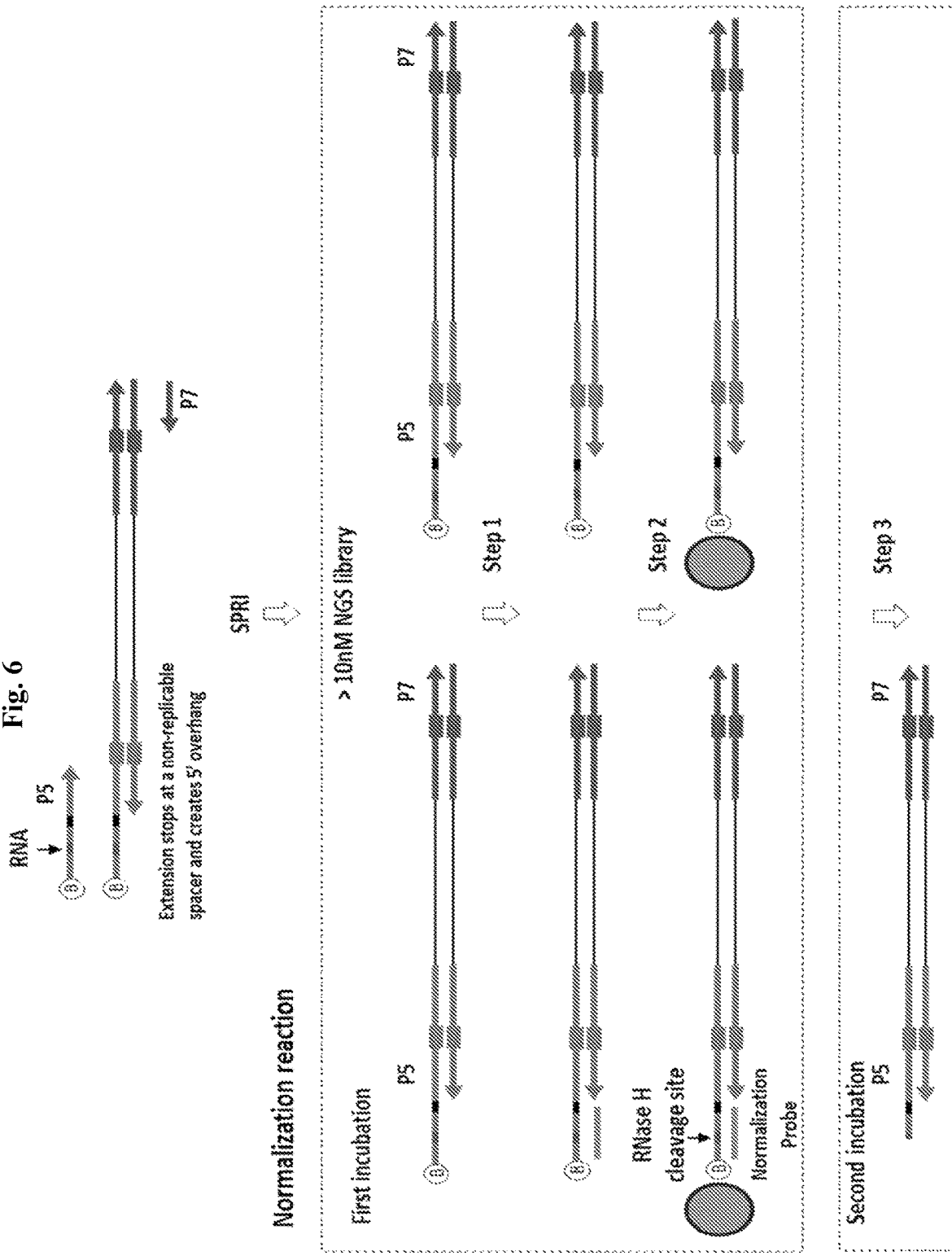

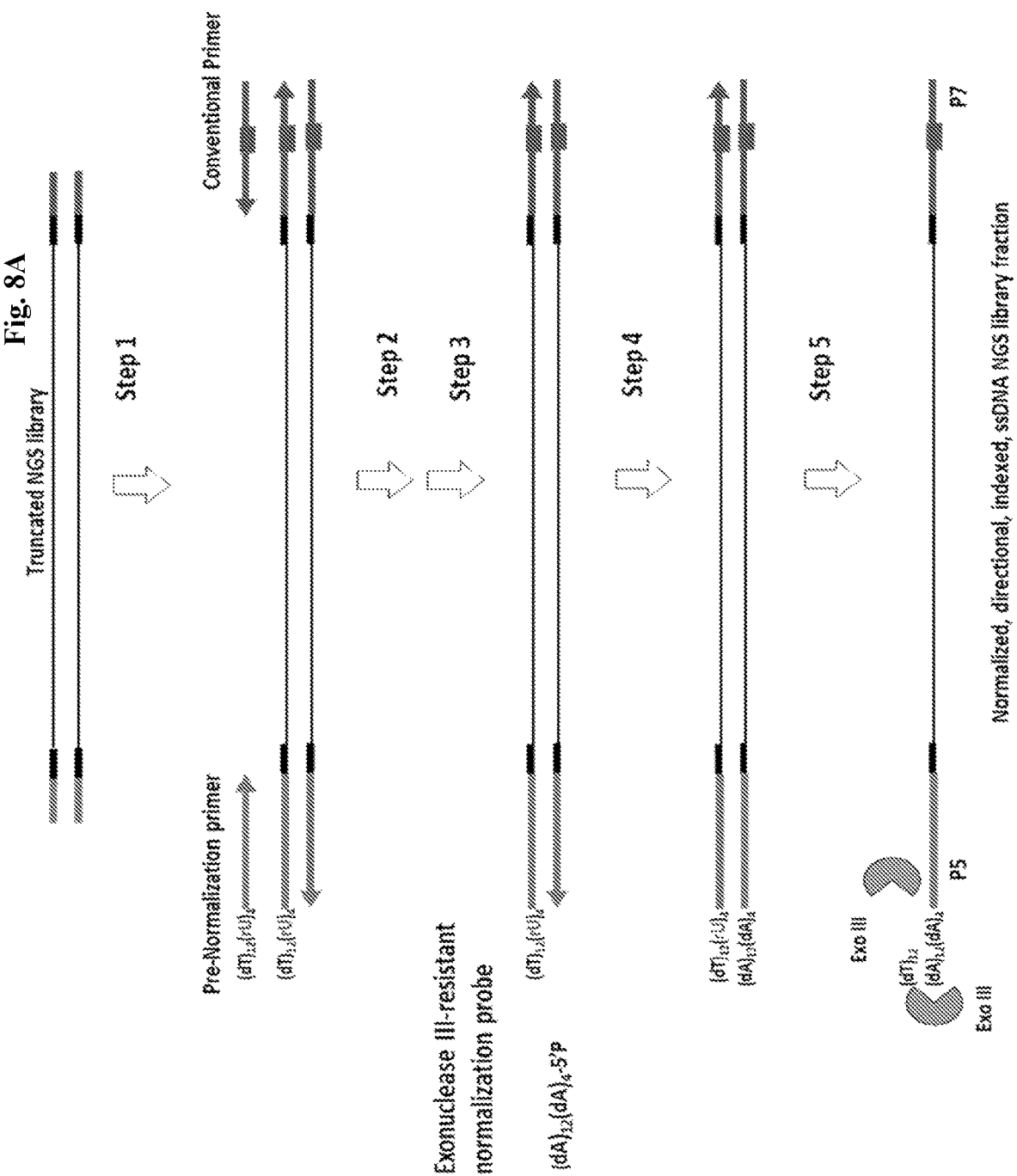

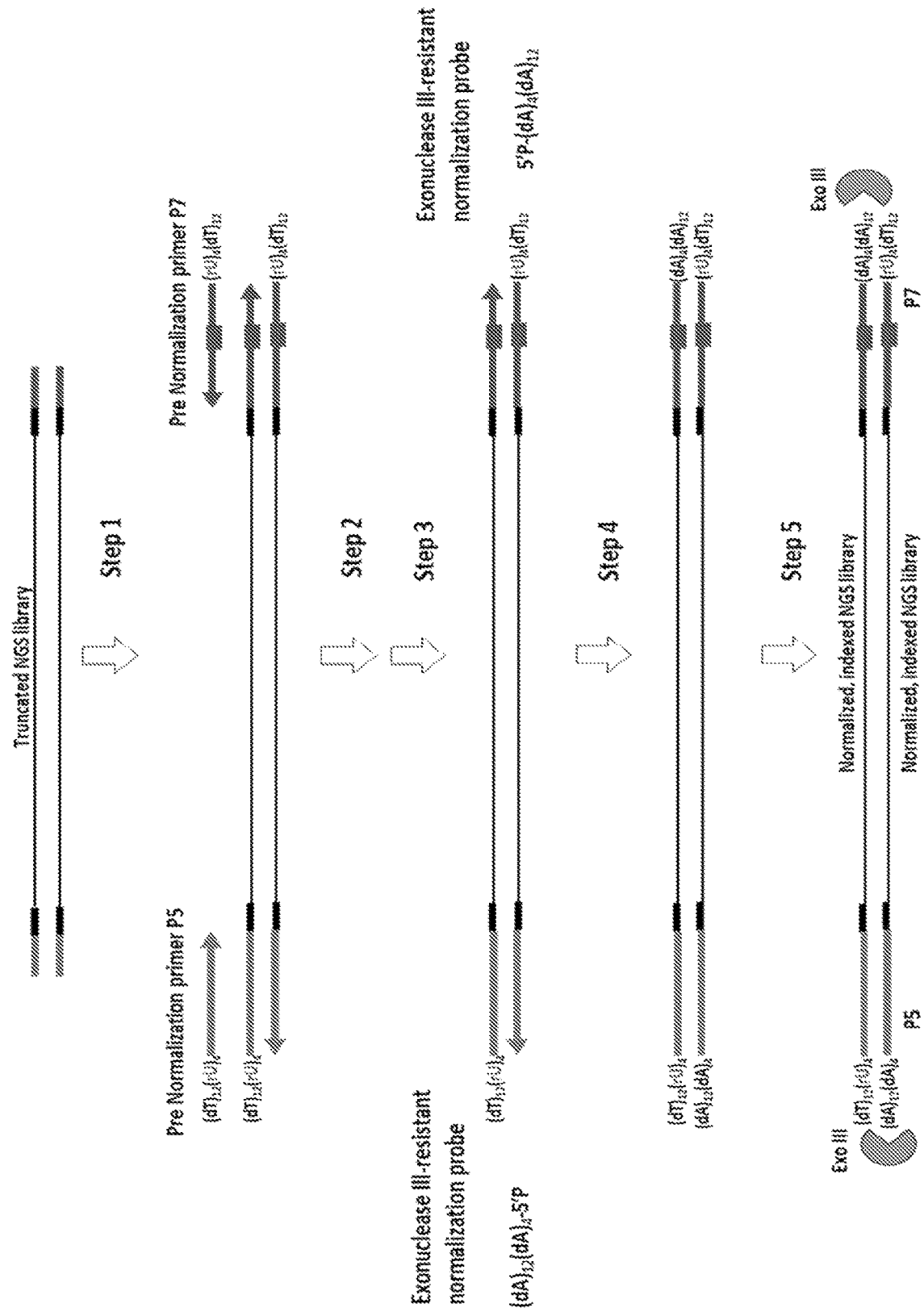

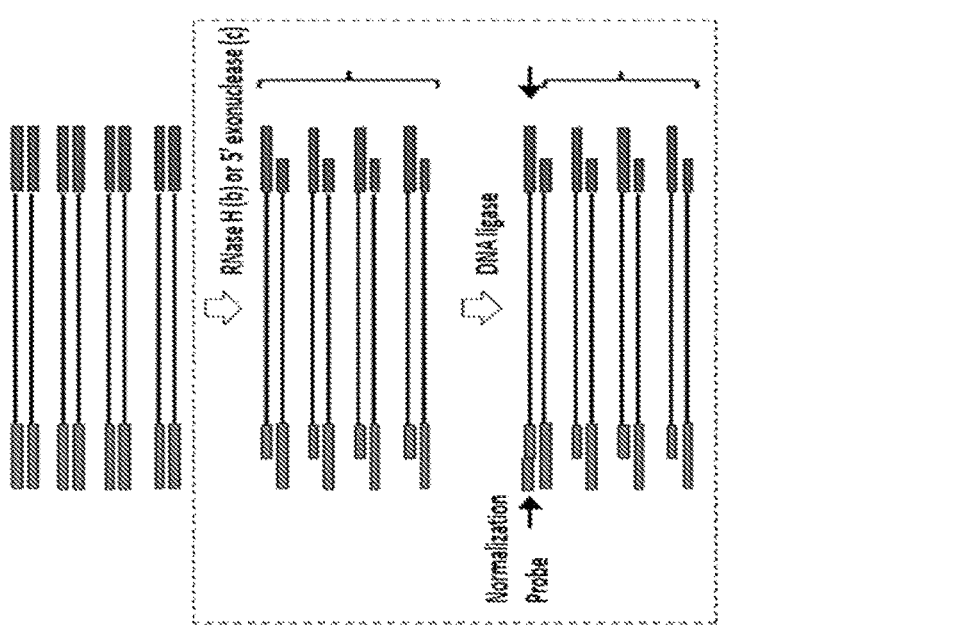
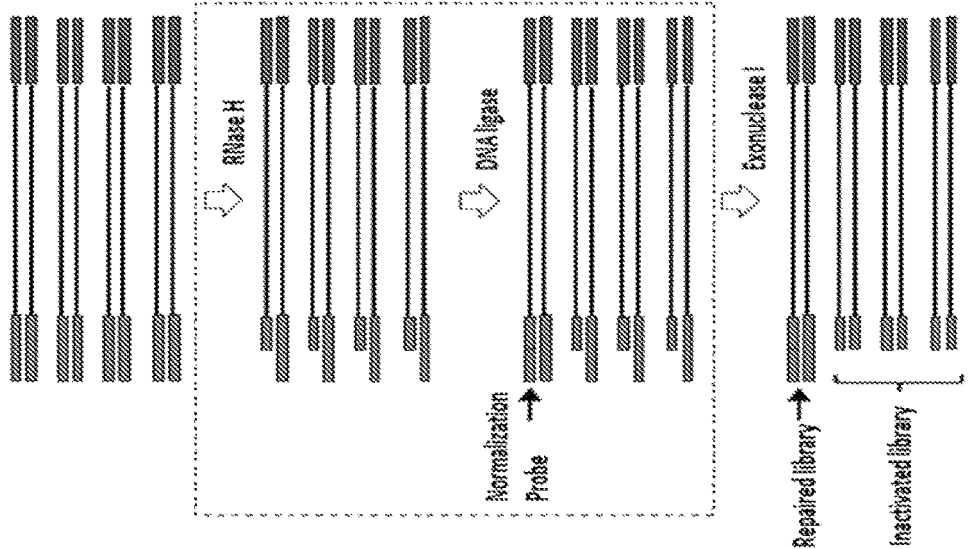
Fig. 13

Fig. 21B
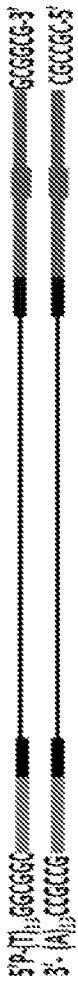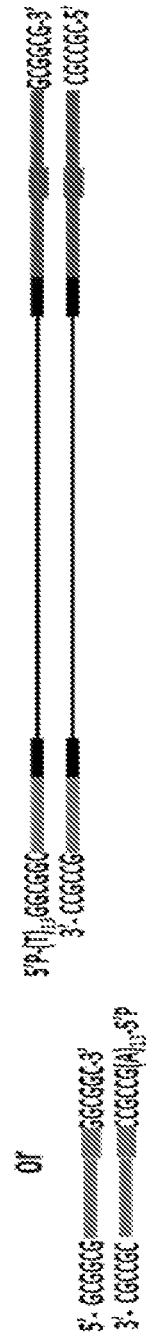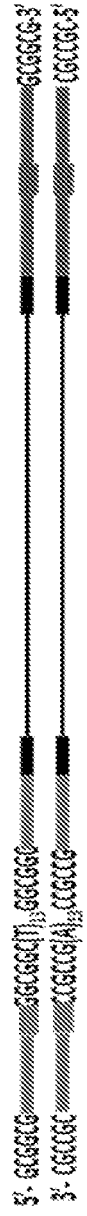

Fig. 23A
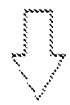
40 nM NGS library
10-fold dilution

Fig. 23B
40 nM P5
$(T)_{25}$ ⟶
⟵ $(A)_{25}$
40 nM P7
40 nM NGS library
10-fold dilution Fig. 29C
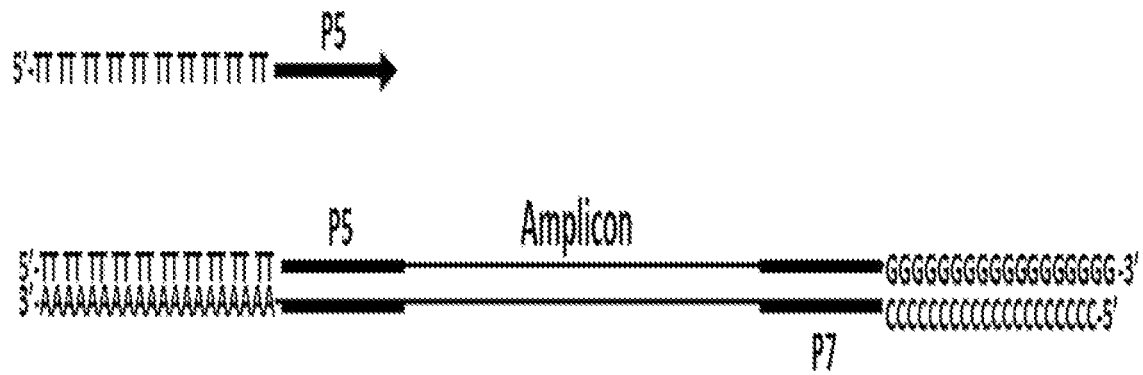
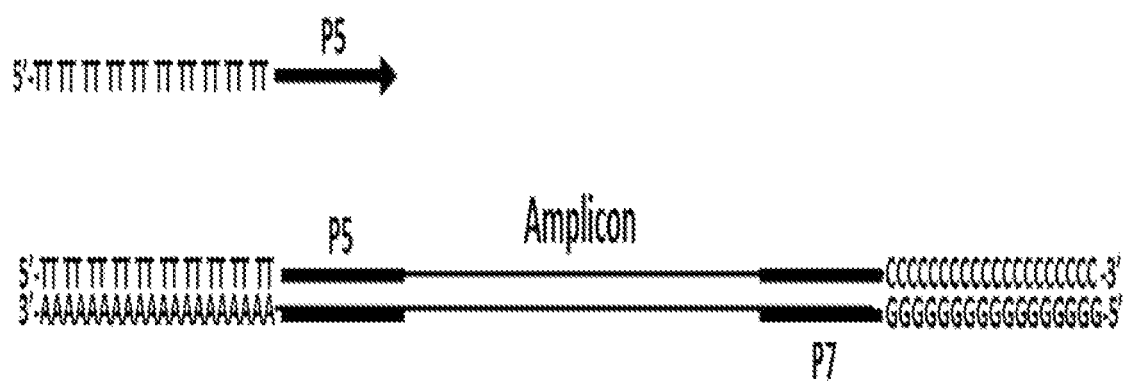
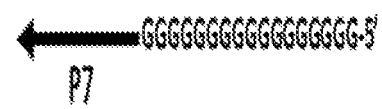

Fig. 29D

5'-TGTGTGTGTGTGTGTGTGTG ⟶ 3'

5'-AGAGAGAGAGAGAGAGAG ⟶ 3'

5'-CTCTCTCTCTCTCTCTCTCT ⟶ 3'

5'-CACACACACACACACACA ⟶ 3'

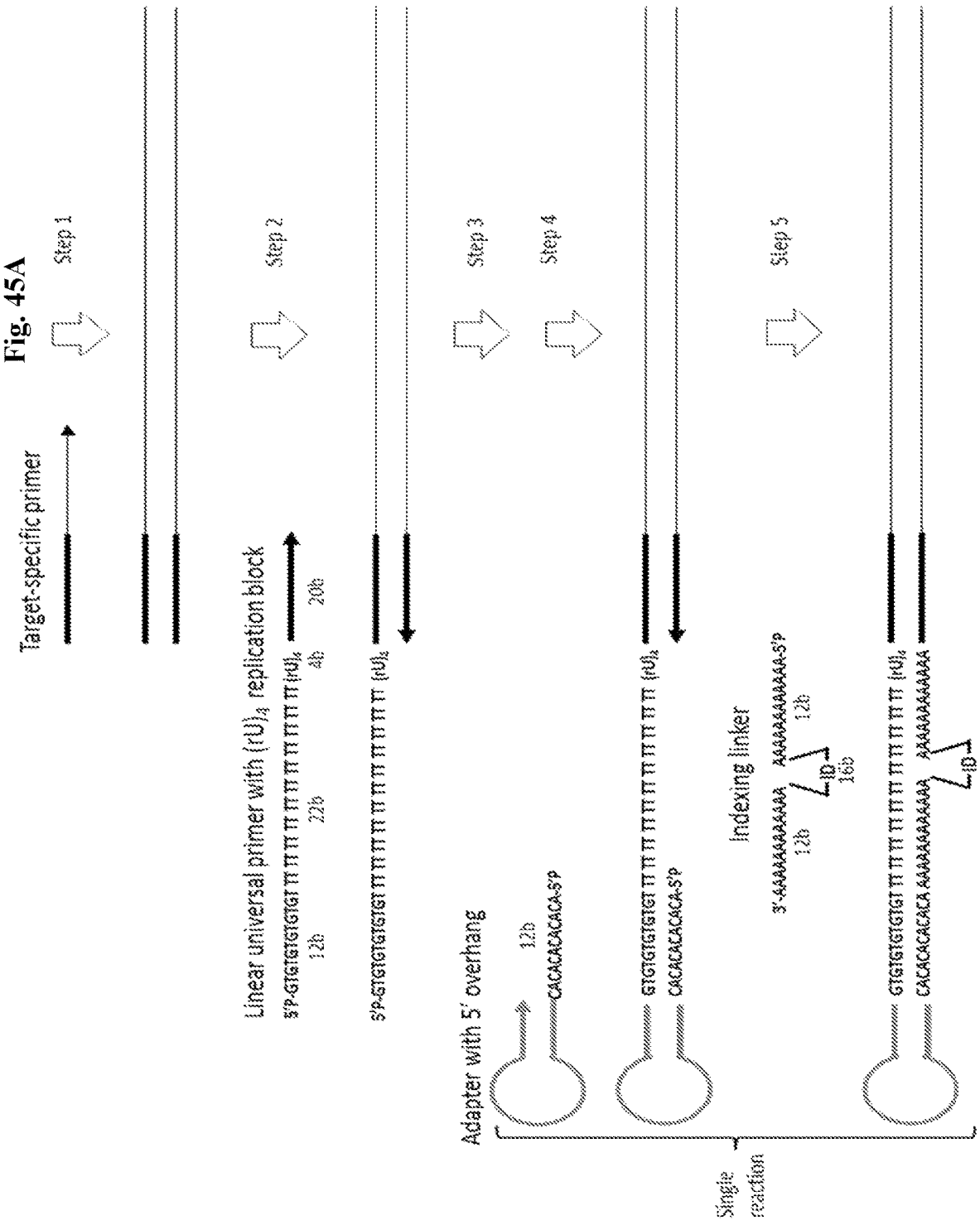

\* - Designated product

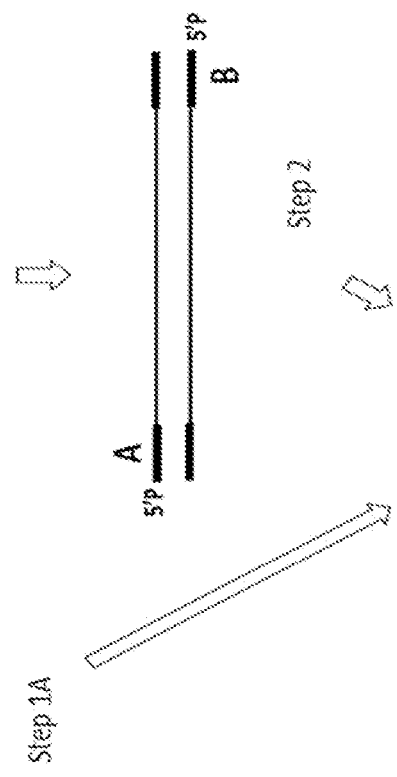
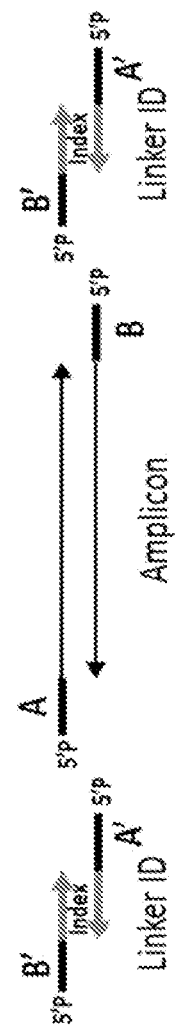
Fig. 48B

Fig. 50A

SEQUENCE LISTING

```
Sequence total quantity: 117
SEQ ID NO: 1           moltype = DNA  length = 46
FEATURE                Location/Qualifiers
misc_feature           1..46
                       note = Description of Artificial Sequence: Synthetic
                        oligonucleotide
misc_feature           1..46
                       note = Description of Combined DNA/RNA Molecule: Synthetic
                        oligonucleotide
source                 1..46
                       mol_type = other DNA
                       organism = synthetic construct
SEQUENCE: 1
gcggagagag gagaggaagg agccctaatg atacggcgac caccga                          46

SEQ ID NO: 2           moltype = DNA  length = 47
FEATURE                Location/Qualifiers
misc_feature           1..47
```

```
                        note = Description of Artificial Sequence: Synthetic
                            oligonucleotide
misc_feature            1..47
                        note = Description of Combined DNA/RNA Molecule: Synthetic
                            oligonucleotide
source                  1..47
                        mol_type = other DNA
                        organism = synthetic construct
SEQUENCE: 2
gcggagagag gagaggaagg agcccttaat gatacggcga ccaccga            47

SEQ ID NO: 3            moltype = DNA   length = 48
FEATURE                 Location/Qualifiers
misc_feature            1..48
                        note = Description of Artificial Sequence: Synthetic
                            oligonucleotide
misc_feature            1..48
                        note = Description of Combined DNA/RNA Molecule: Synthetic
                            oligonucleotide
source                  1..48
                        mol_type = other DNA
                        organism = synthetic construct
SEQUENCE: 3
gcggagagag gagaggaagg agccctttaa tgatacggcg accaccga           48

SEQ ID NO: 4            moltype = DNA   length = 49
FEATURE                 Location/Qualifiers
misc_feature            1..49
                        note = Description of Artificial Sequence: Synthetic
                            oligonucleotide
misc_feature            1..49
                        note = Description of Combined DNA/RNA Molecule: Synthetic
                            oligonucleotide
source                  1..49
                        mol_type = other DNA
                        organism = synthetic construct
SEQUENCE: 4
gcggagagag gagaggaagg agccctttta atgatacggc gaccaccga          49

SEQ ID NO: 5            moltype = DNA   length = 51
FEATURE                 Location/Qualifiers
misc_feature            1..51
                        note = Description of Artificial Sequence: Synthetic
                            oligonucleotide
misc_feature            1..51
                        note = Description of Combined DNA/RNA Molecule: Synthetic
                            oligonucleotide
source                  1..51
                        mol_type = other DNA
                        organism = synthetic construct
SEQUENCE: 5
gcggagagag gagaggaagg agcccttttt taatgatacg gcgaccaccg a       51

SEQ ID NO: 6            moltype = DNA   length = 46
FEATURE                 Location/Qualifiers
misc_feature            1..46
                        note = Description of Artificial Sequence: Synthetic
                            oligonucleotide
misc_feature            1..46
                        note = Description of Combined DNA/RNA Molecule: Synthetic
                            oligonucleotide
source                  1..46
                        mol_type = other DNA
                        organism = synthetic construct
SEQUENCE: 6
gcggagagag gagaggaagg agccctaatg atacggcgac caccga             46

SEQ ID NO: 7            moltype = DNA   length = 48
FEATURE                 Location/Qualifiers
misc_feature            1..48
                        note = Description of Artificial Sequence: Synthetic
                            oligonucleotide
misc_feature            1..48
                        note = Description of Combined DNA/RNA Molecule: Synthetic
                            oligonucleotide
source                  1..48
                        mol_type = other DNA
                        organism = synthetic construct
SEQUENCE: 7
```

```
gcggagagag gagaggaagg agcccaaaaa tgatacggcg accaccga                48

SEQ ID NO: 8          moltype = DNA   length = 48
FEATURE               Location/Qualifiers
misc_feature          1..48
                      note = Description of Artificial Sequence: Synthetic
                      oligonucleotide
misc_feature          1..48
                      note = Description of Combined DNA/RNA Molecule: Synthetic
                      oligonucleotide
source                1..48
                      mol_type = other DNA
                      organism = synthetic construct
SEQUENCE: 8
gcggagagag gagaggaagg agccccccaa tgatacggcg accaccga                48

SEQ ID NO: 9          moltype = DNA   length = 48
FEATURE               Location/Qualifiers
misc_feature          1..48
                      note = Description of Artificial Sequence: Synthetic
                      oligonucleotide
misc_feature          1..48
                      note = Description of Combined DNA/RNA Molecule: Synthetic
                      oligonucleotide
source                1..48
                      mol_type = other DNA
                      organism = synthetic construct
SEQUENCE: 9
gcggagagag gagaggaagg agcccgggaa tgatacggcg accaccga                48

SEQ ID NO: 10         moltype = DNA   length = 25
FEATURE               Location/Qualifiers
misc_feature          1..25
                      note = Description of Artificial Sequence: Synthetic
                      oligonucleotide
source                1..25
                      mol_type = other DNA
                      organism = synthetic construct
SEQUENCE: 10
aaaaaagtat cggtggtcgc cgtat                                         25

SEQ ID NO: 11         moltype = DNA   length = 70
FEATURE               Location/Qualifiers
misc_feature          1..70
                      note = Description of Artificial Sequence: Synthetic
                      oligonucleotide
source                1..70
                      mol_type = other DNA
                      organism = synthetic construct
SEQUENCE: 11
aatgatacgg cgaccaccga gatctacact atagcctaca ctctttccct acacgacgct   60
cttccgatct                                                          70

SEQ ID NO: 12         moltype = DNA   length = 40
FEATURE               Location/Qualifiers
misc_feature          1..40
                      note = Description of Artificial Sequence: Synthetic
                      oligonucleotide
misc_feature          1..40
                      note = Description of Combined DNA/RNA Molecule: Synthetic
                      oligonucleotide
source                1..40
                      mol_type = other DNA
                      organism = synthetic construct
SEQUENCE: 12
ggagaggaag gagccccttt aatgatacgg cgaccaccga                         40

SEQ ID NO: 13         moltype = DNA   length = 22
FEATURE               Location/Qualifiers
misc_feature          1..22
                      note = Description of Artificial Sequence: Synthetic
                      oligonucleotide
source                1..22
                      mol_type = other DNA
                      organism = synthetic construct
SEQUENCE: 13
agatcggaag agcgtcgtgt ag                                            22

SEQ ID NO: 14         moltype = DNA   length = 38
```

| | |
|---|---|
| FEATURE | Location/Qualifiers |
| misc_feature | 1..38 |
| | note = Description of Artificial Sequence: Synthetic oligonucleotide |
| misc_feature | 1..38 |
| | note = Description of Combined DNA/RNA Molecule: Synthetic oligonucleotide |
| source | 1..38 |
| | mol_type = other DNA |
| | organism = synthetic construct |

SEQUENCE: 14
ttttttttt tttttaatg atacggcgac caccgaga                        38

| | |
|---|---|
| SEQ ID NO: 15 | moltype = DNA length = 40 |
| FEATURE | Location/Qualifiers |
| misc_feature | 1..40 |
| | note = Description of Artificial Sequence: Synthetic oligonucleotide |
| misc_feature | 1..40 |
| | note = Description of Combined DNA/RNA Molecule: Synthetic oligonucleotide |
| source | 1..40 |
| | mol_type = other DNA |
| | organism = synthetic construct |

SEQUENCE: 15
tttttttttt tttttcaag cagaagacgg catacgagat                      40

| | |
|---|---|
| SEQ ID NO: 16 | moltype = DNA length = 16 |
| FEATURE | Location/Qualifiers |
| misc_feature | 1..16 |
| | note = Description of Artificial Sequence: Synthetic oligonucleotide |
| source | 1..16 |
| | mol_type = other DNA |
| | organism = synthetic construct |

SEQUENCE: 16
aaaaaaaaaa aaaaaa                                              16

| | |
|---|---|
| SEQ ID NO: 17 | moltype = DNA length = 42 |
| FEATURE | Location/Qualifiers |
| misc_feature | 1..42 |
| | note = Description of Artificial Sequence: Synthetic oligonucleotide |
| source | 1..42 |
| | mol_type = other DNA |
| | organism = synthetic construct |

SEQUENCE: 17
ggttgtgggt gtcaaacaaa caaatgatac ggcgaccacc ga                  42

| | |
|---|---|
| SEQ ID NO: 18 | moltype = DNA length = 12 |
| FEATURE | Location/Qualifiers |
| misc_feature | 1..12 |
| | note = Description of Artificial Sequence: Synthetic oligonucleotide |
| source | 1..12 |
| | mol_type = other DNA |
| | organism = synthetic construct |

SEQUENCE: 18
acacccacaa cc                                                  12

| | |
|---|---|
| SEQ ID NO: 19 | moltype = DNA length = 43 |
| FEATURE | Location/Qualifiers |
| misc_feature | 1..43 |
| | note = Description of Artificial Sequence: Synthetic oligonucleotide |
| misc_feature | 1..43 |
| | note = Description of Combined DNA/RNA Molecule: Synthetic oligonucleotide |
| source | 1..43 |
| | mol_type = other DNA |
| | organism = synthetic construct |

SEQUENCE: 19
tttttttttt tttttacat cggtgactgg agttcagacg tgt                  43

| | |
|---|---|
| SEQ ID NO: 20 | moltype = DNA length = 16 |
| FEATURE | Location/Qualifiers |
| misc_feature | 1..16 |
| | note = Description of Artificial Sequence: Synthetic oligonucleotide |

```
source                  1..16
                        mol_type = other DNA
                        organism = synthetic construct
SEQUENCE: 20
aaaaaaaaaa aaaaaa                                                          16

SEQ ID NO: 21           moltype = DNA   length = 22
FEATURE                 Location/Qualifiers
misc_feature            1..22
                        note = Description of Artificial Sequence: Synthetic
                            oligonucleotide
source                  1..22
                        mol_type = other DNA
                        organism = synthetic construct
SEQUENCE: 21
aatgatacgg cgaccaccga ga                                                   22

SEQ ID NO: 22           moltype = DNA   length = 42
FEATURE                 Location/Qualifiers
misc_feature            1..42
                        note = Description of Artificial Sequence: Synthetic
                            oligonucleotide
source                  1..42
                        mol_type = other DNA
                        organism = synthetic construct
SEQUENCE: 22
gtgtgtgtgt gtgtgtgtgt aatgatacgg cgaccaccga ga                             42

SEQ ID NO: 23           moltype = DNA   length = 42
FEATURE                 Location/Qualifiers
misc_feature            1..42
                        note = Description of Artificial Sequence: Synthetic
                            oligonucleotide
source                  1..42
                        mol_type = other DNA
                        organism = synthetic construct
SEQUENCE: 23
tctcggtggt cgccgtatca ttacacacac acacacacac ac                             42

SEQ ID NO: 24           moltype = DNA   length = 22
FEATURE                 Location/Qualifiers
misc_feature            1..22
                        note = Description of Artificial Sequence: Synthetic
                            oligonucleotide
source                  1..22
                        mol_type = other DNA
                        organism = synthetic construct
SEQUENCE: 24
aatgatacgg cgaccaccga ga                                                   22

SEQ ID NO: 25           moltype = DNA   length = 24
FEATURE                 Location/Qualifiers
misc_feature            1..24
                        note = Description of Artificial Sequence: Synthetic
                            oligonucleotide
source                  1..24
                        mol_type = other DNA
                        organism = synthetic construct
SEQUENCE: 25
caagcagaag acggcatacg agat                                                 24

SEQ ID NO: 26           moltype = DNA   length = 42
FEATURE                 Location/Qualifiers
misc_feature            1..42
                        note = Description of Artificial Sequence: Synthetic
                            oligonucleotide
source                  1..42
                        mol_type = other DNA
                        organism = synthetic construct
SEQUENCE: 26
gtgtgtgtgt gtgtgtgtgt aatgatacgg cgaccaccga ga                             42

SEQ ID NO: 27           moltype = DNA   length = 48
FEATURE                 Location/Qualifiers
misc_feature            1..48
                        note = Description of Artificial Sequence: Synthetic
                            oligonucleotide
source                  1..48
                        mol_type = other DNA
```

```
                              organism = synthetic construct
SEQUENCE: 27
gagagagaga gagagagaga gagacaagca gaagacggca tacgagat              48

SEQ ID NO: 28           moltype = DNA   length = 43
FEATURE                 Location/Qualifiers
misc_feature            1..43
                        note = Description of Artificial Sequence: Synthetic
                          oligonucleotide
source                  1..43
                        mol_type = other DNA
                        organism = synthetic construct
SEQUENCE: 28
tgtgtgtgtg tgtgtgtgtg taatgatacg gcgaccaccg aga                   43

SEQ ID NO: 29           moltype = DNA   length = 48
FEATURE                 Location/Qualifiers
misc_feature            1..48
                        note = Description of Artificial Sequence: Synthetic
                          oligonucleotide
source                  1..48
                        mol_type = other DNA
                        organism = synthetic construct
SEQUENCE: 29
gagagagaga gagagagaga gagacaagca gaagacggca tacgagat              48

SEQ ID NO: 30           moltype = DNA   length = 32
FEATURE                 Location/Qualifiers
misc_feature            1..32
                        note = Description of Artificial Sequence: Synthetic
                          oligonucleotide
source                  1..32
                        mol_type = other DNA
                        organism = synthetic construct
SEQUENCE: 30
gccgtatcat tacacacaca cacacacaca ca                               32

SEQ ID NO: 31           moltype = DNA   length = 21
FEATURE                 Location/Qualifiers
misc_feature            1..21
                        note = Description of Artificial Sequence: Synthetic
                          oligonucleotide
source                  1..21
                        mol_type = other DNA
                        organism = synthetic construct
SEQUENCE: 31
caagcagaag acggcatacg a                                           21

SEQ ID NO: 32           moltype = DNA   length = 33
FEATURE                 Location/Qualifiers
misc_feature            1..33
                        note = Description of Artificial Sequence: Synthetic
                          oligonucleotide
misc_feature            1..33
                        note = Description of Combined DNA/RNA Molecule: Synthetic
                          oligonucleotide
source                  1..33
                        mol_type = other DNA
                        organism = synthetic construct
SEQUENCE: 32
acactctttc cctacacgac gctcttccga tct                              33

SEQ ID NO: 33           moltype = DNA   length = 25
FEATURE                 Location/Qualifiers
misc_feature            1..25
                        note = Description of Artificial Sequence: Synthetic
                          oligonucleotide
source                  1..25
                        mol_type = other DNA
                        organism = synthetic construct
SEQUENCE: 33
aatgatacgg cgaccaccga gatct                                       25

SEQ ID NO: 34           moltype = DNA   length = 34
FEATURE                 Location/Qualifiers
misc_feature            1..34
                        note = Description of Artificial Sequence: Synthetic
                          oligonucleotide
source                  1..34
```

```
                        mol_type = other DNA
                        organism = synthetic construct
SEQUENCE: 34
aaagagtgta gatctcggtg gtcgccgtat catt                              34

SEQ ID NO: 35           moltype = DNA   length = 57
FEATURE                 Location/Qualifiers
misc_feature            1..57
                        note = Description of Artificial Sequence: Synthetic
                          oligonucleotide
misc_feature            1..57
                        note = Description of Combined DNA/RNA Molecule: Synthetic
                          oligonucleotide
source                  1..57
                        mol_type = other DNA
                        organism = synthetic construct
SEQUENCE: 35
aaaaaaaaaa aaaatgcgag atctacactc tttccctaca cgacgctctt ccgatct     57

SEQ ID NO: 36           moltype = DNA   length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 36
aaagagtgta gatctcggtg gtcgccgtat cattttttt tttttt                  46

SEQ ID NO: 37           moltype = DNA   length = 45
FEATURE                 Location/Qualifiers
misc_feature            1..45
                        note = Description of Artificial Sequence: Synthetic
                          oligonucleotide
source                  1..45
                        mol_type = other DNA
                        organism = synthetic construct
SEQUENCE: 37
agcaggatcg gtatggctag tgtccgcaag gtcatcgcta agtaa                  45

SEQ ID NO: 38           moltype = DNA   length = 47
FEATURE                 Location/Qualifiers
misc_feature            1..47
                        note = Description of Artificial Sequence: Synthetic
                          oligonucleotide
source                  1..47
                        mol_type = other DNA
                        organism = synthetic construct
SEQUENCE: 38
agcaggatcg gtatggctag tgtcagggtt agacgtgtca aggtatc                47

SEQ ID NO: 39           moltype = DNA   length = 61
FEATURE                 Location/Qualifiers
misc_feature            1..61
                        note = Description of Artificial Sequence: Synthetic
                          oligonucleotide
misc_feature            1..61
                        note = Description of Combined DNA/RNA Molecule: Synthetic
                          oligonucleotide
source                  1..61
                        mol_type = other DNA
                        organism = synthetic construct
SEQUENCE: 39
gtgtgtgtgt gttttttttt tttttttttt tttttttag caggatcggt atggctagtg  60
t                                                                 61

SEQ ID NO: 40           moltype = DNA   length = 94
FEATURE                 Location/Qualifiers
misc_feature            1..94
                        note = Description of Artificial Sequence: Synthetic
                          oligonucleotide
misc_feature            1..94
                        note = Description of Combined DNA/RNA Molecule: Synthetic
                          oligonucleotide
source                  1..94
                        mol_type = other DNA
                        organism = synthetic construct
SEQUENCE: 40
```

```
atctctctct tttcctcctc ctccgttgtt gttgttgaga gagatttttt tttttttttt    60
ttttttttt tagcaggatc ggtatggcta gtgt                                 94

SEQ ID NO: 41          moltype = DNA   length = 57
FEATURE                Location/Qualifiers
misc_feature           1..57
                       note = Description of Artificial Sequence: Synthetic
                       oligonucleotide
source                 1..57
                       mol_type = other DNA
                       organism = synthetic construct
SEQUENCE: 41
acacacacac acatctctct cttttcctcc tcctccgttg ttgttgttga gagagat       57

SEQ ID NO: 42          moltype = DNA   length = 40
FEATURE                Location/Qualifiers
misc_feature           1..40
                       note = Description of Artificial Sequence: Synthetic
                       oligonucleotide
source                 1..40
                       mol_type = other DNA
                       organism = synthetic construct
SEQUENCE: 42
aaaaaaaaaa aatcagacga tgcgtcataa aaaaaaaaaa                          40

SEQ ID NO: 43          moltype = DNA   length = 58
FEATURE                Location/Qualifiers
misc_feature           1..58
                       note = Description of Artificial Sequence: Synthetic
                       oligonucleotide
source                 1..58
                       mol_type = other DNA
                       organism = synthetic construct
SEQUENCE: 43
aatgatacgg cgaccaccga gatctacact ctttccctac acgacgctct ccgatct       58

SEQ ID NO: 44          moltype = DNA   length = 63
FEATURE                Location/Qualifiers
misc_feature           1..63
                       note = Description of Artificial Sequence: Synthetic
                       oligonucleotide
misc_difference        34..39
                       note = a, c, t, g, unknown or other
source                 1..63
                       mol_type = other DNA
                       organism = synthetic construct
SEQUENCE: 44
gatcggaaga gcacacgtct gaactccagt cacnnnnnna tctcgtatgc cgtcttctgc    60
ttg                                                                  63

SEQ ID NO: 45          moltype = DNA   length = 30
FEATURE                Location/Qualifiers
misc_feature           1..30
                       note = Description of Artificial Sequence: Synthetic
                       oligonucleotide
source                 1..30
                       mol_type = other DNA
                       organism = synthetic construct
SEQUENCE: 45
ccatctcatc cctgcgtgtc tccgactcag                                     30

SEQ ID NO: 46          moltype = DNA   length = 41
FEATURE                Location/Qualifiers
misc_feature           1..41
                       note = Description of Artificial Sequence: Synthetic
                       oligonucleotide
source                 1..41
                       mol_type = other DNA
                       organism = synthetic construct
SEQUENCE: 46
atcaccgact gcccatagag aggaaagcgg aggcgtagtg g                        41

SEQ ID NO: 47          moltype = DNA   length = 45
FEATURE                Location/Qualifiers
misc_feature           1..45
                       note = Description of Artificial Sequence: Synthetic
                       oligonucleotide
source                 1..45
                       mol_type = other DNA
```

```
                       organism = synthetic construct
SEQUENCE: 47
atctctctct tttcctcctc ctccgttgtt gttgttgaga gagat            45

SEQ ID NO: 48           moltype = DNA  length = 47
FEATURE                 Location/Qualifiers
misc_feature            1..47
                        note = Description of Artificial Sequence: Synthetic
                          oligonucleotide
source                  1..47
                        mol_type = other DNA
                        organism = synthetic construct
SEQUENCE: 48
tttttttttt ttggcggcaa ttgcgatcga tgcactgtgg cggcggc          47

SEQ ID NO: 49           moltype = DNA  length = 47
FEATURE                 Location/Qualifiers
misc_feature            1..47
                        note = Description of Artificial Sequence: Synthetic
                          oligonucleotide
source                  1..47
                        mol_type = other DNA
                        organism = synthetic construct
SEQUENCE: 49
gccgccgcca cagtgcatcg atcgcaattg ccgccaaaaa aaaaaaa          47

SEQ ID NO: 50           moltype = DNA  length = 45
FEATURE                 Location/Qualifiers
misc_feature            1..45
                        note = Description of Artificial Sequence: Synthetic
                          oligonucleotide
source                  1..45
                        mol_type = other DNA
                        organism = synthetic construct
SEQUENCE: 50
tttttttttt ttggcgaatt gcgatcgatg cactgtggcg gcggc            45

SEQ ID NO: 51           moltype = DNA  length = 45
FEATURE                 Location/Qualifiers
misc_feature            1..45
                        note = Description of Artificial Sequence: Synthetic
                          oligonucleotide
source                  1..45
                        mol_type = other DNA
                        organism = synthetic construct
SEQUENCE: 51
gccgccgcca cagtgcatcg atcgcaattc gccaaaaaaa aaaaa            45

SEQ ID NO: 52           moltype = DNA  length = 43
FEATURE                 Location/Qualifiers
misc_feature            1..43
                        note = Description of Artificial Sequence: Synthetic
                          oligonucleotide
source                  1..43
                        mol_type = other DNA
                        organism = synthetic construct
SEQUENCE: 52
tttttttttt ttggaattgc gatcgatgca ctgtggcggc ggc              43

SEQ ID NO: 53           moltype = DNA  length = 43
FEATURE                 Location/Qualifiers
misc_feature            1..43
                        note = Description of Artificial Sequence: Synthetic
                          oligonucleotide
source                  1..43
                        mol_type = other DNA
                        organism = synthetic construct
SEQUENCE: 53
gccgccgcca cagtgcatcg atcgcaattc caaaaaaaaa aaa              43

SEQ ID NO: 54           moltype = DNA  length = 42
FEATURE                 Location/Qualifiers
misc_feature            1..42
                        note = Description of Artificial Sequence: Synthetic
                          oligonucleotide
source                  1..42
                        mol_type = other DNA
                        organism = synthetic construct
SEQUENCE: 54
```

-continued

```
tttttttttt ttgaattgcg atcgatgcac tgtggcggcg gc                42

SEQ ID NO: 55           moltype = DNA  length = 42
FEATURE                 Location/Qualifiers
misc_feature            1..42
                        note = Description of Artificial Sequence: Synthetic
                          oligonucleotide
source                  1..42
                        mol_type = other DNA
                        organism = synthetic construct
SEQUENCE: 55
gccgccgcca cagtgcatcg atcgcaattc aaaaaaaaaa aa                42

SEQ ID NO: 56           moltype = DNA  length = 12
FEATURE                 Location/Qualifiers
misc_feature            1..12
                        note = Description of Artificial Sequence: Synthetic
                          oligonucleotide
source                  1..12
                        mol_type = other DNA
                        organism = synthetic construct
SEQUENCE: 56
tttttttttt tt                                                 12

SEQ ID NO: 57           moltype = DNA  length = 20
FEATURE                 Location/Qualifiers
misc_feature            1..20
                        note = Description of Artificial Sequence: Synthetic
                          oligonucleotide
misc_feature            1..20
                        note = This sequence may encompass 6-20 bases
source                  1..20
                        mol_type = other DNA
                        organism = synthetic construct
SEQUENCE: 57
tttttttttt tttttttttt                                         20

SEQ ID NO: 58           moltype = DNA  length = 20
FEATURE                 Location/Qualifiers
misc_feature            1..20
                        note = Description of Artificial Sequence: Synthetic
                          oligonucleotide
misc_feature            1..20
                        note = This sequence may encompass 6-20 bases
source                  1..20
                        mol_type = other DNA
                        organism = synthetic construct
SEQUENCE: 58
aaaaaaaaaa aaaaaaaaaa                                         20

SEQ ID NO: 59           moltype = DNA  length = 20
FEATURE                 Location/Qualifiers
misc_feature            1..20
                        note = Description of Artificial Sequence: Synthetic
                          oligonucleotide
misc_feature            1..20
                        note = This sequence may encompass 10-20 bases
source                  1..20
                        mol_type = other DNA
                        organism = synthetic construct
SEQUENCE: 59
aaaaaaaaaa aaaaaaaaaa                                         20

SEQ ID NO: 60           moltype = DNA  length = 20
FEATURE                 Location/Qualifiers
misc_feature            1..20
                        note = Description of Artificial Sequence: Synthetic
                          oligonucleotide
misc_feature            1..20
                        note = This sequence may encompass 10-20 bases
source                  1..20
                        mol_type = other DNA
                        organism = synthetic construct
SEQUENCE: 60
tttttttttt tttttttttt                                         20

SEQ ID NO: 61           moltype = DNA  length = 38
FEATURE                 Location/Qualifiers
misc_feature            1..38
```

```
                        note = Description of Artificial Sequence: Synthetic
                          oligonucleotide
misc_feature            1..38
                        note = Description of Combined DNA/RNA Molecule: Synthetic
                          oligonucleotide
source                  1..38
                        mol_type = other DNA
                        organism = synthetic construct
SEQUENCE: 61
gtgtgtgtgt gtttttttt tttttttttt tttttttt                                  38

SEQ ID NO: 62           moltype = DNA   length = 26
FEATURE                 Location/Qualifiers
misc_feature            1..26
                        note = Description of Artificial Sequence: Synthetic
                          oligonucleotide
misc_feature            1..26
                        note = Description of Combined DNA/RNA Molecule: Synthetic
                          oligonucleotide
source                  1..26
                        mol_type = other DNA
                        organism = synthetic construct
SEQUENCE: 62
tttttttttt tttttttttt tttttt                                              26

SEQ ID NO: 63           moltype = DNA   length = 12
FEATURE                 Location/Qualifiers
misc_feature            1..12
                        note = Description of Artificial Sequence: Synthetic
                          oligonucleotide
source                  1..12
                        mol_type = other DNA
                        organism = synthetic construct
SEQUENCE: 63
gtgtgtgtgt gt                                                             12

SEQ ID NO: 64           moltype = DNA   length = 12
FEATURE                 Location/Qualifiers
misc_feature            1..12
                        note = Description of Artificial Sequence: Synthetic
                          oligonucleotide
source                  1..12
                        mol_type = other DNA
                        organism = synthetic construct
SEQUENCE: 64
acacacacac ac                                                             12

SEQ ID NO: 65           moltype = DNA   length = 16
FEATURE                 Location/Qualifiers
misc_feature            1..16
                        note = Description of Artificial Sequence: Synthetic
                          oligonucleotide
misc_feature            1..16
                        note = This sequence may encompass 10-16 bases
source                  1..16
                        mol_type = other DNA
                        organism = synthetic construct
SEQUENCE: 65
tttttttttt tttttt                                                         16

SEQ ID NO: 66           moltype = DNA   length = 20
FEATURE                 Location/Qualifiers
misc_feature            1..20
                        note = Description of Artificial Sequence: Synthetic
                          oligonucleotide
misc_feature            1..20
                        note = Description of Combined DNA/RNA Molecule: Synthetic
                          oligonucleotide
misc_feature            5..20
                        note = This region may encompass 12-16 bases
source                  1..20
                        mol_type = other DNA
                        organism = synthetic construct
SEQUENCE: 66
tttttttttt tttttttttt                                                     20

SEQ ID NO: 67           moltype = DNA   length = 16
FEATURE                 Location/Qualifiers
misc_feature            1..16
```

```
                        note = Description of Artificial Sequence: Synthetic
                            oligonucleotide
misc_feature            1..16
                        note = Description of Combined DNA/RNA Molecule: Synthetic
                            oligonucleotide
source                  1..16
                        mol_type = other DNA
                        organism = synthetic construct
SEQUENCE: 67
tttttttttt tttttt                                                             16

SEQ ID NO: 68           moltype = DNA  length = 16
FEATURE                 Location/Qualifiers
misc_feature            1..16
                        note = Description of Artificial Sequence: Synthetic
                            oligonucleotide
source                  1..16
                        mol_type = other DNA
                        organism = synthetic construct
SEQUENCE: 68
aaaaaaaaaa aaaaaa                                                             16

SEQ ID NO: 69           moltype = DNA  length = 18
FEATURE                 Location/Qualifiers
misc_feature            1..18
                        note = Description of Artificial Sequence: Synthetic
                            oligonucleotide
source                  1..18
                        mol_type = other DNA
                        organism = synthetic construct
SEQUENCE: 69
tttttttttt ttssssss                                                           18

SEQ ID NO: 70           moltype = DNA  length = 18
FEATURE                 Location/Qualifiers
misc_feature            1..18
                        note = Description of Artificial Sequence: Synthetic
                            oligonucleotide
source                  1..18
                        mol_type = other DNA
                        organism = synthetic construct
SEQUENCE: 70
ssssssaaaa aaaaaaaa                                                           18

SEQ ID NO: 71           moltype = DNA  length = 24
FEATURE                 Location/Qualifiers
misc_feature            1..24
                        note = Description of Artificial Sequence: Synthetic
                            oligonucleotide
source                  1..24
                        mol_type = other DNA
                        organism = synthetic construct
SEQUENCE: 71
ssssssttttt tttttttttss ssss                                                  24

SEQ ID NO: 72           moltype = DNA  length = 24
FEATURE                 Location/Qualifiers
misc_feature            1..24
                        note = Description of Artificial Sequence: Synthetic
                            oligonucleotide
source                  1..24
                        mol_type = other DNA
                        organism = synthetic construct
SEQUENCE: 72
ssssssaaaa aaaaaaaass ssss                                                    24

SEQ ID NO: 73           moltype = DNA  length = 19
FEATURE                 Location/Qualifiers
misc_feature            1..19
                        note = Description of Artificial Sequence: Synthetic
                            oligonucleotide
source                  1..19
                        mol_type = other DNA
                        organism = synthetic construct
SEQUENCE: 73
tttttttttt tttggcggc                                                          19

SEQ ID NO: 74           moltype = DNA  length = 19
FEATURE                 Location/Qualifiers
```

```
misc_feature              1..19
                          note = Description of Artificial Sequence: Synthetic
                            oligonucleotide
source                    1..19
                          mol_type = other DNA
                          organism = synthetic construct
SEQUENCE: 74
gccgccaaaa aaaaaaaaa                                                      19

SEQ ID NO: 75             moltype = DNA   length = 19
FEATURE                   Location/Qualifiers
misc_feature              1..19
                          note = Description of Artificial Sequence: Synthetic
                            oligonucleotide
source                    1..19
                          mol_type = other DNA
                          organism = synthetic construct
SEQUENCE: 75
aaaaaaaaaa aaagccgcc                                                      19

SEQ ID NO: 76             moltype = DNA   length = 25
FEATURE                   Location/Qualifiers
misc_feature              1..25
                          note = Description of Artificial Sequence: Synthetic
                            oligonucleotide
source                    1..25
                          mol_type = other DNA
                          organism = synthetic construct
SEQUENCE: 76
ggcggctttt tttttttttg gcggc                                               25

SEQ ID NO: 77             moltype = DNA   length = 25
FEATURE                   Location/Qualifiers
misc_feature              1..25
                          note = Description of Artificial Sequence: Synthetic
                            oligonucleotide
source                    1..25
                          mol_type = other DNA
                          organism = synthetic construct
SEQUENCE: 77
gccgccaaaa aaaaaaaaag ccgcc                                               25

SEQ ID NO: 78             moltype = DNA   length = 24
FEATURE                   Location/Qualifiers
misc_feature              1..24
                          note = Description of Artificial Sequence: Synthetic
                            oligonucleotide
source                    1..24
                          mol_type = other DNA
                          organism = synthetic construct
SEQUENCE: 78
gagagagaga gagagagaga gaga                                                24

SEQ ID NO: 79             moltype = DNA   length = 20
FEATURE                   Location/Qualifiers
misc_feature              1..20
                          note = Description of Artificial Sequence: Synthetic
                            oligonucleotide
source                    1..20
                          mol_type = other DNA
                          organism = synthetic construct
SEQUENCE: 79
gtgtgtgtgt gtgtgtgtgt                                                     20

SEQ ID NO: 80             moltype = DNA   length = 20
FEATURE                   Location/Qualifiers
misc_feature              1..20
                          note = Description of Artificial Sequence: Synthetic
                            oligonucleotide
source                    1..20
                          mol_type = other DNA
                          organism = synthetic construct
SEQUENCE: 80
acacacacac acacacacac                                                     20

SEQ ID NO: 81             moltype = DNA   length = 24
FEATURE                   Location/Qualifiers
misc_feature              1..24
                          note = Description of Artificial Sequence: Synthetic
```

```
                    oligonucleotide
source              1..24
                    mol_type = other DNA
                    organism = synthetic construct
SEQUENCE: 81
tctctctctc tctctctctc tctc                                              24

SEQ ID NO: 82       moltype = DNA   length = 25
FEATURE             Location/Qualifiers
misc_feature        1..25
                    note = Description of Artificial Sequence: Synthetic
                    oligonucleotide
source              1..25
                    mol_type = other DNA
                    organism = synthetic construct
SEQUENCE: 82
tttttttttt tttttttttt ttttt                                             25

SEQ ID NO: 83       moltype = DNA   length = 25
FEATURE             Location/Qualifiers
misc_feature        1..25
                    note = Description of Artificial Sequence: Synthetic
                    oligonucleotide
source              1..25
                    mol_type = other DNA
                    organism = synthetic construct
SEQUENCE: 83
aaaaaaaaaa aaaaaaaaaa aaaaa                                             25

SEQ ID NO: 84       moltype = DNA   length = 24
FEATURE             Location/Qualifiers
misc_feature        1..24
                    note = Description of Artificial Sequence: Synthetic
                    oligonucleotide
source              1..24
                    mol_type = other DNA
                    organism = synthetic construct
SEQUENCE: 84
tttttttttt tttttttttt tttt                                              24

SEQ ID NO: 85       moltype = DNA   length = 20
FEATURE             Location/Qualifiers
misc_feature        1..20
                    note = Description of Artificial Sequence: Synthetic
                    oligonucleotide
source              1..20
                    mol_type = other DNA
                    organism = synthetic construct
SEQUENCE: 85
aaaaaaaaaa aaaaaaaaaa                                                   20

SEQ ID NO: 86       moltype = DNA   length = 21
FEATURE             Location/Qualifiers
misc_feature        1..21
                    note = Description of Artificial Sequence: Synthetic
                    oligonucleotide
source              1..21
                    mol_type = other DNA
                    organism = synthetic construct
SEQUENCE: 86
cccccccccc cccccccccc c                                                 21

SEQ ID NO: 87       moltype = DNA   length = 17
FEATURE             Location/Qualifiers
misc_feature        1..17
                    note = Description of Artificial Sequence: Synthetic
                    oligonucleotide
source              1..17
                    mol_type = other DNA
                    organism = synthetic construct
SEQUENCE: 87
gggggggggg ggggggg                                                      17

SEQ ID NO: 88       moltype = DNA   length = 20
FEATURE             Location/Qualifiers
misc_feature        1..20
                    note = Description of Artificial Sequence: Synthetic
                    oligonucleotide
source              1..20
```

```
                            mol_type = other DNA
                            organism = synthetic construct
SEQUENCE: 88
tgtgtgtgtg tgtgtgtgtg                                                  20

SEQ ID NO: 89           moltype = DNA  length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 89
agagagagag agagagag                                                    18

SEQ ID NO: 90           moltype = DNA  length = 22
FEATURE                 Location/Qualifiers
misc_feature            1..22
                        note = Description of Artificial Sequence: Synthetic
                          oligonucleotide
source                  1..22
                        mol_type = other DNA
                        organism = synthetic construct
SEQUENCE: 90
ctctctctct ctctctctct ct                                               22

SEQ ID NO: 91           moltype = DNA  length = 20
FEATURE                 Location/Qualifiers
misc_feature            1..20
                        note = Description of Artificial Sequence: Synthetic
                          oligonucleotide
source                  1..20
                        mol_type = other DNA
                        organism = synthetic construct
SEQUENCE: 91
cacacacaca cacacacaca                                                  20

SEQ ID NO: 92           moltype = DNA  length = 21
FEATURE                 Location/Qualifiers
misc_feature            1..21
                        note = Description of Artificial Sequence: Synthetic
                          oligonucleotide
source                  1..21
                        mol_type = other DNA
                        organism = synthetic construct
SEQUENCE: 92
cagcagcagc agcagcagca g                                                21

SEQ ID NO: 93           moltype = DNA  length = 21
FEATURE                 Location/Qualifiers
misc_feature            1..21
                        note = Description of Artificial Sequence: Synthetic
                          oligonucleotide
source                  1..21
                        mol_type = other DNA
                        organism = synthetic construct
SEQUENCE: 93
tgatgatgat gatgatgatg a                                                21

SEQ ID NO: 94           moltype = DNA  length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 94
ggaggaggag gaggagga                                                    18

SEQ ID NO: 95           moltype = DNA  length = 21
FEATURE                 Location/Qualifiers
misc_feature            1..21
                        note = Description of Artificial Sequence: Synthetic
                          oligonucleotide
source                  1..21
                        mol_type = other DNA
                        organism = synthetic construct
```

```
SEQUENCE: 95
caacaacaac aacaacaaca a                                              21

SEQ ID NO: 96           moltype = DNA  length = 24
FEATURE                 Location/Qualifiers
misc_feature            1..24
                        note = Description of Artificial Sequence: Synthetic
                        oligonucleotide
source                  1..24
                        mol_type = other DNA
                        organism = synthetic construct
SEQUENCE: 96
tgtgtgtgtg tgtgtgtgtg ttgt                                           24

SEQ ID NO: 97           moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 97
gagagagaga gagagagaga                                                20

SEQ ID NO: 98           moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 98
tctctctctc tctctctctc                                                20

SEQ ID NO: 99           moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 99
tttttttttt tttttttttt                                                20

SEQ ID NO: 100          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 100
gggggggggg gggggggg                                                  18

SEQ ID NO: 101          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 101
cccccccccc cccccccccc                                                20

SEQ ID NO: 102          moltype = DNA  length = 58
FEATURE                 Location/Qualifiers
misc_feature            1..58
                        note = Description of Artificial Sequence: Synthetic
                        oligonucleotide
source                  1..58
                        mol_type = other DNA
                        organism = synthetic construct
SEQUENCE: 102
agatcggaag agcgtcgtgt agggaaagag tgtagatctc ggtggtcgcc gtatcatt      58
```

```
SEQ ID NO: 103          moltype = DNA  length = 24
FEATURE                 Location/Qualifiers
misc_feature            1..24
                        note = Description of Artificial Sequence: Synthetic
                        oligonucleotide
source                  1..24
                        mol_type = other DNA
                        organism = synthetic construct
SEQUENCE: 103
agatcggaag agcgtcgtgt aggg                                                24

SEQ ID NO: 104          moltype = DNA  length = 58
FEATURE                 Location/Qualifiers
misc_feature            1..58
                        note = Description of Artificial Sequence: Synthetic
                        oligonucleotide
misc_feature            1..58
                        note = Description of Combined DNA/RNA Molecule: Synthetic
                        oligonucleotide
source                  1..58
                        mol_type = other DNA
                        organism = synthetic construct
SEQUENCE: 104
aatgatacgg cgaccaccga gatctacact ctttccctac acgacgctct tccgatct      58

SEQ ID NO: 105          moltype = DNA  length = 54
FEATURE                 Location/Qualifiers
misc_feature            1..54
                        note = Description of Artificial Sequence: Synthetic
                        oligonucleotide
misc_feature            1..54
                        note = Description of Combined DNA/RNA Molecule: Synthetic
                        oligonucleotide
source                  1..54
                        mol_type = other DNA
                        organism = synthetic construct
SEQUENCE: 105
aaaaaaaaaa aaaatggatc tacactcttt ccctacacga cgctcttccg atct          54

SEQ ID NO: 106          moltype = DNA  length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 106
agatcggaag agcgtcgtgt agggaaagag tgtagatcca ttttttttttt tttt         54

SEQ ID NO: 107          moltype = DNA  length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 107
tcggtggtcg ccgtat                                                         16

SEQ ID NO: 108          moltype = DNA  length = 12
FEATURE                 Location/Qualifiers
misc_feature            1..12
                        note = Description of Artificial Sequence: Synthetic
                        oligonucleotide
source                  1..12
                        mol_type = other DNA
                        organism = synthetic construct
SEQUENCE: 108
acacacacac ac                                                             12

SEQ ID NO: 109          moltype = DNA  length = 12
FEATURE                 Location/Qualifiers
misc_feature            1..12
                        note = Description of Artificial Sequence: Synthetic
                        oligonucleotide
source                  1..12
```

```
                        mol_type = other DNA
                        organism = synthetic construct
SEQUENCE: 109
aaaaaaaaaa aa                                                              12

SEQ ID NO: 110          moltype = DNA   length = 24
FEATURE                 Location/Qualifiers
misc_feature            1..24
                        note = Description of Artificial Sequence: Synthetic
                          oligonucleotide
source                  1..24
                        mol_type = other DNA
                        organism = synthetic construct
SEQUENCE: 110
aaaaaaaaaa aaacacacac acac                                                 24

SEQ ID NO: 111          moltype = DNA   length = 38
FEATURE                 Location/Qualifiers
misc_feature            1..38
                        note = Description of Artificial Sequence: Synthetic
                          oligonucleotide
misc_feature            1..38
                        note = Description of Combined DNA/RNA Molecule: Synthetic
                          oligonucleotide
source                  1..38
                        mol_type = other DNA
                        organism = synthetic construct
SEQUENCE: 111
acacacacac actttttttt tttttttttt ttttttt                                   38

SEQ ID NO: 112          moltype = DNA   length = 50
FEATURE                 Location/Qualifiers
misc_feature            1..50
                        note = Description of Artificial Sequence: Synthetic
                          oligonucleotide
misc_feature            1..50
                        note = Description of Combined DNA/RNA Molecule: Synthetic
                          oligonucleotide
source                  1..50
                        mol_type = other DNA
                        organism = synthetic construct
SEQUENCE: 112
aaaaaaaaaa aagtgtgtgt gtgttttttt tttttttttt tttttttttt                     50

SEQ ID NO: 113          moltype = DNA   length = 50
FEATURE                 Location/Qualifiers
misc_feature            1..50
                        note = Description of Artificial Sequence: Synthetic
                          oligonucleotide
misc_feature            1..50
                        note = Description of Combined DNA/RNA Molecule: Synthetic
                          oligonucleotide
source                  1..50
                        mol_type = other DNA
                        organism = synthetic construct
SEQUENCE: 113
aaaaaaaaaa aaacacacac acactttttt tttttttttt tttttttttt                     50

SEQ ID NO: 114          moltype = DNA   length = 16
FEATURE                 Location/Qualifiers
misc_feature            1..16
                        note = Description of Artificial Sequence: Synthetic
                          oligonucleotide
misc_feature            1..16
                        note = Description of Combined DNA/RNA Molecule: Synthetic
                          oligonucleotide
source                  1..16
                        mol_type = other DNA
                        organism = synthetic construct
SEQUENCE: 114
tttttttttt tttttt                                                          16

SEQ ID NO: 115          moltype = DNA   length = 35
FEATURE                 Location/Qualifiers
misc_feature            1..35
                        note = Description of Artificial Sequence: Synthetic
                          oligonucleotide
source                  1..35
                        mol_type = other DNA
```

```
                        organism = synthetic construct
SEQUENCE: 115
gccgccgcca cagtgcatcg atcgcaattg ccgcc                              35

SEQ ID NO: 116          moltype = DNA  length = 33
FEATURE                 Location/Qualifiers
misc_feature            1..33
                        note = Description of Artificial Sequence: Synthetic
                         oligonucleotide
source                  1..33
                        mol_type = other DNA
                        organism = synthetic construct
SEQUENCE: 116
gccgccgcca cagtgcatcg atcgcaattc gcc                                33

SEQ ID NO: 117          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 117
gccgccgcca cagtgcatcg atcgc                                         25
```

NORMALIZATION OF NGS LIBRARY CONCENTRATION

CROSS-REFERENCE TO RELATED APPLICATIONS

The present application is a continuation of U.S. application Ser. No. 17/214,251, filed Mar. 26, 2021, the entire contents of which is hereby incorporated herein by reference. U.S. application Ser. No. 17/214,251 is a continuation of U.S. application Ser. No. 16/294,561, filed Mar. 6, 2019, the entire contents of which is hereby incorporated herein by reference. U.S. application Ser. No. 16/294,561 is a continuation of International Application No. PCT/US2017/050354, filed Sep. 6, 2017, which claims priority to U.S. Provisional Application No. 62/384,118, filed Sep. 6, 2016, the disclosure of each of which is incorporated herein by reference in its entirety.

SEQUENCE LISTING

The instant application contains a Sequence Listing which has been submitted electronically in XML format and is hereby incorporated by reference in its entirety. Said XML copy, created on May 27, 2023, is named 85563-390540_SL.xml and is 165,800 bytes in size.

BACKGROUND

To maximize high-quality next-generation sequencing (NGS) data, loading the sequencing instrument with a precise quantity of library DNA is essential. Loading an insufficient quantity of library DNA will result in low cluster density (Illumina)/low template-positive ISPs (Ion Torrent) and reduced sequencing output while an overabundance of library DNA will result in chimeric clusters (Illumina)/polyclonal ISPs (Ion Torrent) and result in reduced data of lower quality. When libraries are pooled for multiplex sequencing, inaccurate quantification leads to unbalanced sequence data, where under-quantified libraries are over-sequenced and over-quantified libraries are under-sequenced. For these reasons, accurate quantification of the number of sequenceable library molecules is a critical step in the NGS workflow. Accurate library quantification is also necessary when pooling libraries to create multiplex pools for hybridization-capture. Current methods for library quantification include chip electrophoresis (e.g. Agilent Bioanalyzer), fluorometric methods for dsDNA (e.g. Qubit), and qPCR (various commercially available kits). Both chip electrophoresis and fluorometric methods can only accurately quantify PCR amplified libraries enriched for fully adapted library molecules because these methods cannot distinguish functional (fragments containing both NGS adapters) from non-functional (fragments containing only 1 or no NGS adapters) molecules that exist in PCR-free library preparations. qPCR is widely used in the NGS workflow because it allows accurate quantification of functional library molecules but the protocol involves multiple pipetting steps and takes a substantial amount of time. Each library must be serially diluted and qPCR assays run in triplicate along side a standard curve, followed by qPCR data analysis. The qPCR quantification procedure takes almost 2 hours with at least 45 minutes of hands-on time. Finally, all of these methods require manual concentration adjustment for each NGS library when pooling samples. Additionally, all current library quantification methods are dependent on the library insert size to convert mass to molarity, and if libraries have a broad size distribution or an undefined size, molar quantification will not be accurately determined.

SUMMARY

The present disclosure provides novel procedures for molar normalization of NGS library concentration that are independent of library insert size. The methods provide a simple alternative to library quantification followed by manual adjustment of library concentration (FIG. 1A). The disclosed library normalization occurs in either a single step or in several steps to produce a plurality of samples possessing equimolar NGS library quantity.

The method requiring a single step is a PCR-based normalization (N-PCR), where amplification of each NGS library is performed using a limited concentration of normalization primers (N-PCR primers) with accelerated annealing kinetics and amplification conditions for complete primer utilization during the PCR reaction, thus providing a specified molar quantity of each NGS library.

The method requiring several steps is an enzyme-based normalization which entails:
a. PCR amplification to an excess quantity of each NGS library using pre-Normalization primers (pre-N primers) that result in a 5' or 3' overhang at one or both ends, either during PCR or a post-PCR enzymatic digest, followed by a purification step;
b. incubation of each amplified library with a limiting specified molar quantity of normalization probe (N-probe) and in some embodiments a DNA ligase, where probe annealing and ligation to the 5' or 3' overhang selects a library fraction that is equimolar to the N-probe; and
c. for some embodiments, isolation of the probe selected fraction is performed by enzymatic digestion of the non selected library fraction or by enzyme-mediated release of the probe selected fraction from solid phase immobilization.

An exemplary workflow of the enzyme-based normalization methods is shown in FIG. 1B. As can be seen, the process can involve less hands on and less total time than qPCR quantification and manual adjustment as shown in FIG. 1A.

Therefore, by either limiting Normalization PCR primer concentration or by limiting N-probe concentration, library normalization is achieved (see, e.g., FIG. 2 for simulated library normalization, the dotted line representing the quantity of normalization probe). As shown in FIG. 2, libraries can be normalized using the methods of the present disclosure such that excess quantities of library can be eliminated, resulting in equimolar library concentrations. The disclosed NGS library normalization is fast, requires no serial dilution or manual concentration adjustment, thereby saving up to 1 h of hands-on time and up to 2 h of total prep time when compared to qPCR quantification. This method can be used for NGS library molar adjustment before loading a sequencing instrument or for pooling prior to hybridization-capture (FIGS. 3A and 3B, respectively). It is compatible with any NGS library (DNA or RNA), using Illumina, Ion Torrent or other platforms that sequence PCR amplified DNA libraries. The disclosed options do not utilize a limited streptavidin bead binding step which requires a vast excess of library input and results in poor consistency of recovery that leads to a variable output range of molarity. Also, the simple, incubations of the disclosed methods have few pipetting steps and are easily automatable.

The disclosed methods require library amplification by PCR and cannot be used directly with PCR-free library protocols, although can be adjusted to work with PCR-free NGS libraries. Also, for enzyme-based normalization, libraries with post-PCR yields below the specified molar threshold will retain a reduced molar quantity after the normalization procedure, thereby resulting in an under-represented library with reduced data output in the sequence or hybridization capture workflows (FIG. 2, Sample 3). For this reason, producing an excess molar quantity of each library relative to a lesser molar quantity of N-probe is recommended to avoid under-represented samples.

Some of the disclosed normalization methods require a PCR amplification step that results in either a normalized amplified library (in the case of N-PCR) or results in a 5' or 3' overhang at one or both adapter ends (in the case of enzyme-based normalization). In some instances, an overhang is not necessarily required. The overhang is generated either during the PCR or post-PCR enzymatic digestion to enable N-probe annealing to dsDNA substrates. The enzymatic normalization methods have a limiting, specified molar quantity of N-probe that anneals to an equivalent molar quantity of NGS library molecules, in some instances by a 5' or 3' overhang of the double-stranded NGS library. In some instances, an overhang is not required and the probe can be ligated to library molecules in the amplified library by methods such as, by way of example but not limitation, blunt end ligation, TA ligation and cohesive end ligation. Therefore, precise N-probe quantity selects the number of library molecules that will be recovered during the enzyme-based normalization process. The PCR-based normalization method has a limiting, specified molar quantity of N-PCR primers that amplify an equivalent molar quantity of NGS library. Therefore, precise N-PCR primer quantity selects the number of library molecules that will be generated during the N-PCR process.

PCR-Based Normalization

When using conventional reagents to try to control the amount of PCR product by limiting primer concentration, several factors reduce the utility of such a method. First, conventional PCR primer concentration ranges from 200 nM to greater than 1 uM and complete utilization of primers with such high concentration would result in 10-50 pmol of PCR product that would require a high DNA polymerase concentration and result in significant over-amplification of samples which is not desirable as replication errors and base composition bias can be introduced, of particular importance when amplifying NGS libraries. Alternatively, PCR can be performed at reduced 20-40 nM primer concentration to result in 1-2 pmol of amplified product, but in this case, primer annealing time would need to be increased accordingly by 10 fold to ensure efficient primer annealing, extension and unbiased amplification of a high complexity template such as an NGS library, where excessive thermocycling incubation times would also be undesirable as they could induce DNA damage and reduce NGS library quality. In certain embodiments of the present disclosure, a novel normalization PCR primer composition is introduced that addresses these problems (N-PCR primers). The normalization PCR primer composition increases primer annealing hybridization rate, reduces annealing time and allows efficient and complete utilization of PCR primers using amplification cycles with conventional annealing time, thus providing reproducible generation of a specified molar quantity of NGS libraries by limiting PCR primer concentration.

To increase the primer hybridization rate, a 5' tail comprising a low complexity sequence is introduced on each N-PCR primer of the pair, where the 3' portion of each primer anneals to the NGS adapter sequences already present on the library template. In some embodiments, the forward and reverse N-PCR primers have different 5' tail sequences. In other embodiments, the forward and reverse N-PCR primers have the same 5' tail sequence. The low complexity 5' tail can be comprised of a homopolymer repeat sequence such as (A)n, (T)n, (G)n or (C)n, a dinucleotide repeat sequence such as (AG)n, (AC)n, (GT)n, (CT)n, (AT)n or (GC)n, a trinucleotide, tetranucleotide, pentanucleotide or even larger repeat sequence element. The 5' tail of the N-PCR primer can be 8 to 50 bases or more in length, comprised of deoxynucleotides or ribonucleotides with or without additional modifications, or be a mixture thereof. In some embodiments, the 3' portion of the N-PCR primers anneal to adapter sequences that are different for the forward and reverse primer, when they are amplifying an NGS library that comprises unique adapter sequences at each terminus, whereas in other embodiments, the forward and reverse N-PCR primer anneal to the same adapter sequence when they are amplifying an NGS library with the same adapter at both library ends.

During the first two cycles when using a limited concentration of N-PCR primers, primer annealing to the template occurs only by the 3' portion of the N-PCR primer that is complementary to the NGS adapter. For this reason, the annealing time for the first cycles should be extended in length to ensure priming and extension of all library molecules when at low primer concentration. Once the reverse complement of the low complexity/repetitive tail sequence is incorporated into the amplicons, both the 5' and 3' portions of the N-PCR primer can participate in annealing to the template, which due to the low complexity composition, significantly accelerates annealing and as a result, conventional annealing times can be used for subsequent cycles, thus enabling efficient PCR amplification of the library. Accelerated primer hybridization occurs due to the fast annealing of the low complexity/repetitive 5' tail sequence followed by annealing of the high complexity 3' adapter sequence. Once utilization of the N-PCR primers has been completed, the specified molar quantity of NGS library has been generated. The resulting amplified library may be predominantly single stranded due to the limiting primer concentration, but where re-annealing of adapter sequences can occur to produce partially double stranded heteroduplex molecules. Optionally, the low complexity tail sequence can be cleaved from the libraries prior to sequencing if desired. Alternatively, the low complexity sequence complementary to the 5' tail of each N-PCR primer can be introduced during the adapter ligation step in library preparation by incorporating the sequence at the terminus of the NGS adapter. In this embodiment, conventional annealing times can be performed during every cycle of the N-PCR amplification because the low complexity sequence is already present on the completed NGS library substrate prior to PCR.

Enzyme-Based Normalization

In this method, PCR amplification using pre-Normalization primers (pre-N primers) is used to produce an excess molar quantity to the amount of normalization probe (N-probe) that will be utilized to select a fraction of the library. The N-probe can be utilized in multiple methods (FIG. 4 depicts exemplary methods). In one embodiment, the pre-N PCR primer has a biotin group and at least one RNA base, and the biotin-labeled NGS library is captured in its entirety using streptavidin beads, where only a select molar fraction that has the annealed N-probe is released from the bead immobilization as it overlaps with the RNA base and creates a substrate for RNase H enzymatic cleavage (Method 1; controlled release). In other embodiments, the annealing and ligation of the N-probe to a selected library fraction confers nuclease resistance of this library fraction against enzymatic digestion (Method 2; controlled protection). In these options, the N-probe contains bases, groups or conformations that confer resistance to enzymatic digestion. In other embodiments, the annealing and ligation of the N-probe to a selected library fraction occurs following enzymatic digestion and removal of specific, functional library sequences, where N-probe ligation results in the restoration of library functionality for a selected library fraction (Method 3; controlled repair). In yet another embodiment, N-probe ligation completes library synthesis, where only the specified probe ligated molar fraction produces functional library molecules (Method 4; controlled synthesis). Method 1 requires 3 normalization steps, Method 2 requires 2 steps, and Methods 3 and 4 have a single step, all of which are post-PCR. Without limitation, it is understood that aspects of these different methods can be used in any combination thereof to achieve molar normalization of NGS libraries.

To enable N-probe annealing to a dsDNA library substrate, there are at least three ways a 5' overhang can be generated for the normalization step. In some embodiments, the 5' overhang at one or both library ends is created during PCR using pre-Normalization primers (pre-N primers) with a 5' tail for N-probe annealing and a non-replicable spacer located between the tail and adapter sequence, the non-replicable group including but not limited to a dU base (for archael DNA polymerases), a stable, abasic site such as dSpacer, rSpacer, spacers C3, C6 or C12, hexanediol, triethylene glycol Spacer 9 and hexaethylene glycol Spacer 18. In other embodiments, the 5' overhang at one or both library ends is created during PCR using a thermostable DNA polymerase with 3' exonuclease proofreading activity and pre-N primers with a 5' tail for N-probe annealing and a novel non-replicable spacer comprising a consecutive stretch of 3 or more riboU or riboA bases located between the tail and adapter sequences, where the high fidelity DNA polymerase is incapable of extending through the $(riboU)_n$ or $(riboA)_n$ template, where n=3 or more. The $(riboU)_n/(riboA)_n$ replication block disclosed herein is unique in that it can be replicated by non proofreading polymerases such as Taq DNA Polymerase, and also allows ligation of a probe oligonucleotide complementary to the 5' tail and the poly (rU) or poly(rA) stretch, unlike other replication blocking groups which generate a non-ligatable junction. In yet other embodiments, the 5' overhang at one or both library ends is created after PCR using T4 DNA Polymerase. In this case, pre-N PCR primers incorporate a 5' tail and 3' adjacent buffer region. The tail region is 10-20 bases and comprises a homopolymer, di- or tri-nucleotide composition followed by a 5-10 base buffer region containing a nucleotide composition that is excluded from the 5' tail region. When an NGS library comprising such sequences is incubated with T4 DNA Polymerase and a nucleotide mix restricted to only bases complementary to the buffer region but not the tail region, the 3' exonuclease proofreading activity of T4 DNA Polymerase will irreversibly trim the 3' complementary tail region until it reaches the buffer region where it can reversibly remove and replace nucleotides, thus creating a 5' overhang defined by the buffer region.

Alternatively, there are at least two different ways a 3' overhang can be generated for N-probe annealing. In some embodiments, the 3' overhang at one or both library ends is created after PCR by incubation with such enzymes as RNase H, a mix of UDG and abasic endonuclease, or endonuclease V by cleaving RNA, deoxyuracil or deoxyinosine bases that were incorporated by modified pre-N PCR primers that comprise such cleavable bases. In other embodiments, the 3' overhang at one or both library ends is created after PCR by incubation with a 5' exonuclease such as T7 Exonuclease or Lambda Exonuclease. The length of the 3' overhang in these embodiments is controlled by the position of the cleavable/nuclease-resistant bases or linkages within the pre-N PCR primer and overall primer length.

In some embodiments, the N-probe is ligated to the 3' or the 5' end of the NGS library, where the DNA ligase is T4 DNA ligase, T3 DNA ligase, T7 DNA ligase, or *E. coli* DNA ligase, a thermostable DNA ligase such as Taq ligase, Ampligase, 9° N DNA ligase, or Pfu DNA ligase. In other embodiments, N-probe ligation is not performed. In yet other embodiments, probe ligation can also involve displacement and cleavage of residual 5' RNA bases left after cleavage with RNase H, or residual deoxyuracil or deoxyinosine modified bases from an incomplete digestion with a mix of UDG and abasic endonuclease or endonuclease V, or nuclease-resistant bases left after T7 exonuclease or lambda exonuclease digestion. In this case, the ligation reaction can be supplemented by Taq DNA Polymerase or DNA Polymerase I and, if necessary, a restricted nucleotide mix to allow a limited nick-translation reaction.

Some embodiments require an additional step of probe selected library isolation following N-probe ligation. For Method 1, enzymes used for probe selected library cleavage (release from immobilization) include RNase H enzymes, including *E. coli* RNase H1 and RNase H2, or thermostable RNase H. In other embodiments (Method 2), enzymes used for non-probe selected library digestion include 3' exonucleases, such as Exonuclease III, T4 DNA Polymerase, Exonuclease I, as well as 5' exonucleases, such as Exonuclease T7 or Lambda Exonuclease. Without limitation, it is understood that aspects of the different methods for 5' and 3' overhang creation, N-probe ligation, and enrichment or depletion of a library fraction can be used in any combination thereof to achieve molar normalization of NGS libraries.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein.

In the following FIGURES, P5 and P7 are used to refer to the P5 and P7 NGS adaptors, respectively.

FIG. 2 depicts the results of a normalization method of the present disclosure producing equimolar concentrations of each sample without manual adjustment of individual sample volumes.

FIG. 6 depicts an exemplary method of enzyme-based normalization by Method 1 (controlled release). "B" represents biotin. The red bar indicates the portion of RNA bases. The black bar indicates the position of a DNA spacer that is non-replicable. In the first incubation, normalization probe and streptavidin beads are added. Step 1: Annealing a specified quantity of normalization cleavage probe to an equal molar quantity of 5' overhang. Step 2: Binding of all NGS library molecules to streptavidin magnetic beads. Step 3: Add RNase H. Wash beads and release the probe specified NGS library fraction by RNase H cleavage.

FIG. 8A depicts an exemplary method of enzyme-based normalization by Method 2(a) targeting 1 library strand using 1 pre-N PCR primer. Step 1: PCR to yield an indexed, full length NGS library with a 5' overhang at 1 end when using a single normalization primer with a conventional primer. Step 2: Exonuclease I (optional unused primer digestion).
Step 3: SPRI. Step 4: T4 DNA ligase covalently attached a specified quantity of nuclease resistant normalization probe. Step 5: Exonuclease III digests the 3' termini lacking nuclease resistant probe. Figure discloses "$(dT)_{12}(rU)_4$" as SEQ ID NO: 67, "$(dA)_{12}(dA)_4$" as SEQ ID NO: 68 and "$(dT)_{12}$" as SEQ ID NO: 56.

FIG. 8C depicts an exemplary method of enzyme-based normalization by Method 2(a) targeting both library strands using 2 pre-N PCR primers. Step 1: PCR to yield an indexed, full length NGS library with two identical 5' overhangs when 2 normalization primers are used. Step 2: Exonuclease I (optional unused primer digestion). Step 3: SPRI. Step 4: T4 DNA ligase. Step 5: Exonuclease III. Figure discloses "$(dT)_{12}(rU)_4$" as SEQ ID NO: 67 and "$(dA)_{12}(dA)_4$" as SEQ ID NO: 68.

FIG. 13 depicts exemplary methods for enzyme-based normalization by controlled NGS adapter repair by Methods 3(a), 3(b) and 3(c).

FIG. 21B depicts an exemplary method for single indexing or dual indexing using normalization probes for Method 4 (controlled synthesis). Figure discloses SEQ ID NOS 73, 74, 75, 73, 75, 76, and 77, respectively, in order of appearance.

FIG. 23A depicts an exemplary method for PCR-based normalization by controlled amplification using a dinucleotide repeat 5' tail regions of the N-PCR primers. Figure discloses SEQ ID NOS 78, 79, 78, 80, 81, and 79, respectively, in order of appearance.

FIG. 23B depicts and exemplary method for PCR-based normalization by controlled amplification using homopolymer repeat 5' tail regions of the N-PCR primers. Figure discloses SEQ ID NOS 82, 83, 82, 82, 83, and 83, respectively, in order of appearance.

FIG. 29C depicts a proposed mechanism for failed replication when using N-PCR primers with non-complementary homopolymer tails due to the formation of non-Watson-Crick secondary structures. Figure discloses "TTTTTTTTTTTTTTTTTTTT" as SEQ ID NO: 99, "GGGGGGGGGGGGGGGGGGG" as SEQ ID NO: 100, "AAAAAAAAAAAAAAAAAAAA" as SEQ ID NO: 85, and "CCCCCCCCCCCCCCCCCCCC" as SEQ ID NO: 101.

FIG. 29D depicts exemplary N-PCR primers with dinucleotide repeat tails. Figure discloses SEQ ID NOS 88-91, respectively, in order of appearance.

FIG. 45A depicts Example 14. Step 1: 1st PCR (multiplex). Step 2: 2nd PCR with a high fidelity DNA polymerase and universal primer containing non-replicable poly (rU) linker creates DNA molecule with 5' overhangs at both ends (only one end is shown). Step 3: SPRI removes non-incorporated primers. Step 4: Stem-loop adapter anneals and become ligated to the 5' end of DNA. Step 5: Linker molecule containing indexing sequence ID and polyA tails at both ends anneals to the gap regions on both DNA strands and becomes ligated.
Figure discloses SEQ ID NOS 61, 61, 108, 61, 108, 109, 109, 61, 110, and 109, respectively, in order of appearance.

FIG. 48B depicts Example 15. Step 1A: PCR with primers containing tail sequences A and B with $(rU)_n$ replication block (not shown). Step 1B: PCR with primers containing a reduced complexity tail sequences A and B with the adjacent buffer region containing bases that are not present in the tail (not shown). Step 2: T4 DNA polymerase in the presence of nucleotides present in the buffer region but absent in the tail region. Linkers also have buffer regions on both ends to prevent their degradation by T4 DNA polymerase (not shown). Step 3: Ligation reaction occurs at equal molar concentrations of amplicons and linkers.

FIG. 50A depicts Example 17. Figure discloses SEQ ID NOS 48, 48, 49, 115, 50, 50, 51, 116, 52, 52, 53, 117, 54, 54, and 55, respectively, in order of appearance.

DESCRIPTION

Figure 1A:
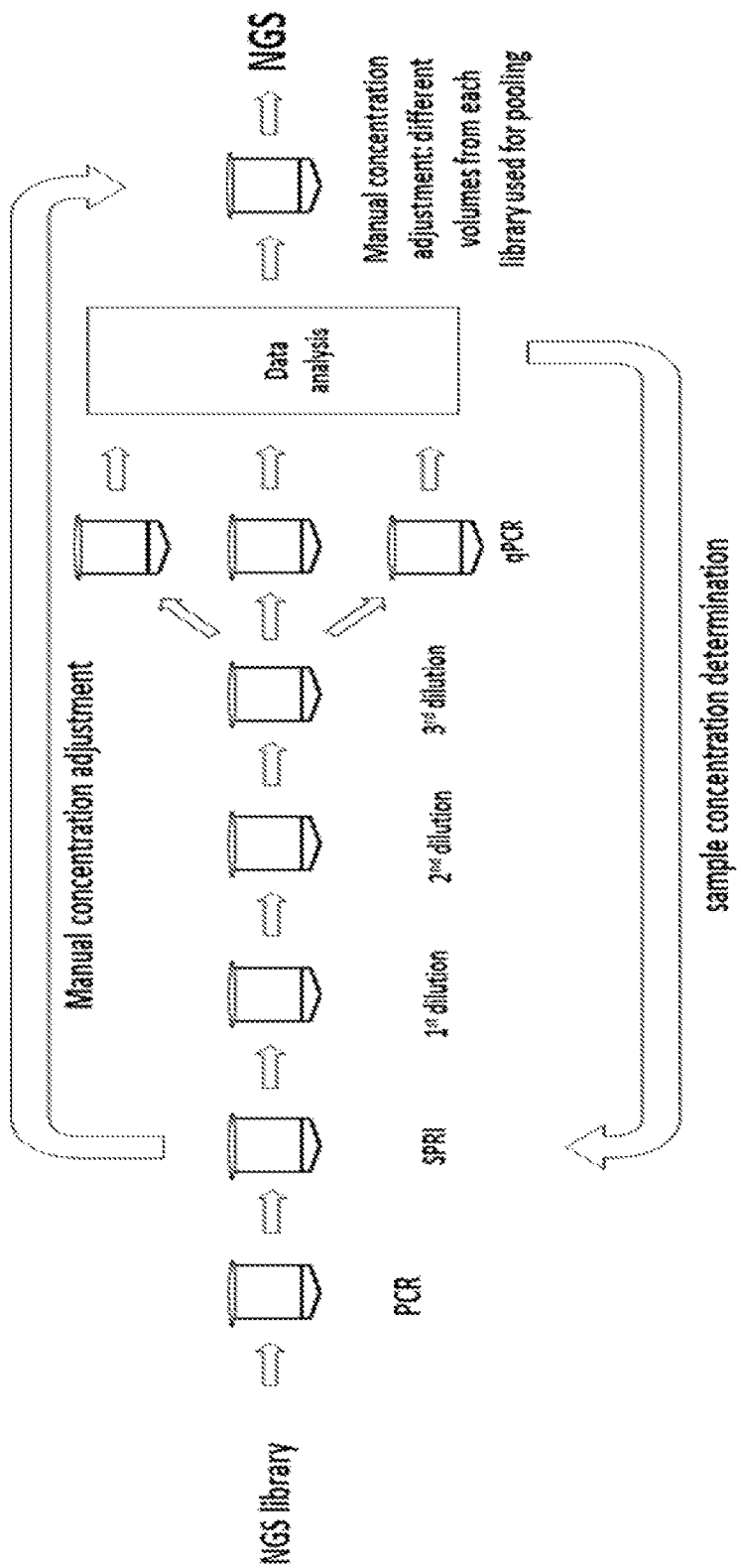
FIGS. 1A and 1B compare qPCR library quantification (FIG. 1A) to a normalization reaction by enzymatic treatment of the present disclosure (FIG. 1B).
Figure 1B:
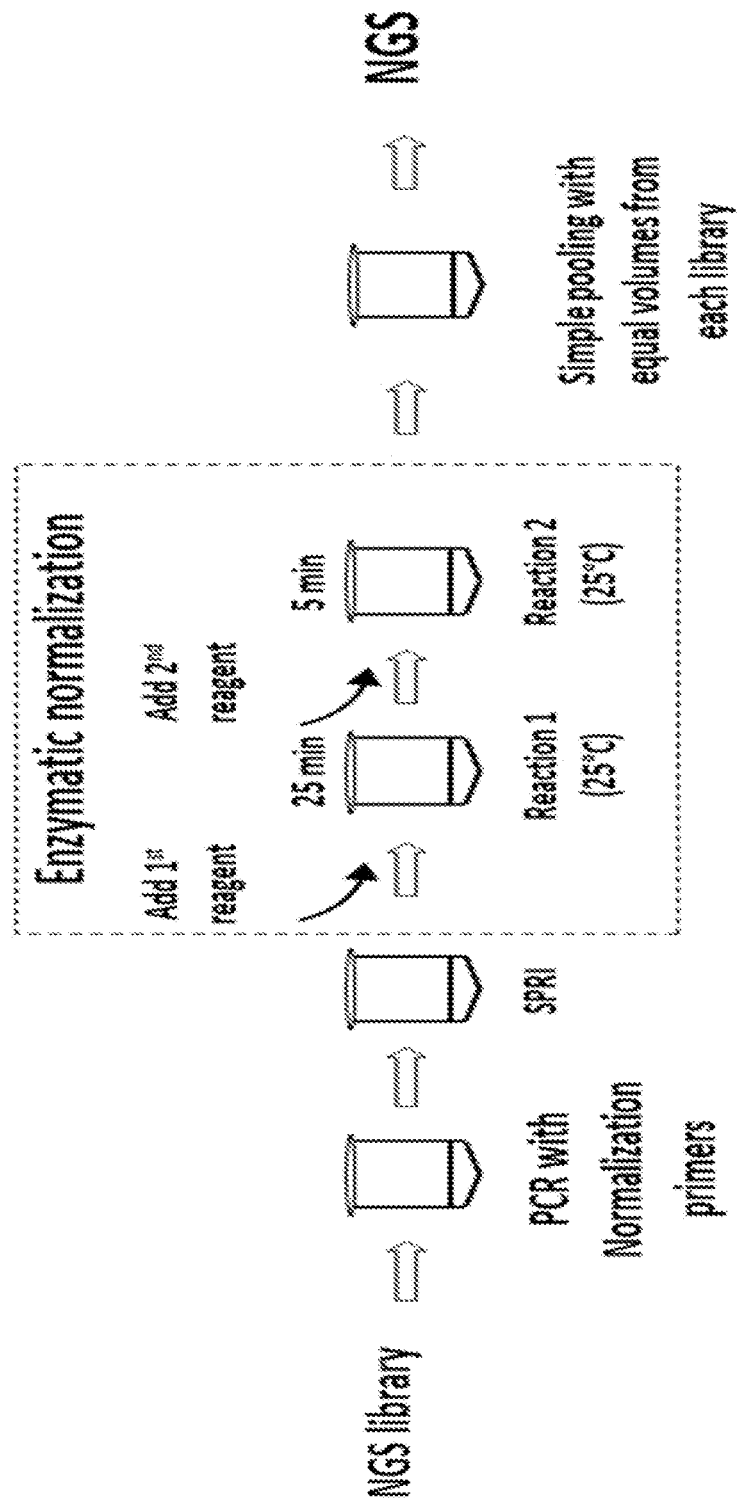
Figure 3A:
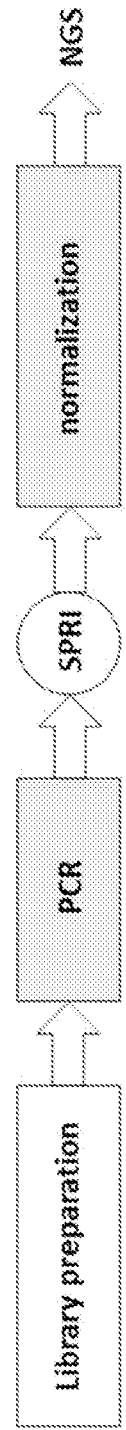
FIG. 3A depicts an exemplary workflow for a normalization method of the present disclosure whereby, following library preparation, the library is subjected to PCR followed by purification by SPRI and normalization to yield the normalized sample for NGS.
Figure 3B:
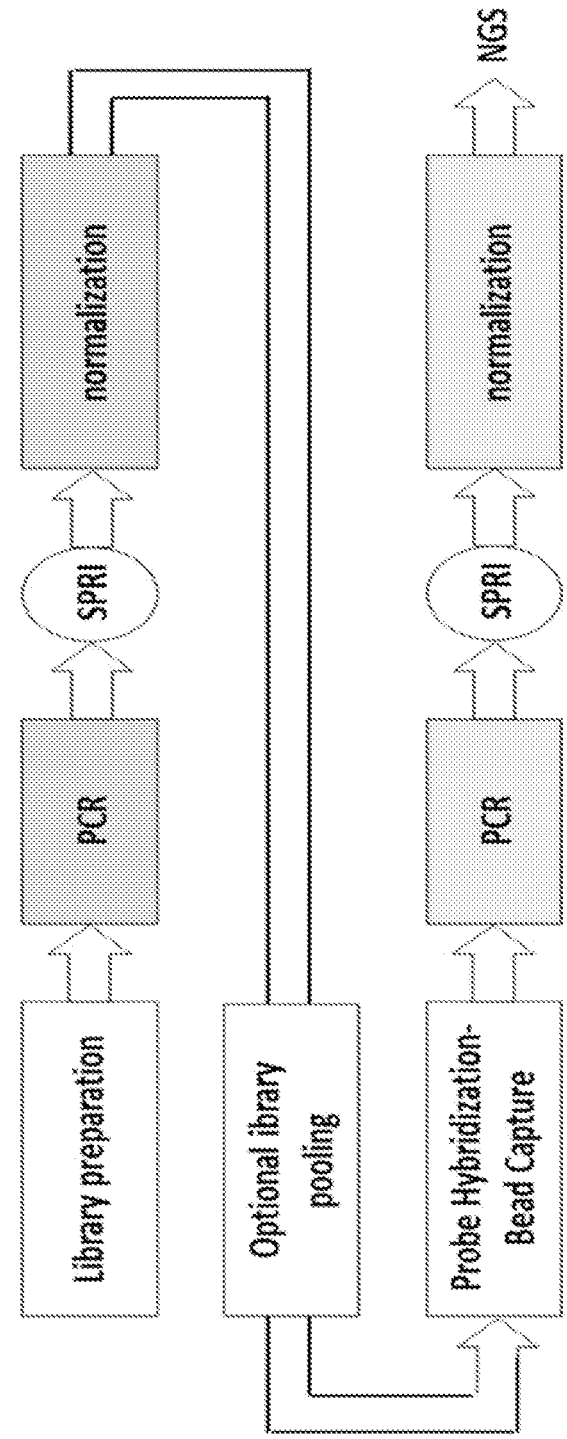
FIG. 3B depicts an exemplary multiplex workflow incorporating the normalization process.
Figure 4:
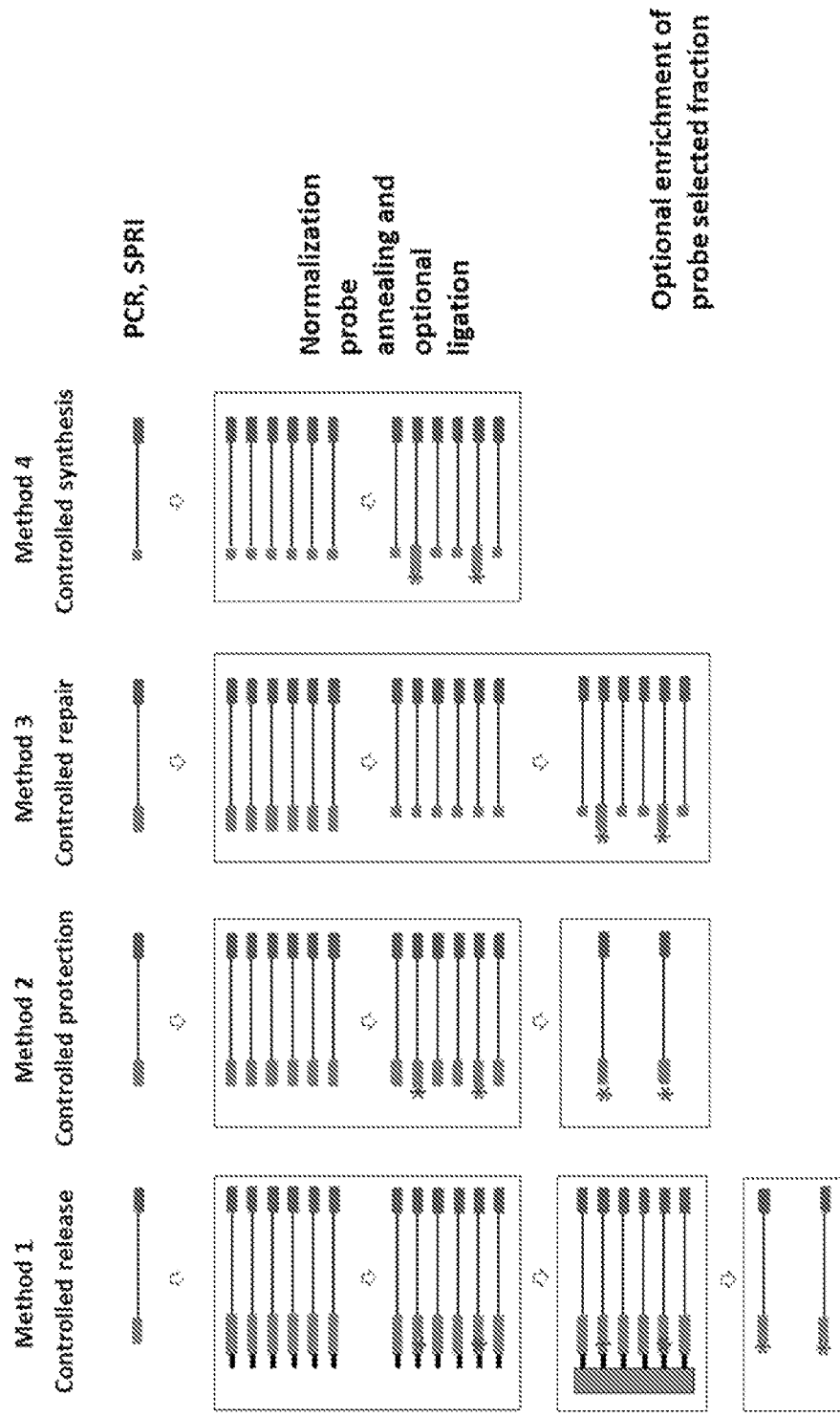
FIG. 4 depicts four exemplary methods of the present disclosure for normalization wherein the first step involves PCR of the NGS library and purification of the amplified NGS library by SPRI, followed by normalization probe annealing and optional ligation, followed by enrichment for the probe selected fraction.

The present disclosure describes particular embodiments and with reference to certain drawings, but the subject matter is not limited thereto. The drawings described are only schematic and are non-limiting. In the drawings, the size of some of the elements may be exaggerated or distorted and not drawn on scale for illustrative purposes. Where the elements of the disclosure are designated as "a" or "an" in first appearance and designated as "the" or "said" for second or subsequent appearances unless something else is specifically stated.

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Certain terminology is used in the following description for convenience only and is not limiting. Certain words used herein designate directions in the drawings to which reference is made. Unless specifically set forth herein, the terms "a," "an" and "the" are not limited to one element, but instead should be read as meaning "at least one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about", when used with a numerical value, is intended to include +/−10%. For example, if a number of amino acids is identified as about 200, this would include 180 to 220 (plus or minus 10%).

Unless otherwise defined, all technical and scientific terms used herein have the same meaning as commonly understood by one of ordinary skill in the art.

Figure 5:
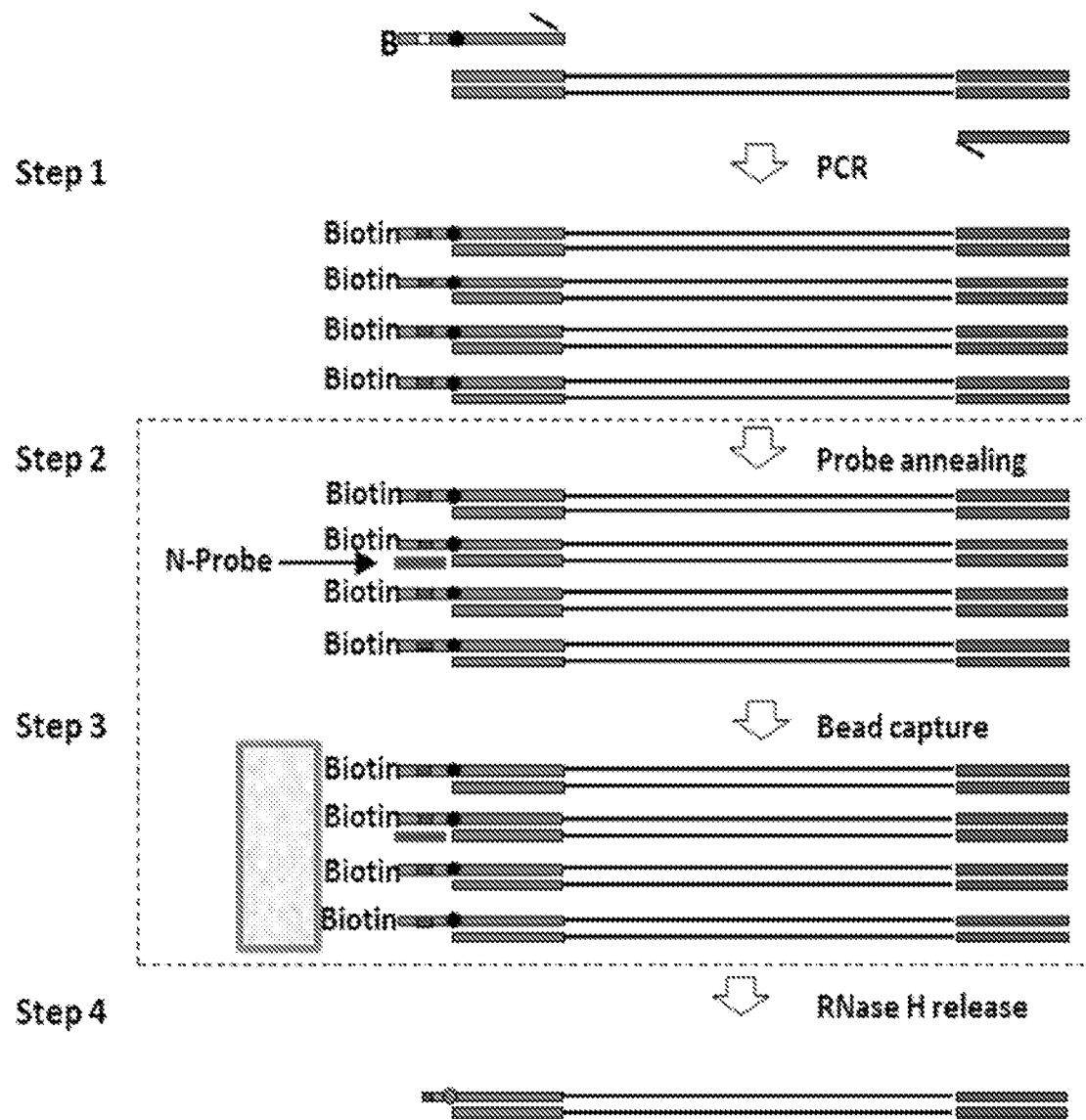
FIG. 5 depicts an exemplary method of enzyme-based normalization by Method 1 (controlled release). "B" represents biotin.

Enzyme-based Library Normalization Methods
Method 1: Enzyme-Based Library Normalization by Controlled Release from Immobilization This method utilizes enzymatic release of a specified molar quantity of library from magnetic bead immobilization. This method has at least 3 steps: a pre-N PCR step followed by a purification, then a capture step and a controlled elution step. Without limitation, it is understood that aspects of this method and alternate embodiments can be used in any combination thereof to achieve molar normalization of NGS libraries. FIG. 5 shows an exemplary four-step version of the method which includes the following steps: (1) PCR amplification using primers with non-replicable spacers to introduce a 5'-overhang with a biotin at the 5' end and an RNA cleavage site at one of the NGS adapter ends and SPRI purification;
(2) selecting a specified number of library molecules by annealing to the 5' overhang a specified quantity of Normalization Probe; (3) bead capture of the entire library (steps 2 and 3 can be performed in the same reaction or in either order-2 then 3 or 3 then 2); and (4) bead release of the specified molar fraction of library containing Normalization Probe by incubation with RNase H (cleavage at the RNA base).

This method requires PCR amplification of the NGS library in molar excess to the quantity of N-probe that will be used. For the PCR, the pre-N primer introduces a 5' or 3' overhang at one end of the amplified NGS library, and for some embodiments, a thermostable DNA polymerase possessing 3' exonuclease proofreading activity is used. The 5' or 3' overhang can be generated using any of the disclosed methods (a replication block is depicted in the primer used in FIG. 6). For this method, the pre-N primer also requires a biotin group and at least one RNA base, preferably positioned in the middle of the resulting 5' or 3' overhang. Following amplification, a purification step is performed, then streptavidin magnetic bead capture of the entire amplified library is performed, and in the same capture reaction, a limiting specified molar quantity of N-probe is included that is complementary to the 5' or 3' overhang, preferably comprising a homopolymer sequence, and is annealed to an equivalent molar quantity of the immobilized library, where the homopolymer sequence facilitates annealing in the absence of a significant molar excess of either probe or substrate relative to a probe with a complex sequence composition. In the final step, elution of the specified molar quantity of dsDNA library is performed by enzymatic cleavage using RNase H, where only the selected N-probe bound fraction is a substrate for RNase H cleavage and release from solid phase immobilization, as the probe hybridizes to the overhang comprising the RNA base.

Figure 7A:
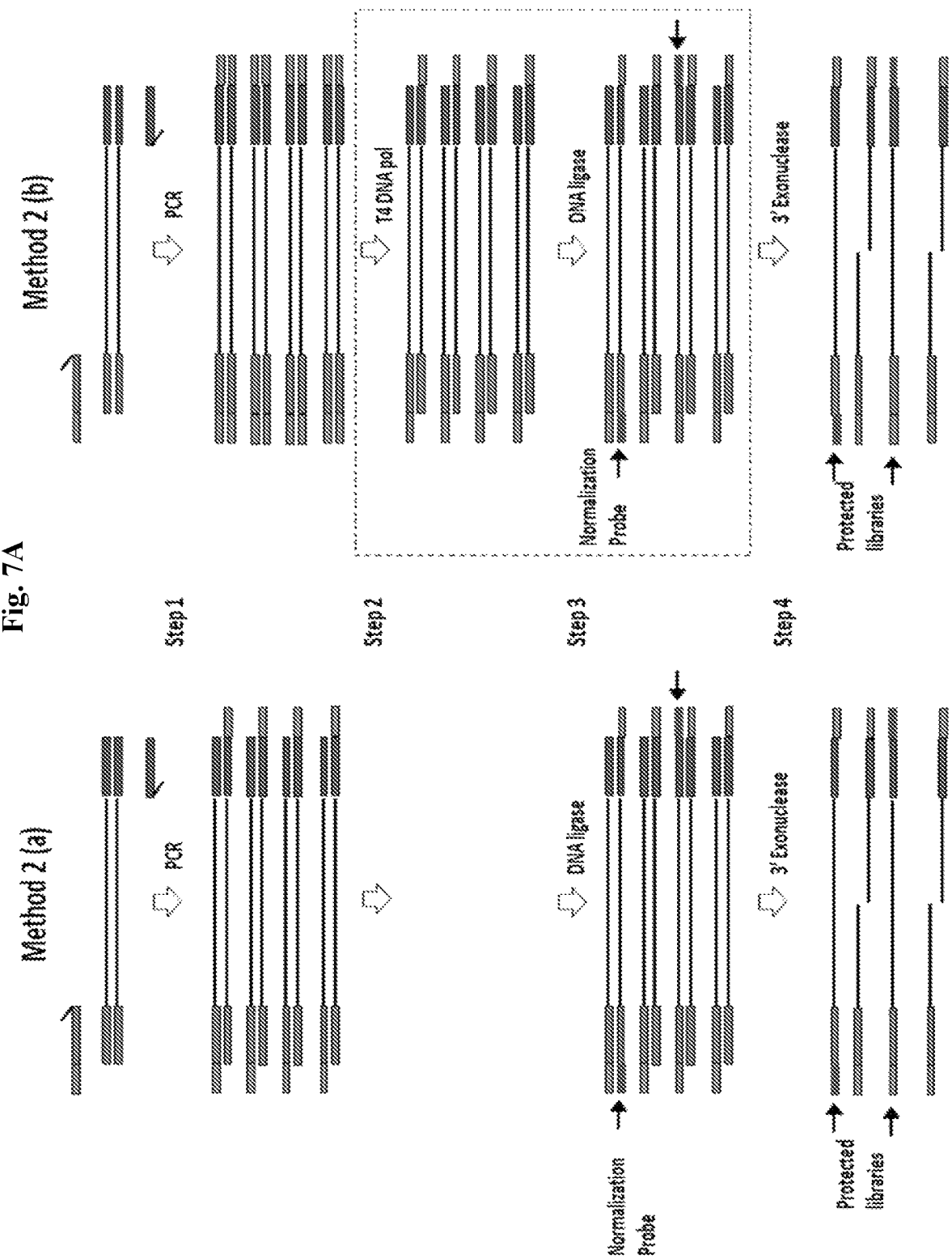
FIG. 7A depicts exemplary methods of enzyme-based normalization by Method 2(a) (controlled protection) and Method 2(b) (controlled protection).
Figure 7B:
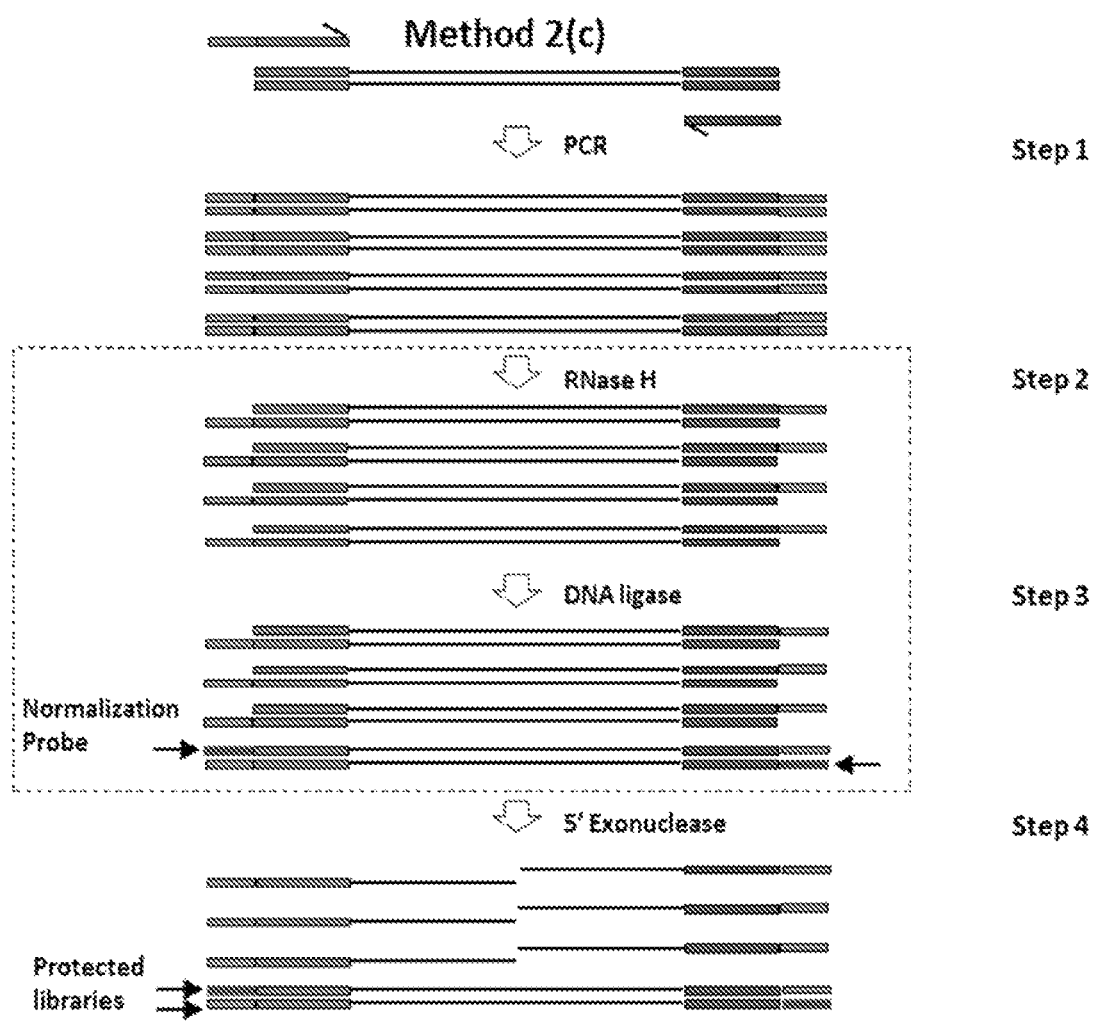
FIG. 7B depicts an exemplary method of enzyme-based normalization by Method 2(c) (controlled protection).

Method 2: Enzyme-Based Library Normalization by Controlled Protection from Exonuclease Digestion FIGS. 7A-7B summarize three exemplary options for performing Method 2, where following pre-N PCR amplification, Method 2a has a ligation step and a digestion step and Methods 2b and c have a cleavage/ligation step and a digestion step. In Methods 2a and b, a 5' overhang is generated whereas in Method 2c, a 3' overhang is generated, where the overhangs are generated using any of the disclosed methods. All three normalization options require PCR amplification of the NGS library in molar excess compared to the molar amount of N-probe that will be used. The pre-N primer introduces a 5' or 3' overhang at one end of the dsDNA library if one pre-N primer is used with a conventional primer, or at both ends of the dsDNA library if two pre-N primers are used. In Method 2a, the 5' overhang is generated during PCR using a pre-N primer comprising a consecutive stretch of 3 or more riboU or riboA bases that block replication by a thermostable DNA polymerase possessing 3' exonuclease proofreading activity. In Method 2b, the 5' overhang is generated following PCR by T4 DNA Polymerase 3' exonuclease activity based on specific nucleotide composition of the pre-N primer and dNTP composition in the normalization reaction. In Method 2c, a 3' overhang is generated following PCR by enzymatic cleavage of the incorporated primer sequence, where the pre-N primer introduces cleavable bases into the PCR product. For all three methods, following PCR amplification, a purification step is performed, and in the first enzyme-based normalization step, a limiting, specified molar quantity of N-probe is added with a ligase; a cleavage enzyme is also added to this reaction for Methods 2b and c. The N-probe is complementary to the 5' or 3' overhang, comprising nuclease resistant modifications and preferably comprising a low complexity sequence such as a homopolymer, and is annealed and ligated to an equivalent molar quantity of the amplified library. The homopolymer sequence facilitates annealing in the absence of a significant molar excess of either probe or substrate relative to a probe with a complex sequence composition. In the second enzyme-based normalization step, enzymatic digestion of the excess library fraction lacking probe ligation is performed, where the N-probe specified molar quantity of library remains nuclease resistant and is protected from digestion. For Methods 2a and b, a 3' exonuclease is used, whereas for Method 2c, a 5' exonuclease is used.

Formation of a 5' or 3' overhang is not a requirement for N-probe ligation, but the overhang significantly facilitates probe and library ligation at low concentrations. In one embodiment, ligation of a double stranded normalization probe with a single T-base 3' overhang requires a library with a single A-base 3' overhang created during PCR by Taq DNA polymerase. In another embodiment, a double stranded normalization probe has a blunt end and is ligated to a blunt end library amplified using a high fidelity DNA polymerase. Ligation of a limited amount of blunt end or single T-base 3' overhang normalization probe to the truncated adapter end of the library can be facilitated by a high library concentration created during PCR. Prevention of probe ligation to the adapter at the opposite end of the NGS library can be controlled by the lack of a 5' phosphate group on the adapter end or lack of a compatible blunt or single A-base overhang, or both a lack of a 5' phosphate and a compatible end for probe ligation.

Specifically, in FIG. 7A, Methods 2(a) and 2(b) include 4 steps: (1) PCR amplification to introduce a probe binding sequence at one or both adapter ends with a PCR primer containing either a non-replicable base or base combination to create a 5' overhang during PCR (Method 2a), or a special base composition to allow a 5' overhang by T4 DNA polymerase (Method 2b), followed by SPRI purification; (2) generation of the 5' overhang by T4 DNA polymerase mediated 3'-5' exonuclease digestion (Method 2b only); (3) protection of a specified number of library molecules by annealing and ligation of a specified quantity of Normalization Probe to the 5' overhang; and (4) 3' exonuclease digestion of the non probe protected library fraction.

Figure 8B:
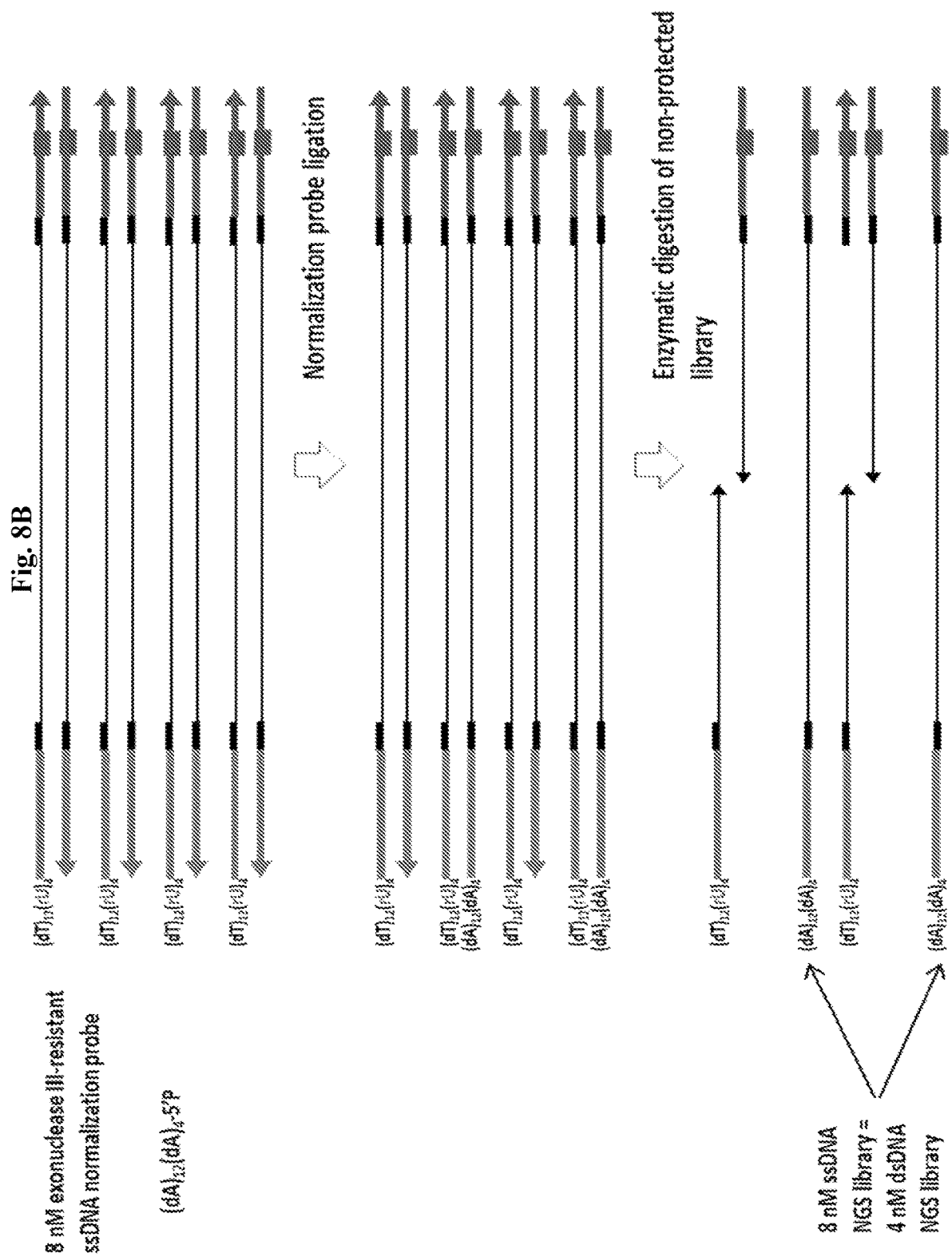
FIG. 8B depicts an exemplary method of enzyme-based normalization by Method 2(a) targeting 1 library strand, resulting in a single-stranded DNA library. Figure discloses "$(dT)_{12}(rU)_4$" as SEQ ID NO: 67 and "$(dA)_{12}(dA)_4$" as SEQ ID NO: 68.

Specifically, in FIG. 7B, Method 2(c) includes 4 steps: (1) PCR amplification to introduce a probe binding sequence at one or both adapter ends with a PCR primer containing cleavable bases to allow a 3' overhang generation by enzymatic cleavage, followed by SPRI purification; (2) generation of the 3' overhang by enzymatic cleavage of the incorporated PCR primer portion containing cleavable bases; (3) protection of a specified number of library molecules by annealing and ligation of a specified quantity of Normalization Probe to the 3' overhang; and (4) 5' exonuclease digestion of the non probe protected library fraction.
Method 2a Further details of Method 2a are found in FIGS. 8A-8D, 9A-9B and 10A-10B; FIG. 8A depicts a reaction using a single 5' overhang where the complementary probe sequence is either complex sequence S (comprising any 2, 3 or 4 base composition, not shown) or is a low complexity homopolymer sequence, by way of example but not limitation (dT)$_{12}$ (SEQ ID NO: 56) as shown in FIG. 8A. In this example, only one pre-N primer is used with a conventional reverse primer, which targets the normalization reaction to only one of the two NGS library strands. An excess quantity of NGS library is included in the first normalization step, where a limiting specified molar quantity of N-probe is added in addition to a DNA ligase. The annealing will occur more rapidly for the low complexity homopolymer sequence compared to high complexity sequence S. Due to the use of the consecutive stretch of riboU bases as a replication block, the 5' overhang is preferably a poly(T) homopolymer and the N-probe is preferably a poly(A) homopolymer that is complementary to both T and riboU bases; in other embodiments where the replication block is comprised of riboA bases, the 5' overhang is preferable poly(A) and the N-probe is preferable a poly(T) homopolymer. The N-probe additionally comprises 1 or more nuclease resistant modifications such as phosphorothioate linkages that can be positioned consecutively within the probe sequence at its 3' terminus, internally or near its 5' terminus, in addition to an optional 3' terminal block such as a C3 carbon spacer to provide resistance to exonuclease III digestion after probe annealing and ligation to the library end(s). Optionally, the N-probe is longer in length than the 5' overhang to generate a single stranded 3' overhang following ligation to the NGS library, in order to confer further resistance to Exonuclease III digestion which has double stranded DNA specific activity.

Following the annealing and ligation of the limiting, specified molar quantity of N-probe, the second normalization step is performed where Exonuclease III is added to digest the excess non probe-protected library fraction. Due to its dsDNA specific 3' to 5' exonuclease activity, completely unprotected library molecules are digested from the 3' terminus until the opposite strand digestion is met, resulting in two single stranded partial library fragments that are non-functional and are unable to be amplified or sequenced. For the single strand protected fraction of the NGS library, the unprotected strand is fully digested and the probe-protected strand is nuclease resistant. As a result, a two-fold greater molar quantity of ssDNA N-probe is required to protect a corresponding specified molar quantity of dsDNA library, where the resulting library is single stranded and directional with regard to adapter sequence (FIG. 8B), In FIG. 8B, by way of example, 8 nM of Normalization Probe will yield 8 nM of single-stranded DNA NGS library which is equivalent to 4 nM of double-stranded DNA NGS library.

Figure 8D:
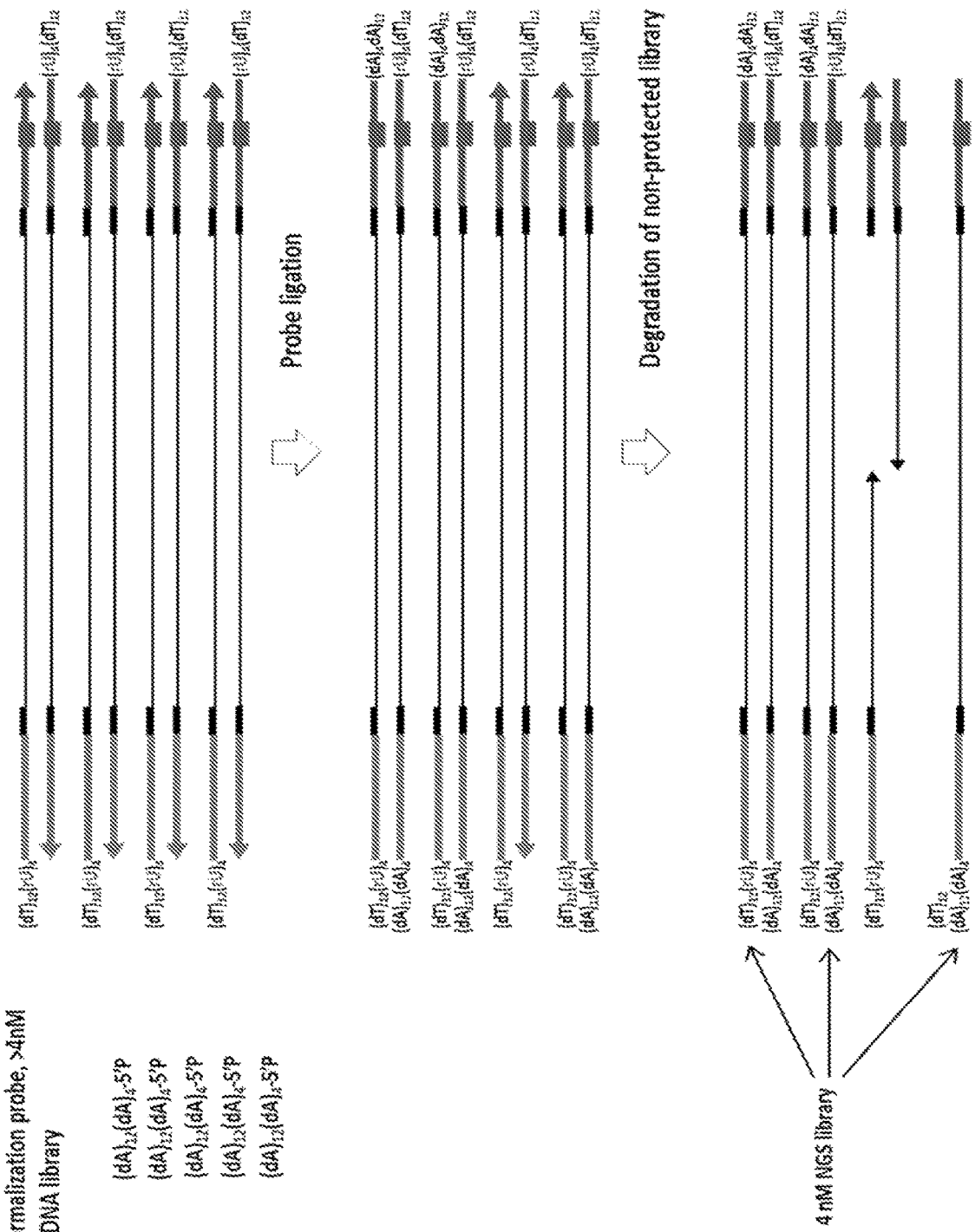
FIG. 8D depicts an exemplary method of enzyme-based normalization by Method 2(a) targeting both library strands using 1 pre-N PCR primer which results in both single-stranded DNA and double-stranded DNA in the library. Figure discloses "$(dT)_{12}(rU)_4$" as SEQ ID NO: 67 and "$(dA)_{12}(dA)_4$" as SEQ ID NO: 68.

Alternatively, Method 2a can be performed using two pre-N primers that generate a 5' overhang at both NGS library termini, resulting in recovery of both strands following normalization (FIGS. 8C and 8D). In this example, from an excess quantity of library to N-probe molarity, the desired quantity of dsDNA library recovered also requires using twice the molarity of ssDNA N-probe. And although a corresponding dsDNA library quantity is recovered, the normalized library comprises both ssDNA and dsDNA library molecules, depending on whether one or both strands of each duplex were protected, as the N-probe is limiting relative to input NGS library. For example, in FIG. 8C, 8 nM single-stranded probe and more than 4 nM PCR-amplified dsDNA library would be required to produce a 4 nM dsDNA NGS library quantity.

Figure 9A:
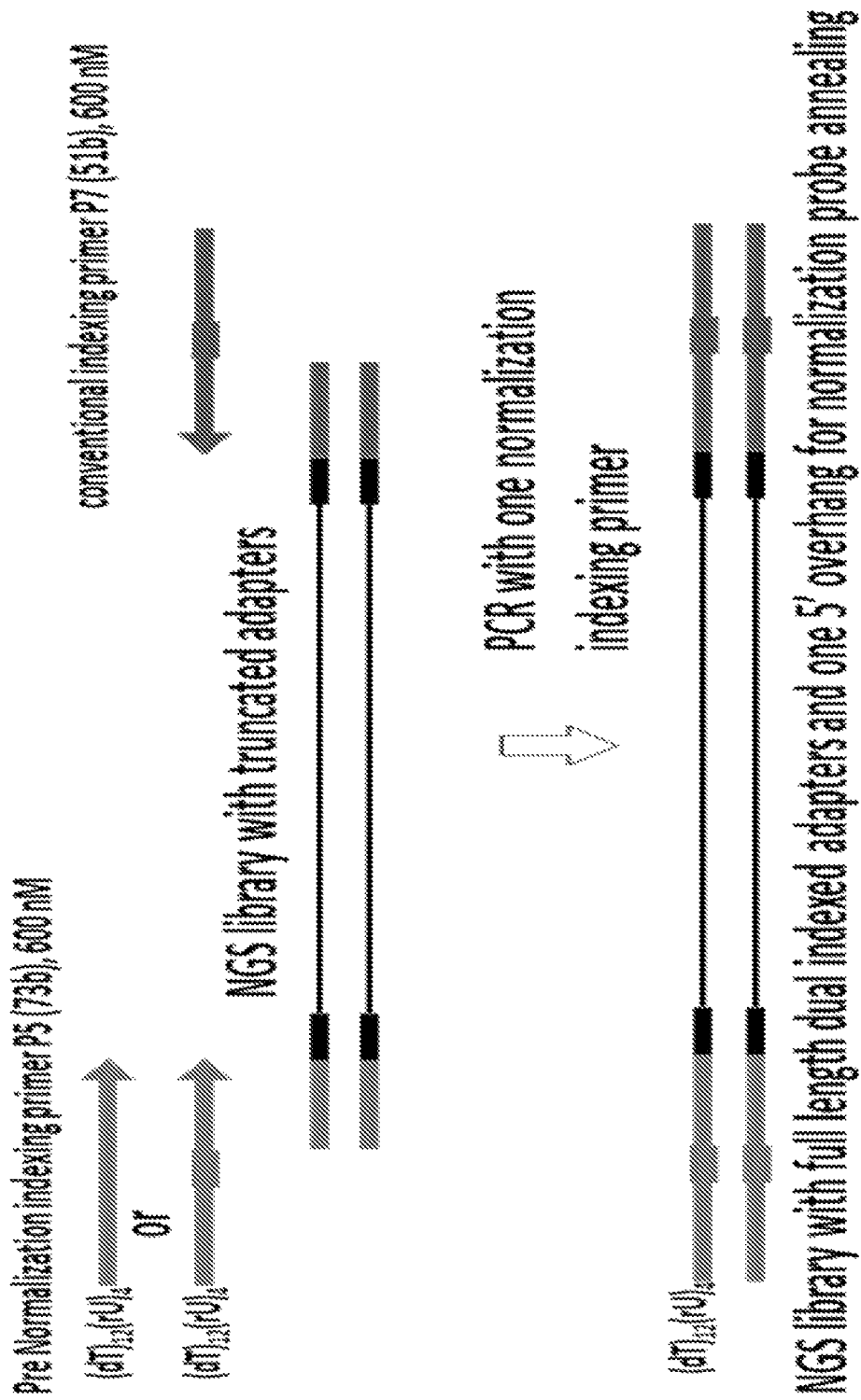
FIG. 9A depicts an exemplary method for PCR amplification for Method 2(a) targeting 1 library strand using a pre-N PCR primer and a conventional primer. Figure discloses "$(dT)_{12}(rU)_4$" as SEQ ID NO: 67.
Figure 9B:
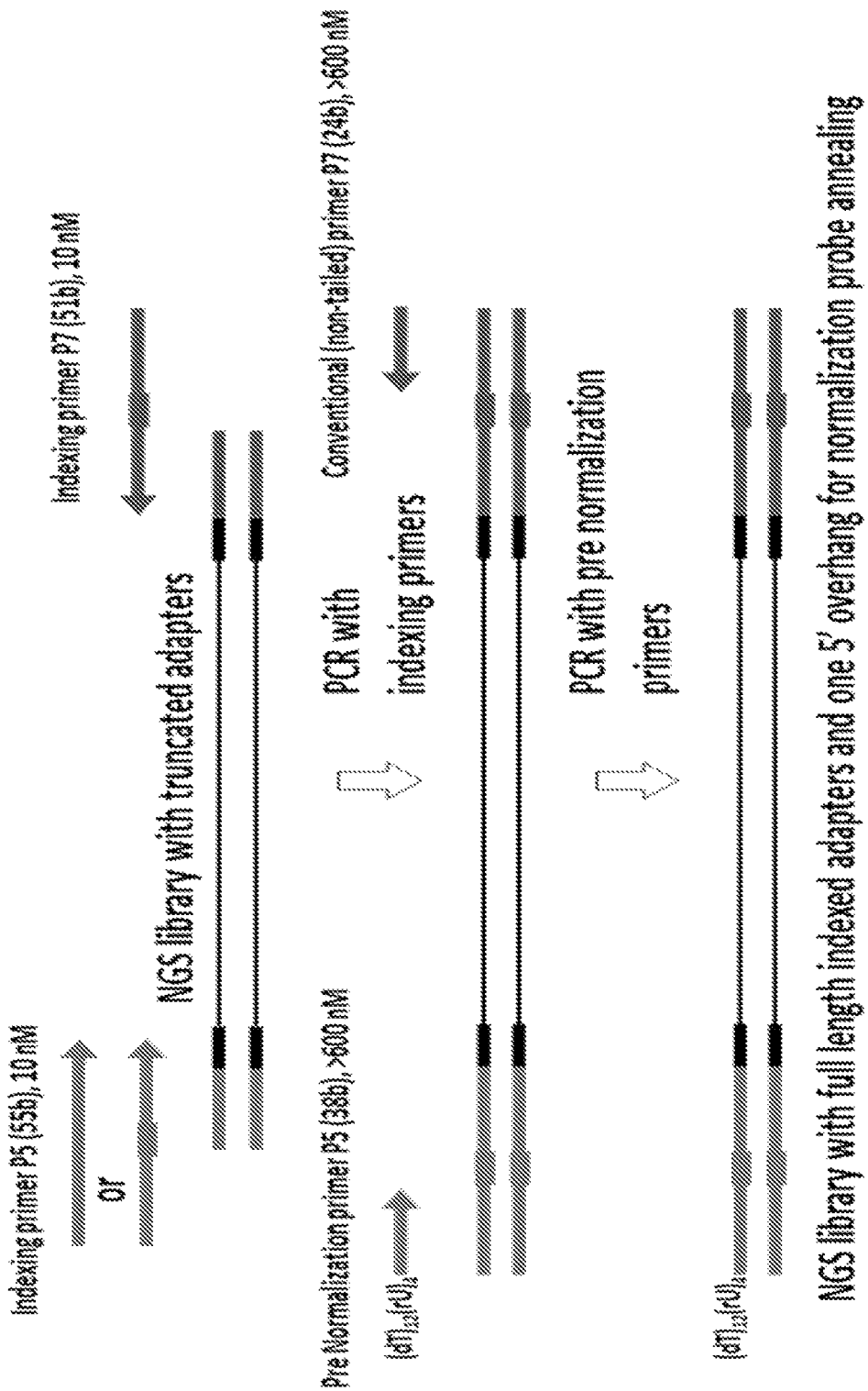
FIG. 9B depicts an exemplary method for PCR amplification for Method 2(a) targeting 1 library strand using a pre-N PCR primer and a conventional primer with a prior PCR step using indexing primers to complete a NGS library with truncated adapters. Figure discloses "$(dT)_{12}(rU)_4$" as SEQ ID NO: 67.

For Method 2a, PCR amplification using pre-N primers can be performed using 2 or 4 primers (FIGS. 9A and 10A, and 9B and 10B, respectively). When targeting only one NGS library strand to create a single 5' overhang per dsDNA library molecule, in the 2 primer PCR, a single pre-N primer is used with a conventional reverse primer that has no 5' tail sequence. Although FIGS. 9A-9B depict a primer pair where both primers comprise a long 5' tail that incorporate indexing sequences and complete the adapters when a truncated NGS adapter ligated library is used as a template (and where the pre-N primer introduces an additional 5' tail region that incorporates the N-probe annealing tail region), the 2 primers can also be designed to amplify completed, full length indexed libraries where the primers only anneal to the terminal adapter sequences used for library amplification, and only the pre-N primer comprises a 5' tail sequence which comprises the N-probe annealing tail region whereas the conventional primer does not have a 5' tail (not shown).

The 4 primer PCR amplification (FIG. 9B) is limited to truncated NGS adapter ligated library as template, and instead of incorporating long 5' tails on the pre-N and conventional primers to complete the NGS adapter sequence and simultaneously introduce the tail region for N-probe annealing, the sequence incorporations are performed sequentially, where a first indexing primer pair is used to complete the NGS adapter, both primers comprising a 5' tail that complete the NGS adapter, and then a second pre-N primer pair introduces the tail region for N-probe annealing on the amplification products of the first primer pair, where in this case the pre-N primer is used with a conventional primer to target one strand of the NGS library. In the 4 primer reaction, the indexing primer pair can be used at a lower concentration that leads to their consumption and the pre-N primer pair is used at a higher concentration for library amplification to reduce the likelihood of finished library products from being primed with the first primer pair (which would eliminate the tail region for N-probe annealing).

Although FIGS. 9A-9B depicts only a first NGS adapter orientation being used to generate a 5' overhang for targeting a single strand, alternatively, the opposite, second NGS adapter can be used to generate a 5' overhang, where a conventional primer is then used on the first NGS adapter (not shown).

Figure 10A:
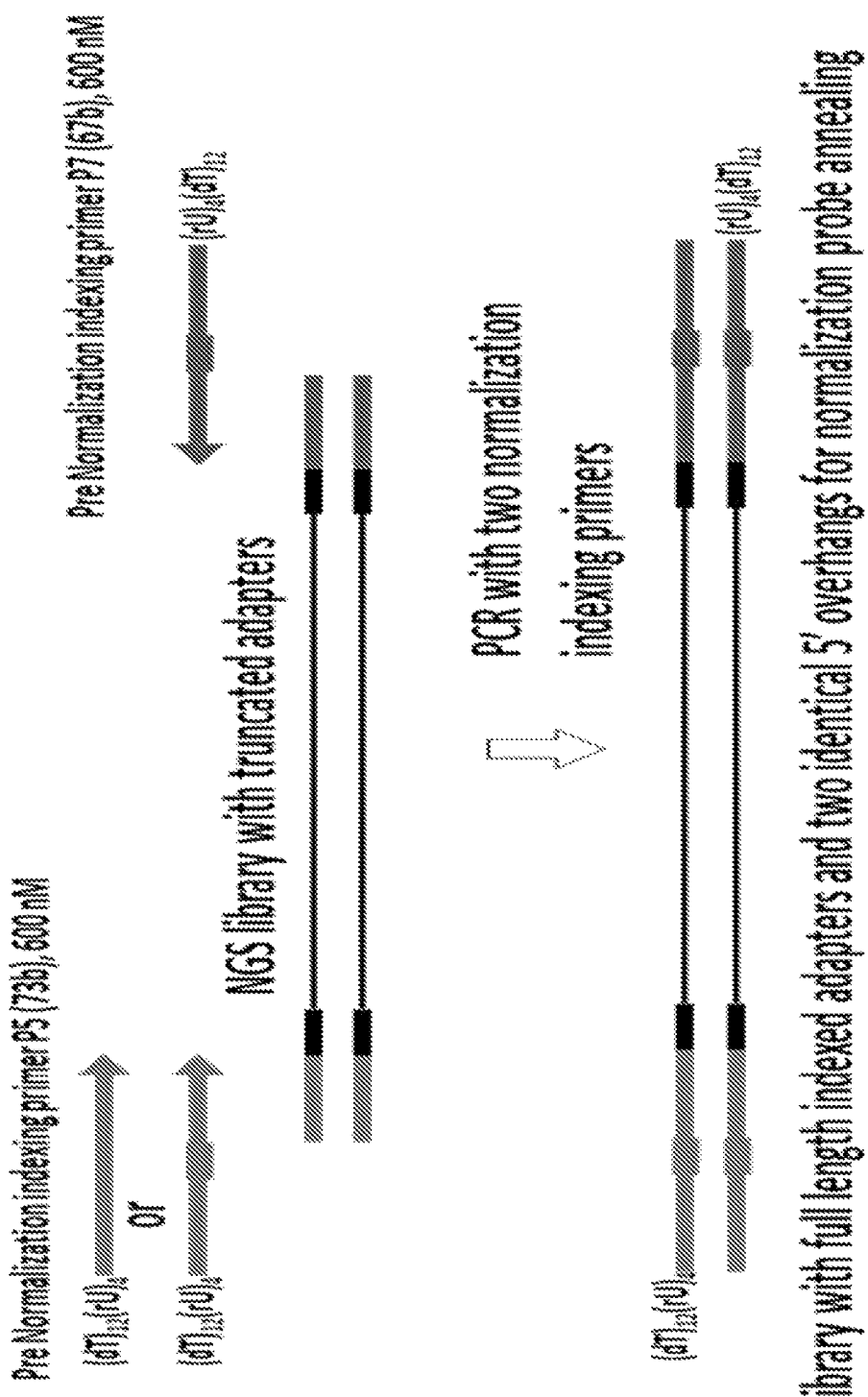
FIG. 10A depicts an exemplary method for PCR amplification for Method 2(a) targeting both library strands using 2 pre-N PCR primers. Figure discloses "$(dT)_{12}(rU)_4$" as SEQ ID NO: 67.
Figure 10B:
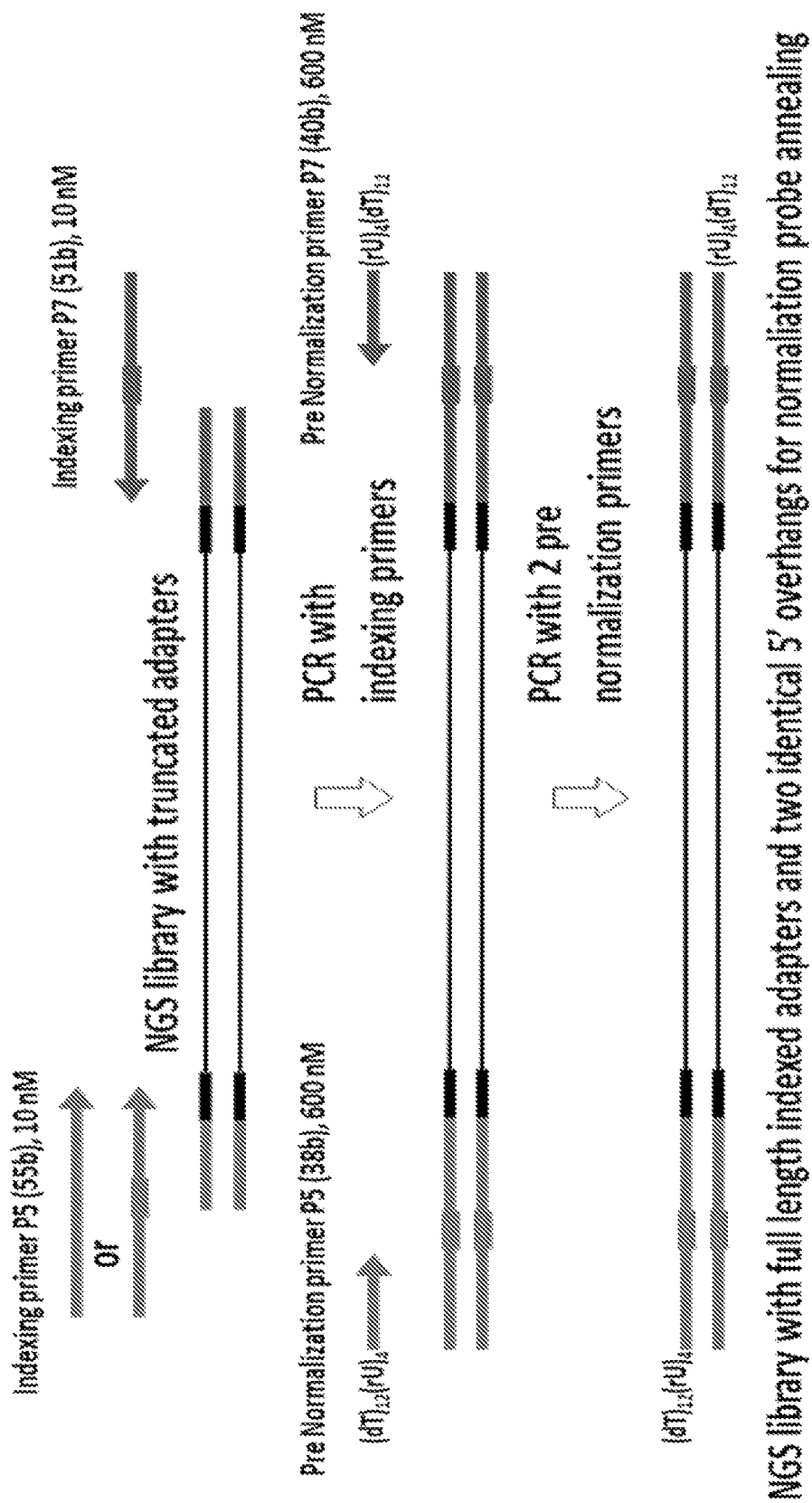
FIG. 10B depicts an exemplary method for PCR amplification for Method 2(a) targeting both library strands using two pre-N PCR primers with a prior PCR step using indexing primers to complete a NGS library with truncated adapters. Figure discloses "$(dT)_{12}(rU)_4$" as SEQ ID NO: 67.

As shown in FIGS. 10A-10B, when Method 2a is designed to target both DNA strands of the NGS library, whether 2 primers or 4 primers are used, in both cases, there are two pre-N primers, both of which introduce a 5' terminal tail region with identical composition, except each of the two primers anneal specifically to either the first or second NGS adapter sequence and optionally incorporates the terminal portion of the adapter sequence, to generate a symmetrical 5' overhang at both library ends, instead of a pre-N and conventional primer pair being used.

In FIGS. 9B and 10B the PCR reaction starts with the indexing primers and continues with normalization primers when the indexing primers have been consumed (for example, at 10 nM concentration of the NGS library as shown in FIGS. 9B and 10B).

Method 2b

Figure 11:
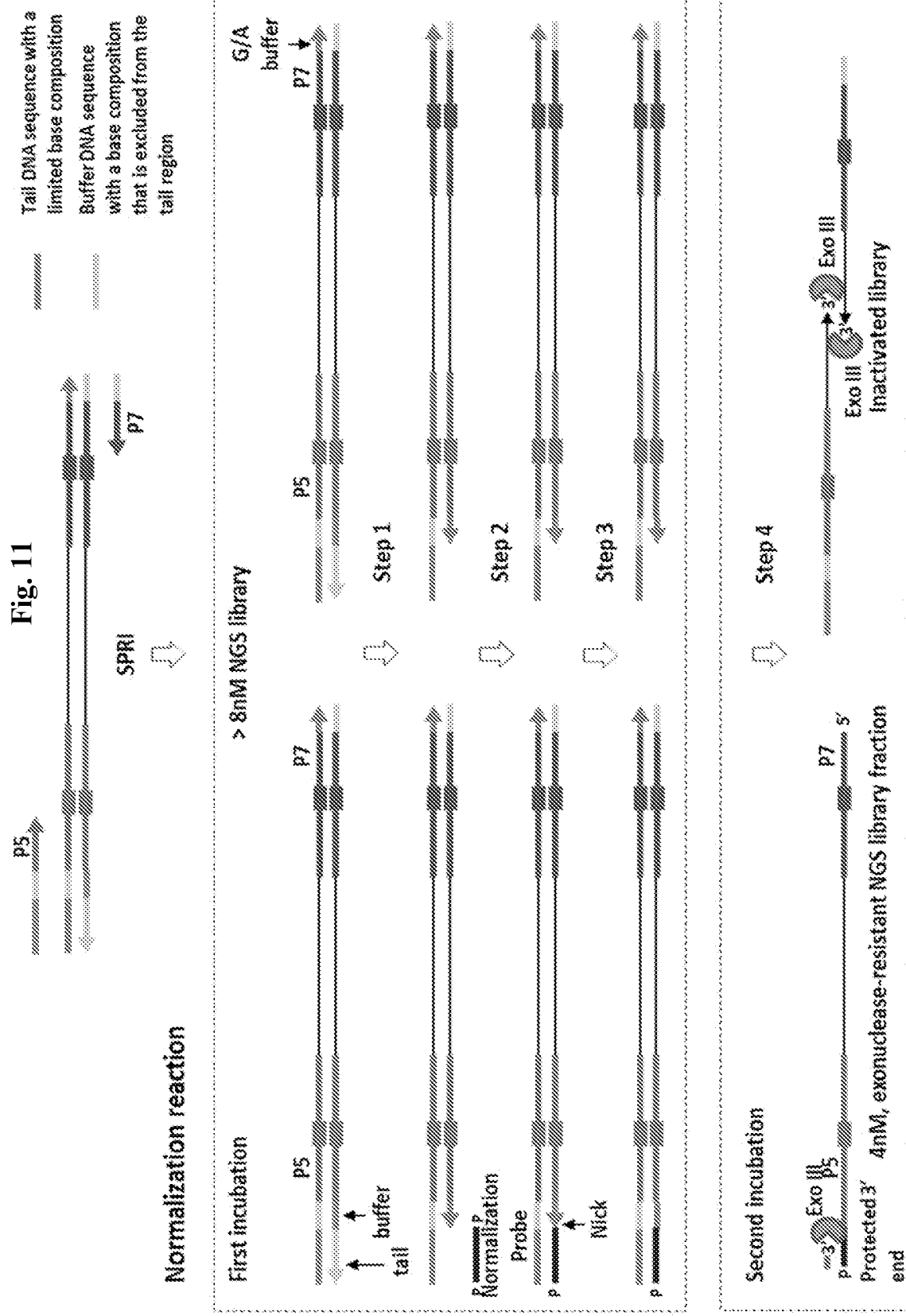
FIG. 11 depicts an exemplary method for generating a 5' overhang using T4 DNA polymerase by Method 2(b) (controlled protection) followed by digestion for normalization of an NGS library. PCR with Pre Normalization Primers and proofreading DNA Polymerase. In the first incubation, normalization probe, T4 DNA polymerase, a nucleotide mix complementary to the buffer region and T4 DNA ligase are added. Step 1: Incubation with T4 DNA polymerase creates 5' overhang at the P5 adapter; it removes 3' bases from the tail region but stops at the buffer region. The opposite end remains blunt due to the buffer region at the 3' end. Step 2: Annealing a specified quantity of Normalization Probe to the 5' overhang created by T4 DNA polymerase. Step 3: Ligation of Normalization Probe to the 3' end of NGS library by T4 DNA ligase. Step 4: Add Exonuclease III or Apyrase; Degradation of non-protected NGS library fraction by Exonuclease III, or by T4 DNA Pol after nucleotide degradation by Apyrase.

Further details of Method 2b, where the 5' overhang is generated by T4 DNA polymerase, are found in FIG. 11; this figure depicts exonuclease protection of one library strand using a single pre-N primer with a conventional reverse primer with a 5' buffer region, but exonuclease protection of both library strands is possible if two pre-N primers are used (not shown). In FIG. 11, only one pre-N primer containing a 5' terminal tail region and 3' adjacent buffer region is used with a reverse primer containing a 5' terminal buffer region identical in base composition to the first buffer region, in the PCR amplification step. The base composition of the buffer regions is restricted to nucleotides that are excluded from the tail region. Following a purification step after generating an excess molar quantity of library relative to the quantity of N-probe to be used, the first normalization step is performed by adding a limiting molar quantity of N-probe that is complementary to the tail region in addition to T4DNA Polymerase, a nucleotide mix complementary to the buffer region but not complementary to the tail region, and a DNA ligase. Use of a low complexity N-probe sequence is preferred, such as a homopolymer, di- or tri-nucleotide sequence, as low complexity probe annealing will occur more rapidly to the complementary overhang compared to a high complexity sequence. The N-probe additionally comprises 1 or more nuclease resistant modifications such as phosphorothioate linkages that can be positioned consecutively within the probe sequence at its 3' terminus, internally or near its 5' terminus to provide resistance to exonuclease III digestion after N-probe annealing and ligation to the library end(s). It also comprises a protection group such as a 3' phosphate or a secondary structure such as a combination of a 3' self-complementary hairpin and a replication block, or any other modification that confers resistance of the N-probe to T4 DNA polymerase 3' exonuclease activity.

Within this first enzyme-based normalization reaction, T4 DNA Polymerase generates a 5' overhang over the previously dsDNA tail region to enable N-probe annealing to the amplified library, where under appropriate reaction conditions, T4 DNA Polymerase irreversibly removes 3' bases from the complementary tail region whose dNTPs are absent from the reaction but reversibly removes and replaces bases at the 3' adjacent buffer region due to the presence of dNTPs complementary to the buffer region. The opposite terminus of the amplified library remains double stranded due to the presence of the second buffer region with the same nucleotide composition as the first buffer region, where bases are reversibly removed and replaced by T4 DNA Polymerase due to the presence of the appropriate nucleotide mix. This thereby defines the limits of the 5' overhang at the buffer region at the first end where at the opposite end the second buffer region prevents formation of an overhang.

Following the annealing and ligation of the limiting N-probe quantity, the second enzyme-based normalization step is performed by addition of Exonuclease III to digest the excess non probe-protected library fraction. Due to its dsDNA specific 3' to 5' exonuclease activity, completely unprotected library molecules are digested from the 3' terminus until the opposite strand digestion is met, resulting in two single stranded partial library fragments that are non-functional and are unable to be amplified or sequenced. For the single strand protected fraction of the NGS library, the unprotected strand is fully digested and the probe-protected strand is nuclease resistant. As a result, a two-fold greater molarity of ssDNA N-probe quantity is required to protect a corresponding dsDNA library quantity, where the resulting library is single stranded and directional with regard to adapter sequence (FIG. 11). In an alternate embodiment of this method, instead of adding Exonuclease III to digest the non probe-selected fraction, the Apyrase diphosphatase enzyme can be added to hydrolyze phosphates from the dNTP mixture present in the reaction, which will then lead to uncontrolled 3'-5' exonuclease activity of T4 DNA polymerase in the absence of any functional dNTPs for replacement of excised bases, and the non-probe selected library fraction will be digested accordingly and rendered non-sequenceable, where the N-probe-selected fraction remains nuclease resistant and sequenceable.

In other aspects, Method 2b can be performed using two pre-N primers, both containing tail and buffer regions, to generate a 5' overhang at both NGS library termini, resulting in recovery of both NGS library strands following N-probe ligation and library digestion. In one embodiment, a homopolymer tail region is used with a dinucleotide buffer region, but any low complexity sequence could be used in the tail region as long as the base composition of the buffer region is excluded from the tail region. A linear N-probe can be used which comprises nuclease resistant modifications at its 3' terminus, internally or near its 5' terminus, or an optional N-probe with a 3' self-complementary hairpin and non-replicable spacer can be used to confer further resistance to T4 DNA Polymerase 3' exonuclease activity and Exonuclease III. In both cases, the probe confers resistance to 3' exonuclease digestion. Following these two enzyme-based normalization steps, from an excess molarity of library input relative to N-probe, the desired molar quantity of dsDNA library is recovered, but twice the molarity of single stranded DNA N-probe is used. And although a dsDNA molar library quantity is recovered, the normalized library comprises both ssDNA and dsDNA library molecules, depending on whether one or both strands of each duplex are protected, as the N-probe is limiting.

Method 2c

Figure 12:
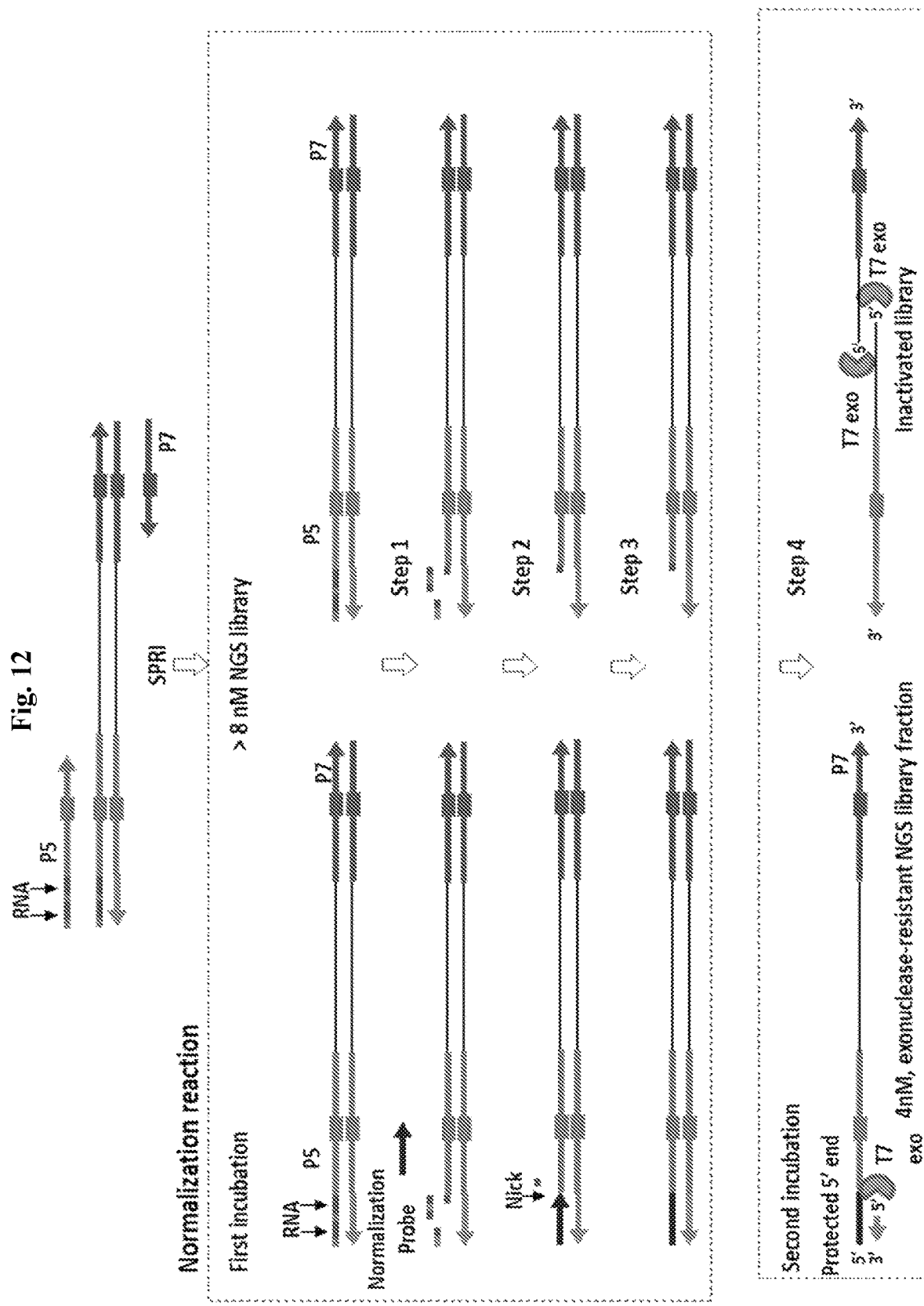
FIG. 12 depicts an exemplary method for generating a 3' overhang and using a 5' exonuclease for Method 2(c) (controlled protection). PCR with Pre Normalization Primers and proofreading DNA Polymerase. The pre-normalization primer comprises RNA bases that can be cleaved from the PCR product using RNase H. In the first incubation, normalization probe, primer digestion enzyme (RNase H) and a DNA ligase are added. Step 1: Incubation with RNase H creates 3' overhang at one or both adapter ends. Step 2: Annealing a specified quantity of Normalization Probe to the 3' overhang created by RNase H treatment. Step 3: Ligation of the Normalization Probe to the 5' end of NGS library by T4 DNA ligase. Step 4: Add T7 exonuclease or lambda exonuclease; Degradation of non-protected NGS library ends by T7 or lambda exonuclease.
Figure 14:
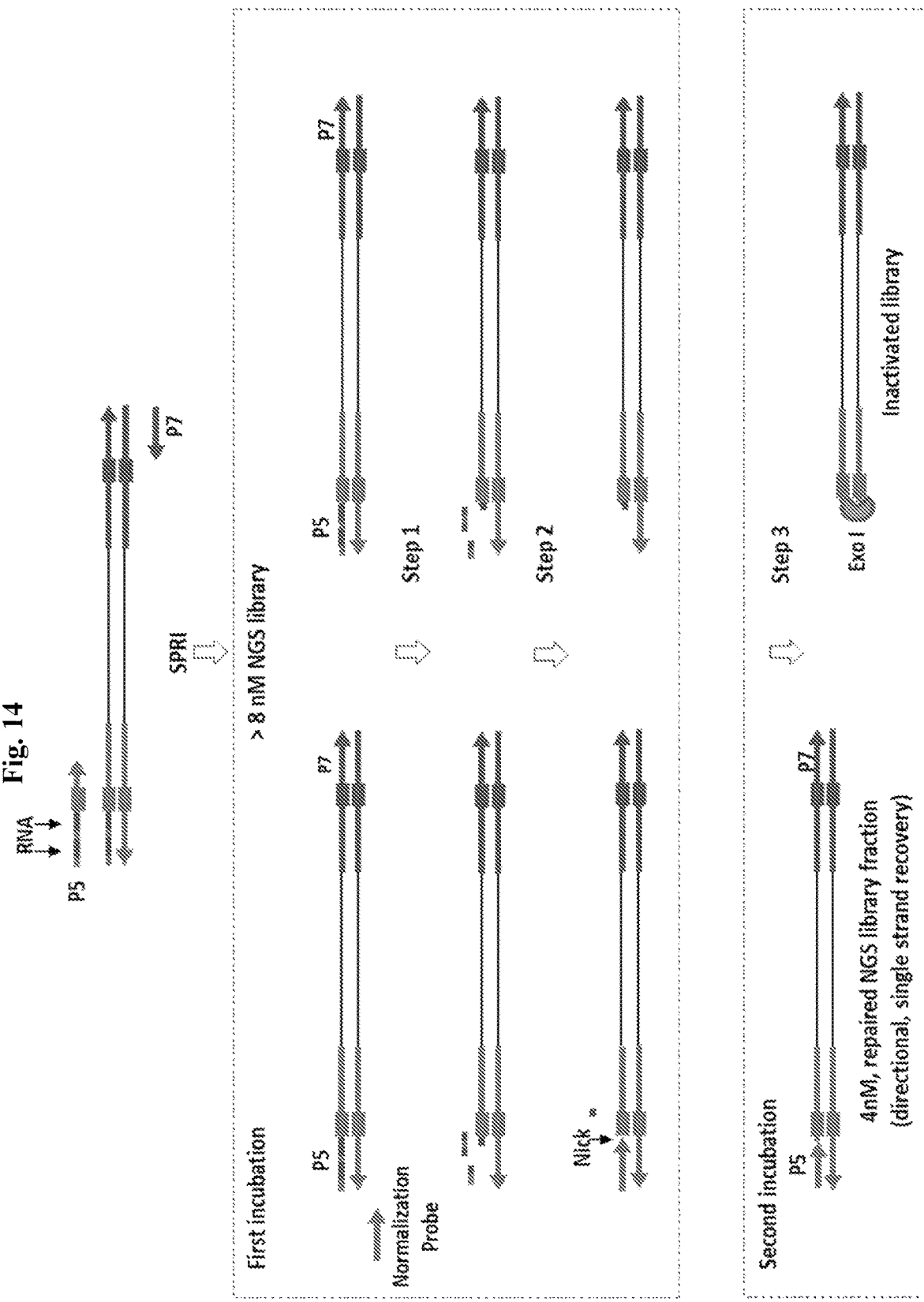
FIG. 14 depicts an exemplary method for normalization using RNaseH, a ligase and Exonuclease I by Method 3a (controlled repair). PCR with Pre Normalization Primers and proofreading DNA Polymerase. Arrows indicate position of RNA bases that can be cleaved from the PCR product using RNase H. In the first incubation, normalization probe, RNase H and T4 DNA ligase (Taq DNA Polymerase is optional) are added. Step 1: Incubation with RNase H inactivates 50% of the library and creates a 3' overhang at one adapter end. Step 2: Annealing and ligating a specified quantity of Normalization Probe to the 3' overhang protects the dsDNA end from digestion with exonuclease I, where the library fraction lacking probe is exonuclease I sensitive. Step 3: Add Exonuclease I; Digestion of the non probe protected single-stranded NGS library ends by Exonuclease I.
Figure 15:
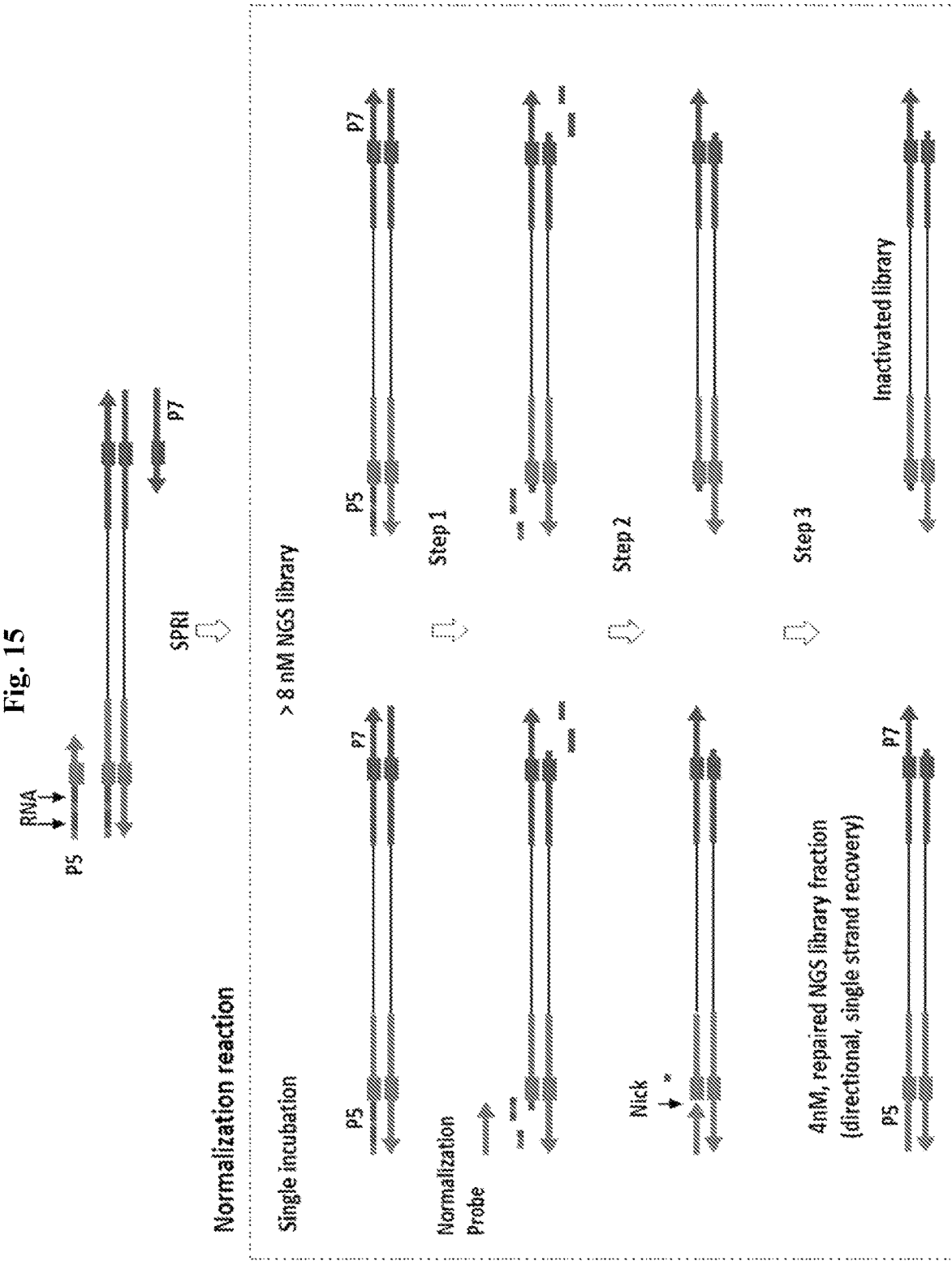
FIG. 15 depicts an exemplary method for normalization using RNaseH and a ligase by Method 3b (controlled repair). PCR with Pre Normalization Primers and proofreading DNA Polymerase. Arrows indicate position of RNA bases that can be cleaved from the PCR product using RNase H. In the single incubation, normalization probe, RNase H and T4 DNA ligase (Taq DNA Polymerase is optional) are added. Step 1: Incubation with RNase H inactivates the library and creates 3' overhangs at both adapter ends. Step 2: Annealing of a specified quantity of normalization probe to the P5 3' overhang only. Step 3: Recovery of a specified quantity of NGS library by ligation of the normalization probe to the P5 adapter 5' end (with displacement and cleavage of remaining RNA bases by a 5'-flap endonuclease activity of Taq DNA Pol, if necessary).
Figure 16:
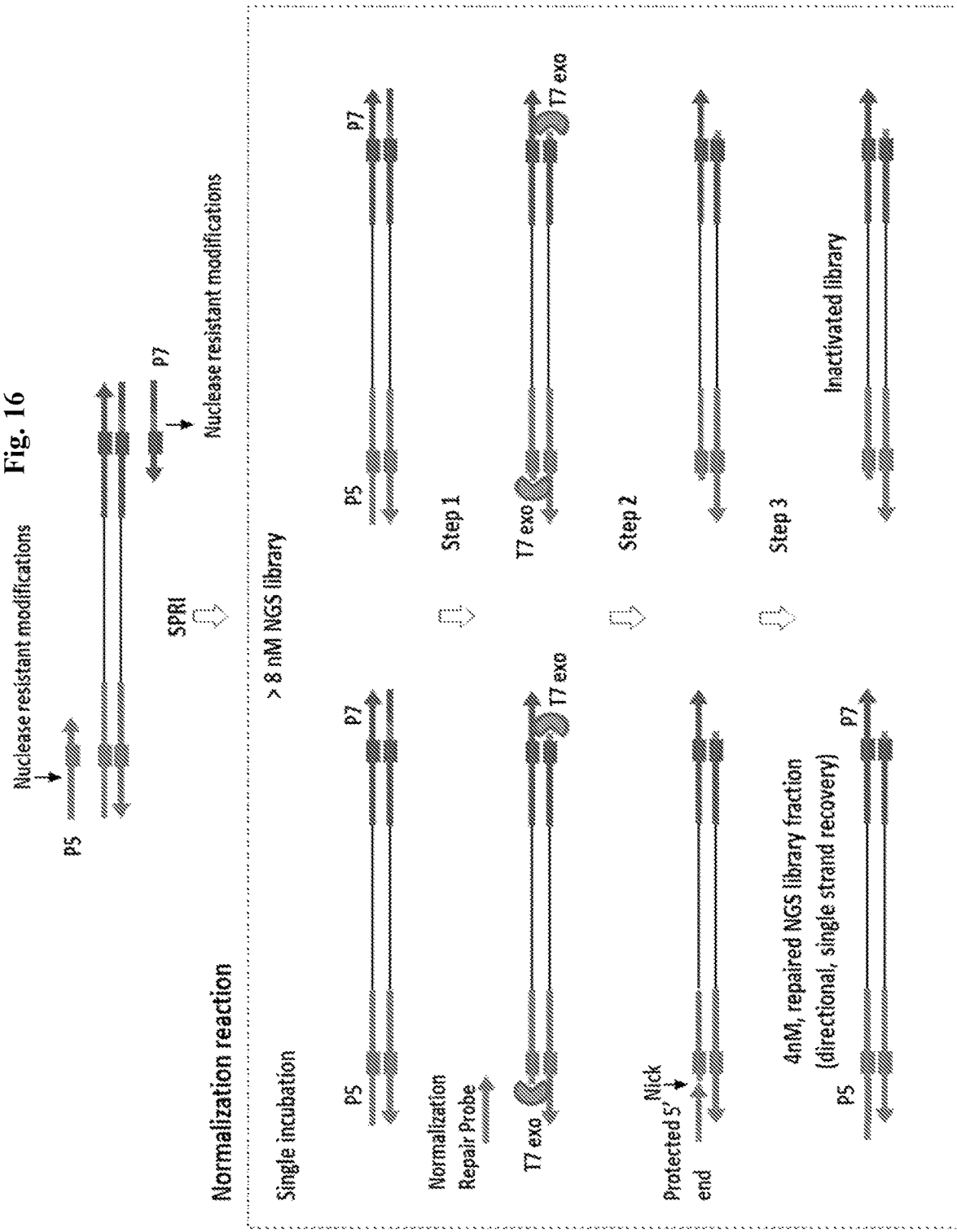
FIG. 16 depicts an exemplary method for normalization using a 5' exonuclease and a ligase by Method 3c (controlled repair). PCR with Pre Normalization Primers and proofreading DNA Polymerase. Arrow indicates position of the nuclease-resistant bases or linkages (6 or more). In the single incubation, normalization probe, T7 exonuclease (5') and T4 DNA ligase (Taq DNA Pol is optional) are added. Step 1: Incubation with T7 exonuclease inactivates the library and creates 3' overhangs at both adapter ends. Digestion stops at nuclease-resistant bases introduced during PCR amplification. Step 2: Annealing of a specified quantity of normalization probe to the 3' overhang created by 5' exonuclease digestion. Step 3: Recovery of a specified quantity of NGS library by ligation of the normalization probe.

This method, where alternatively a 3' overhang for N-probe ligation is generated post PCR by a cleavage enzyme, can be found in FIG. 12. Although this figure depicts only one cleavable pre-N primer being used to generate a single 3' overhang on one NGS library strand, if both PCR primers contain cleavable bases, a 3' overhang can be generated at both library termini to protect both NGS library strands from 5' exonuclease digestion following annealing and ligation of the nuclease resistant N-probe. The cleavable base incorporated into the pre-N primer can be RNA, deoxyuracil or deoxyinosine, where the incorporated primer sequence can be cleaved from the resulting amplicon by cleavage with RNAse H, Uracil DNA glycosylase and apurinic endonuclease, or Endonuclease V, respectively.

Following a purification step after generating an excess molar quantity NGS library relative to N-probe molar quantity to be used, the first normalization reaction is performed by adding a specified molar quantity of N-probe in addition to a cleavage enzyme and a DNA ligase. Use of a low complexity probe sequence that is complementary to the 3' overhang is preferred, such as a homopolymer, di- or tri-nucleotide sequence, as low complexity probe annealing will occur more rapidly compared to a high complexity sequence. The N-probe additionally comprises 1 or more nuclease resistant modifications such as phosphorothioate linkages that can be positioned consecutively within the probe sequence at its 5' terminus, internally or near its 3' terminus to provide resistance to a 5' exonuclease digestion after probe annealing and ligation to the library end(s). Within this reaction, both the length of the pre-N primer and the position and number of cleavable bases define the length of the 3' overhang that is generated by enzymatic cleavage. Therefore, the cleavage enzyme generates a 3' overhang to enable probe annealing and ligation of the limiting, specified probe quantity to the excess quantity of 3' overhangs, which confers 5' exonuclease resistance to a selected library fraction. In the second normalization step, Lambda or T7 Exonuclease is then added to digest the non probe-protected library fraction. Due to their dsDNA specific 5' to 3' exonuclease activity, completely unprotected library molecules are digested from the 5' terminus until the opposite strand digestion is met, resulting in two single stranded partial library fragments that are non-functional and are unable to be amplified or sequenced. For the single strand protected fraction of the NGS library, the unprotected strand is fully digested and the probe protected strand is nuclease resistant. As a result, two-fold greater ssDNA probe molar quantity is required to protect a corresponding desired dsDNA library molar quantity, where the resulting library is single stranded and directional with regard to adapter sequence.

FIGS. 41A-41E also depict different exemplary embodiments for controlled protection from exonuclease digestion. In some instances an overhang is not required (see, e.g. FIG. 41A). In some instances the ligation can be, by way of example but not limitation, blunt-end (FIG. 41A), TA ligation (FIG. 41B) or cohesive end ligation. In all of the methods depicted in FIGS. 41A-41E, the limited and specified amount of N-probe carrying nuclease-resistant bases can become ligated to either the 3' or 5' or both DNA termini thus protecting the specified library fraction from exonuclease degradation. Library molecules can be produced via methods described in the present disclosure and known to those of skill in the art. In instances where an overhang is generated by PCR, the methods of the present disclosure can be used to generate such overhangs.

Figure 41A:
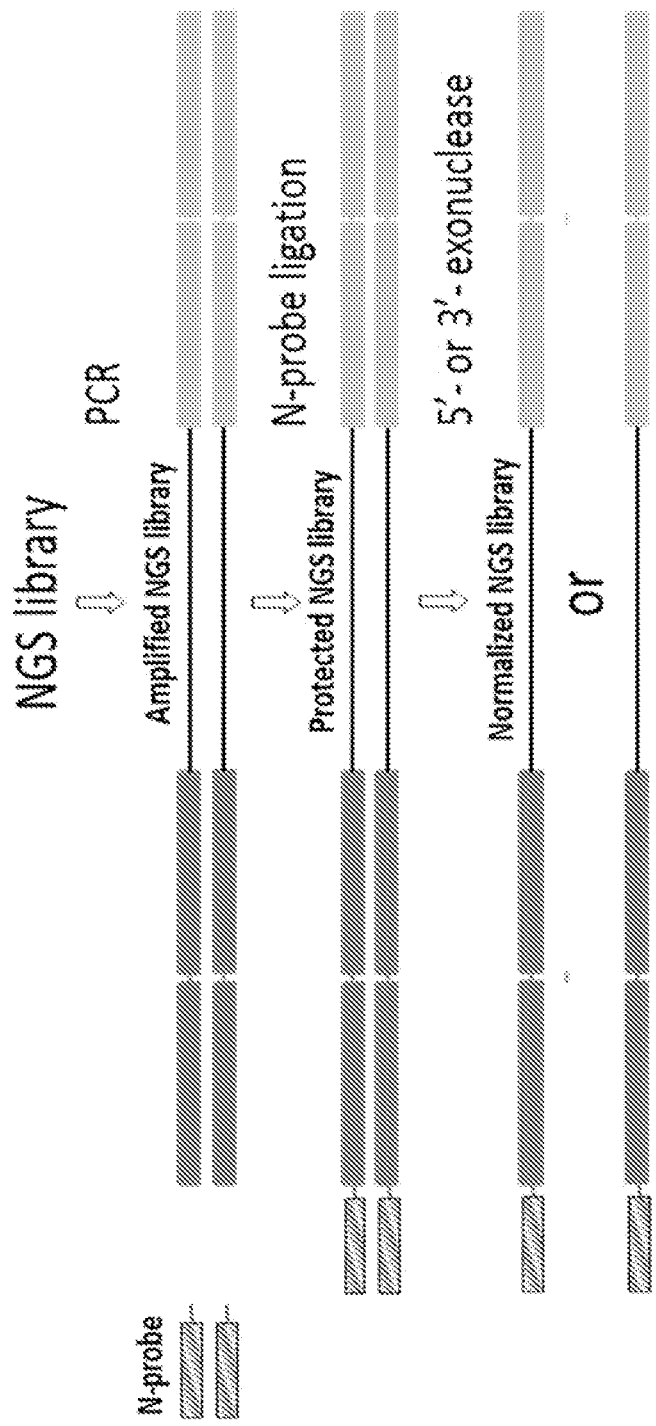
FIG. 41A depicts a schematic representation of an exemplary normalization method of the present disclosure.

In FIG. 41A, the NGS library is amplified with a high fidelity DNA polymerase and conventional primers to yield blunt-end fragments which can then be blunt-end ligated to a specified amount of a double-stranded (or single-stranded, not shown) probe with a modification to provide resistance to digestion by an exonuclease and then exposed to an exonuclease to yield the normalized NGS library. To be efficient, the reaction can proceed at very high library and DNA ligase concentration because there is no low complexity sequence to accelerate probe annealing and ligation.

Figure 41B:
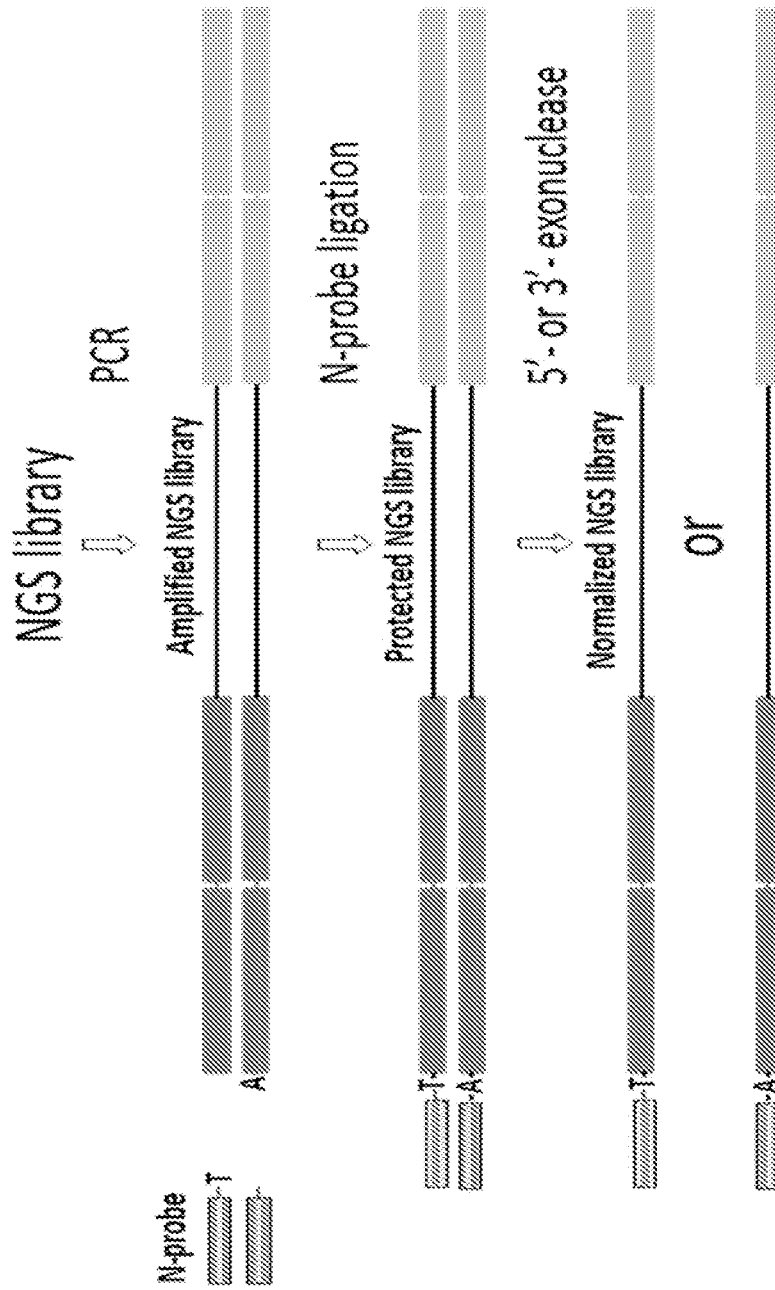
FIG. 41B depicts a schematic representation of an exemplary normalization method of the present disclosure.

In FIG. 41B, the library is amplified with Taq or any other thermostable DNA polymerase lacking 3' proofreading activity and conventional primers to yield fragments with A-tail at the ends which can then be ligated to a normalization probe with a T-tail by TA ligation. As with FIG. 41A, the reaction can proceed at very high library and DNA ligase concentration to be efficient because there is no low complexity sequence to accelerate probe annealing and ligation.

Figure 41C:
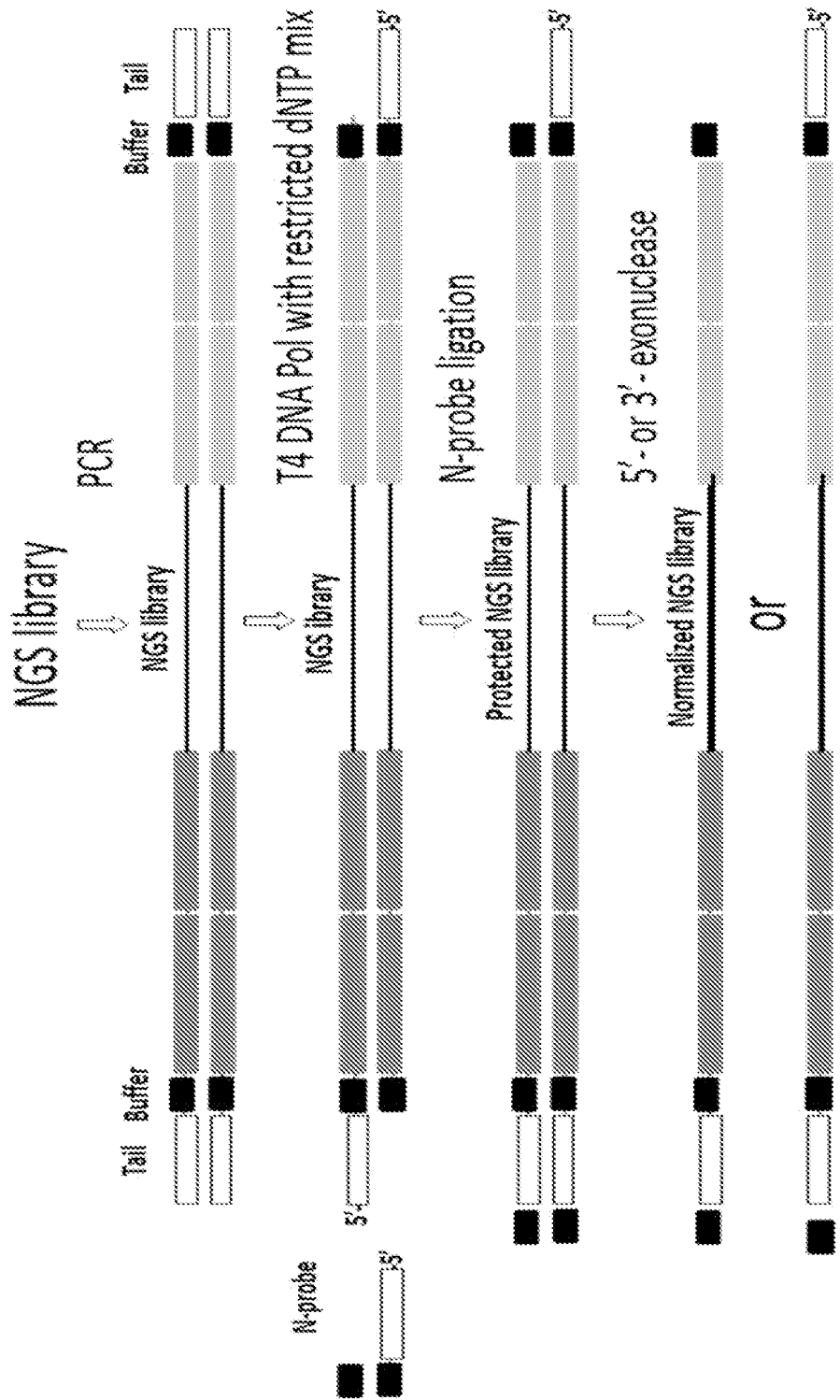
FIG. 41C depicts a schematic representation of an exemplary normalization method of the present disclosure.

In FIG. 41C, the library is amplified using pre-N PCR primers to incorporate a 5' tail and 3' adjacent buffer region. The tail region is 6-20 bases and comprises a homopolymer, di- or tri-nucleotide composition followed by a 5-10 base buffer region containing a nucleotide composition that is excluded from the 5' tail region. When an NGS library comprising such sequences is incubated with T4 DNA Polymerase and a nucleotide mix restricted to only bases complementary to the buffer region but not the tail region, the 3' exonuclease proofreading activity of T4 DNA Polymerase will irreversibly trim the 3' complementary tail region until it reaches the buffer region where it can reversibly remove and replace nucleotides, thus creating a 5' overhang defined by the buffer region. Creation of the 5' overhang and ligation of the N-probe with the complementary 5' overhang sequence can be done sequentially after removing or heat inactivating T4 DNA polymerase, or combined into a single incubation reaction when the N-probe contains buffer region with the same base composition 3' adjacent to the 5' tail. The pre-N PCR primer and N-probe complementary tail sequences are homopolymer repetitive sequences such as poly A and poly T to accelerate probe annealing and ligation to enable efficient ligation at low probe concentration.

Figure 41D:
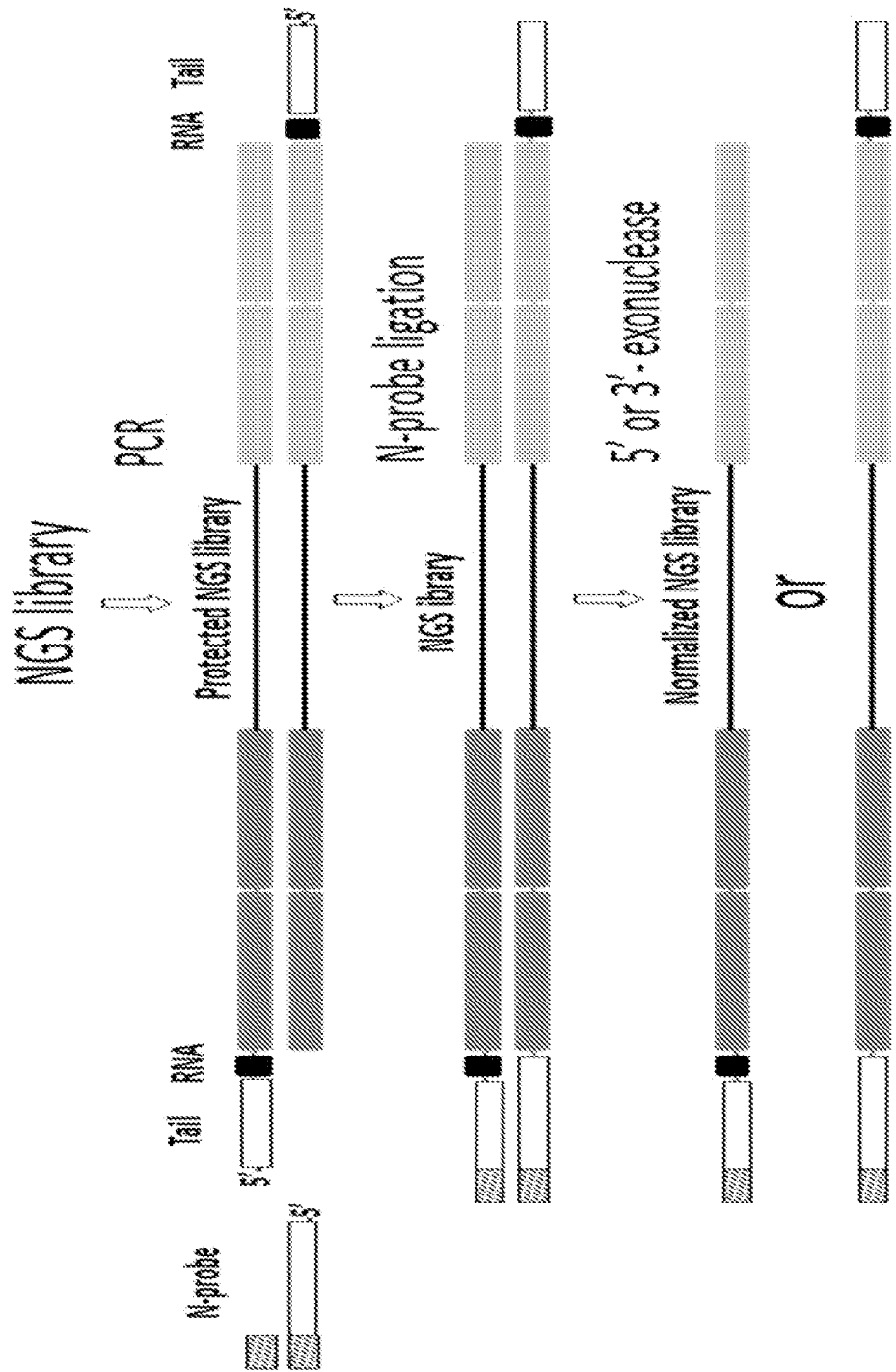
FIG. 41D depicts a schematic representation of an exemplary normalization method of the present disclosure.

In FIG. 41D, the library is amplified using pre-N PCR primers with a 5' tail and located between the tail and adapter sequence, the non-replicable group including a dU base (for archael DNA polymerases), or a non-replicable spacer comprising a consecutive stretch of 3 or more riboU or riboA bases, where the high fidelity DNA polymerase is incapable of extending through the $(riboU)_n$ or $(riboA)_n$ template, where n=3 or more. When riboU and ribo A bases are flanked with the poly(dT) and poly(dA) 6-20 base tail sequences (SEQ ID NOS 57 and 58, respectively), respectively, the PCR results in library molecules with the corresponding homopolymer 5' overhangs for homopolymer N-probe ligation. The repetitive sequences such as poly A and poly T accelerate probe annealing and ligation to enable efficient ligation at low probe concentration.

Figure 41E:
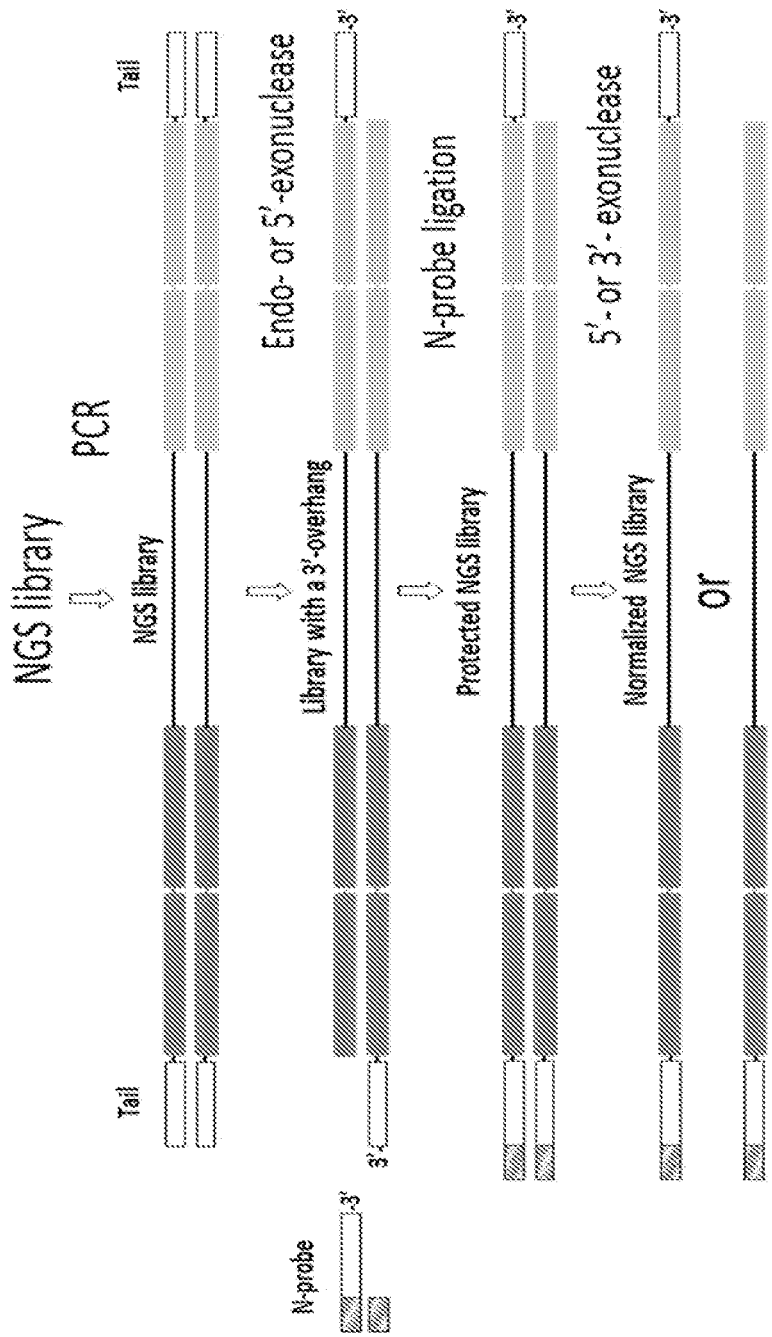
FIG. 41E depicts a schematic representation of an exemplary normalization method of the present disclosure.

In FIG. 41E, the library is amplified using pre-N PCR primers with modified bases comprising either cleavable or nuclease-resistant bases. Cleavable bases can be located evenly within a 5' tail or within the 5' portion of the adapter sequence and include but not limited to dU base, RNA and deoxyinosine. Nuclease resistant bases such as phosphorothioate bases can be located within the 3' portion of the 5' tail or, if tail is absent (not shown), within the adapter sequence. Incubation with UDG/abasic endonuclease mix, RNase H or endonuclease V (in the case of cleavable bases) and 5' exonuclease such as T7 exonuclease, lambda exonuclease or exonuclease V (in the case of nuclease-resistant bases) would result in the 3' overhang whose length is controlled by the position of the cleavable/nuclease-resistant bases or linkages within the pre-N PCR primer. The tail sequence can be either a complex sequence or a homopolymer low complexity sequence.

Method 3: Enzyme-Based Library Normalization by Controlled Repair

The three controlled repair methods are summarized in FIGS. 13-16, where following pre-N primer PCR amplification, Method 3a has two normalization steps: a cleavage/ligation followed by an exonuclease step whereas Methods 3b and c have only a single cleavage/ligation step. Similar to Method 2c, Methods 3a and b utilize pre-N PCR primers that comprise cleavable bases to generate a 3' overhang on the excess molar quantity of NGS library post-PCR, whereas Method 3c generates a 3' overhang using a 5' exonuclease with a pre-N primer comprising nuclease-resistant modifications. In Method 3a, using a single pre-N primer with a conventional primer, the single 3' overhang that is generated comprises a functional portion of the NGS adapter, such that cleavage of the incorporated primer sequence results in partial library inactivation of 50% of the library molecules, in that without the 5' portion of the adapter, the cleaved library strand is rendered incapable of forming clusters on the Illumina sequencing platform or supporting emulsion PCR on Ion instruments, whereas the second NGS strand remains intact and functional. If two pre-N primers are used instead of one (Method 3b), then both library strands or 100% of the library molecules are inactivated by the cleavage reaction. In either method, RNA, dexoyuracil or deoxyinosine cleavable bases are included in the normalization primer, in conjunction with RNaseH, UDG and an apurinic endonuclease, or Endonuclease V cleavage. The length of the 3' overhang is controlled by the position of the cleavable bases within the primer as well as overall primer length. In other embodiments (Method 3c), the 3' overhang at one or both library ends is created after PCR by incubation with a 5' exonuclease such as T7 or Lambda Exonuclease, which will digest the 5' ends of the amplified library molecule until nuclease resistant linkages such as phosphorothioate bonds or other modifications are encountered internally. The length of the 3' overhang is controlled by the position of the digestable vs. nuclease-resistant bases or linkages within the pre-N PCR primer as well as overall primer length.

The enzyme-based normalization step also has a limiting molar quantity of N-probe and a ligase present. Optionally an enzyme such as Taq DNA polymerase or a flap endonuclease is also included to displace and cleave any residual cleavable bases from an incomplete primer digestion reaction that would otherwise interfere with the N-probe fully annealing and ligating. Within this step, following enzymatic removal of either one (Method 3a) or both (Methods 3b,c) 5' termini to inactivate one or both library strands, a selected fraction of the excess molar quantity of library is ligated to a limiting molar quantity of N-probe that corresponds to the NGS adapter sequence that was removed by cleavage, thus restoring the functional NGS adapter and its ability to be sequenced. This completes the enzyme-based normalization process for Methods 4b and c, as the selected library fraction with restored functionality is a molar quantity that corresponds to the limiting molar quantity of N-probe. Method 3a requires an additional normalization step where a single strand specific 3' to 5' exonuclease such as Exonuclease I is used to digest the 3' overhang on the library strand that was left intact but which its complementary strand did not ligate to a N-probe, thus inactivating all library strands with the exception of those library strands ligated to N-probe, which normalizes the molarity of the NGS library to correspond to the N-probe molar quantity.

Specifically, in FIG. 13 there are 4 steps that describe the three methods: (1) PCR amplification to generate an NGS library with cleavable (Methods 3a or 3b), or nuclease-resistant bases (Method 3c) at one (Method 3a) or both (Methods 3b or 3c) adapter ends, followed by SPRI purification; (2) partial library inactivation by digestion of the 5' portion of one NGS adapter (Method 3a), or complete library inactivation by enzymatic digestion of the 5' portion of both NGS adapters (Method 3b), or by 5' exonuclease digestion (Method 3c), to generate a 3' overhang; (3) restoration of a specified number of library molecules by annealing and ligation of a specified quantity of Normalization Probe to the 3' overhang; and (4) complete inactivation of the non-repaired library fraction by digestion of the 3' overhang using a single-stand-specific exonuclease such as exonuclease I (Method 3a only).

Method 4: Enzyme-Based Library Normalization by Controlled Synthesis

Figure 17:
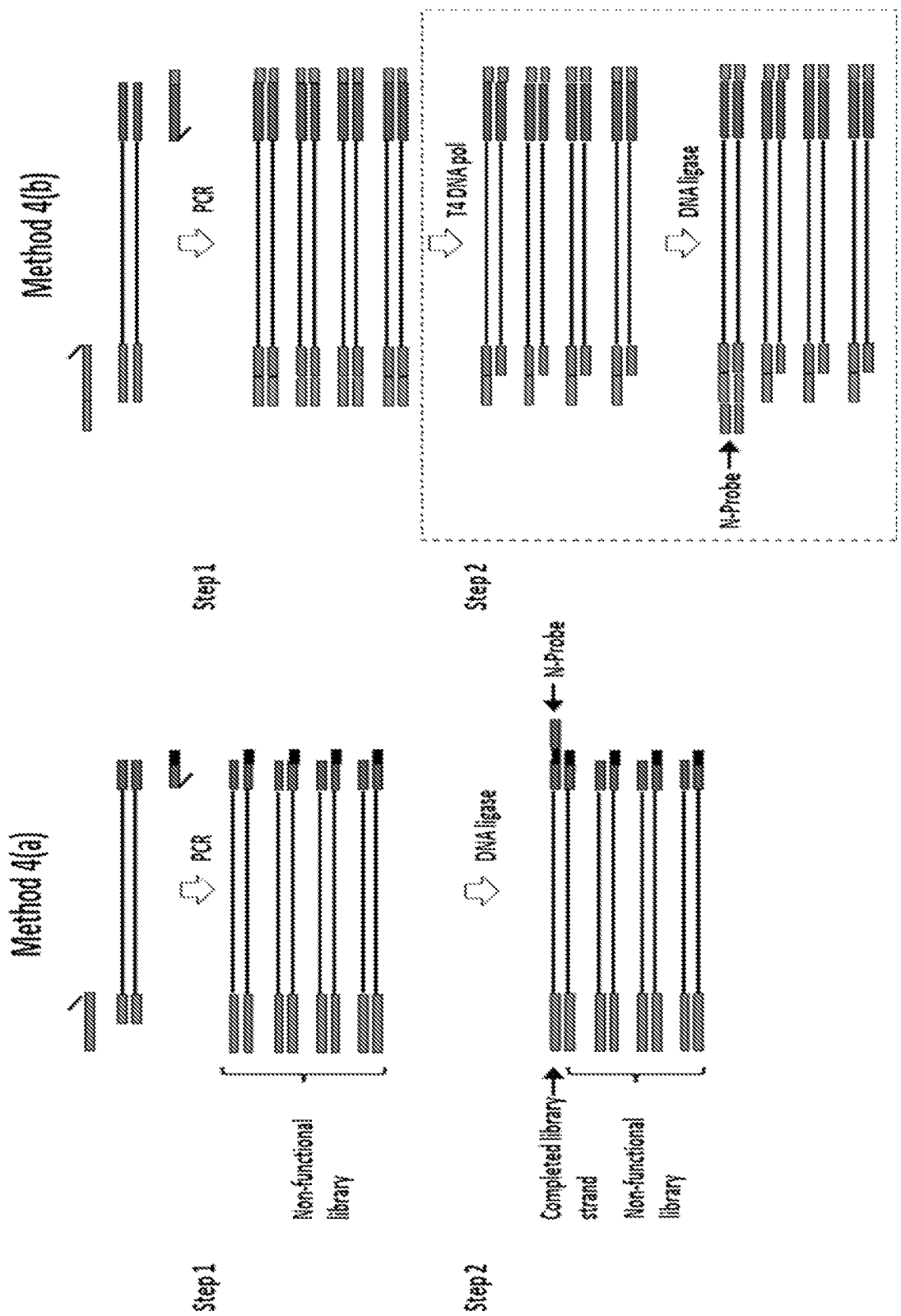
FIG. 17 depicts exemplary methods for normalization by controlled post-PCR library synthesis by Methods 5(a) and 5(b) (controlled synthesis).

Two controlled synthesis methods for enzyme-based library normalization are summarized in FIG. 17, which entail constructing and amplifying an NGS library that has a truncated or incomplete, non-functional adapter sequence at one or both ends, followed by ligation of a limited N-probe quantity that completes functional library construction for a selected molar fraction of the library. In Method 4a, a 5' overhang is generated during PCR using a non-replicable moiety in the pre-N primer, or in Method 4b a 5' overhang is generated by T4 DNA Polymerase post-PCR as described previously (limited base composition in the tail that is excluded from the buffer regions of the pre-N PCR primers followed by limited dNTP composition in the post-PCR 3'-5' exonuclease reaction that is excluded from the complementary tail region but included in the complementary buffer region). In other aspects, the 5' overhang can be generated by other disclosed methods herein. Alternatively, controlled synthesis normalization could be performed following generation of a 3' overhang by any of the disclosed methods for N-probe annealing and ligation disclosed in Method 2c (not shown). Following formation of a 5' or 3' overhang, in one embodiment (Method 4a), a single stranded N-probe is used, conferring library functionality to only the strand to which it ligates. In another embodiment (Method 4b), a partially double-stranded N-probe is used, conferring library functionality to both strands to which it ligates.

Figure 42A:
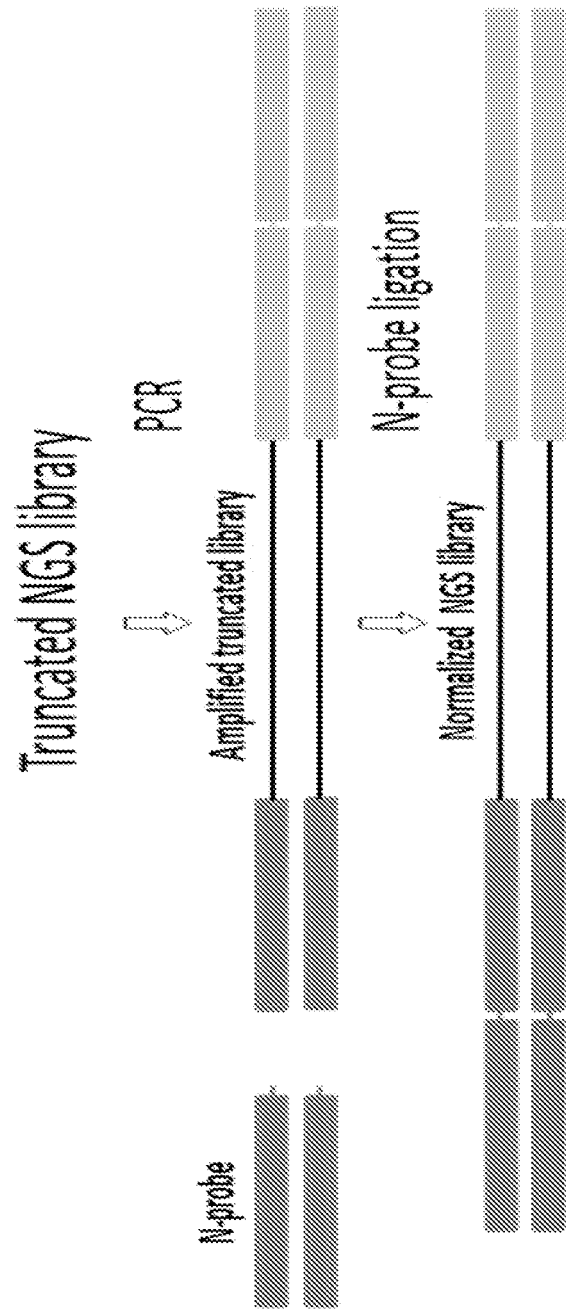
FIG. 42A depicts a schematic representation of an exemplary normalization method of the present disclosure.
Figure 42B:
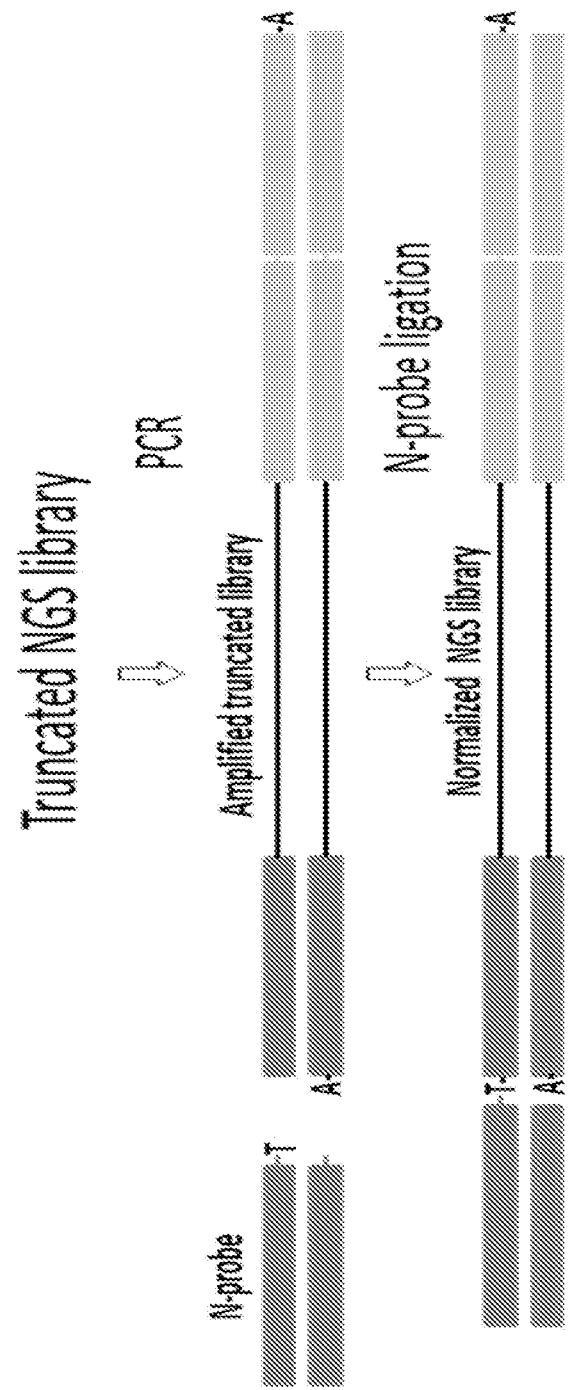
FIG. 42B depicts a schematic representation of an exemplary normalization method of the present disclosure.

Formation of 5' and 3' overhangs is not a requirement for N-probe ligation, but the overhangs significantly facilitate probe and library ligation at low concentrations. In one embodiment, ligation of double stranded normalization probe with a single T-base 3' overhang requires a library with a single A-base 3' overhang created during PCR by Taq DNA Polymerase (FIG. 42B). In another embodiment, a double stranded normalization probe has a blunt end and is ligated to the library amplified using a high fidelity DNA polymerase (FIG. 42A). Ligation of a limited amount of blunt end or single T-base 3' overhang normalization probe to the truncated adapter end can be facilitated by high library concentration created during PCR. Prevention of probe ligation to the adapter at the opposite end of the NGS library can be controlled by lack of a 5' phosphate group or lack of a compatible blunt or single A-base 3' overhang, or lack of both a 5' phosphate and a compatible end.

Specifically, in FIG. 17, the two steps shown include: (1) PCR amplification to generate non-functional library molecules with a 5' overhang at a truncated adapter end using a PCR primer containing a non-replicable base or base combination (method 4), or with special base composition at both ends to allow 5' overhang generation by T4 DNA polymerase (method 4), followed by SPRI purification; and (2) synthesis of a specified number of functional library molecules by annealing and ligation to the 5' overhang a specified amount of Normalization Synthesis Probe (method 4), or first, producing a 5' overhang at the truncated adapter end by T4 DNA polymerase in the presence of limited nucleotide composition, and second, annealing and ligation to the 5' overhang a specified quantity of double-stranded Normalization Synthesis Probe (method 4).

Figure 18:
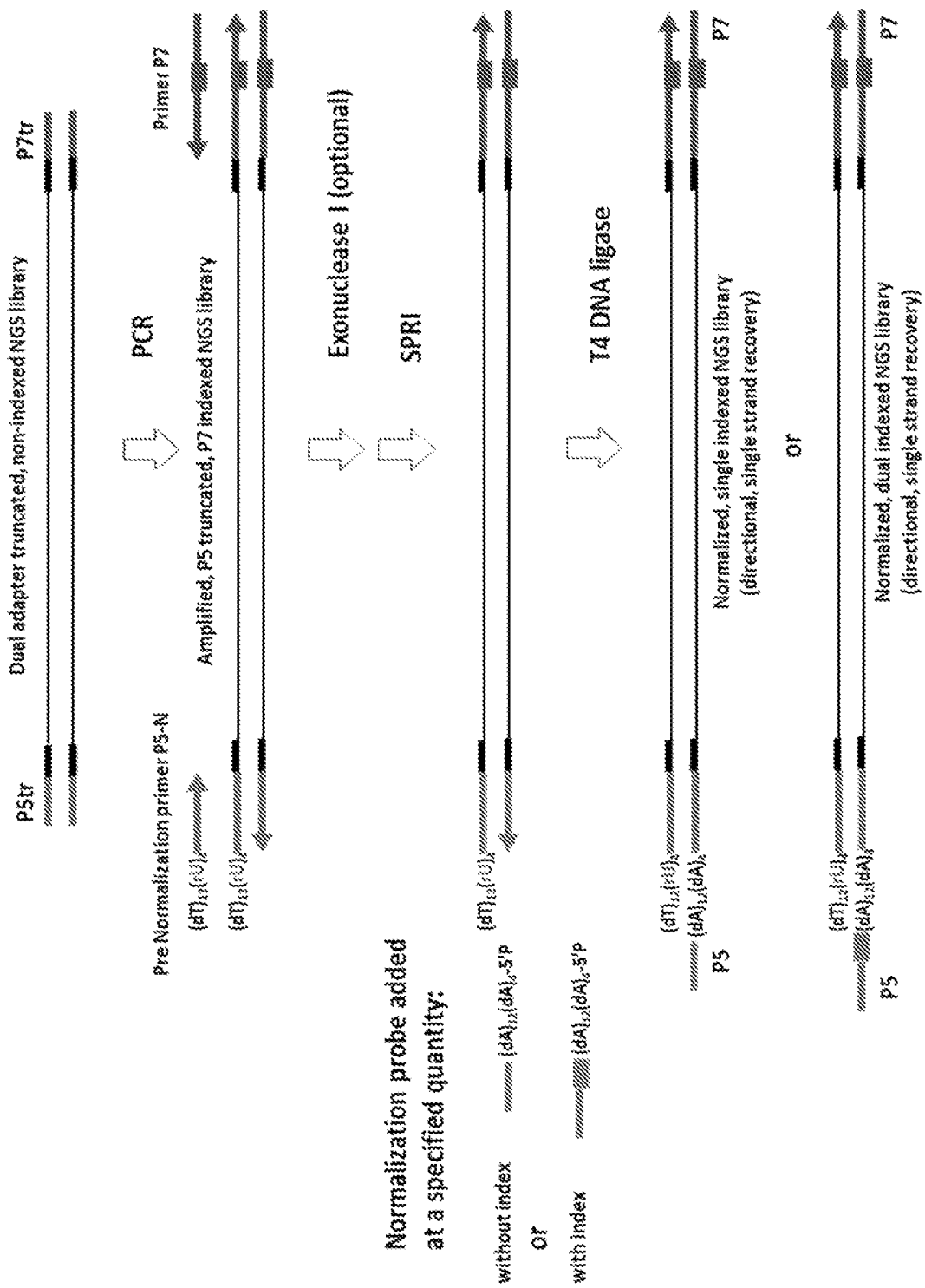
FIG. 18 depicts an exemplary method for normalization by synthesis that targets 1 NGS library strand using Method 4 (controlled synthesis). Figure discloses "$(dT)_{12}(rU)_4$" as SEQ ID NO: 67 and "$(dA)_{12}(dA)_4$" as SEQ ID NO: 68.

FIGS. 18-42I demonstrate details of when one or two library strands are targeted for controlled synthesis based normalization. FIGS. 18, 20 and 42D depict options when targeting one library strand with a single pre-N primer that maintains a truncated first NGS adapter but introduces a low complexity (including but not limited to a homopolymer) probe annealing site as a 5' overhang, combined with a conventional reverse primer that produces a blunt end and can introduce sample indexing such as required for Illumina sequencing. Following PCR, a purification step is performed prior to incubating the PCR product with the N-probe and a DNA ligase. In this case, the N-probe comprises a sequence complementary to the low complexity sequence and introduces the missing portion of the truncated NGS adapter upon ligation to confer a functional NGS library. The resulting library comprises a fully functional adapter with an internal low complexity insertion. In an alternative embodiment (FIGS. 42E-42H), the 5' overhang probe annealing region corresponds to the functional adapter sequence instead of introducing a low complexity sequence to facilitate rapid annealing. In this case, creation of a 5' overhang can be produced by replacing some nucleotides within the adapter sequence with ribonucleotides. In one such embodiment, three consecutive thymine bases within the pre-N-primer are replaced with three consecutive ribouridine bases (FIG. 42E and FIGS. 43B-43). In this case, following N-probe ligation, a functional NGS library is generated without incorporation of a low complexity sequence. In yet another embodiment, ligation of a single stranded N-probe comprising an adapter sequence can be accelerated by adding mutually complementary low complexity sequences, for example, polyA and polyT to the 5' and 3' ends of the pre-N-primer and the N-probe, respectively (FIGS. 42G and 43C). In this case, following N-probe ligation, a functional NGS library is generated with incorporation of a low complexity sequence at the terminus of the adapter instead of being incorporated within the adapter. Following ligation of the limiting molar quantity of single stranded or double stranded N-probe to the resulting 5' overhang, a single-stranded functional library is generated that corresponds to the molarity of the N-probe. It is understood that a two fold higher ssDNA probe concentration is required to generate a specified molar concentration of dsDNA library equivalent quantity.

Figure 19:
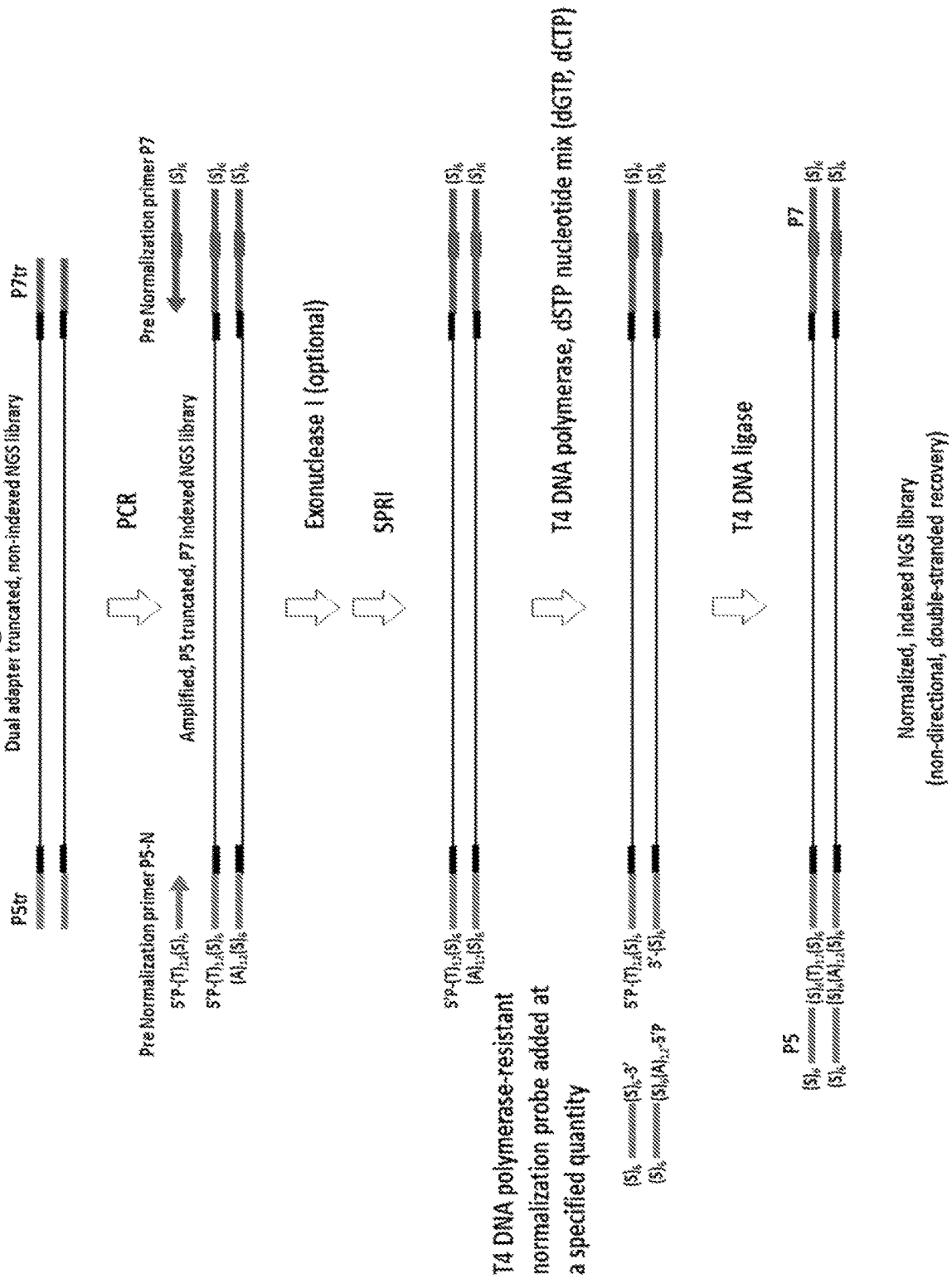
FIG. 19 depicts an exemplary method for normalization by synthesis that targets both NGS library strands using Method 4 (controlled synthesis). Figure discloses "$(T)_{12}(S)_6$" as SEQ ID NO: 69, "$(S)_6(A)_{12}$" as SEQ ID NO: 70, "$(S)_6(T)_{12}(S)_6$" as SEQ ID NO: 71, and "$(S)_6(A)_{12}(S)_6$" as SEQ ID NO: 72.
Figure 21A:
FIG. 21A depicts an exemplary method for PCR amplification for normalization by Method 4 (controlled synthesis) targeting both library strands. Figure discloses SEQ ID NOS 73, 73, and 74, respectively, in order of appearance.

FIG. 19 and FIG. 21A depict options when targeting both library strands with two pre-N-primers where one pre-N-primer maintains a truncated first NGS adapter but introduces additional sequences that facilitate T4 DNA polymerase-mediated 5' overhang creation while the second pre-N-primer introduces an index sequence and a buffer region to the terminus of the second NGS adapter to confer resistance to T4 DNA polymerase 3' exonuclease activity to maintain a blunt end. Following PCR amplification with the pre-N-primers, followed by a purification step to removed unused primers and perform a buffer exchange, the purified PCR products are incubated with T4 DNA polymerase and a limited deoxynucleotide composition that are complementary to the buffer sequence and not complementary to the tail sequence, thereby generating a product with a 5' overhang at the truncated first adapter end and a blunt end at the complete second adapter end. Following heat inactivation of T4 DNA Polymerase, a limiting molar quantity of the N-probe comprising a sequence complementary to the low complexity tail sequence and the missing portion of the NGS adapter needed to confer functionality are ligated to the 5' overhang. In an alternative embodiment, the N-probe additionally comprises buffer regions at its 3' termini for 3' exonuclease resistance to enable simultaneous 5' overhang generation using T4 DNA Polymerase and ligation.

Figure 20A:
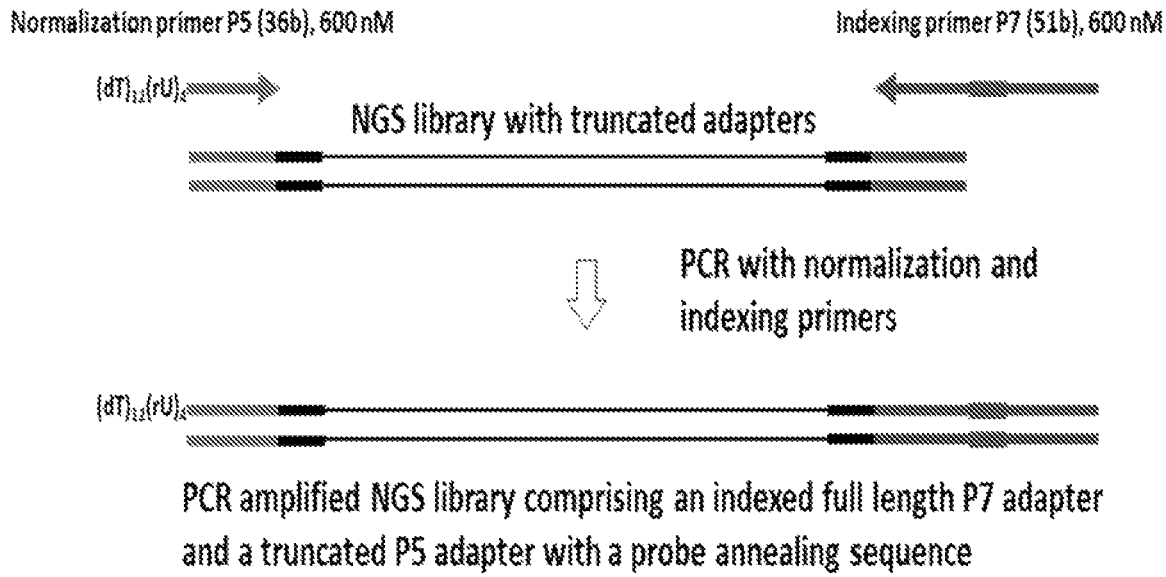
FIG. 20A depicts an exemplary method for PCR amplification for normalization by Method 4 targeting 1 library strand using P5 end normalization, single indexing (dual indexing with the indexed probe). Figure discloses "$(dT)_{12}(rU)_4$" as SEQ ID NO: 67.
Figure 20B:
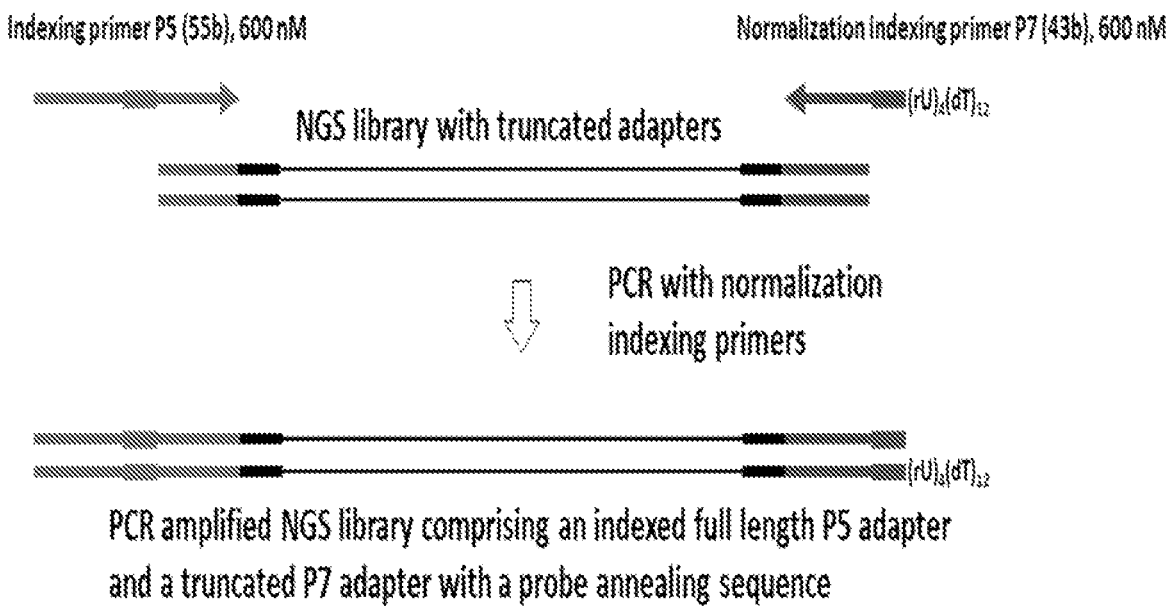
FIG. 20B depicts an exemplary method for PCR amplification for normalization by Method 4 targeting 1 library strand using P7 end normalization, dual indexing.

FIGS. 20A-20B demonstrate that when using a single pre-N primer (Method 4a), either adapter end can be used to introduce the 5' overhang for N-probe annealing and ligation; additionally, either single or dual indexing can be incorporated in either embodiment whether targeting normalization to the first or second adapter end. In FIG. 21A the PCR amplified NGS library comprises an indexed full length P7 adapter and a truncated P5 adapter, where P5 has a terminal probe annealing and buffer sequence and P7 has a buffer sequence (buffer sequence blocks T4 DNA polymerase exonuclease digestion with the appropriate dNTP composition). In FIG. 21B the completely synthesized NGS library has a P7 index and optional P5 dual index, where the P5 adapter comprises an internal normalization probe sequence.

In an alternative embodiment, producing a truncated adapter library is not required for normalization by controlled synthesis. This is because insertion of ribonucleotide bases into the adapter sequence can confer the library non-functional due to incompatibility of ribonucleotides with the sequencing workflow. Therefore, a full-length adapter can be non-functional if it comprises internal ribonucleotides. As it is illustrated by FIG. 42H, a pre-N-primer with ribo-bases can have a full size adapter sequence but the product of PCR can still be non-functional for at least the Illumina sequencing platform because one strand (bottom) of the PCR product is truncated and non-functional and the other (upper) strand is not completely replicable by a high fidelity DNA polymerase used for cluster formation on the Illumina flow cell so it is also non-functional. Subsequent ligation of the N-probe to the bottom strand of the PCR product produces a functional library, and the amount of this library is controlled by the amount of normalization probe.

In one aspect, a kit for PCR-based or enzyme-based NGS library normalization comprises components required to perform a method or a combination of methods disclosed herein and embodiments thereof. In another aspect, a kit for enzyme-based NGS library normalization comprises components required for Method 2a, including pre-N primers, a polymerase, an N-probe, a ligase, and a nuclease. In an alternative embodiment, a kit for PCR-based library normalization comprises an N-PCR primer pair and a polymerase.

Alternative methods for controlled synthesis are depicted in FIGS. 42A-42H which include embodiments where a truncated NGS library having a truncated adapter at one end is produced by any of a variety of methods and the probe provides the missing portion of the adapter to restore functionality of the NGS library for NGS.

In FIG. 42A, the library is amplified with a high fidelity DNA polymerase and conventional primers to produce blunt-end fragments and then ligated to a blunt-end N-probe. To be efficient such reaction should proceed at very high library and DNA ligase concentration to enable ligation at low probe concentration in the absence of a low complexity sequence. Non-deficient end can avoid such ligation by placing a bulky spacer to the 5' end of corresponding PCR primer. The amplified library is initially truncated by having a defective adapter end which is ligated to the probe which includes the missing portion of the adapter to yield a functional normalized NGS library.

In FIG. 42B, the library is amplified with Taq or any other thermostable DNA polymerase lacking 3' proofreading activity and conventional primers to produce fragments with A-tail at the ends and then ligated to the N-probe with T-tail. As in the case A such reaction should proceed at very high library and DNA ligase concentration to enable ligation at low probe concentration in the absence of a low complexity sequence. Non-deficient end can avoid such ligation by placing a bulky spacer to the 5' end of corresponding PCR primer. The amplified library is initially truncated by having a defective adapter end which is ligated to the probe which includes the missing portion of the adapter to yield a functional normalized NGS library.

Figure 42C:
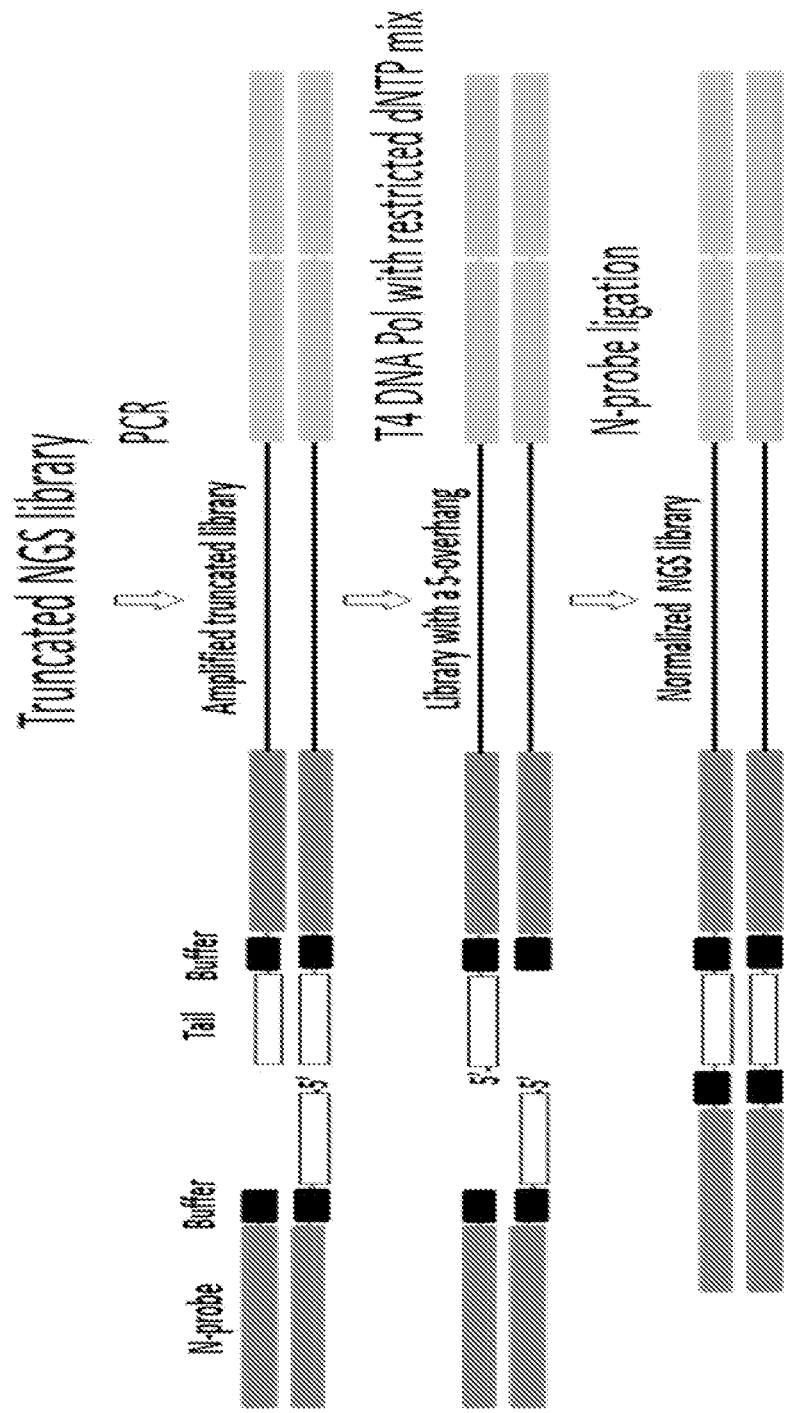
FIG. 42C depicts a schematic representation of an exemplary normalization method of the present disclosure.
Figure 42D:
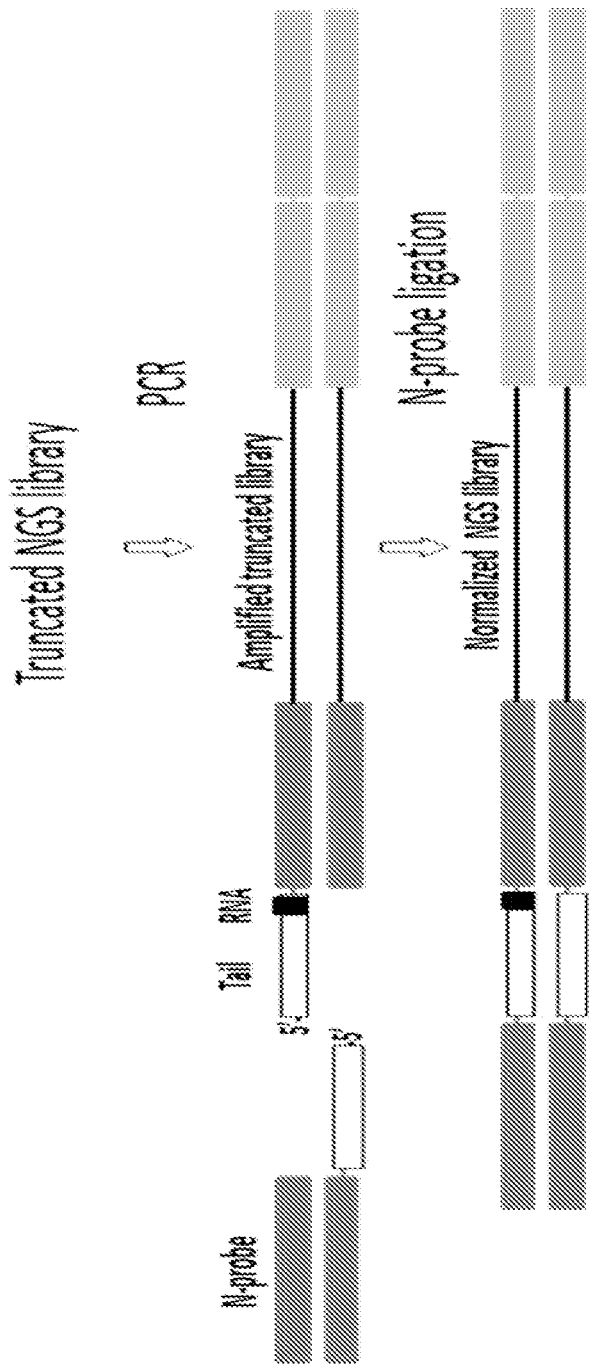
FIG. 42D depicts a schematic representation of an exemplary normalization method of the present disclosure.
Figure 42E:
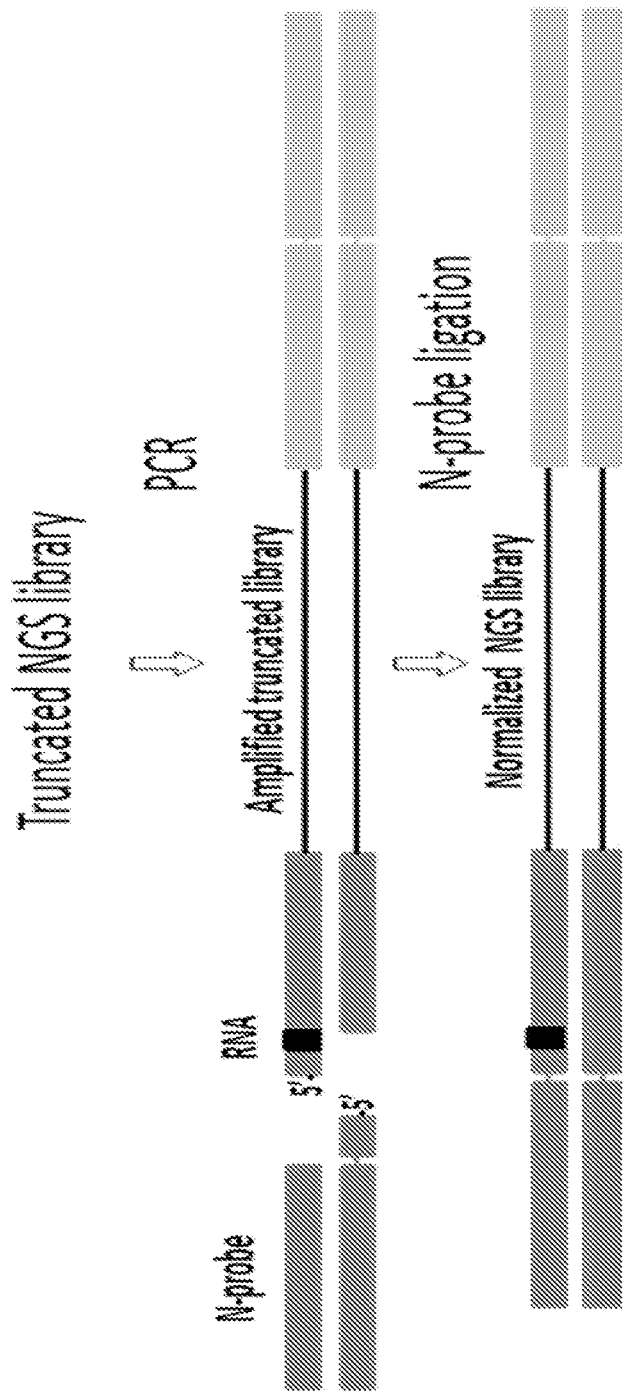
FIG. 42E depicts a schematic representation of an exemplary normalization method of the present disclosure.

In FIG. 42C, the library is amplified using pre-N PCR primer to incorporate a 5' tail and 3' adjacent buffer region at the truncated adapter end of NGS library. The tail region is 6-20 bases and comprises a homopolymer, or di-nucleotide composition followed by a 5-10 base buffer region containing a nucleotide composition that is excluded from the 5' tail region. When an NGS library comprising such sequences is incubated with T4 DNA Polymerase and a nucleotide mix restricted to only bases complementary to the buffer region but not the tail region, the 3' exonuclease proofreading activity of T4 DNA Polymerase will irreversibly trim the 3' complementary tail region until it reaches the buffer region where it can reversibly remove and replace nucleotides, thus creating a 5' overhang defined by the buffer region. Creation of the 5' overhang and ligation of the N-probe with the complementary 5' overhang sequence can be done sequentially after removing or heat inactivating T4 DNA polymerase, or combined into a single incubation reaction when the N-probe contains buffer region with the same base composition 3' adjacent to its 5' tail. In best scenario, pre-N PCR primer and N-probe complementary tail sequences are homo-nucleotide repetitive sequences such as poly A and poly T to accelerate probe annealing and ligation at low probe concentration. The amplified library is initially truncated by having a defective adapter end which is ligated to the probe which includes the missing portion of the adapter to yield a functional normalized NGS library.

In FIG. 42D, the library is amplified using pre-N PCR primers with a 5' tail and located between the tail and adapter sequence, the non-replicable group including a dU base (for archael DNA polymerases), or a non-replicable spacer comprising a consecutive stretch of 3 or more riboU or riboA bases, where the high fidelity DNA polymerase is incapable of extending through the (riboU)$_n$ or (riboA)$_n$ template, where n=3 or more. When riboU and ribo A bases are flanked with the poly(dT) and poly(dA) 6-20 base tail sequences (SEQ ID NOS 57 and 58, respectively), respectively, the PCR results in library molecules with the corresponding homopolymer 5' overhangs for ligation of N probe with a homopolymer 5' tail. The repetitive sequences such as poly A and poly T accelerate probe annealing and ligation to enable efficient ligation at low probe concentration. The amplified library is initially truncated by having a defective adapter end which is ligated to the probe which includes the missing portion of the adapter to yield a functional normalized NGS library.

In FIG. 42E, the library is amplified using pre-N PCR primer with the consecutive stretch of 3 or more ribo bases replacing deoxyribonucleotides within the original NGS adapter sequence. N-probe is double stranded. The amplified library is initially truncated by having a defective adapter end which is ligated to the probe which includes the missing portion of the adapter to yield a functional normalized NGS library. This method allows for generation of a truncated library with a 5' overhang when a polymerase without 3' proofreading activity is used without adding additional sequence to the truncated adapter sequence.

Figure 42F:
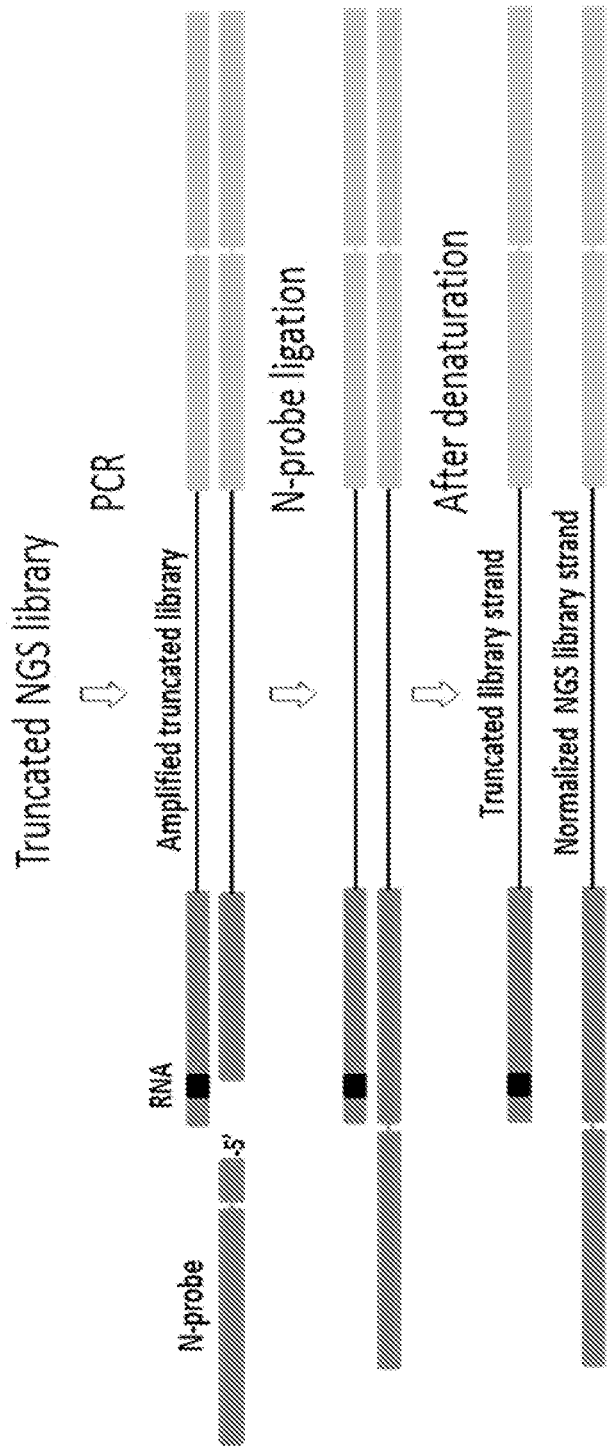
FIG. 42F depicts a schematic representation of an exemplary normalization method of the present disclosure.
Figure 42G:
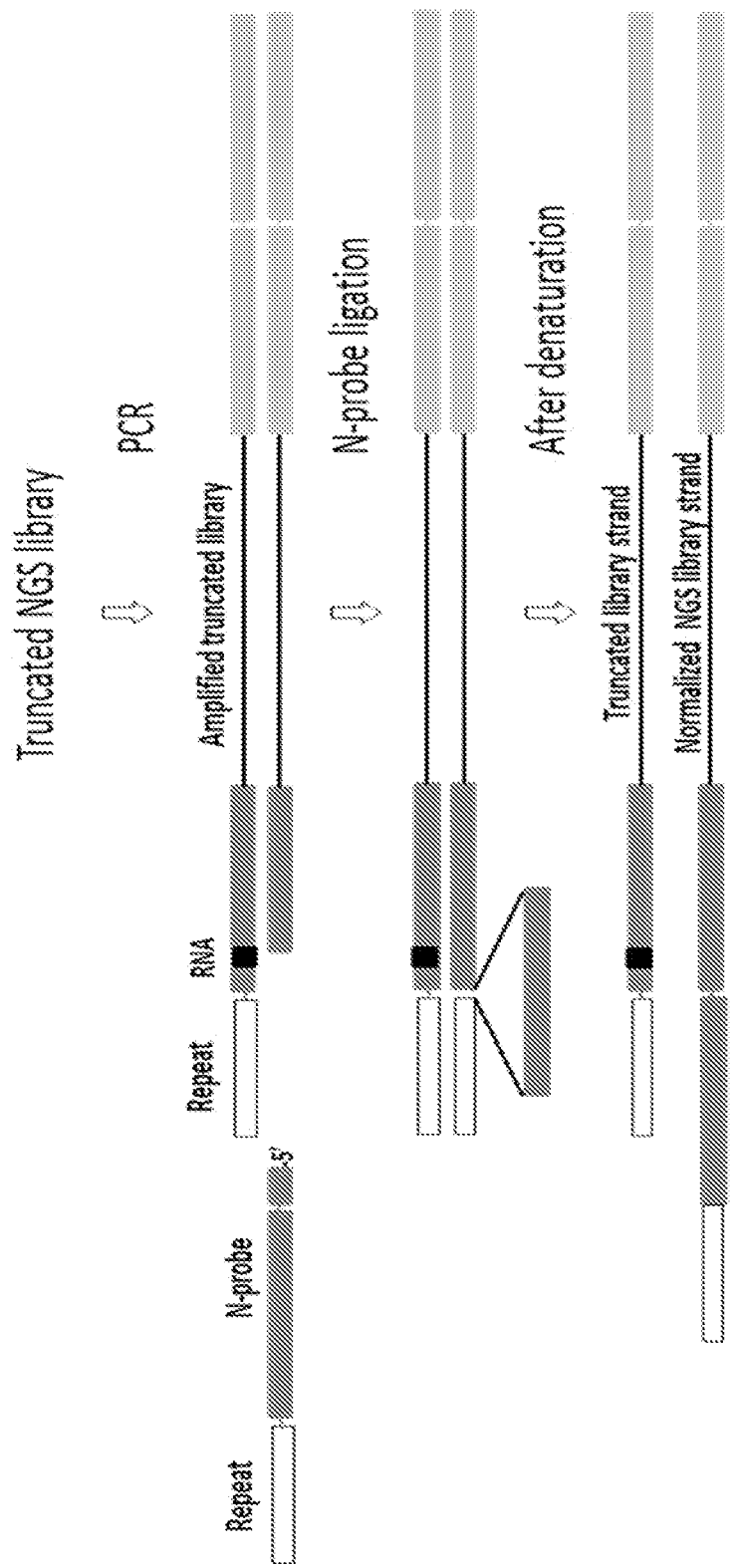
FIG. 42G depicts a schematic representation of an exemplary normalization method of the present disclosure.
Figure 42H:
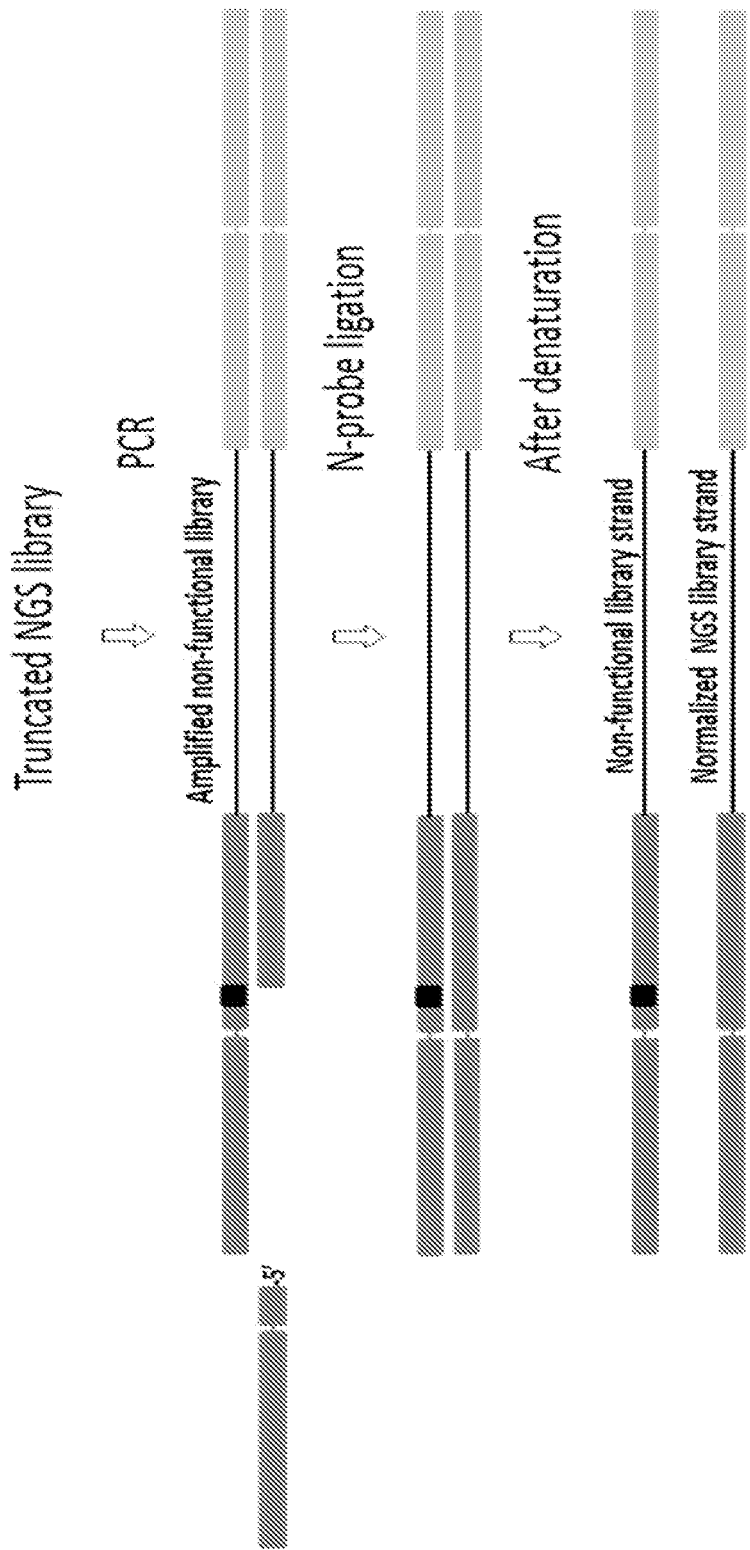
FIG. 42H depicts a schematic representation of an exemplary normalization method of the present disclosure.
Figure 42I:
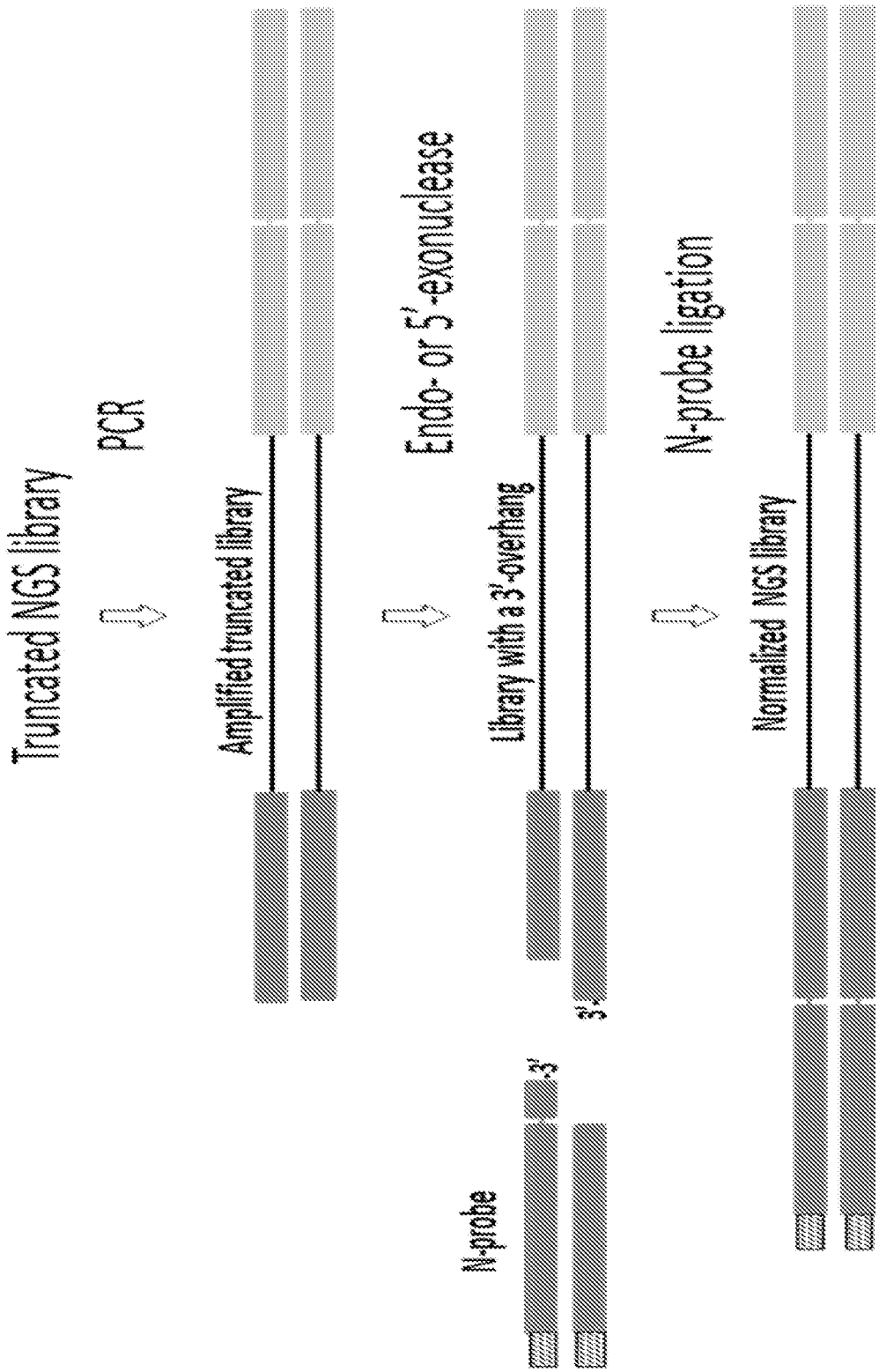
FIG. 42I depicts a schematic representation of an exemplary normalization method of the present disclosure.

In FIG. 42F, the library is amplified using pre-N PCR primer with the consecutive stretch of 3 or more ribo bases replacing deoxyribonucleotides within the original NGS adapter sequence. N-probe is single stranded. The amplified library is initially truncated by having a defective adapter end which is ligated to the probe which includes the missing portion of the adapter to yield a functional normalized NGS library.

In FIG. 42G, the library is amplified using pre-N PCR primer with the consecutive stretch of 3 or more ribo bases replacing deoxyribonucleotides within the original NGS adapter sequence and the homo-, di, tri-nucleotide repetitive sequence at the 5' end. N-probe is single stranded with a complementary repetitive sequence at the 5' end to accelerate probe annealing and ligation at low probe concentration. The amplified library is initially truncated by having a defective adapter end which is ligated to the probe which includes the missing portion of the adapter to yield a functional normalized NGS library. The N-probe can have 10-20 poly A or poly T bases (SEQ ID NOS 59 and 60, respectively) at its 3' end. Thus, in some embodiments, the truncated NGS library can comprise an overhang, in cases a 5' overhang, which also comprises a low complexity sequence as described in the present disclosure which can facilitate accelerated annealing for amplification of the library while also permitting the re-incorporation of the missing adapter portion by the probe which is present in a loop when the probe is ligated to the truncated NGS library. This can restore functionality of the truncated NGS library for those library molecules ligated to the probe but perform at a faster and more efficient rate because of binding between the low complexity sequence and a complementary sequence on the probe.

In FIG. 42H, the library is amplified using pre-N PCR primers with modified bases comprising either cleavable or nuclease-resistant bases. Cleavable bases are located evenly within the 5' portion of the adapter sequence and include but not limited to dU base, RNA and deoxyinosine. Nuclease resistant bases such as phosphorothioate bases can be located within the 3' portion of the 5' tail or, if tail is absent, within the adapter sequence. Incubation with UDG/abasic endonuclease mix, RNase H or endonuclease V (in the case of cleavable bases) and 5' exonuclease such as T7 exonuclease, lambda exonuclease or exonuclease V (in the case of nuclease-resistant bases) would result in the 3' overhang whose length is controlled by the position of the cleavable/nuclease-resistant bases or linkages within the pre-N PCR primer. Creation of the 5' overhang and ligation of the N-probe with the complementary 5' overhang sequence can be done sequentially after removing or heat inactivating of cleavage enzymes, or combined into a single incubation reaction. In the case of exonuclease digestion the N-probe contains protection region with nuclease resistant bases within the terminal portion distal to the 3' overhang. The amplified library is initially truncated by having a defective adapter end which is ligated to the probe which includes the missing portion of the adapter to yield a functional normalized NGS library.

N-PCR: A PCR-Based NGS Library Normalization Method

Normalization of NGS library concentration by PCR (N-PCR) relies on the assumption that all PCR primers can be utilized during amplification and converted into NGS library, thus producing a molar quantity of NGS library equal to the molar quantity of N-PCR primers. To ensure efficient amplification of an NGS library and preserve its complexity, the primer concentration in a conventional PCR reaction is usually varying from 200 nM to >1,000 nM. With this primer concentration, the PCR amplification reaction conducted in the 50 ul reaction volume should result in 30 to 50 pmol of NGS library assuming complete utilization of PCR primers. Production of this quantity of library would require an additional amount of DNA polymerase that is not practical, but even in this case the reaction would still suffer at later PCR cycles from inhibition by a large quantity of DNA. It would also require more PCR cycles to convert all the primers into the library resulting in substantial increase of PCR duplicates and additional exposure of DNA to heat with the risk of damaging DNA and introducing heat-induced mutations.

The problem can potentially be addressed by lowering primer concentration, but at reduced primer concentration the priming efficiency and library complexity can be low if standard annealing and extension times are used; alternatively, the PCR reaction would go for several hours if the annealing and extension time was increased to compensate for reduced primer concentration.

Figure 22:
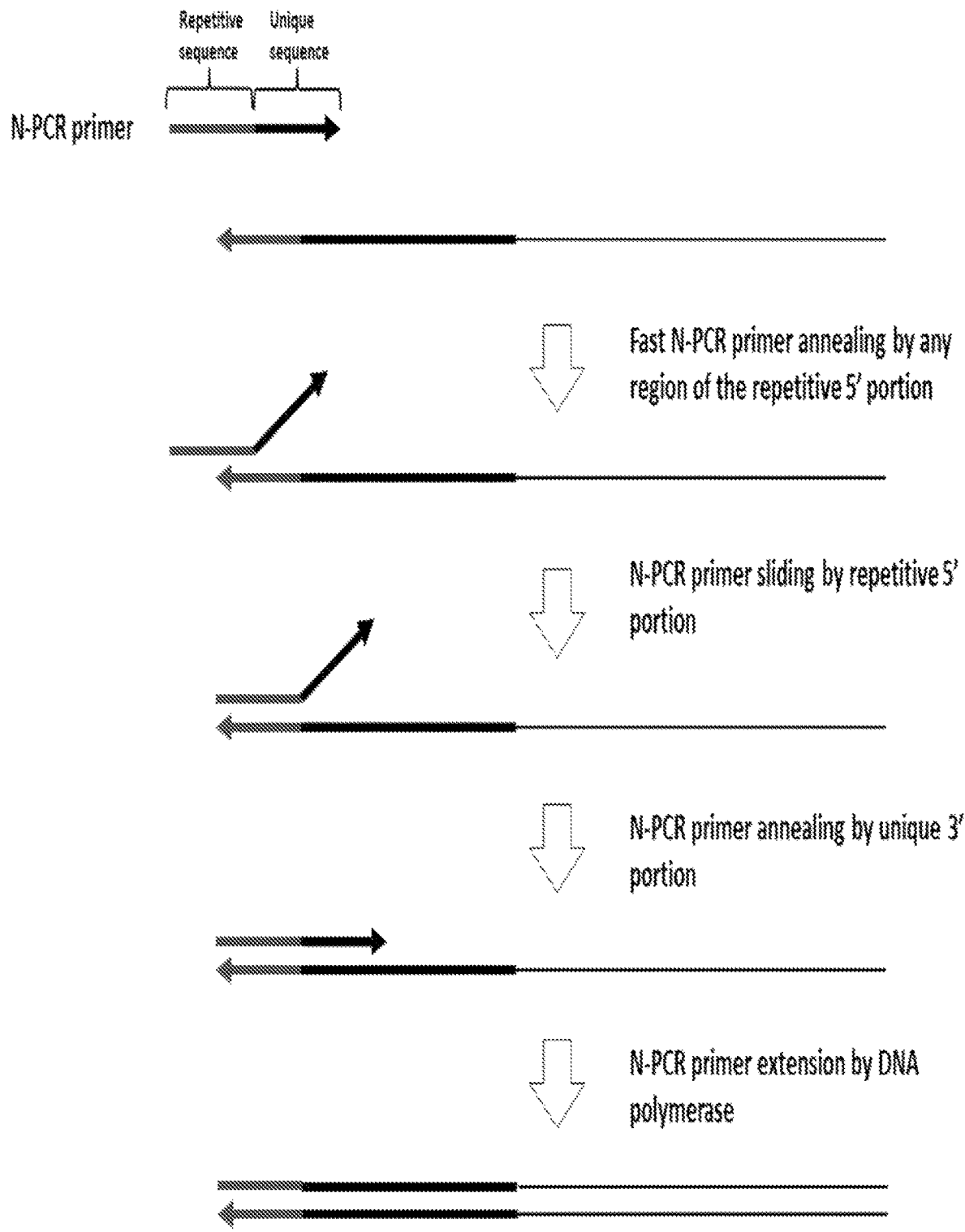
FIG. 22 depicts an exemplary method for using N-PCR primers with an accelerated annealing rate for normalization by controlled amplification.

PCR-based library normalization can be achieved by using a novel primer design disclosed herein that leads to efficient primer annealing at low primer concentration to enable use of conventional annealing times. These modified N-PCR primers can perform at reduced concentration and conventional annealing time without a reduction in priming efficiency or NGS library complexity. A schematic representation of the accelerated annealing process is shown in FIG. 22.

The modified N-PCR primers with accelerated annealing time have two domains, a 3' domain that anneals to the NGS adapter sequence for library amplification and a 5' domain that is an additional feature added to an otherwise conventional library amplification primer to increase its annealing rate and reduce annealing time. The 5' domain comprises a DNA sequence with a low sequence complexity, such as mono-, di-, tri, tetra-nucleotide repeats. When a DNA substrate has a reduced complexity repetitive sequence complementary to the repetitive sequence of the 5' domain of the primer (and additionally a sequence complementary to the 3' portion of the primer), primer annealing occurs rapidly by its 5' repetitive domain to the complementary, repetitive counterpart in the template, where this anchoring allows the primer to anneal by its 3' domain to the higher complexity sequence. Anchoring of the 5' domain generates a high local primer concentration and results in rapid annealing and extension of the 3' domain of the primer.

Figure 24A:
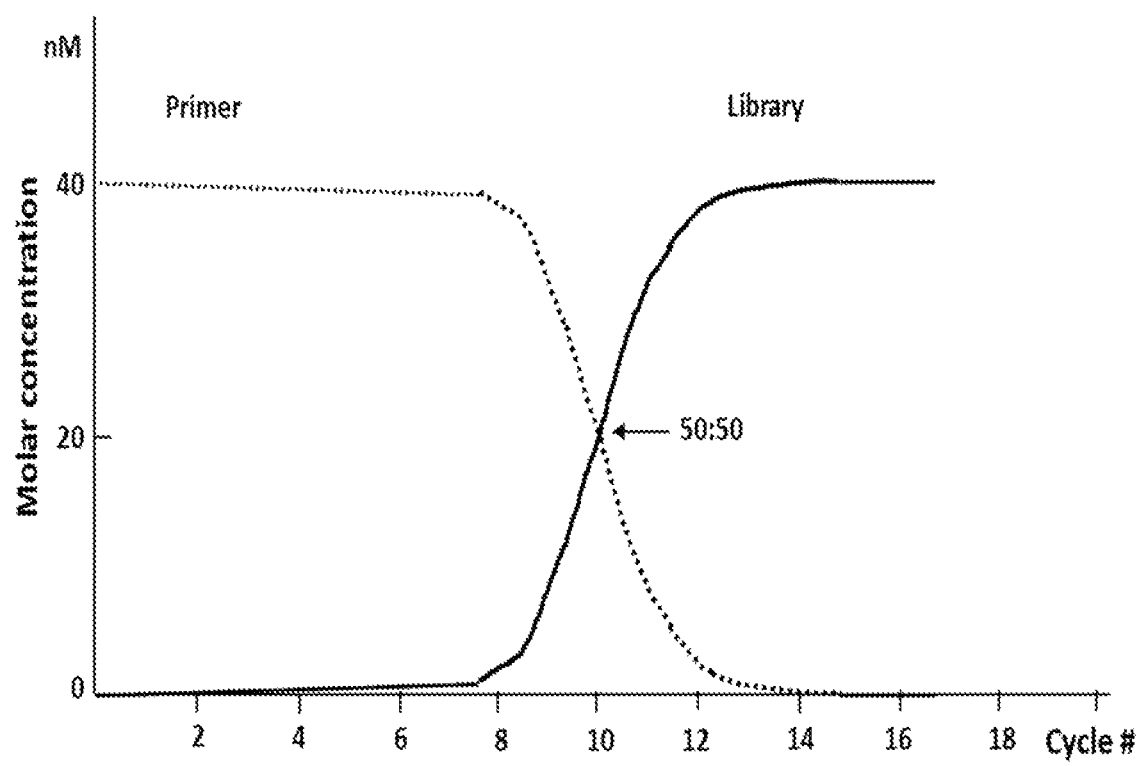
FIG. 24A depicts a graph of N-PCR primer and library concentration during N-PCR.
Figure 24B:
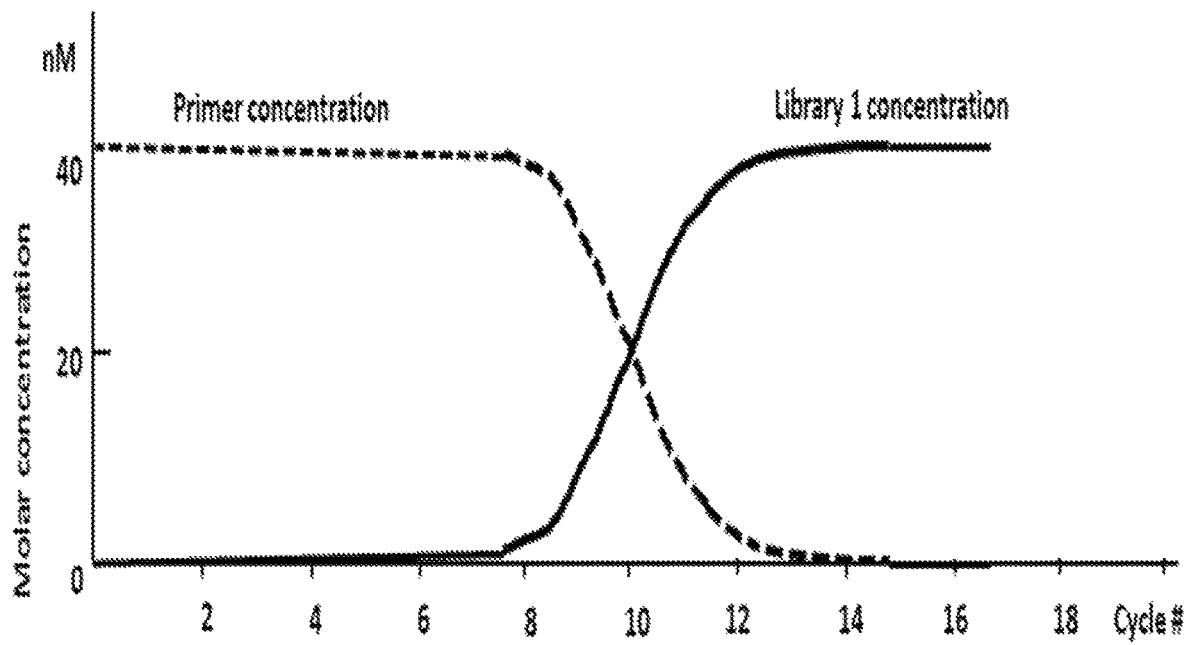
FIG. 24B depicts a graph of N-PCR primer and library concentration during N-PCR.
Figure 24C:
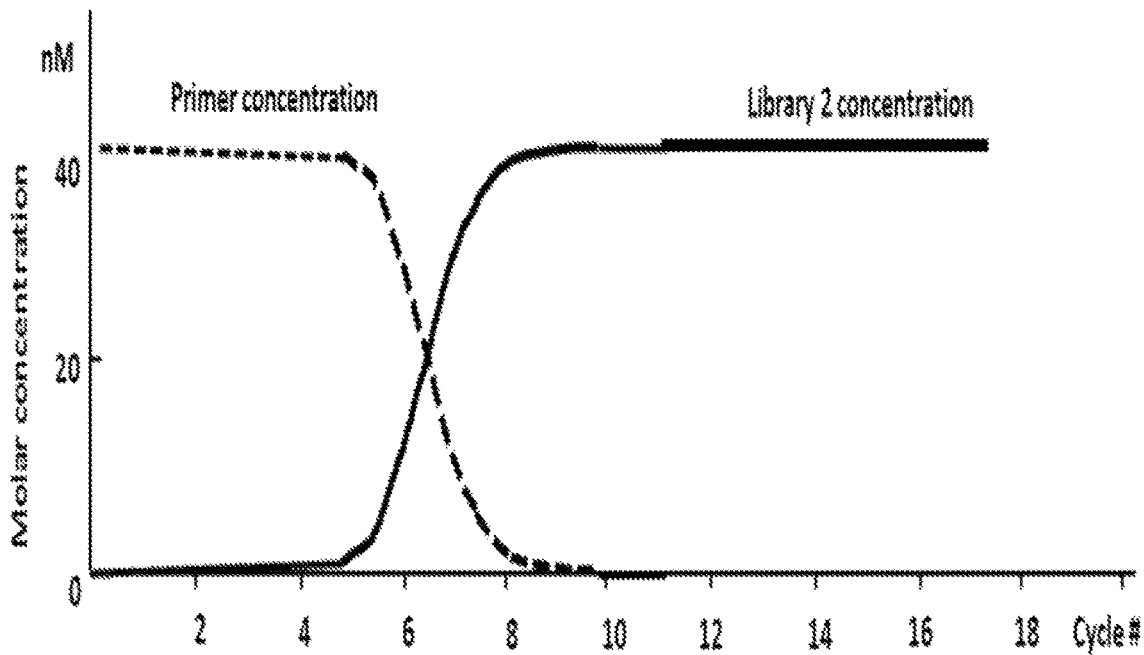
FIG. 24C depicts a graph of N-PCR primer and library concentration during N-PCR.
Figure 24D:
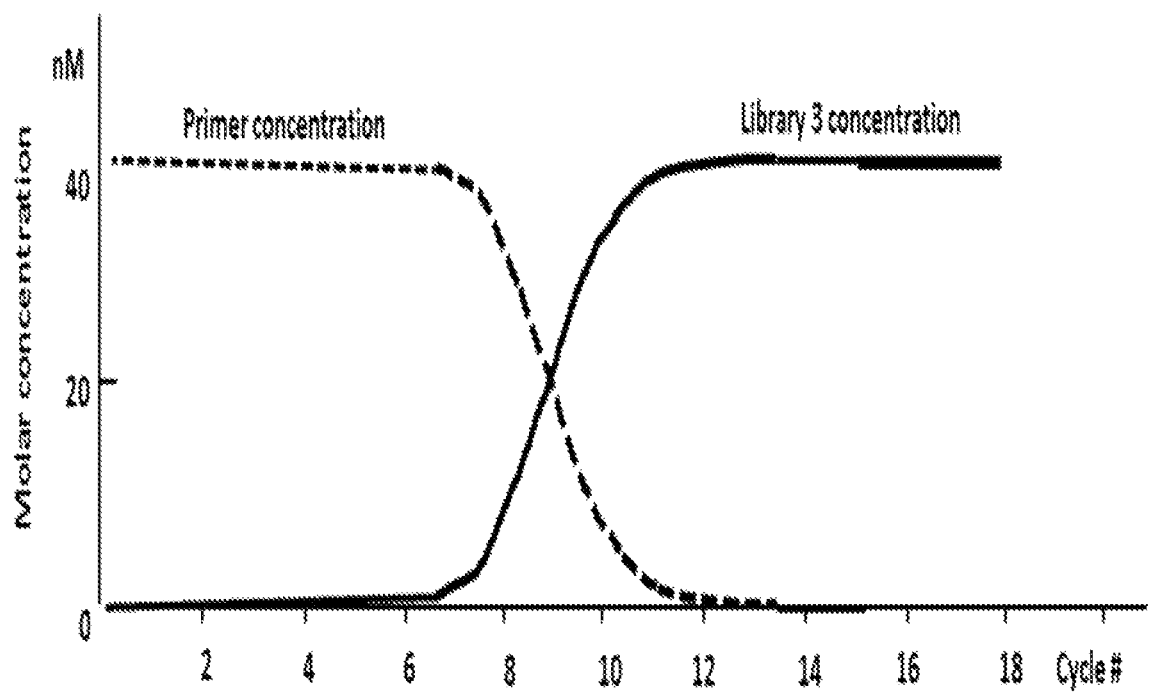
FIG. 24D depicts a graph of N-PCR primer and library concentration during N-PCR.
Figure 25:
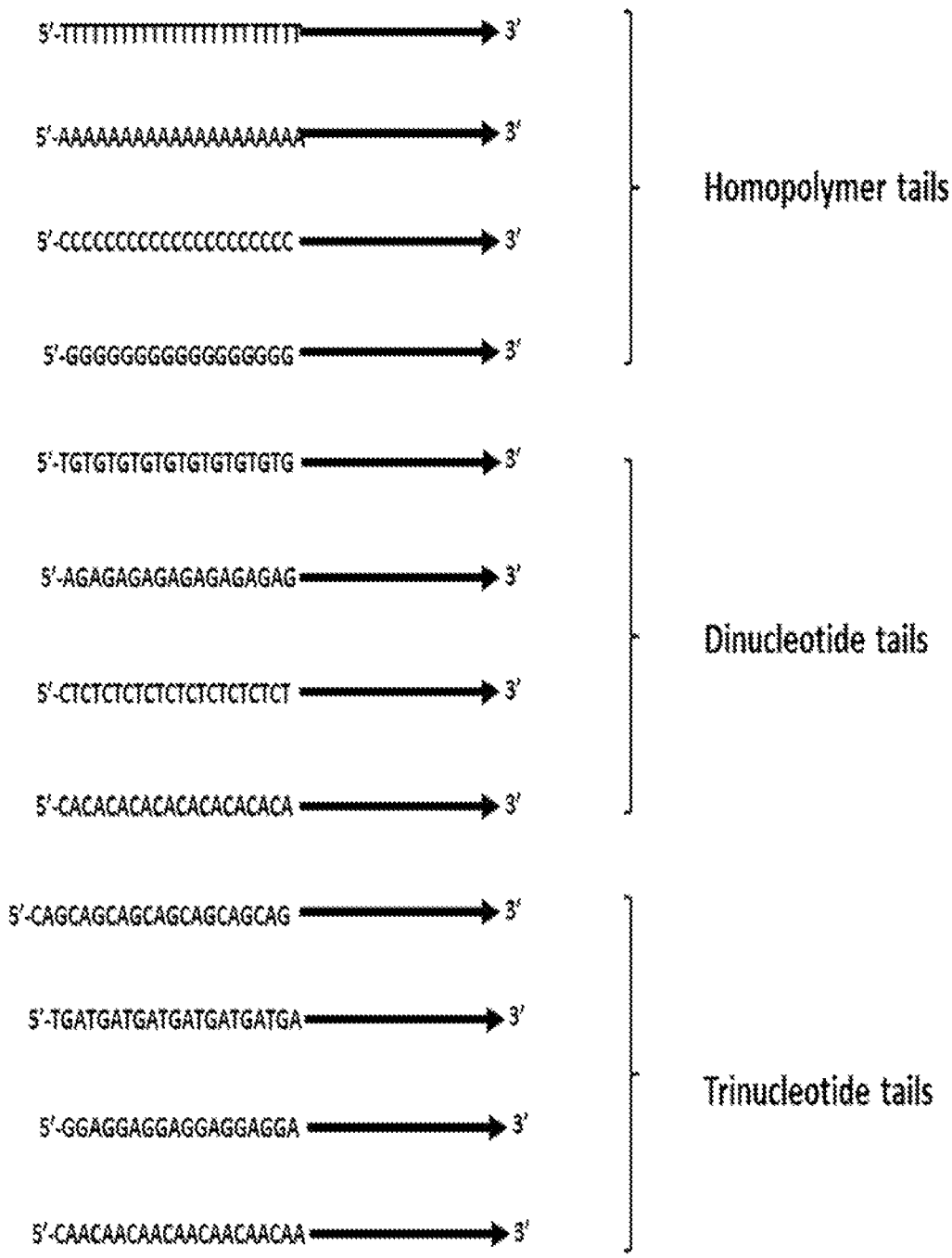
FIG. 25 depicts exemplary N-PCR primers having either homopolymer tails, dinucleotide tails or trinucleotide tails. Figure discloses SEQ ID NOS 84-95, respectively, in order of appearance.

There are a number of simple repetitive sequences for use in the 5' domain of N-PCR primers with increased annealing rate but not all of them are useful. To avoid cross-interaction between N-PCR primers, the 5' domain sequences should be selected from two non-complementary repeats, for example, poly A and poly C, or poly T and poly G for homopolymer sequences. In the case of dinucleotide repeats, the 5' domain sequences of the primer pair are selected from two non-complementary sequences such as poly GT and poly GA, poly GT and poly CT, poly AG and poly CA, or poly CT and poly CA. Selection of complementary tail sequences such as poly A and poly T, or poly GT and poly CA is not desirable because it would lead to annealing the 5' domains of primers and reduction of the acceleration effect. 5' domain sequences can also be selected from tri-nucleotide, tetra-nucleotide, penta-nucleotide and hexa-nucleotide repeat combinations with the same principle to avoid complementarity between the 5' domains. N-PCR Primers with the same repetitive sequence such as poly A, poly GT, poly ACG, etc. at the 5' end would lead to the creation of amplicon strands folding into a self-complementary stem-loop structure and also to the competition between two PCR primers for the same repetitive binding site. Therefore, the 5' domain of the N-PCR primer can also contain a non-repetitive portion if such a portion is necessary for another function. FIG. 23A shows an exemplary method using poly(GA) and poly(GT) tails at the 5' end of N-PCR primers which results in controlled amplification with limited primer concentration. FIG. 23B shows an exemplary method using poly(A) and poly(T) tails for the same purpose. FIG. 24A shows a hypothetical graph of the molar concentration of primer and library as a function of time. FIG. 24B shows the same types of graphs for three different library input concentrations. FIG. 25 provides examples of N-PCR primers with homopolymer tails, dinucleotide tails and trinucleotide tails.

Figure 26:
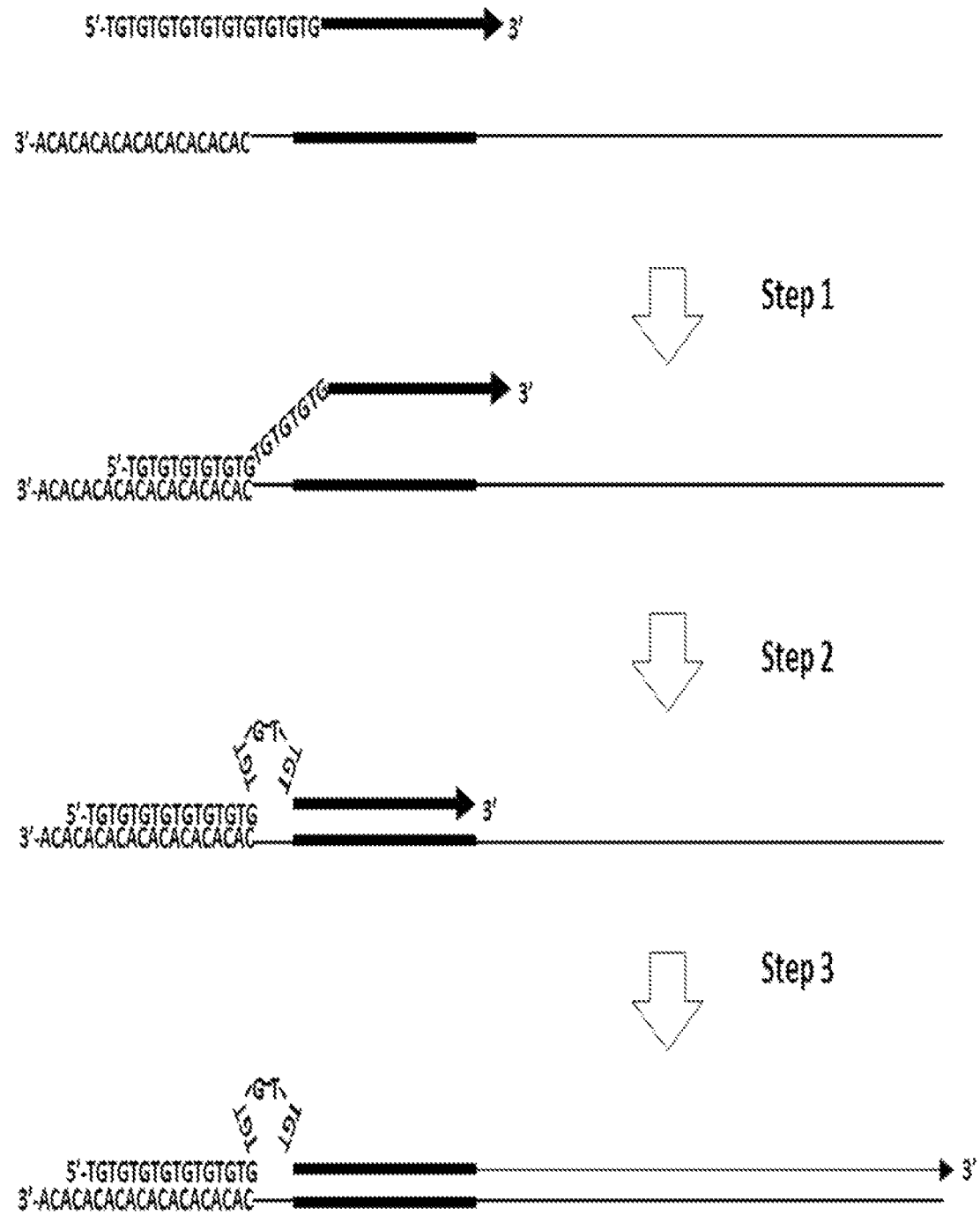
FIG. 26 depicts a proposed mechanism for accelerated annealing of N-PCR primers. Step 1: N-PCR Primer anchors to the target template by its repetitive 5' portion. Step 2: N-PCR primer anneals by its 3' portion. Step 3: N-PCR Primer becomes extended by DNA polymerase. Figure discloses SEQ ID NOS 88, 91, 88, 91, 96, 91, 96, and 91, respectively, in order of appearance.
Figure 27:
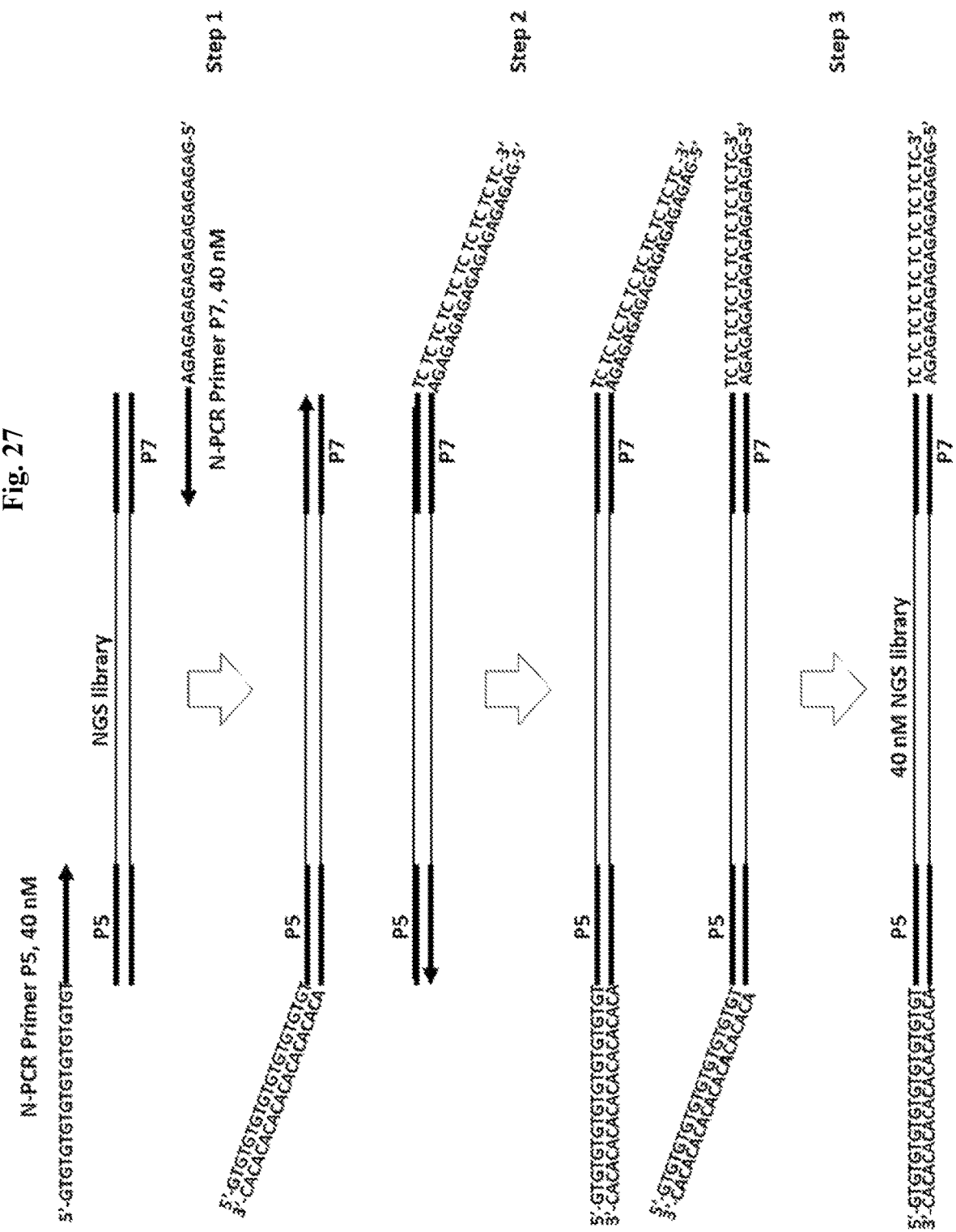
FIG. 27 depicts an exemplary method for amplification and normalization of a NGS library using N-PCR primers. Step 1: 1st long annealing/extension cycle adds repetitive tail to one side of NGS library. Step 2: 2nd long annealing/extension cycle adds repetitive tail to both sides of NGS library. Step 3: Subsequent fast annealing-extension cycles utilize all N-PCR primers and create molar amount of PCR-amplified NGS library equal to the molar amount of N-PCR primers. Figure discloses "GTGTGTGTGTGTGTGTGTGT" as SEQ ID NO: 79, "ACACACACACACACACACAC" as SEQ ID NO: 80, "GAGAGAGAGAGAGAGAGAGA" as SEQ ID NO: 97, and "TCTCTCTCTCTCTCTCTCTC" as SEQ ID NO: 98.
Figure 28:
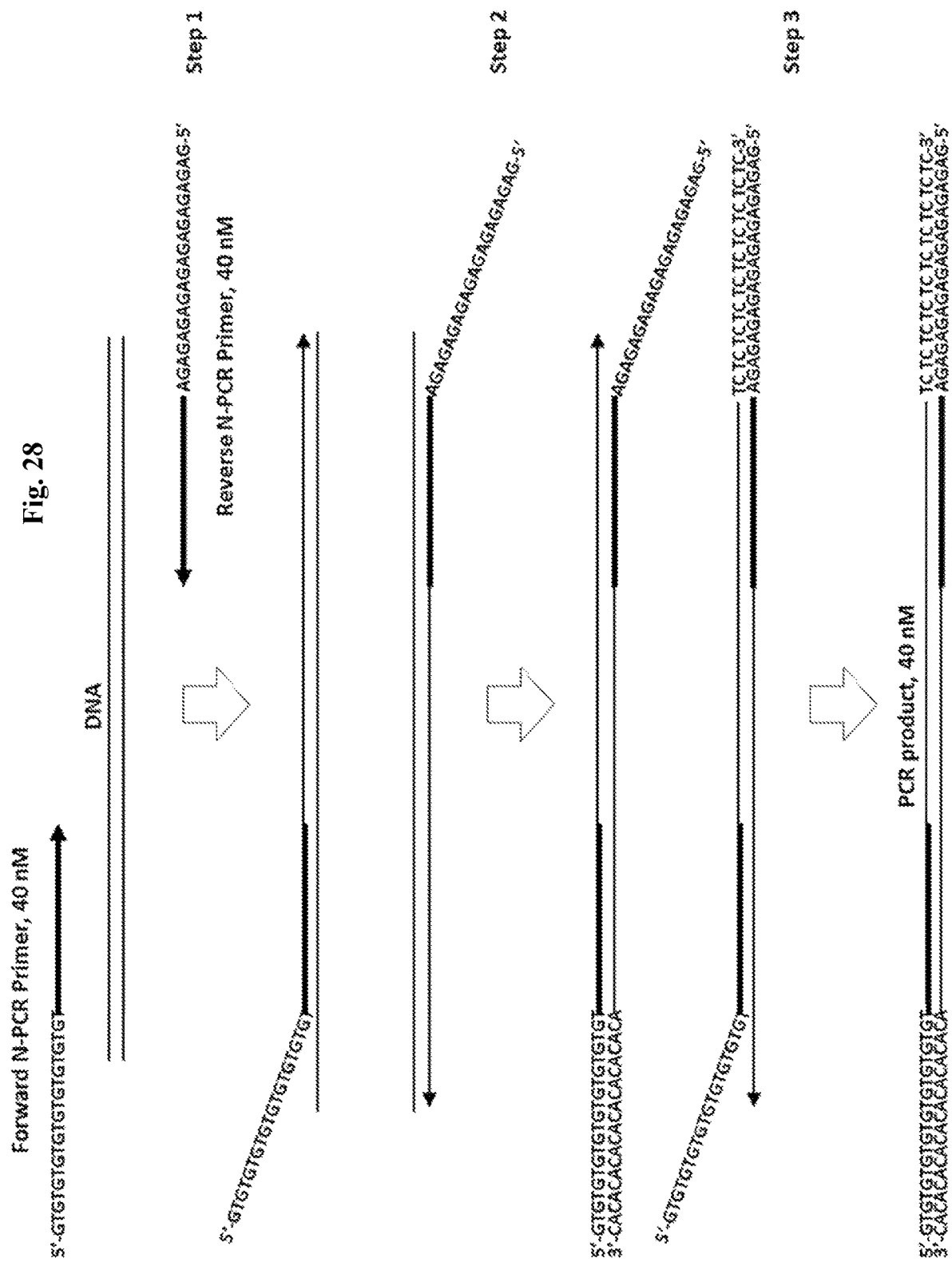
FIG. 28 depicts an exemplary method for PCR using N-PCR primers for a predicted yield of PCR product. Step 1: 1st long annealing/extension cycle creates one-sided DNA amplicon. Step 2: 2nd long annealing/extension cycle creates two-sided DNA amplicon. Step 3: Subsequent fast annealing-extension cycles utilize all N-PCR Primers and create molar amount of PCR-amplified target DNA equal to the molar amount of N-PCR Primers. Figure discloses "GTGTGTGTGTGTGTGTGTGT" as SEQ ID NO: 79, "ACACACACACACACACACAC" as SEQ ID NO: 80, "GAGAGAGAGAGAGAGAGAGA" as SEQ ID NO: 97, and "TCTCTCTCTCTCTCTCTCTC" as SEQ ID NO: 98.
Figure 29A:
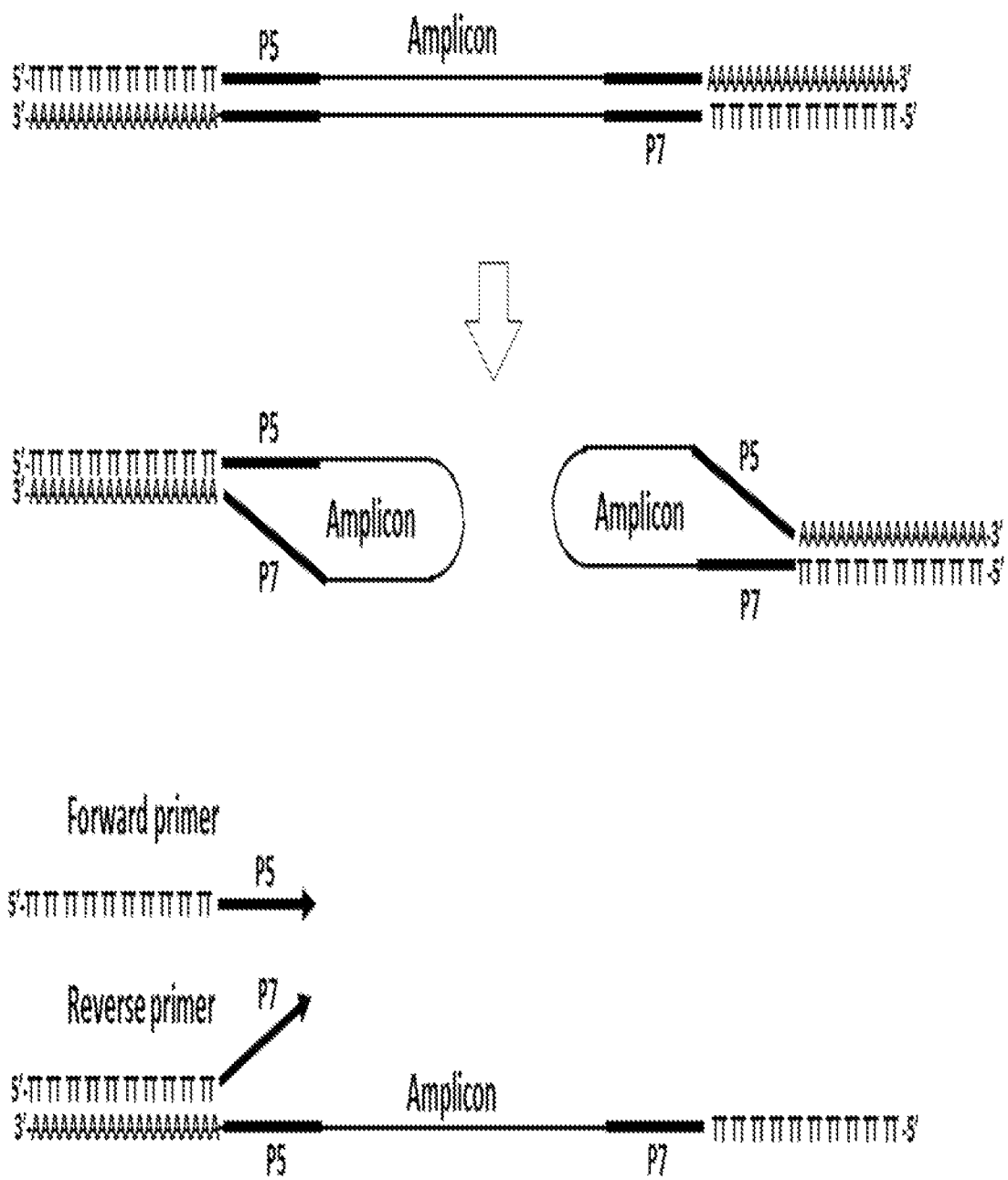
FIG. 29A depicts a proposed mechanism for the formation of secondary structure when both N-PCR primers share the same tail sequence. Figure discloses "TTTTTTTTTTTTTTTTTTTT" as SEQ ID NO: 99 and "AAAAAAAAAAAAAAAAAAAA" as SEQ ID NO: 85.
Figure 29B:
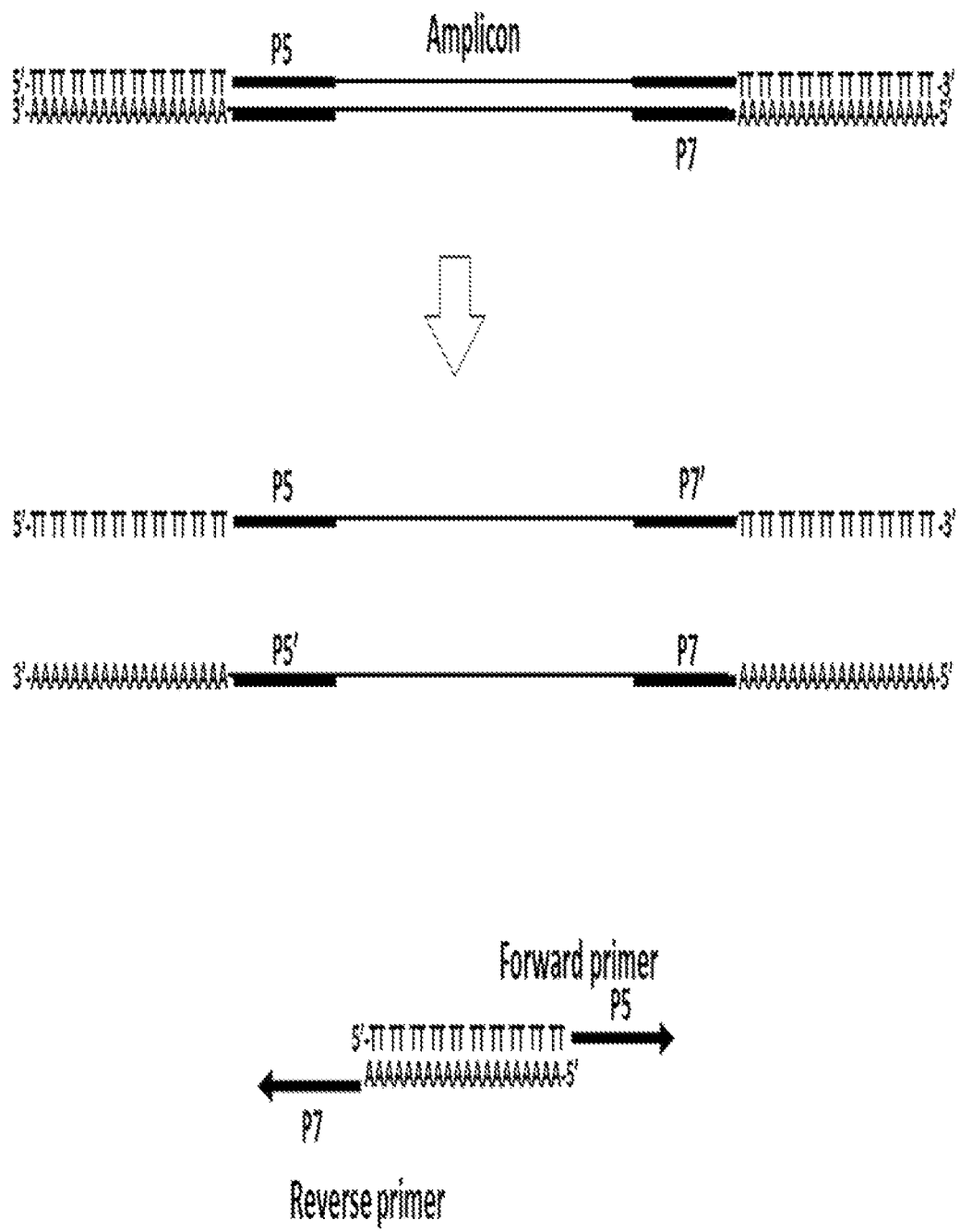
FIG. 29B depicts a proposed mechanism for the interference between N-PCR primers when the N-PCR primers have complementary tail sequences. Figure discloses "TTTTTTTTTTTTTTTTTTTT" as SEQ ID NO: 99 and "AAAAAAAAAAAAAAAAAAAA" as SEQ ID NO: 85.

In addition to a low complexity 5' domain on the N-PCR primer, the corresponding DNA template should have a repetitive sequence that is complementary to the repetitive sequence at the 5' end of primer to allow rapid annealing of the N-PCR primer with the template. These sequences can be added to the ends of NGS library during library synthesis by ligating NGS adaptors containing repetitive sequences. This approach is preferred because it allows library amplification without performing long annealing times in the first two cycles to incorporate the low complexity tails by PCR. Alternatively, when the library does not have the low complexity sequences at the adaptor termini, the repetitive sequences can be introduced during library amplification using primers containing repetitive sequences. In the latter case, at least two first PCR cycles should have extended annealing time to ensure complete annealing (and extension) of the primers in the absence of the complementary repetitive sequences in the DNA template. After 2 PCR cycles, the library amplicons containing repetitive sequences at both ends would be generated and PCR cycling can be continued using reduced, conventional annealing time. FIG. 26 shows a proposed mechanism for the accelerated annealing of the N-PCR primers. FIGS. 27 and 28 show an exemplary methods for amplification and normalization using N-PCR primers. FIG. 29A shows that it is possible for N-PCR primers with homopolymer tails (the lowest complexity) should provide maximal acceleration for annealing but certain problems can arise with the use of such tails: forward and reverse primers with the same homopolymer tail create amplicons with stem-loop structure where mutual complementary 5' and 3' tails form the stem region and become not easily accessible for priming. Even where they are capable of binding to the amplicon, such secondary structure causes the homopolymer tail of the reverse primer to compete with binding of the forward primer and vice versa. FIG. 29B shows that forward and reverse N-PCR primers with complementary homopolymer tails create amplicons that do not form secondary structure but the primers themselves can interact by their tails which makes them inaccessible for binding. FIG. 29C shows that N-PCR primers with non-complementary homopolymer tails such as poly(T) and poly(G), poly(T) and poly(C), poly(A) and poly(G), or poly(A) and poly(C) create amplicons where either the 5' end or the 3' end has the poly G sequence which is capable of forming Watson-Crick secondary structures (like a G-quartet) which are resistant to primer and/or replication. FIG. 29D shows dinucleotide repeat tails for N-PCR primers which are preferable and can be used. However, $(TA)_n$ and $(GC)_n$ should not be used due to their complementarity.

In some embodiments N-PCR primers can be used for other applications, for example in diagnostics for acceleration of PCR amplification of viral and bacterial DNA and RNA templates. When amplification of very low copy viral nucleic acid requires 30 PCR cycles and occurs within ~45 min (assuming 1.5 min per cycle) the same process with primers described in this disclosure could be accomplished almost 6.5 times faster and within only 7 min.

Figure 30:
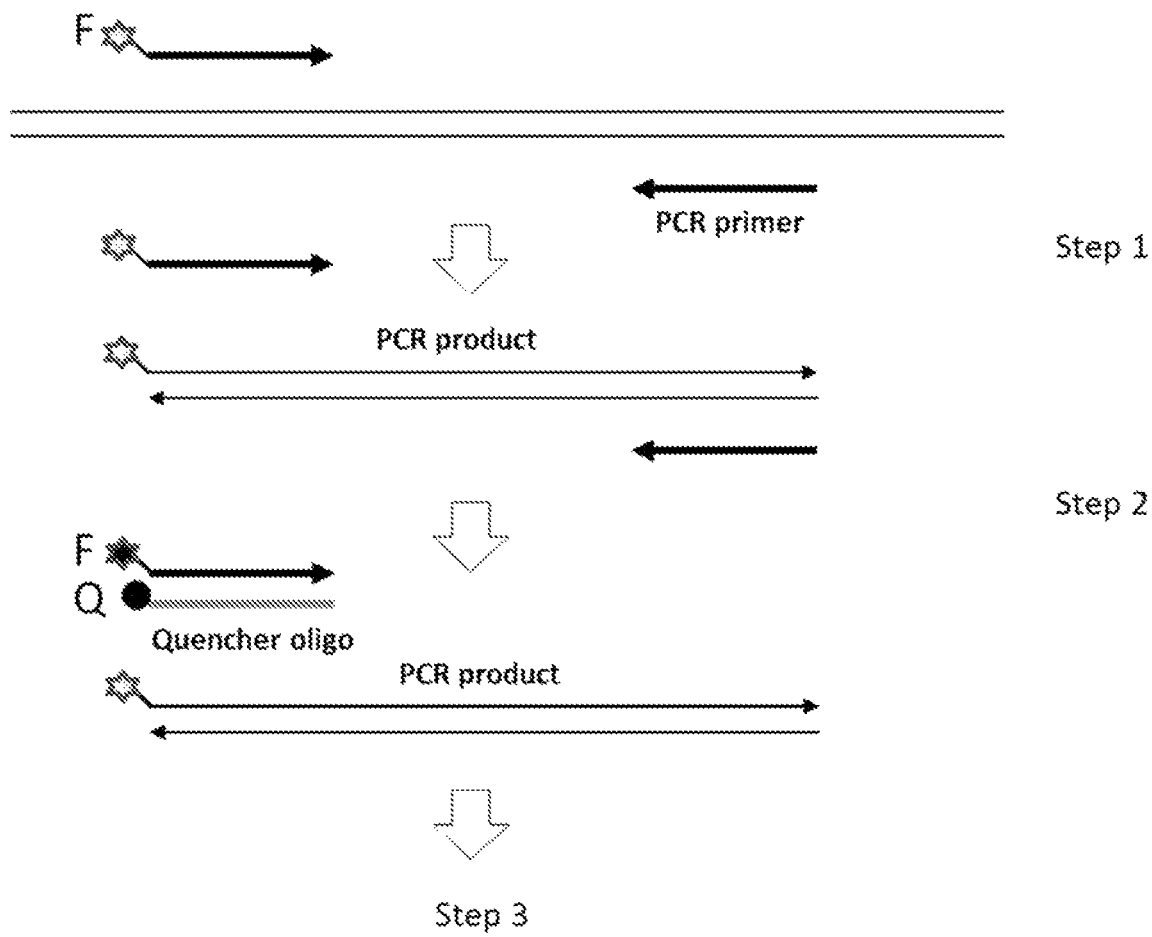
FIG. 30 depicts an exemplary method for post-PCR NGS library molarity quantification. Step 1: PCR with primer containing a fluorophore→Fluorescent reading F1. Step 2: Add quencher oligonucleotide (in excess to primer concentration)→Fluorescent reading F2. Step 3: Determine the molar concentration of the NGS library using formula [NGS library]=F2/F1×[P$_0$], where [P$_0$] is the concentration of the fluorophore-containing primer in the beginning of PCR reaction.

Both the success of the normalization reaction and the molar concentration of the NGS library after N-PCR can be easily determined by measuring fluorescence intensity of library amplified with at least one N-PCR primer containing a fluorophore at the 5' end. Such a measurement is performed before and after addition of an excess molar quantity of quenching oligonucleotide that is complementary to the fluorophore-containing N-PCR primer or its 5' portion and containing a quencher chromophore at the 3' end (two quenching oligonucleotides if both primers have a fluorophore). One advantage of this method over conventional concentration measurements using fluorescent intercalator dyes is that this method is independent of insert size in calculating molarity, so for substrates with a broad or unknown insert size range, the molar quantity can still be accurately measured. Another advantage is that this method of quantification does not require removal of PCR primers prior to measurement, as it can distinguish incorporated vs. free primer concentration. The first fluorescent measurement is performed before addition of the quenching oligonucleotide, which establishes the total fluorescent signal $F_1$ generated by all primers including primers incorporated into the library during PCR and primers that are still present in solution. The second fluorescent measurement is performed after adding quenching oligonucleotide to determine the fluorescent signal $F_2$ that originates from primers incorporated into the library. Based on these two measurements both the library fraction and the non-utilized primer fraction can be determined as $F_2/F_1$ and $(F_1-F_2)/F_1$, respectively. The corresponding molar concentration of the amplified NGS library [Library] and molar concentration of non-incorporated primers [Primer] can be calculated as $[Library]=F_2/F_1 \times [P_0]$ and $[P]=(F_1-F_L)/F_2 \times [P_0]$, respectively, where $[P_0]$ is molar primer concentration in the beginning of the PCR reaction. FIG. 30 shows an exemplary method for applying such a method and calculations to determine the molar concentration of the NGS library.

The above formulas are based on two assumptions, a) that the quantum yield of the fluorophore is the same both in the non-incorporated and incorporated primer, and b) that annealing of the quenching oligonucleotide to the primers remaining in the solution completely suppresses their fluorescence. The first assumption was tested and confirmed by experimental measurement of the fluorescent intensity of PCR primer in the absence and presence of complementary oligonucleotide. As for the second assumption it is well known that suppression of the fluorophore fluorescence by quencher chromophores can be strong but not complete and for real fluorophore-quencher pairs constitutes about 30-100 fold reduction in fluorescence intensity upon quencher oligonucleotide annealing. This reduction can potentially be increased 2-3-fold by selection of the better fluorophore-quencher pair and by using quenching oligonucleotides with multiple quencher groups at the 3' end. However, even current reduction factor can provide very accurate assessment of the success of normalization reaction and give precise measurement of the NGS library concentration without the need to remove non-incorporated primers (see Example 11).

EXAMPLES

TABLE 1

Primer extension reaction oligonucleotides

| Sequence ID | Sequence |
|---|---|
| 1 | GCGGAGAGAGGAGAGGAAGGAGCCC-rU-AATGATACGGCGACCAC*C*G*A*/3SpC3/ |
| 2 | GCGGAGAGAGGAGAGGAAGGAGCCC-rUrU-AATGATACGGCGACCAC*C*G*A*/3SpC3/ |
| 3 | GCGGAGAGAGGAGAGGAAGGAGCCC-rUrUrU-AATGATACGGCGACCAC*C*G*A*/3SpC3/ |
| 4 | GCGGAGAGAGGAGAGGAAGGAGCCC-rUrUrUrU-AATGATACGGCGACCAC*C*G*A*/3SpC3/ |
| 5 | GCGGAGAGAGGAGAGGAAGGAGCCC-rUrUrUrUrUrU-AATGATACGGCGACCAC*C*G*A*/3SpC3/ |
| 6 | GCGGAGAGAGGAGAGGAAGGAGCCC-U-AATGATACGGCGACCAC*C*G*A*/3SpC3/ |
| 7 | GCGGAGAGAGGAGAGGAAGGAGCCC-rArArA-AATGATACGGCGACCAC*C*G*A*/3SpC3/ |
| 8 | GCGGAGAGAGGAGAGGAAGGAGCCC-rCrCrC-AATGATACGGCGACCAC*C*G*A*/3SpC3/ |
| 9 | GCGGAGAGAGGAGAGGAAGGAGCCC-rGrGrG-AATGATACGGCGACCAC*C*G*A*/3SpC3/ |
| 10 | AAAAAA-GTATCGGTGGTCGCCGTAT |

TABLE 2

Amplification oligonucleotides

| Sequence ID | Sequence |
|---|---|
| 11 | AATGATACGGCGACCACCGAGATCTACACTATAGCCTACACTCTTTCCCTACACGACGCTCTTCCGATCT |
| 12 | GGAGAGGAAGGAGCCC-rUrUrUrU-AATGATACGGCGACCAC*C*G*A |
| 13 | AGATCGGAAGAGCGTCGTGTAG |

TABLE 3

Binding kinetics oligonucleotides

| Sequence ID | Sequence |
|---|---|
| 17 | /5IABKFQ/GGTTGTGGGTGTCAAAC AAACAAATGATACGGCGACCACCGA |
| 18 | ACACCCACAACC/36-FAM/ |
| 19 | /5IABKFQ/TTTTTTTTTTT-rUrU rUrU-ACATCG-GTGACTGGAGTTCA GACGTGT |
| 20 | /5Phos/AAAAAAAAAAAAAAA/36-FAM/ |

TABLE 4

Enzymatic-based Library Normalization oligonucleotides

| Sequence ID | Sequence |
|---|---|
| 14 | TTTTTTTTTTT-rUrUrUrU- AATGATACGGCGACCACCGAGA |
| 15 | TTTTTTTTTTT-rUrUrUrU- CAAGCAGAAGACGGCATACGAGAT |
| 16 | /5Phos/A*A*A*A*AAAAAAA AAAA |

TABLE 5

Re-association kinetics oligonucleotides

| Sequence ID | Sequence |
|---|---|
| 21 | AATGATACGGCGACCACCGAGA/ 3IABKFQ/ |
| 22 | GTGTGTGTGTGTGTGTGT-AA TGATACGGCGACCACCGAGA/ 3IABKFQ/ |
| 23 | /56-FAM/TCTCGGTGGTCGCCG TATCATT-ACACACACACACA CACAC |

TABLE 6

PCR-based normalization PCR primers

| Sequence ID | Sequence |
|---|---|
| 24 | AATGATACGGCGACCACCGAGA |
| 25 | CAAGCAGAAGACGGCATACGAGAT |
| 26 | GTGTGTGTGTGTGTGTGT-AAT GATACGGCGACCACCGAGA |
| 27 | GAGAGAGAGAGAGAGAGAGA- CAAGCAGAAGACGGCATACGAGAT |

TABLE 7

Labeled Normalization PCR primers and quencher

| Sequence ID | Sequence |
|---|---|
| 28 | /56-FAM/TGTGTGTGTGTGTGT GTGT-AATGATACGGCGACCACCGA GA |
| 29 | GAGAGAGAGAGAGAGAGAGAGA- CAAGCAGAAGACGGCATACGAGAT |
| 30 | GCCGTATCATT ACACACACACACA CACACACA/3IABKFQ/ |

Where rU—ribo U, dU—deoxyribo U, rA—ribo A, rC—ribo C, rG—ribo G, *—phosphorothioate bond, /3SpC3/—3' end C3 spacer, /5IABkFQ/—5' end Iowa Black® FQ quencher, /36-FAM/—3' end fluorescein, and where/3IABkFQ/—3' end Iowa Black® FQ quencher, /56-FAM/—5' end fluorescein

TABLE 8

Oligonucleotides for library normalization by synthesis method

| Sequence ID | Sequence |
|---|---|
| 31 | CAAGCAGAAGACGGCATACGA |
| 32 | ACACTCrUrUrUCCCTACACGAC GCTCTTCCGATCT |
| 33 | AATGATACGGCGACCACCGAGAT CT |
| 34 | /5Phos/AAAGAGTGTAGATCTC GGTGGTCGCCGTATCATT |
| 35 | AAAAAAAAAAAAATGCGAGATC TACACTCrUrUrUCCCTACACGA CGCTCTTCCGATCT |
| 36 | /5Phos/AAAGAGTGTAGATCTC GGTGGTCGCCGTATCATTTTTTTT TTTTTT |

TABLE 9

Oligonucleotides for PacBio amplicon library synthesis

| Sequence ID | Sequence |
|---|---|
| 37 | AGCAGGATCGGTATGGCTAG TGTCCGCAAGGTCATCGCTA AGTAA |
| 38 | AGCAGGATCGGTATGGCTAG TGTCAGGGTTAGACGTGTCA AGGTATC |
| 39 | /5Phos/GTGTGTGTGTGTT TTTTTTTTTTTTTTTTTTT TrUrUrUrUTAGCAGGATCGG TATGGCTAGTGT |
| 40 | /5Phos/ATCTCTCTCTTTTT CCTCCTCCTCCGTTGTTGTT GTTGAGAGAGATTTTTTTTT |

TABLE 9-continued

Oligonucleotides for PacBio amplicon library synthesis

| Sequence ID | Sequence |
|---|---|
|  | TTTTTTTTTTTTTrUrUrU rUAGCAGGATCGGTATGGCT AGTGT |
| 41 | /5Phos/ACACACACACACA TCTCTCTCTTTTCCTCCTCC TCCGTTGTTGTTGTTGAGAG AGAT |
| 42 | /5Phos/AAAAAAAAAAAT CAGACGATGCGTCATAAAAA AAAAAAA |

Where are: /5Phos/—5' phosphate group, rU— ribo Uridine

TABLE 10

NGS adapter sequences

| Sequence ID | Sequence |
|---|---|
| 43 (Illumina P5) | AATGATACGGCGACCACCGAGATCTA CACTCTTTCCCTACACGACGCTCTTC CGATCT |
| 44 (Illumina P7) | GATCGGAAGAGCACACGTCTGAACTC CAGTCACXXXXXXATCTCGTATGCCG TTCTCTGCTTG |
| 45 (Ion Torrent A) | CCATCTCATCCCTGCGTGTCTCCGAC TCAG |
| 46 Ion (Torrent P1) | ATCACCGACTGCCCATAGAGAGGAAA GCGGAGGCGTAGTGG |
| 47 (PacBio) | ATCTCTCTCTTTTCCTCCTCCGT TGTTGTTGTTGAGAGAGAT |

Where XXXXXX is the index sequence

TABLE 11

Oligonucleotides for Example 17

| Sequence ID | Sequence |
|---|---|
| 48 | TTTTTTTTTTTTGGCGGCAA TTGCGATCGATGCACTGTGG CGGCGGC |
| 49 | GCCGCCGCCACAGTGCATCG ATCGCAATTGCCGCCAAAAA AAAAAAA |
| 50 | TTTTTTTTTTTTGGCGAATT GCGATCGATGCACTGTGGCG GCGGC |
| 51 | GCCGCCGCCACAGTGCATCG ATCGCAATTCGCCAAAAAAA AAAAA |
| 52 | TTTTTTTTTTTTGGAATTGC GATCGATGCACTGTGGCGGC GGC |

TABLE 11-continued

Oligonucleotides for Example 17

| Sequence ID | Sequence |
|---|---|
| 53 | GCCGCCGCCACAGTGCATCG ATCGCAATTCCAAAAAAAAA AAA |
| 54 | TTTTTTTTTTTTGAATTGCG ATCGATGCACTGTGGCGGCG GC |
| 55 | GCCGCCGCCACAGTGCATCG ATCGCAATTCAAAAAAAAAA AA |

Figure 31A:
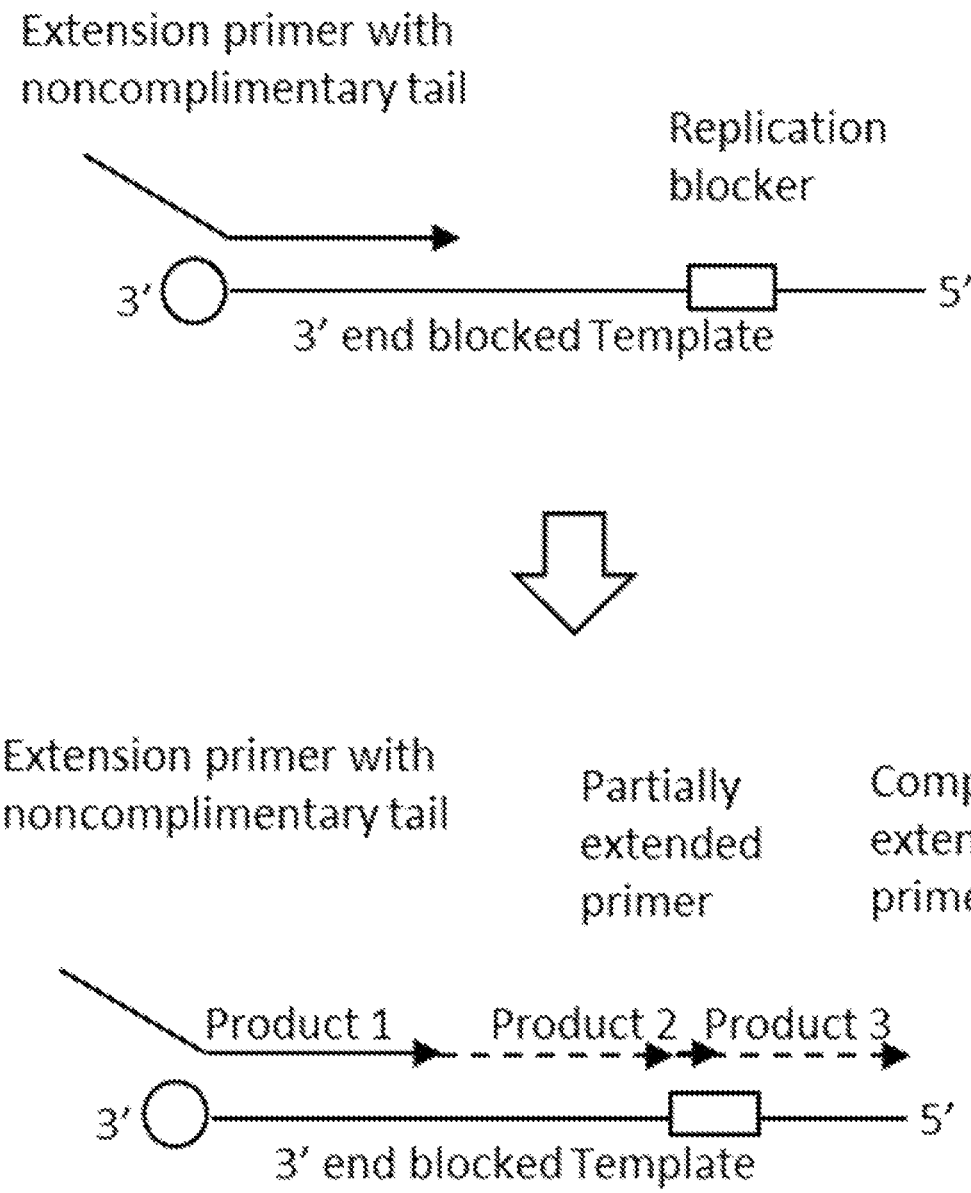
FIG. 31A depicts a schematic representation of a primer extension reaction on a DNA template containing ribonucleotide replication blocker.
Figure 31B:
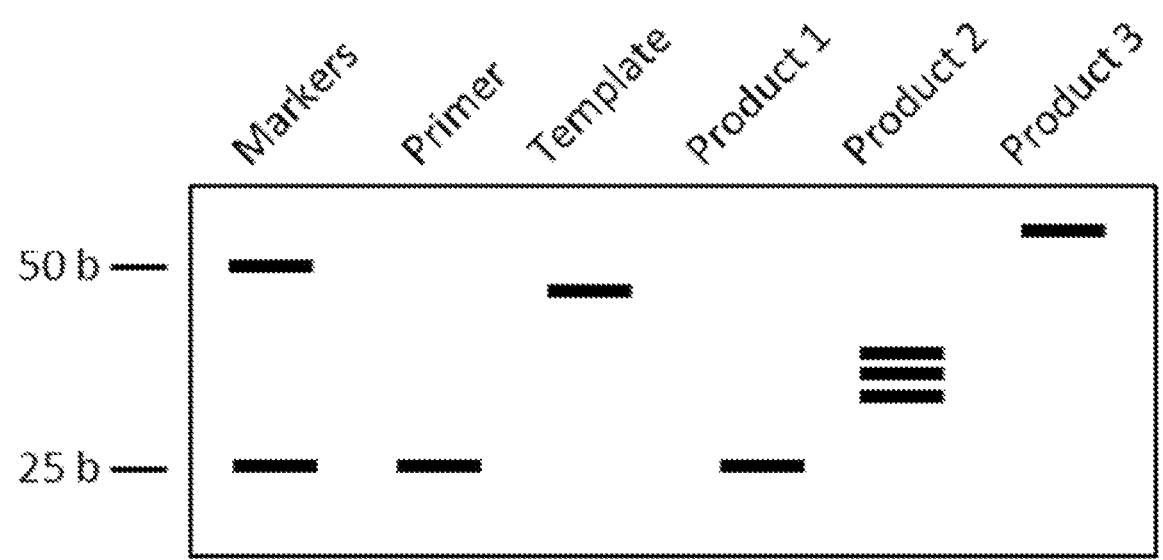
FIG. 31B depicts the expected gel electrophoresis result for the primer extension reaction of FIG. 31A.

Example 1. Schematic Representation of a Primer Extension Reaction on a DNA Template Containing a Ribonucleotide Replication Blocker The primer extension reaction consists of a template DNA oligonucleotide containing an internal RNA replication blocker and also protected at the 3' end to prevent template extension on the 5' end of the primer. Another component of the reaction is an extension primer with a 5' non-complementary end (FIGS. 31A-31B). Three types of products can be formed upon primer extension reaction. If processivity of the polymerase is completely inhibited then no extension will be observed and the non-extended primer will migrate at 25 b size (product 1). If the primer extension reaction stops at the beginning or within the replication blocker, one or multiple extension products migrating above the extension primer but below the template can be observed (product 2). If the polymerase is able to bypass the replication blocker it results in a formation of the product migrating above a template (product 3) (FIG. 31B).

Example 2. A Ribouridine Stretch Incorporated into a DNA Template Blocks Primer Extension by Proofreading DNA Polymerase Q5

Materials
10 μM rU template oligonucleotide (oligonucleotide 1)
10 μM r(U)$_2$ template oligonucleotide (oligonucleotide 2)
10 μM r(U)$_3$ template oligonucleotide (oligonucleotide 3)
10 μM r(U)$_4$ template oligonucleotide (oligonucleotide 4)
10 μM r(U)$_6$ template oligonucleotide (oligonucleotide 5)
10 μM dU template oligonucleotide (oligonucleotide 6)
10 μM extension primer (oligonucleotide 10)
Q5® Hot Start High-Fidelity 2X Master Mix (NEB, cat # M0494S)
Low TE buffer (Teknova cat #TO227)
25 bp ladder DNA size marker (Invitrogen, cat #10488-022)15% TBE-Urea Gel (invitrogen, cat #EC688-52BOX)
SYBR Gold stain (Invitrogen, cat #S11494)

Methods
Extension reactions were performed in 300 reaction volumes, containing 150 2× Q5® Hot Start High-Fidelity Master Mix, 20 of template oligonucleotide, 1 μl of extension primer and 120 of low TE buffer. Reactions were heated at 98° C. for 45 seconds to activate the enzyme followed by 3 minutes extension at 60° C. Samples were boiled in formamide loading buffer and resolved on 15% TBE-Urea Gel at 200 volts. The gel was stained with SYBR Gold stain, visualized on a Dark Reader light box (Clare Chemical Research) and photographed using digital camera.

Results

Figure 32:
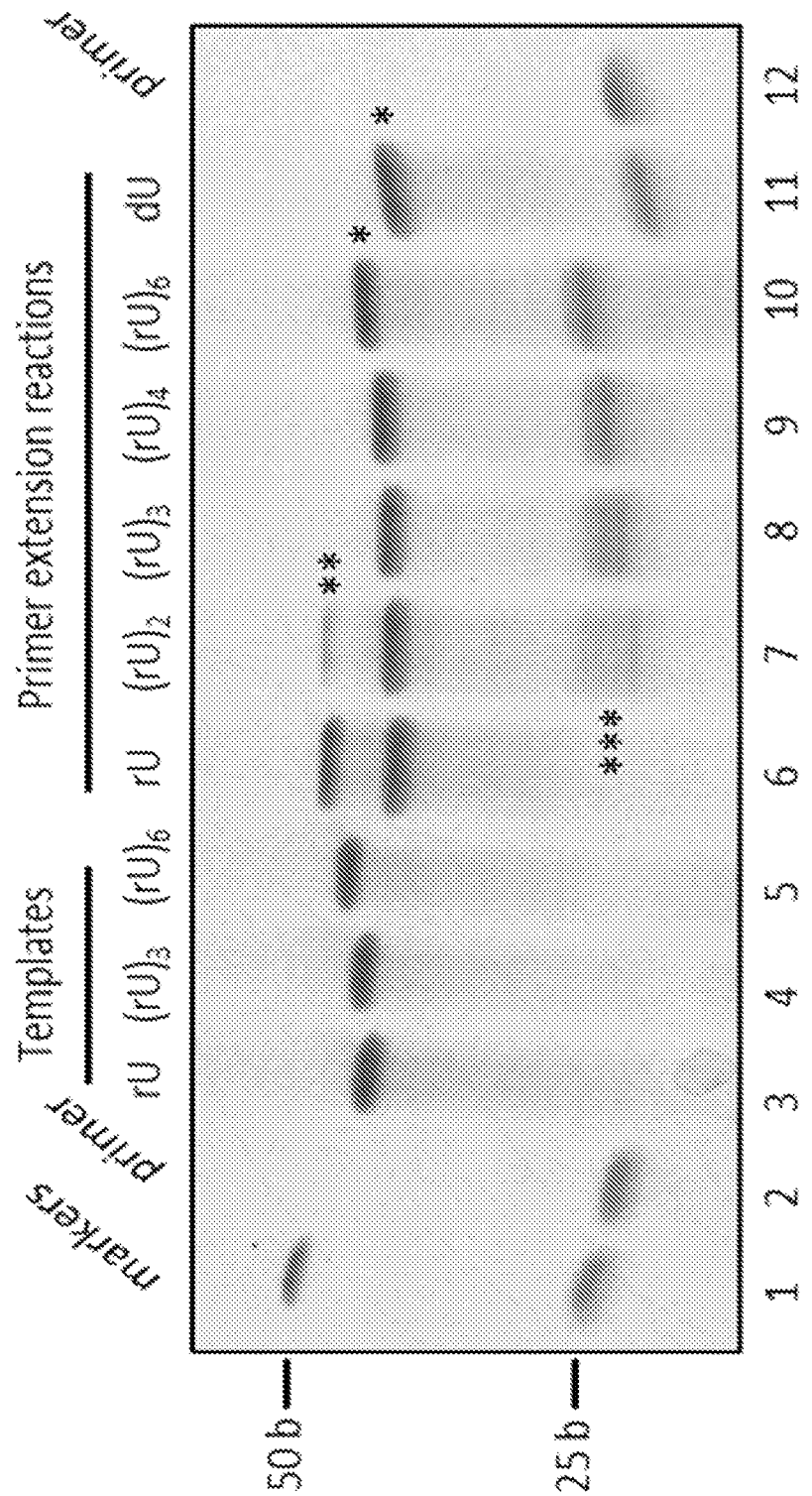
FIG. 32 depicts the products of the extension reactions in Example 2 on a 15% TBE-Urea gel stained with SYBR Gold. "*" indicates the template; "" indicates the fully extended primer; and "*" indicates the partially extended primer.

Electrophoretic analysis of products of extension reactions by Q5® Hot Start High-Fidelity enzyme on templates containing different numbers of ribouridines or deoxyuridine as a replication blocker are shown on FIG. 32. Lane 2 shows migration of an extension primer, lanes 3-5 demonstrate migration of rU, r(U)$_3$ and r(U)$_6$ templates. Lane 6 demonstrates complete extension of the primer on a template containing single ribouridine, lane 7 demonstrates partial and complete extension products on a template containing two ribouridines, lanes 8-10 show only partially extended products on templates which contain more than two (3 to 6) ribouridines. Lane 11 demonstrates completely blocked primer extension by Q5 enzyme on a template containing single deoxyuridine. As can be seen on lane 6, Q5 polymerase can completely bypass the single ribouridine incorporated into the template, creating a complete extension product which migrates above the template and indicated by two asterisks. A noticeable effect on primer extension by Q5 enzyme was observed when more than one ribouridine was incorporated into the DNA template. In particular, very minor complete extension can be observed when two ribouridines are incorporated into the extension template (lane 7). When more than two ribouridines are incorporated into the template oligonucleotide Q5 polymerase cannot bypass the replication blocker creating only partially extended products indicated on a gel by three asterisks (lanes 8-10). As demonstrated on lane 11 deoxyuridine incorporated into the template can completely block Q5 polymerase processivity.

Conclusion

Ribouridines incorporated into a DNA template can inhibit primer extension by proofreading polymerase Q5. In order to archive an efficient blockage of primer extension the replication block should contain three or more ribouridines.

Example 3. Primer Extension Reactions Using Different Thermostable DNA Polymerases on DNA Templates Containing Replication Blockers Comprised of the Four Different Ribonucleotides Materials 10 μM r(U)$_3$ template oligonucleotide (oligonucleotide 3)
10 μM r(A)$_3$ template oligonucleotide (oligonucleotide 7)
10 μM r(C)$_3$ template oligonucleotide (oligonucleotide 8)
10 μM r(G)$_3$ template oligonucleotide (oligonucleotide 9)
10 μM extension primer (oligonucleotide 10)
Taq 2X Master Mix (NEB, cat #M0270L)
2X Q5 dU bypass polymerase (NEB, cat # not available)
Kapa HiFi HotStart ReadyMix (Kapa biosystems, cat #KK2601)
PrimeSTAR® GXL DNA Polymerase (Clontech, cat #R050A)
Q5® Hot Start High-Fidelity 2X Master Mix (NEB, cat #M0494S)
Low TE buffer (Teknova cat #TO227)
25 bp ladder DNA size marker (Invitrogen, cat #10488-022)15% TBE-Urea Gel (invitrogen, cat #EC68852BOX)
SYBR Gold stain (Invitrogen, cat #S11494)

Methods

Primer extension reactions with 2× Taq, 2X Q5 dU bypass polymerase or Q5® Hot Start High-Fidelity 2X Master Mix were performed in 300 reaction volumes, containing 150 of Master Mixes, 20 of template oligonucleotide, 1 μl of extension primer and 120 of low TE buffer. Primer extensions with PrimeSTAR® GXL DNA Polymerase were performed in 300 reaction volumes, containing 60 of 5X PrimeSTAR GXL Buffer, 2.5 μl of dNTP Mixture (2.5 mM each) 20 of template oligonucleotide, 10 of extension primer, 10 of PrimeSTAR GXL DNA Polymerase and 17.50 of low TE buffer. With 2× Taq polymerase reactions were heated at 95° C. for 3 minutes to activate the enzyme followed by 3 minutes extension at 60° C. With 2X Q5 dU Bypass polymerase, Q5® Hot Start High-Fidelity 2X Master Mix or PrimeSTAR® GXL DNA Polymerase reactions were heated at 98° C. for 45 seconds to activate the enzymes followed by 3 minutes extension at 60° C. Samples were boiled in formamide loading buffer and 200 of each reaction was resolved on 15% TBE-Urea Gel at 200 volts. The gel was stained with SYBR Gold stain, visualized on a Dark Reader light box (Clare Chemical Research) and photographed using digital camera.

Results

Figure 33A:
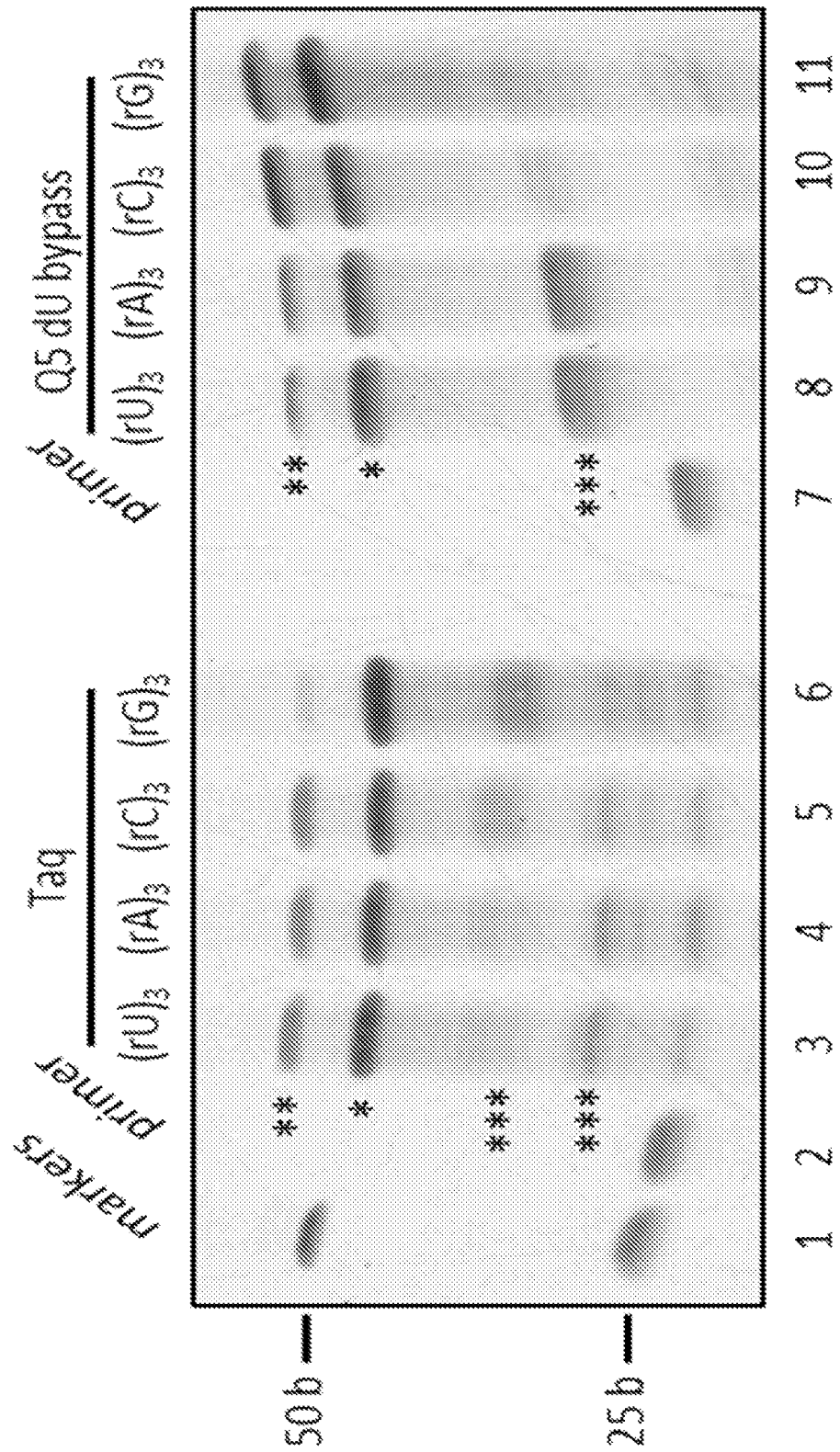
FIG. 33A depicts the products of the extension reactions in Example 3 with Taq and Q5 dU bypass on a 15% TBE-Urea gel stained with SYBR Gold. "*" indicates the template; "" indicates the fully extended primer; and "*" indicates the partially extended primer.

Electrophoretic analysis of products of extension reactions by Taq and Q5 dU bypass enzymes on templates containing different ribonucleotides as a replication blocker are shown on FIG. 33A. Lanes 2 and lane 7 show migration of the extension primer, lanes 3-6 demonstrate the products of primer extension reaction with Taq polymerase on templates containing r(U)$_3$, r(A)$_3$, r(C)$_3$ and r(G)$_3$ stretches. As demonstrated on lanes 3 to 6, Taq polymerase can partially bypass the replication blockers comprised of the three ribouridines, riboadenosines or ribocytosines. Primer extension results in a distinct band corresponding to the completely extended primer () as well as partially extended primers migrating below the templates when replication stops at the beginning or within the replication blocker (*). In contrast, the riboguanosine replication blocker has an ability to nearly completely prevent an extension to the 5' end of the template forming only partially extended products. Lane 8-11 demonstrate the products of the primer extension reaction with Q5 dU bypass polymerase on the templates containing r(U)$_3$, r(A)$_3$, r(C)$_3$ and r(G)$_3$ stretches respectively. This enzyme has a greater ability to bypass ribocytosine and riboguanosine replication blockers compared to Taq polymerase (lanes 10 and 11) whereas extension on templates which contain ribouridine and riboadenosine, blockers lead to mostly partial primer extension (lanes 8 and 9).

Figure 33B:
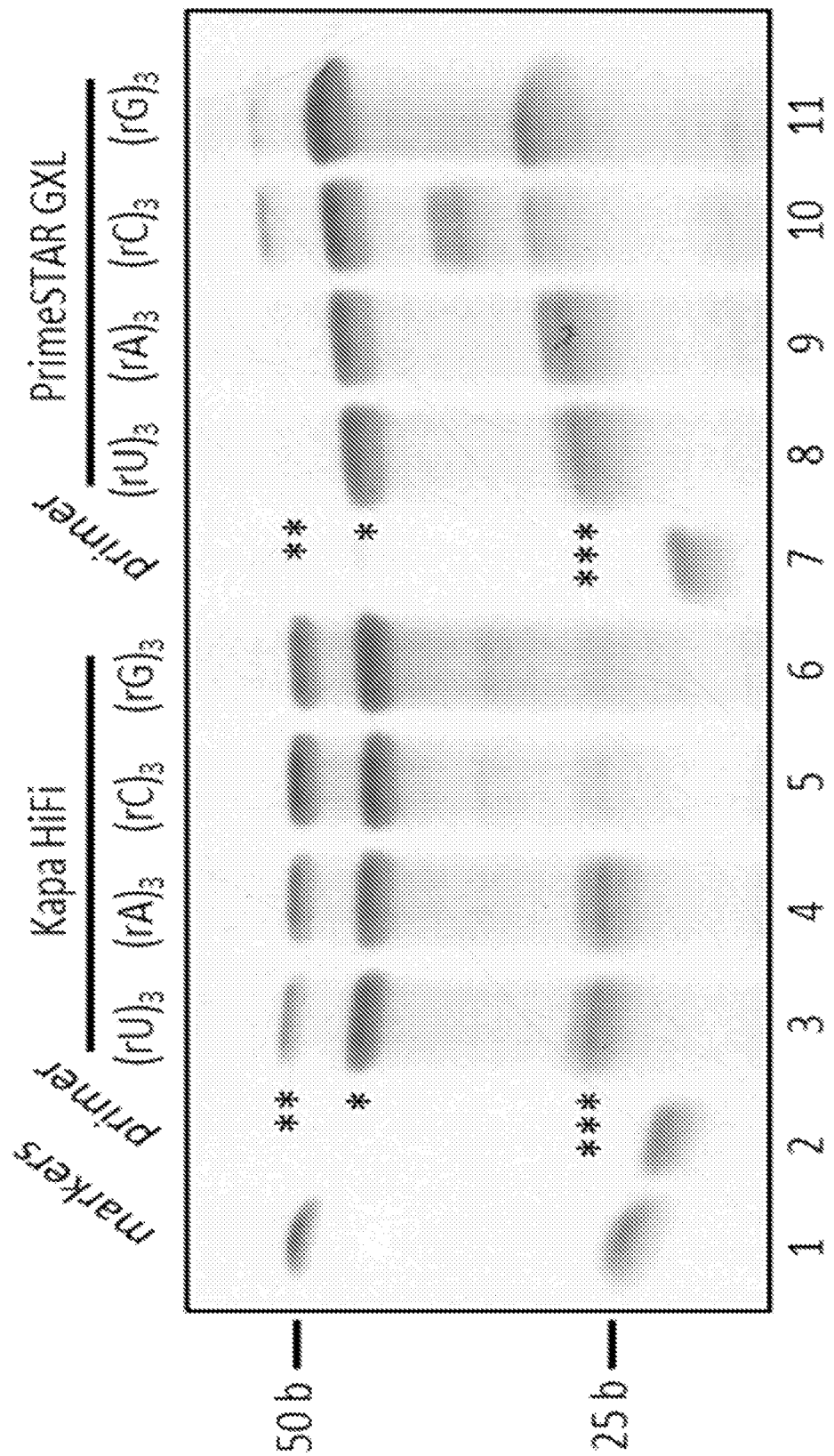
FIG. 33B depicts the products of the extension reactions in Example 3 with Kappa HiFi or PRIMESTAR® GXL on a 15% TBE-Urea gel stained with SYBR Gold. "*" indicates the template; "" indicates the fully extended primer; and "*" indicates the partially extended primer.

Electrophoretic analysis of products of extension reactions by Kapa HiFi and GXL PrimeSTAR enzymes on templates containing different ribonucleotides as a replication blocker are shown on FIG. 33B. Lanes 2 and lane 7 show migration of the extension primer, lanes 3-6 demonstrate the products of primer extension reaction with Kapa HiFi polymerase on the templates containing r(U)$_3$, r(A)$_3$, r(C)$_3$ and r(G)$_3$ stretches. As can be seen on lanes 3 and 4, Kapa HiFi enzyme can partially bypass the replication blockers comprised of the three ribouridines and riboadenosines creating full length as well as truncated primer extension products. Primer extension reaction results in a distinct band corresponding to the completely extended primer () as well as partially extended primers migrating below the templates when replication stops at the beginning or within the replication blocker (*). In contrast, Kapa HiFi Enzyme can completely bypass the ribocytosine and riboguanosine replication blockers forming only full length extension products. Lane 8-11 demonstrate the products of the primer extension reaction with GXL PrimeSTAR polymerase on the templates containing r(U)$_3$, r(A)$_3$, r(C)$_3$ and r(G)$_3$ stretches respectively. Processivity of this enzyme is nearly completely inhibited by all four replication blockers.

Figure 33C:
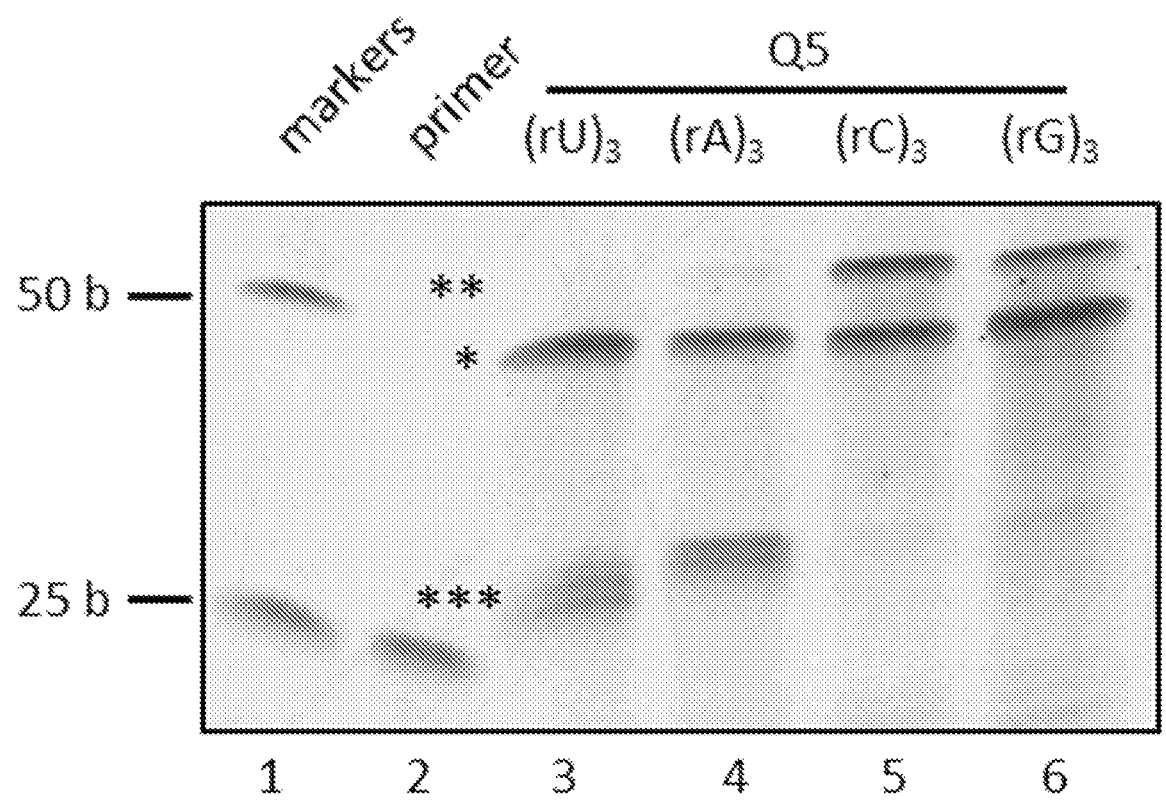
FIG. 33C depicts the products of the extension reactions in Example 3 with Q5 polymerase on a 15% TBE-Urea gel stained with SYBR Gold. "*" indicates the template; "" indicates the fully extended primer; and "*" indicates the partially extended primer.

Electrophoretic analysis of products of extension reactions by Q5 enzyme on templates containing different ribonucleotides as a replication blocker are shown on FIG. 33C. Lane 2 shows migration of the extension primer, lanes 3-6 demonstrate the products of primer extension reaction with Q5 polymerase on the templates containing r(U)$_3$, r(A)$_3$, r(C)$_3$ and r(G)$_3$ stretches. As seen on lanes 3 and 4, Q5 enzyme can not bypass the replication blockers comprised of the three ribouridines or riboadenosines creating only truncated primer extension products. In contrast, Q5 polymerase can completely bypass the ribocytosine and riboguanosine replication blockers forming only full length extension products (lanes 5 and 6).

Conclusions

Different thermostable DNA polymerases have a different ability to bypass the replication blockers composed of 3 ribouridines, riboadenosines, ribocytosines or riboguanosines. For example, Q5 DNA polymerase can easily bypass r(C)$_3$ and r(G)$_3$ replication blockers whereas it completely stalls at r(U)$_3$, r(A)$_3$ sequences. In contrast, Kapa HiFi enzyme has a greater ability to replicate through ribouridine and riboadenosine replication blockers compared to Q5 enzyme. All DNA polymerases except non-proofreading Taq DNA polymerases share the common property to not efficiently replicate through the replication blocker composed of ribouridines making this composition most universal and appealing blocker composition out of four replication blockers tested. At the same time Taq DNA polymerase demonstrates problems with replicating through 3 consecutive ribo G bases.

Example 4. Schematic of an Amplification Experiment with a Normal Amplification Primer and a Primer that Contains the Replication Blocker and a 5' End Non-Complementary Tail As can be seen from FIGS. 34A, a PCR reaction with a normal complementary primer one and primer two which contains an internal replication blocker and non-complementary tail can result in two different scenarios. If the DNA polymerase can bypass the replication blocker, then the 3' end of the template molecule will extend to the 5' end of primer 2 creating two DNA strands of the same size. If the DNA polymerase cannot replicate through the replication blocker, this creates two DNA strands of different sizes which can be visualized on a denaturing gel.

Example 5. Amplification of a Synthetic DNA Template with a Normal Primer and a Primer that Contains a Replication Blocker and a 5' End Non-Complementary Tail Using Taq and PrimeSTAR GXL DNA Polymerases Materials
  10 nM template oligonucleotide (oligonucleotide 11)
  600 nM forward primer with r(U)$_4$ replication blocker and 5' end non-complementary tail
  (oligonucleotide 12)
  600 nM reverse primer (oligonucleotide 13)
  Taq 2X Master Mix (NEB, cat #M0270L)
  PrimeSTAR® GXL DNA Polymerase (Clontech, cat #R050A)
  Low TE buffer (Teknova cat #TO227)
  25 bp ladder DNA size marker (Invitrogen, cat #10488-022)15% TBE-Urea Gel (invitrogen, cat #EC68852BOX)
  SYBR Gold stain (Invitrogen, cat #S11494)

Methods

Amplification reactions with 2× Taq master mix was performed in 500 reaction volume, containing 250 of Master Mix, 20 of template oligonucleotide, 2.50 of each amplification primer and 180 of low TE buffer. The reaction was performed with the following cycling parameters: an initial enzyme activation at 95° C. for 3 min and then 10 cycles consisting of 95° C. for 20 s, 60° C. for 30 s, and 66° C. for 30 s. Amplification with PrimeSTAR® GXL DNA Polymerase also was performed in 500 reaction volume, containing 100 of 5X PrimeSTAR GXL Buffer, 4 μl of dNTP Mixture (2.5 mM each) 20 of template oligonucleotide, 2.50 of each primer, 10 of PrimeSTAR GXL DNA Polymerase and 280 of low TE buffer. Amplification was performed with the following cycling parameters: an initial enzyme activation at 98° C. for 30s and then 10 cycles consisting of 98° C. for 10 s, 60° C. for 30 s, and 68° C. for 30 s. Samples were boiled in formamide loading buffer and 200 of each reaction was resolved on 15% TBE-Urea Gel at 200 volts. Than gel was stained with SYBR Gold stain, visualized on a Dark Reader light box (Clare Chemical Research) and photographed using digital camera.

Results

Electrophoretic analysis of products of amplification reactions by Taq and PrimeSTAR® GXL DNA Polymerasea on a synthetic template with a normal primer and a primer that contains a r(U)$_4$ replication blocker and a 5' end non-complementary tail are shown on FIG. 34. Lane 2 shows migration of the synthetic oligonucleotide template, lane 3 demonstrates migration of primers, lane 4 shows the result of amplification reaction with Taq DNA polymerase where the top band represents the full length amplification product and minor bottom band labeled with single asterisk demonstrates the 3' end truncated product. In contrast, when the amplification reaction was performed with PrimeSTAR® GXL DNA polymerase, two bands of equal intensity corresponding to full size as well as truncated DNA can be seen.

Conclusions

Figure 34A:
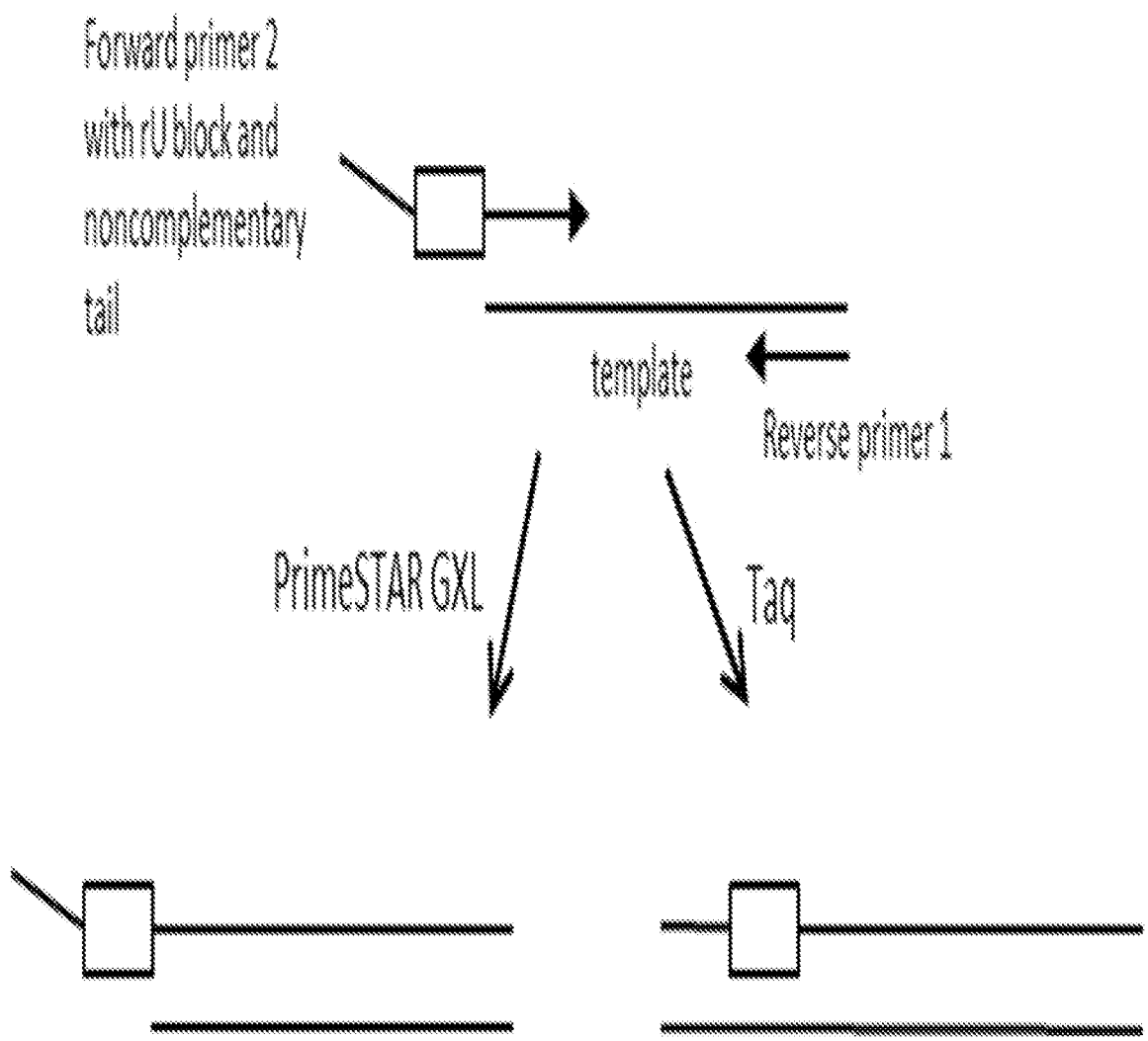
FIG. 34A depicts a schematic representation of an amplification experiment with a normal amplification primer and a primer that contains the replication blocker and a 5' end non-complementary tail.
Figure 34B:
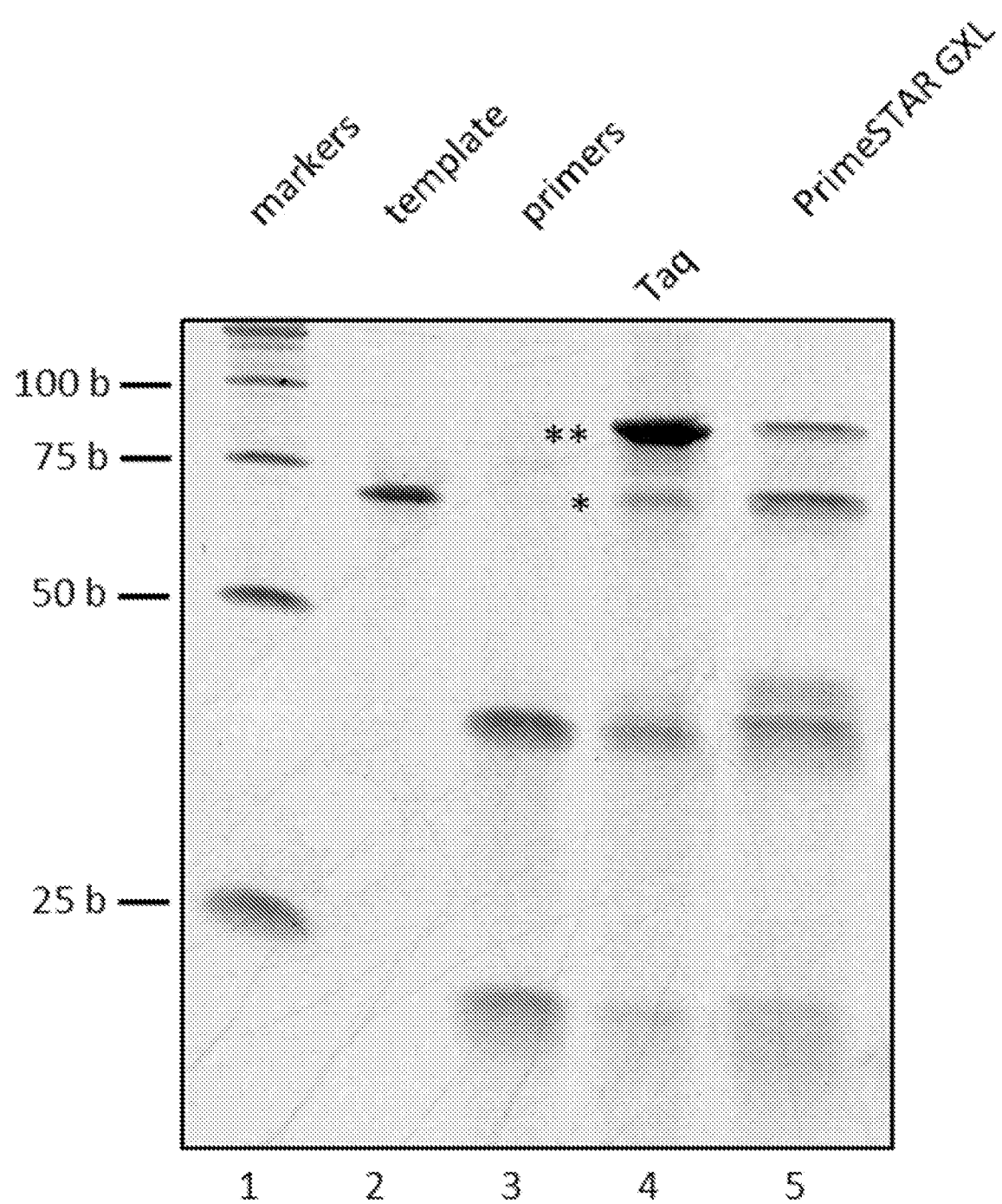
FIG. 34B depicts the products of the extension reactions in Example 5 with Taq and PRIMESTAR® GXL on a 15% TBE-Urea gel stained with SYBR Gold. "" indicates the full length amplification product and "*" indicates the truncated amplification product.

As can be seen from FIG. 34B, lane 5, a ribouridine stretch can serve as an efficient replication blocker for PrimeSTAR® GXL DNA Polymerase (and several others such as Q5 DNA polymerase, data not shown). This phenomenon allows creation of a predefined 5' overhang from one or both ends of double stranded DNA during a PCR reaction. An advantage of using ribouridine as a replication blocker is that the junction that is produced can serve as a substrate in a subsequent ligation reaction, unlike conventional replication blockers.

Example 6. Oligonucleotide Binding Kinetic Analysis for a Complex Sequence and a Homopolymeric Sequence Materials
  500 nM Complex substrate (oligonucleotide 17)
  500 nM Complex probe (oligonucleotide 18)
  500 nM Homopolymeric substrate (oligonucleotide 19)
  500 nM Homopolymeric probe (oligonucleotide 20)
  2X Hybridization buffer: TRIS pH=7.5 20 mM, MgCl$_2$ 10 mM, NaCl 100 mM
  Qubit 2.0 Fluorimeter (Invitrogen cat #Q32866)

Methods

Hybridization reactions were performed in a 2000 volume containing 1000 of 2X Hybridization buffer, 200 of substrate oligonucleotide (50 nM final concentration) and 100 of fluorescent probe (25 nM final concentration). Measurements were taken every 1 minute using Blue excitation (430-495 nm) and Green (510-580 nm) emission filters.

Results

Figure 35A:
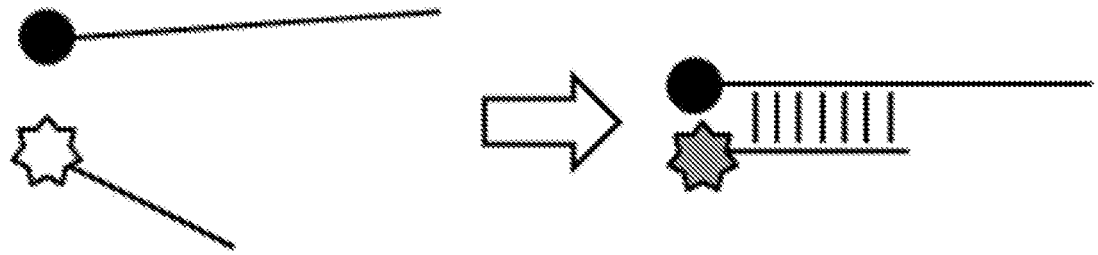
FIG. 35A depicts a schematic representation of binding between a fluorescently-labeled probe to a quencher oligonucleotide.
Figure 35B:
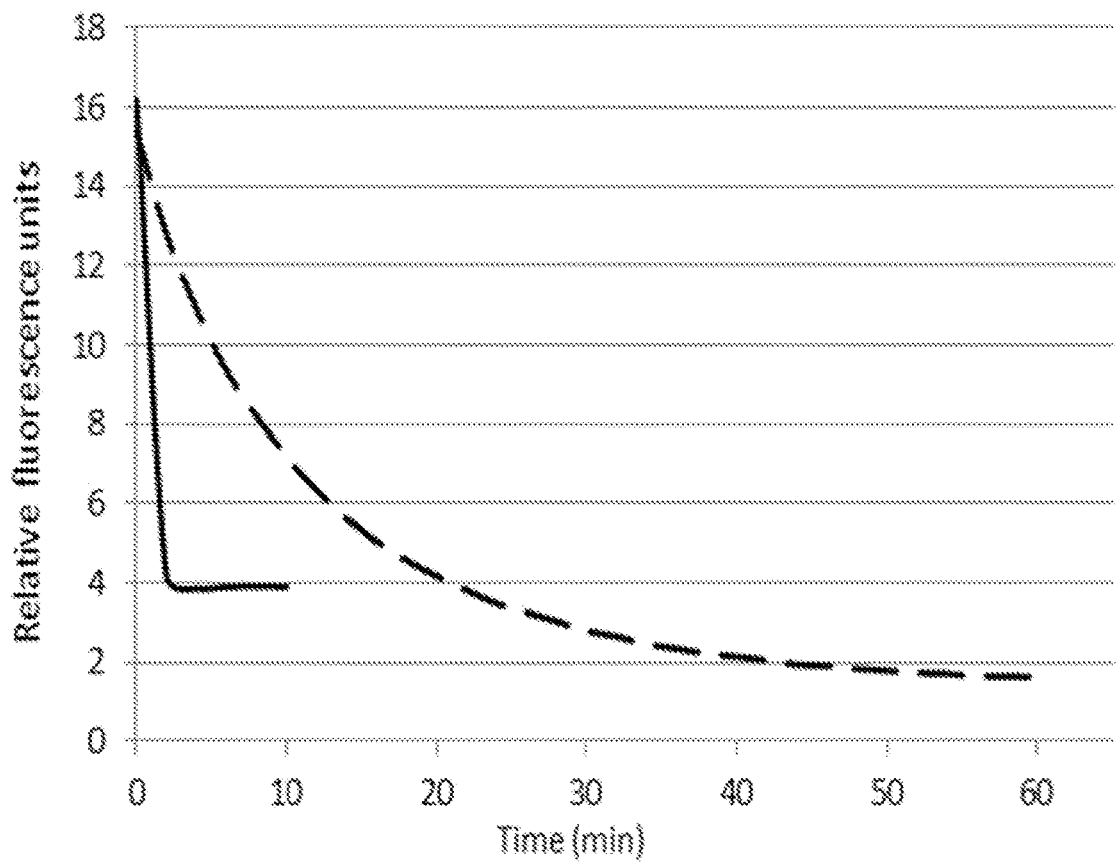
FIG. 35B depicts fluorescence intensity with respect to time for binding of a 25 nM fluorescent complex sequence probe to an excess amount of complementary substrate oligonucleotide with a quencher (dashed line) and of a 25 nM fluorescent homopolymeric sequence probe to its complementary substrate with a quencher (solid line).

FIG. 35A shows a schematic of the binding rate of a fluorescent probe to an excess amount of a corresponding substrate oligonucleotide containing a quencher as a function of time. Binding of the fluorescent probe to the substrate oligonucleotide brings the fluorophore in close proximity to the quencher. This leads to the decay of fluorescent signal and can be measured by fluorimeter. The dashed line demonstrates the binding kinetics of 25 nM complex sequence probe to an excess amount of the complementary substrate oligonucleotide whereas the solid line shows the binding of a 25 nM homopolymeric sequence probe to its complementary substrate (FIG. 35B).

Conclusions

It is evident that the binding rate to the substrate dramatically increases in the case of a homopolymeric oligonucleotide probe compared to the complex sequence probe. As known from previous studies, annealing of two oligonucleotides involves formation of partially paired regions and their expansion. When two complex sequence oligonucleotides approach each other during hybridization, the probability of nucleotide complementary in the initial complex is very low. In contrast, when two complementary homopolymeric oligonucleotides encounter each other, it leads to instantaneous nucleation and duplex formation. This explains the significantly more rapid binding kinetics of the homopolymeric probe compared to the complex sequence probe and allows a much shorter incubation of a corresponding normalization probe or primer to an NGS library in a normalization reaction.

Example 7. Enzyme-Based NGS Library Normalization Using Ligation of a Homopolymeric Probe Comprising Nuclease Resistance Followed by Enzymatic Normalization Using Exonuclease III Materials HapMap DNA NA12878 (Coriell)
Accel-NGS® 2S PCR-Free DNA Library Kit (Swift Biosciences cat #DL-IL2PF-48, SI-ILM2S-48A)
600 nM P5 pre-N primer (oligonucleotide 14)
600 nM P7 pre-N primer (oligonucleotide 15)
Q5® Hot Start High-Fidelity 2X Master Mix (NEB, cat #M0494S)
SPRI select DNA size selection beads (BECKMAN COULTER cat #B23318)
Low TE buffer (Teknova cat #TO227)
480 nM Homopolymeric normalization N-probe (oligonucleotide 16)
Normalization buffer N1: TRIS pH=7.5 62.5 mM, $MgCl_2$ 31.25 mM, ATP 6.25 mM, DTT 62.5 mM NaCl 312.5 mM
Normalization buffer N2: TRIS pH=7.5 10 mM, $MgCl_2$ 1 mM
T4 DNA ligase (Enzymatics cat #L6030-LC-L)
Exonuclease III (Enzymatics cat #X8020F)
0.5M EDTA pH=8.0 (SIGMA-ALDRICH cat #E9884)
KAPA Library Quantification Kit (Kapa Biosystems cat #KK4824)

Methods

An NGS library was constructed from 1 ng Coriell DNA NA12878 using Accel-NGS® 2S PCR-Free DNA Library Kit from Swift Biosciences. The library was eluted in 200 of low TE buffer and subjected to the 10 cycles of amplification with Q5 Hot Start High-Fidelity 2X Master Mix and P5 and P7 pre-N primers. The library was purified on SPRI select DNA size selection beads using library to beads ratio 1.0 and eluted in 500 of low TE DNA resuspension buffer. Amplified library was quantified using KAPA Library Quantification Kit and a set of library dilutions of designated concentrations were prepared (FIG. 36). To normalize the library dilutions to 4 nM final concentration, 200 of libraries were mixed with 40 of N1 normalization buffer, 0.50 of normalization N-probe and 0.50 of T4 DNA ligase and incubated for 20 minutes at 30° C. Then 0.50 of Exonuclease III diluted in 4.50 of N2 buffer was added to each tube and incubated for another 20 minutes at 30° C. At the end of incubation 10 of 0.5M EDTA was added to each tube and then to inactivate enzymes samples were heated at 95° C. for 3 minutes.

Final library concentration was quantified using a qPCR based KAPA Library Quantification Kit according to manufacturers instructions.

Results

Figure 36A:
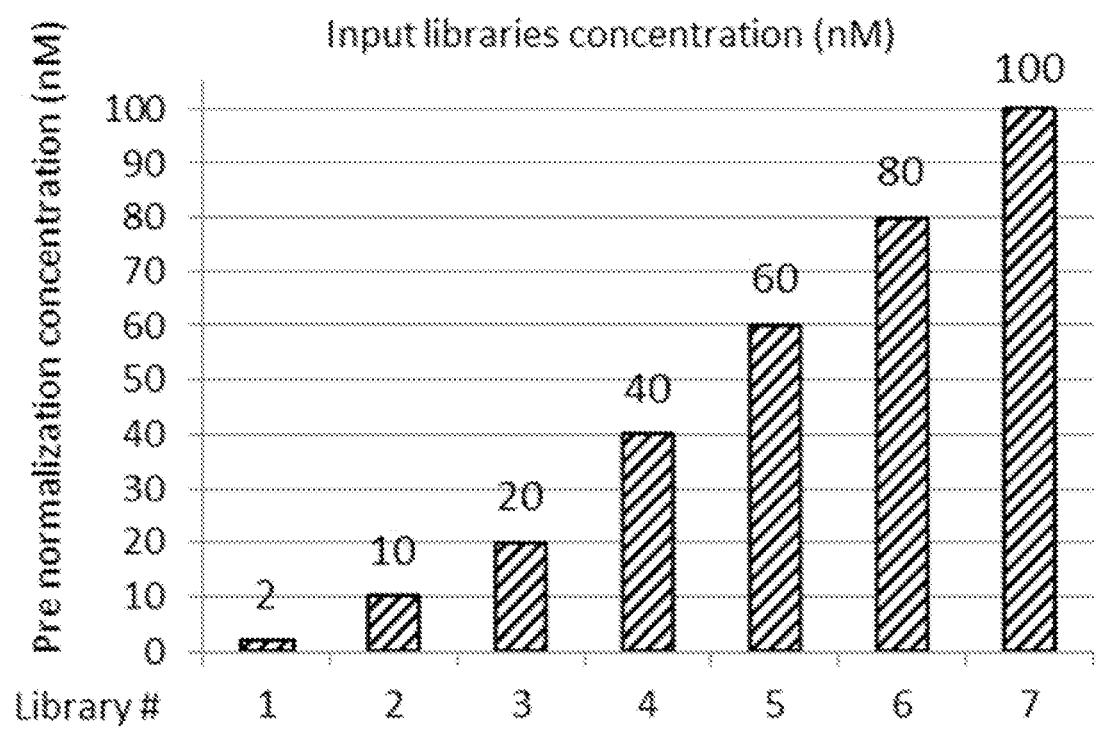
FIG. 36A depicts the pre-normalization concentration of libraries #1-7 in Example 7.
Figure 36B:
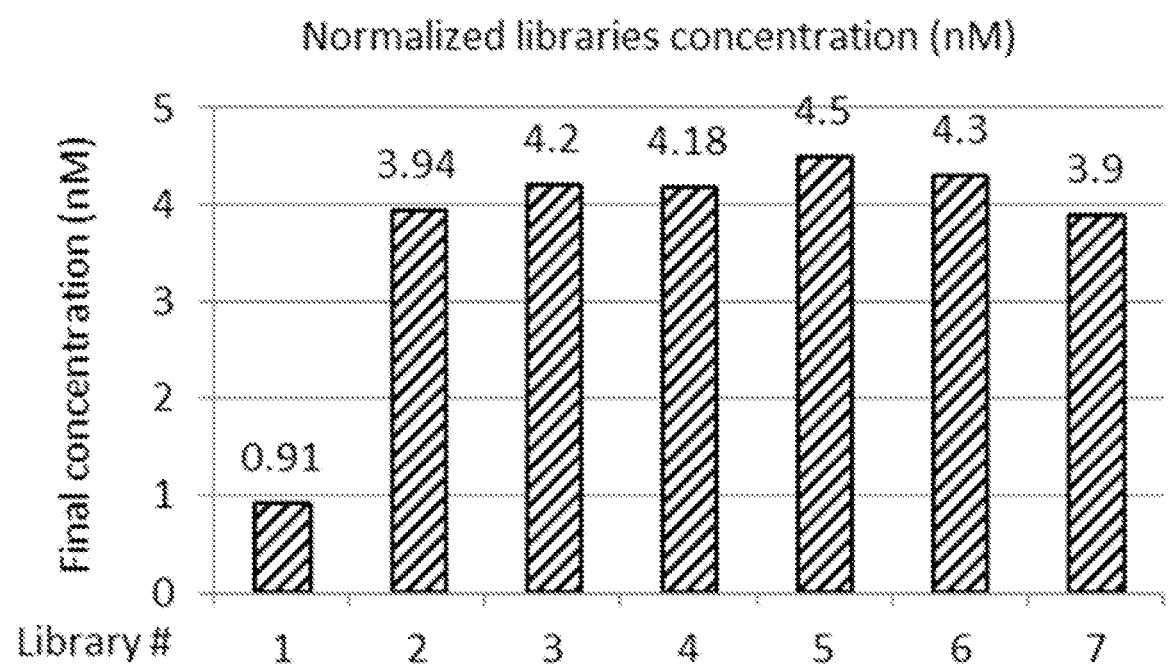
FIG. 36B depicts the post-normalization final concentration of libraries #1-7 in Example 7.

Quantification results of the sequencing libraries before and after normalization are demonstrated on FIGS. 36A-36B. Libraries amplified with Q5 enzyme were quantified and diluted with low TE buffer to create 200 aliquots of designated concentration between 2 and 100 nM. Then each aliquot was subjected to the library normalization procedure as described above. The results of the normalization reactions can be seen at FIGS. 36A-36B. All libraries with the starting concentration of 10 nM and above have been successfully normalized to the 4 nM final concentration with standard deviation of 0.21. As expected the first library with insufficient amount of starting material cannot be normalized to the 4 nM final concentration producing the library with 0.91 nM concentration.

Conclusions

Normalization reactions on NGS libraries with different starting concentrations result in libraries with similar concentrations due to the limited molar quantity of homopolymeric normalization probe, demonstrating a simple, robust method of NGS library normalization prior to sequencing.

Example 8. Re-Association Kinetics Using Oligonucleotides with Fluorescein Dye and Quencher Group Shows that a Primer with a Repetitive Tail Anneals ~10-Time Faster Materials 500 nM conventional template (oligonucleotide 21)
500 nM GT tailed template (oligonucleotide 22)
500 nM AC tailed primer (oligonucleotide 23)
2X Hybridization buffer: TRIS pH=7.5 20 mM, $MgCl_2$ 10 mM, NaCl 100 mM
Synergy HTX multi-mode reader (BioTek)

Methods

Hybridization reactions were performed in 1000 volume containing 500 of 2X Hybridization buffer, 100 of substrate oligonucleotide (50 nM final concentration) and 50 of fluorescent probe (25 nM final concentration). Measurements were taken every 1 minute using Blue excitation and Green emission filters.

Results

Figure 37A:
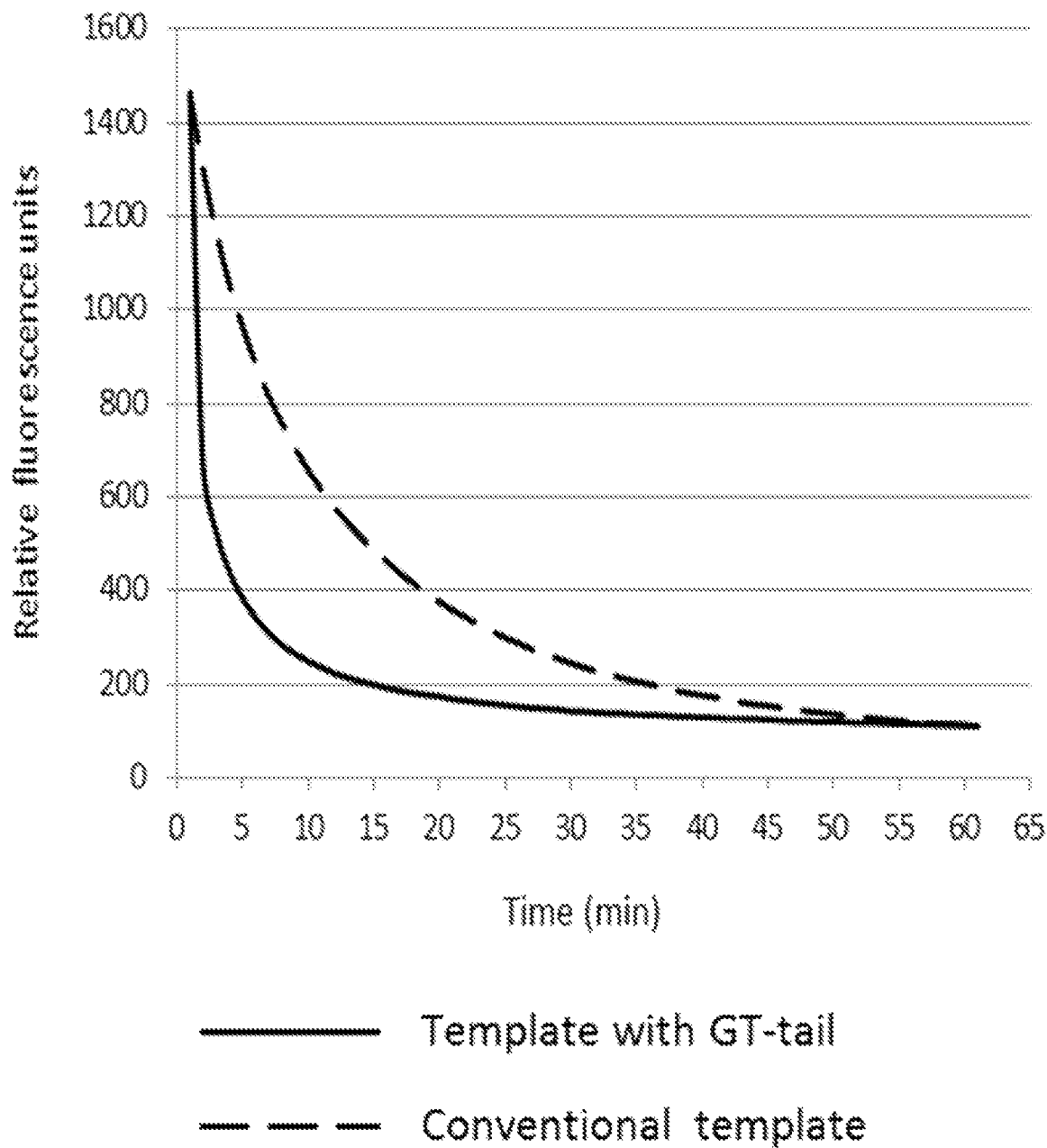
FIG. 37A depicts fluorescence intensity with respect to time for binding of a fluorescent probe to an excess of two different substrate oligonucleotides with quenchers.
Figure 37B:
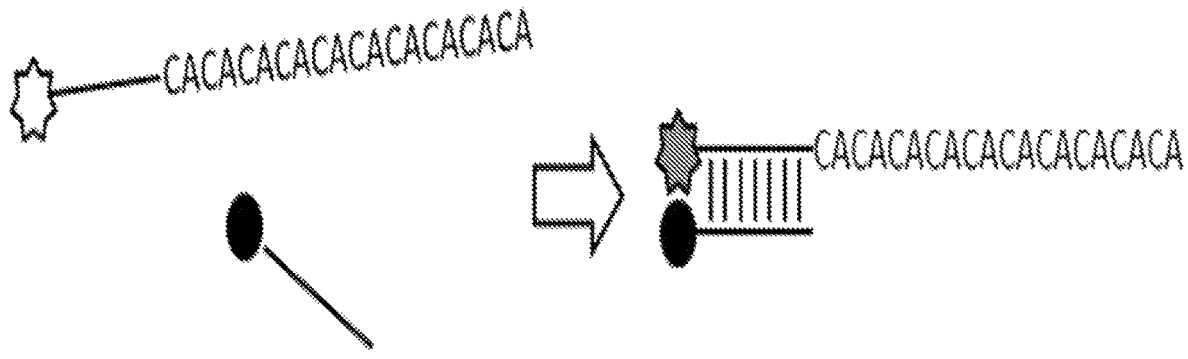
FIG. 37B depicts a schematic representation of the fluorescent probe binding with a conventional template with a quencher. Figure discloses "CACACACACACACACACACA" as SEQ ID NO: 91.
Figure 37C:
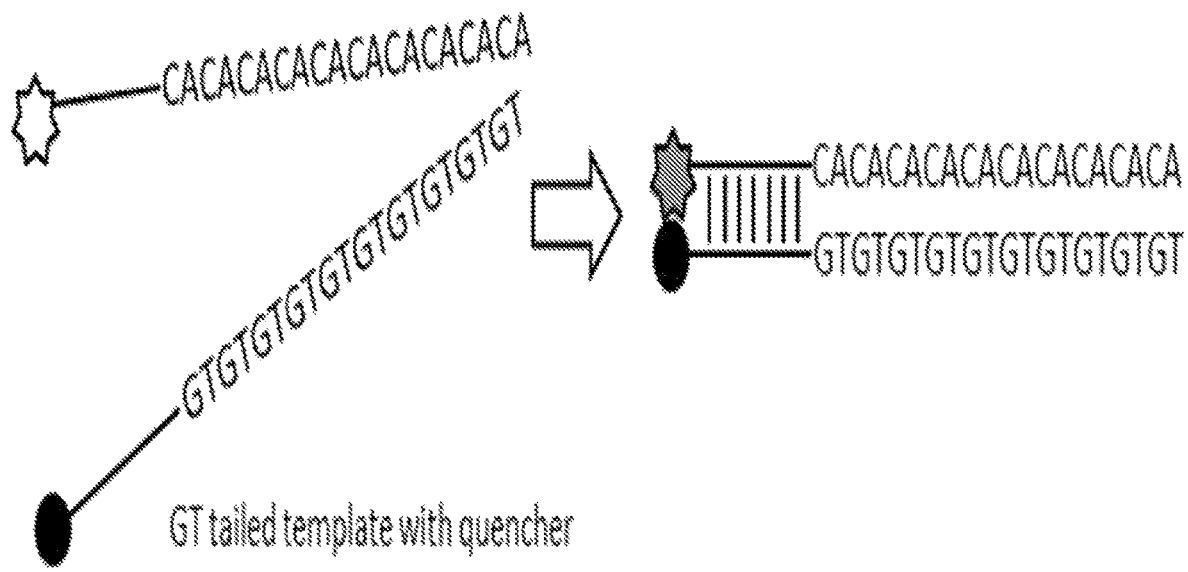
FIG. 37C depicts a schematic representation of the fluorescent probe binding with a GT-tailed template with quencher. Figure discloses "CACACACACACACACACACA" as SEQ ID NO: 91 and "TGTGTGTGTGTGTGTGTGTG" as SEQ ID NO: 88.

FIG. 37A shows the binding rate of the fluorescent probe to the excessive amount of two different substrate oligonucleotides as a function of time. Binding of the fluorescent probe to the substrate oligonucleotide brings the fluorophore to the close proximity of the quencher. This leads to the decay of fluorescent signal and can be measured by fluorimeter FIG. 37. Dashed lane demonstrates the binding kinetic of 25 nM probe to the excessive amount of the conventional template oligo where as solid lane shows the binding of the probe to template oligonucleotide containing GT repeat (see FIGS. 37B-37C for schematic representations of the probe and oligo pairs).

Conclusions

It is apparent that the binding rate to the substrate dramatically increases in case of the template containing GT repeat compare to the conventional complex template. It has been shown previously that the annealing of two oligonucleotides involves formation of partially paired regions and their expansion. When two complex oligonucleotides approaching each other during hybridization the probability a nucleotide match in the initial complex is very low. In contrast when two oligonucleotides containing matching GT and AC repeats encounter each other it leads to the much faster nucleation and duplex formation. This explains faster binding kinetics of the probe to the template containing GT repeat compare to the conventional template and allows much shorter annealing time for the normalization primers and NGS library in a normalization PCR reaction.

Example 9. Normalization of 8 Accel-NGS 2S Libraries Using PCR-Based Normalization (N-PCR Primers)

Materials
  400 nM conventional PCR primer 1 (oligonucleotide 24)
  400 nM conventional PCR primer 2 (oligonucleotide 25)
  400 nM N-PCR primer 1 (oligonucleotide 26)
  400 nM N-PCR primer 2 (oligonucleotide 27)
  HapMap DNA NA12878 (Coriell)
  Accel-NGS® 2S PCR-Free DNA Library Kit (Swift Biosciences cat #DL-IL2PF-48, SI-ILM2S-48A)
  Q5® Hot Start High-Fidelity 2X Master Mix (NEB, cat #M0494S)
  Low TE buffer (Teknova cat #TO227)
  KAPA Library Quantification Kit (Kapa Biosystems cat #KK4824)

Methods

Figure 38A:
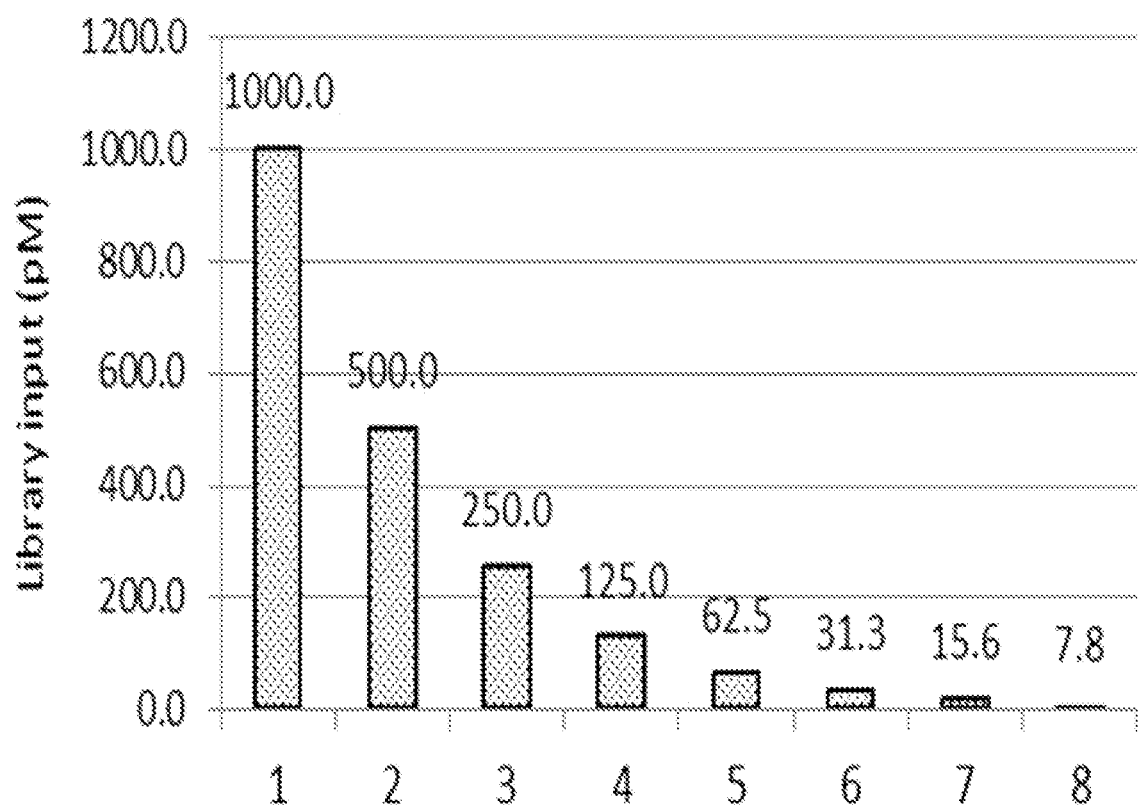
FIG. 38A depicts the library input concentration for libraries #1-7 in Example 9 for use with conventional primers.
Figure 38B:
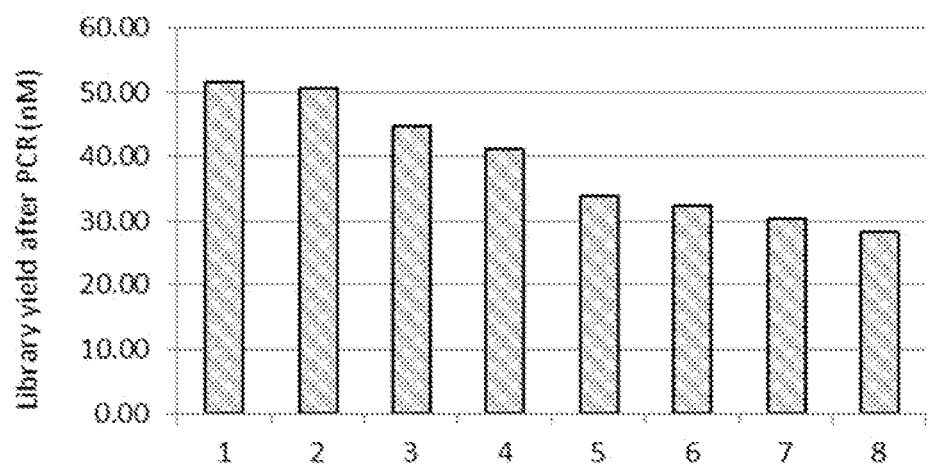
FIG. 38B depicts the yield of libraries #1-7 after PCR using conventional primers in Example 9.
Figure 38C:
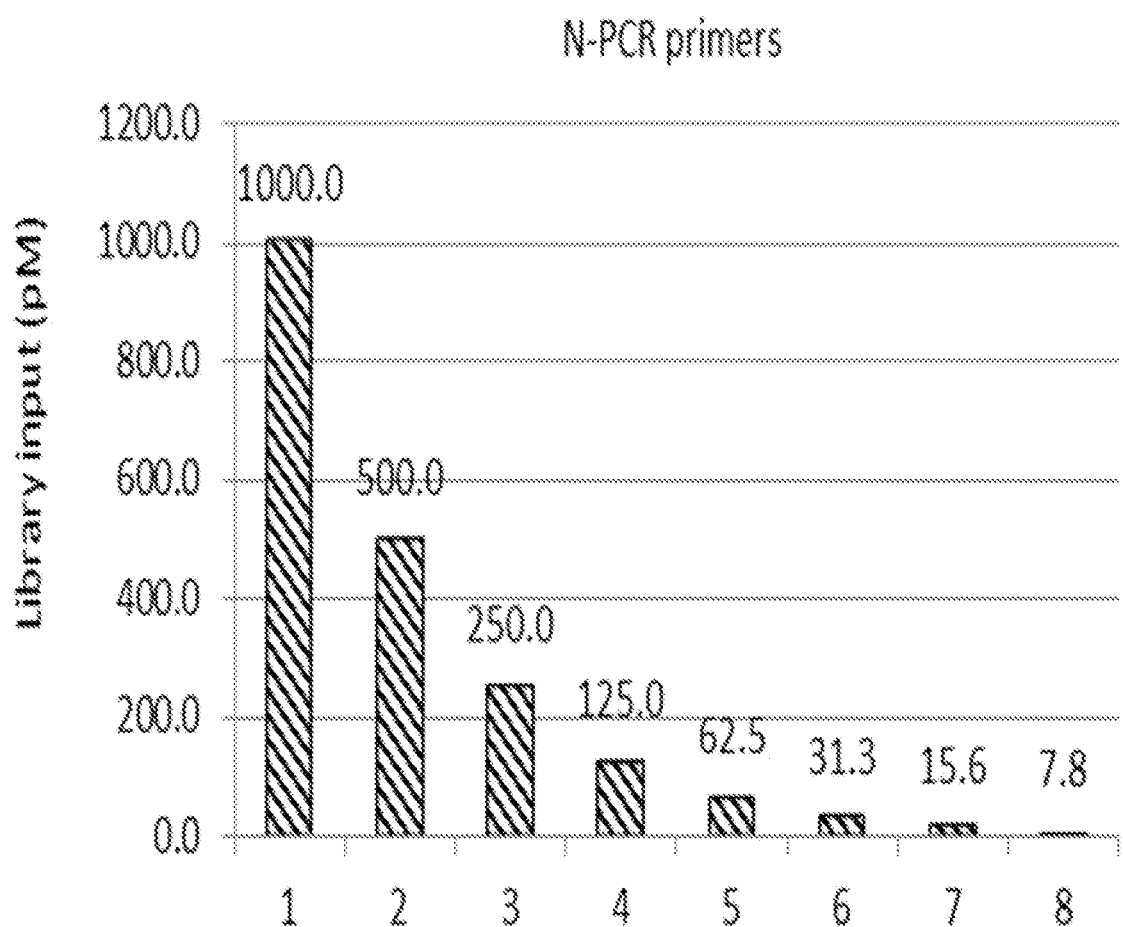
FIG. 38C depicts the library input concentration for libraries #1-7 in Example 9 for use with N-PCR primers.
Figure 38D:
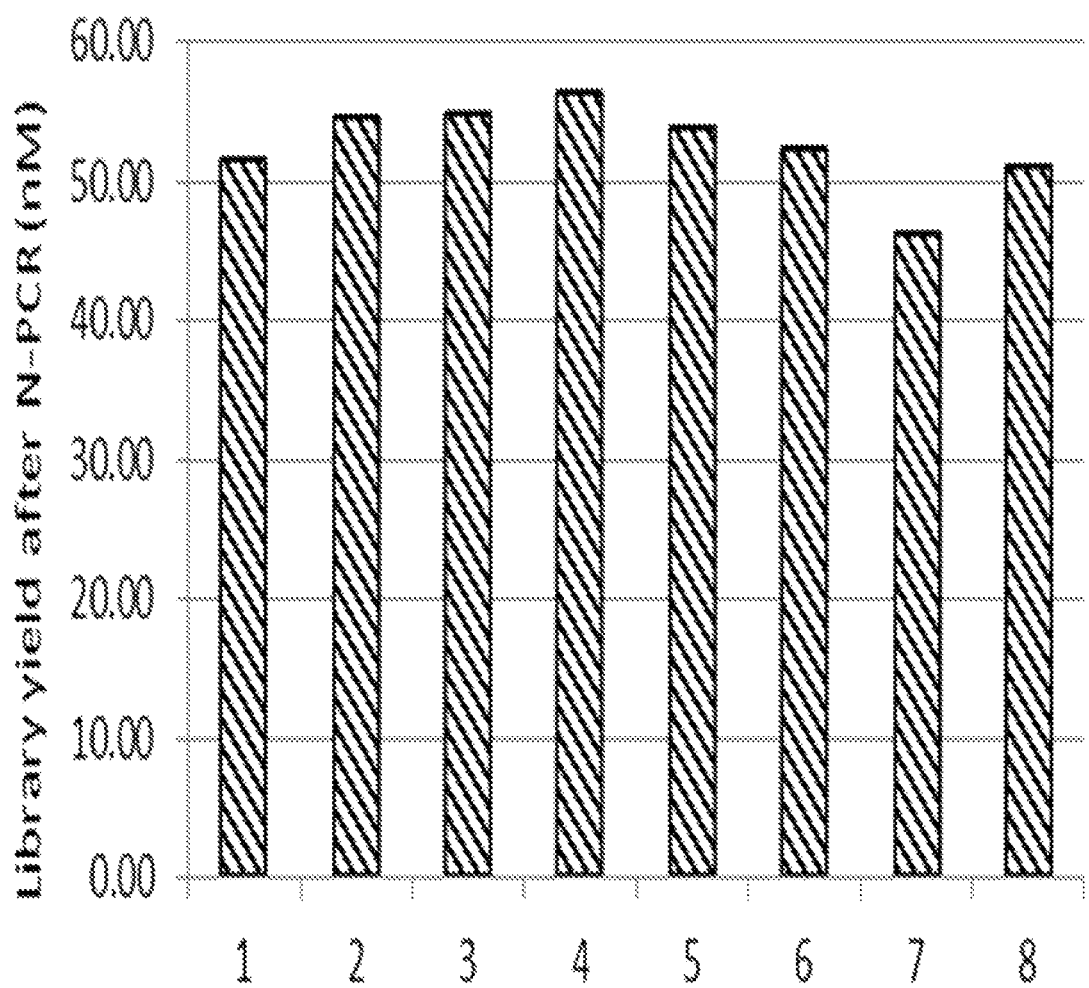
FIG. 38D depicts the yield of libraries #1-7 after N-PCR using N-PCR primers.
Figure 39A:
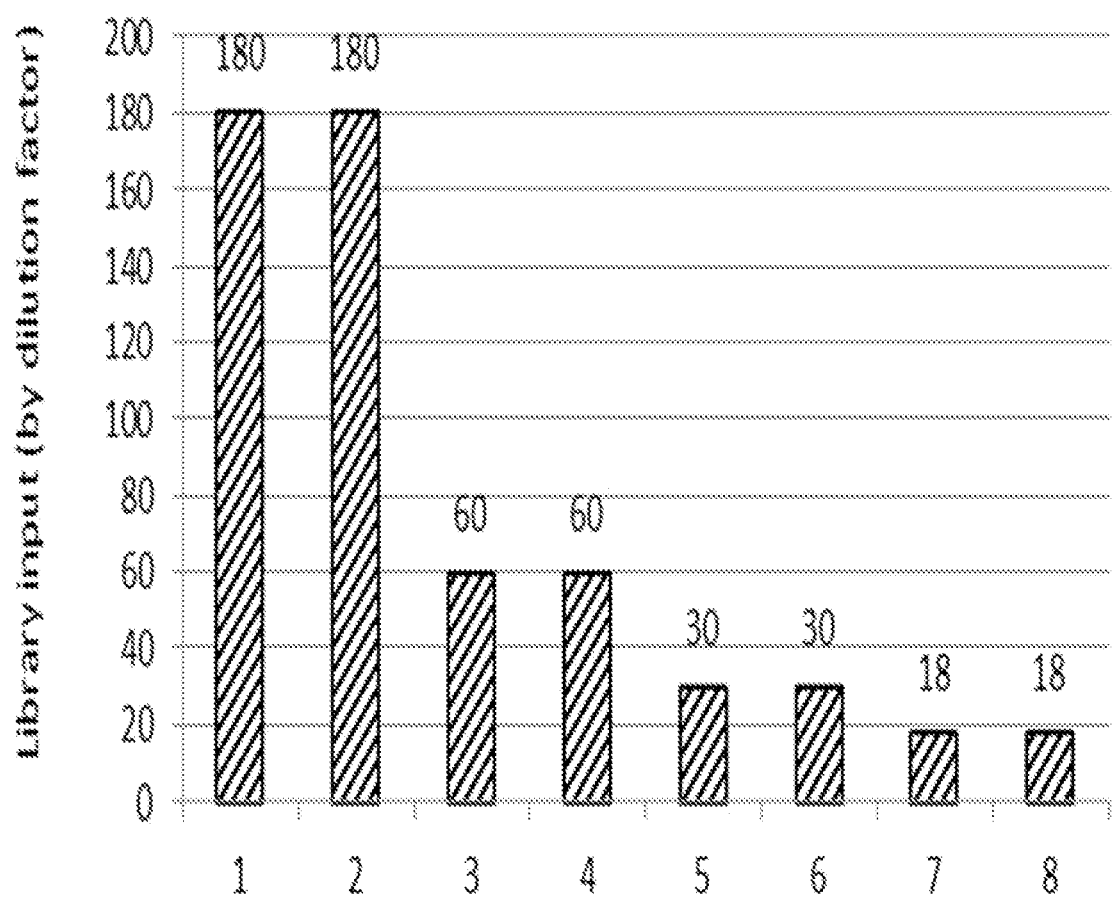
FIG. 39A depicts the library input concentration for libraries #1-8 in Example 10.
Figure 39B:
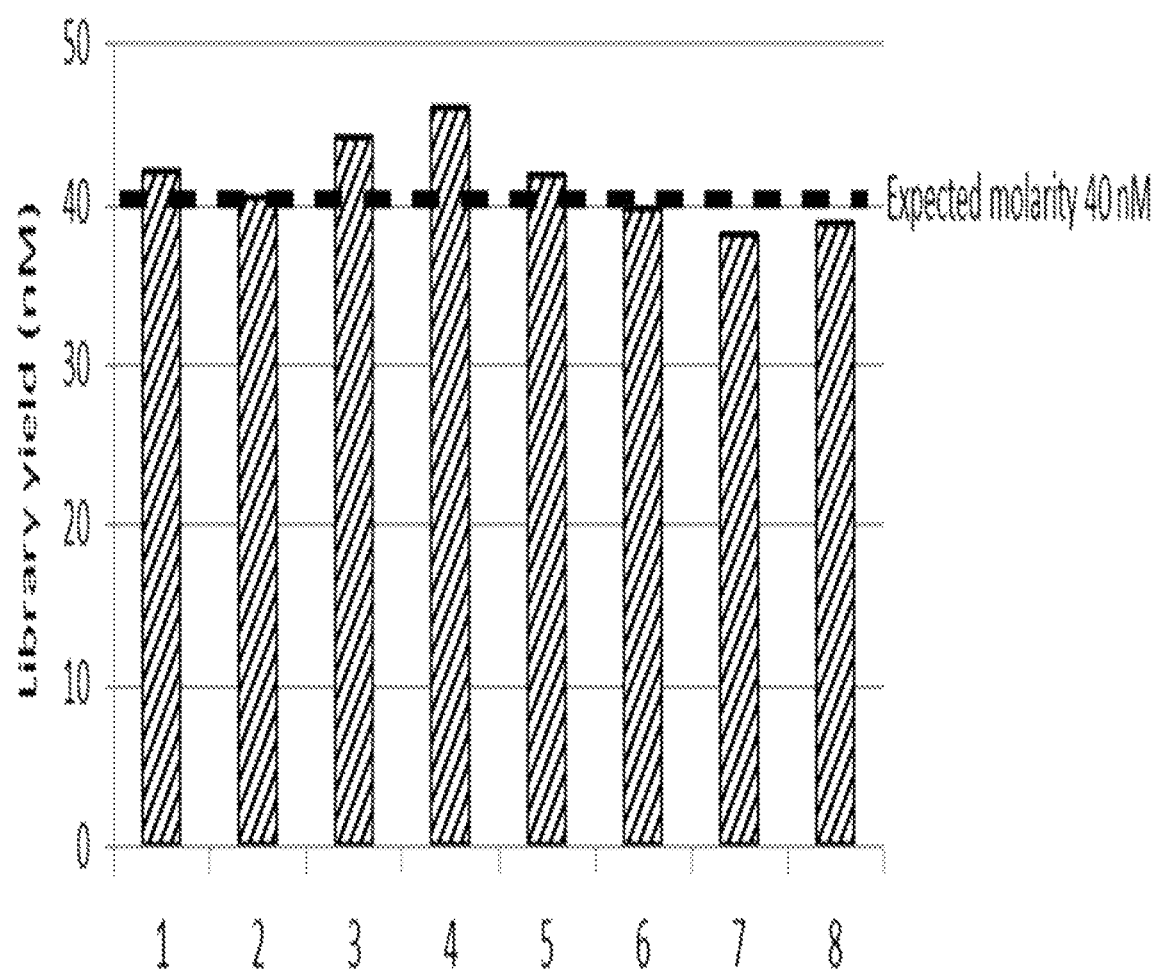
FIG. 39B depicts the yield of libraries #1-8 after N-PCR using N-PCR primers.
Figure 39C:
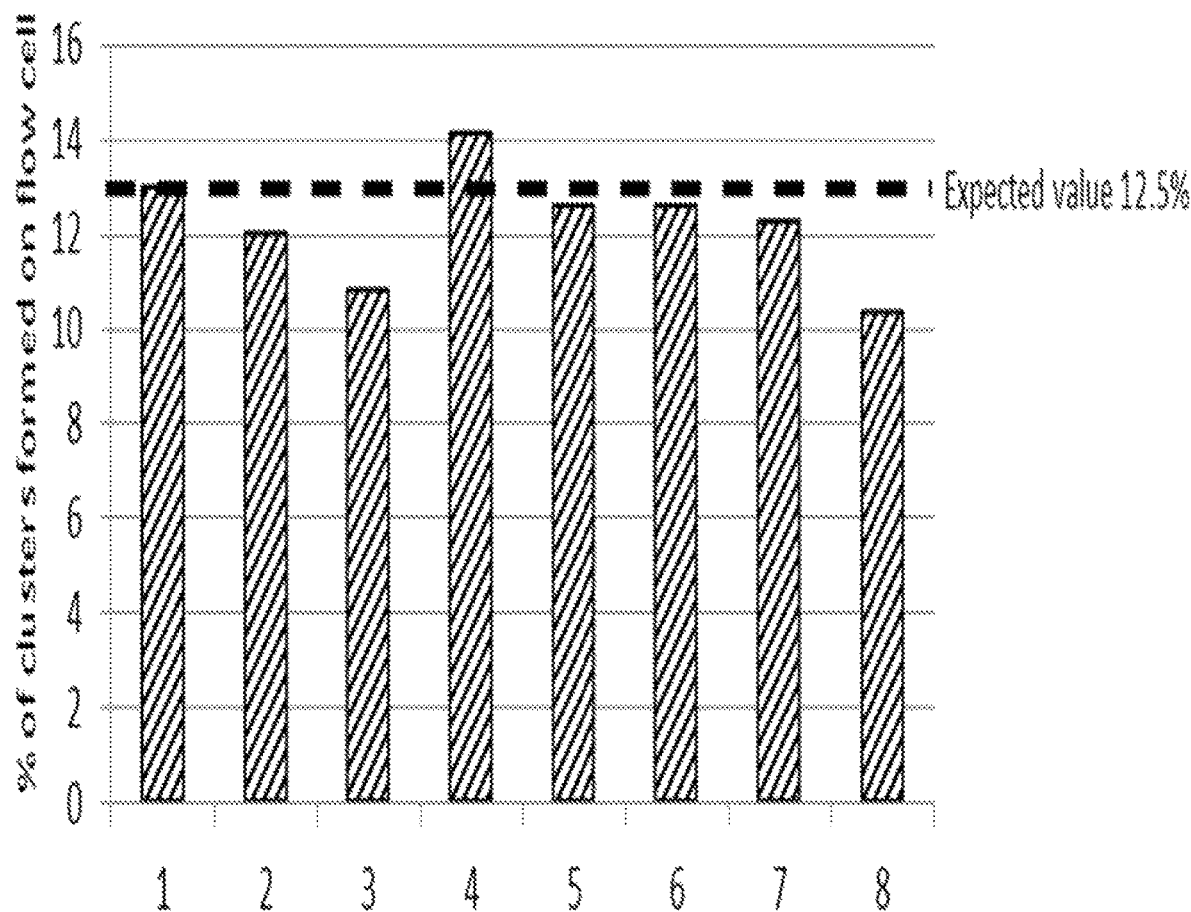
FIG. 39C depicts the % of clusters formed on the flow cell for libraries #1-8 from next-generation sequencing using the N-PCR normalized libraries.
Figure 40A:
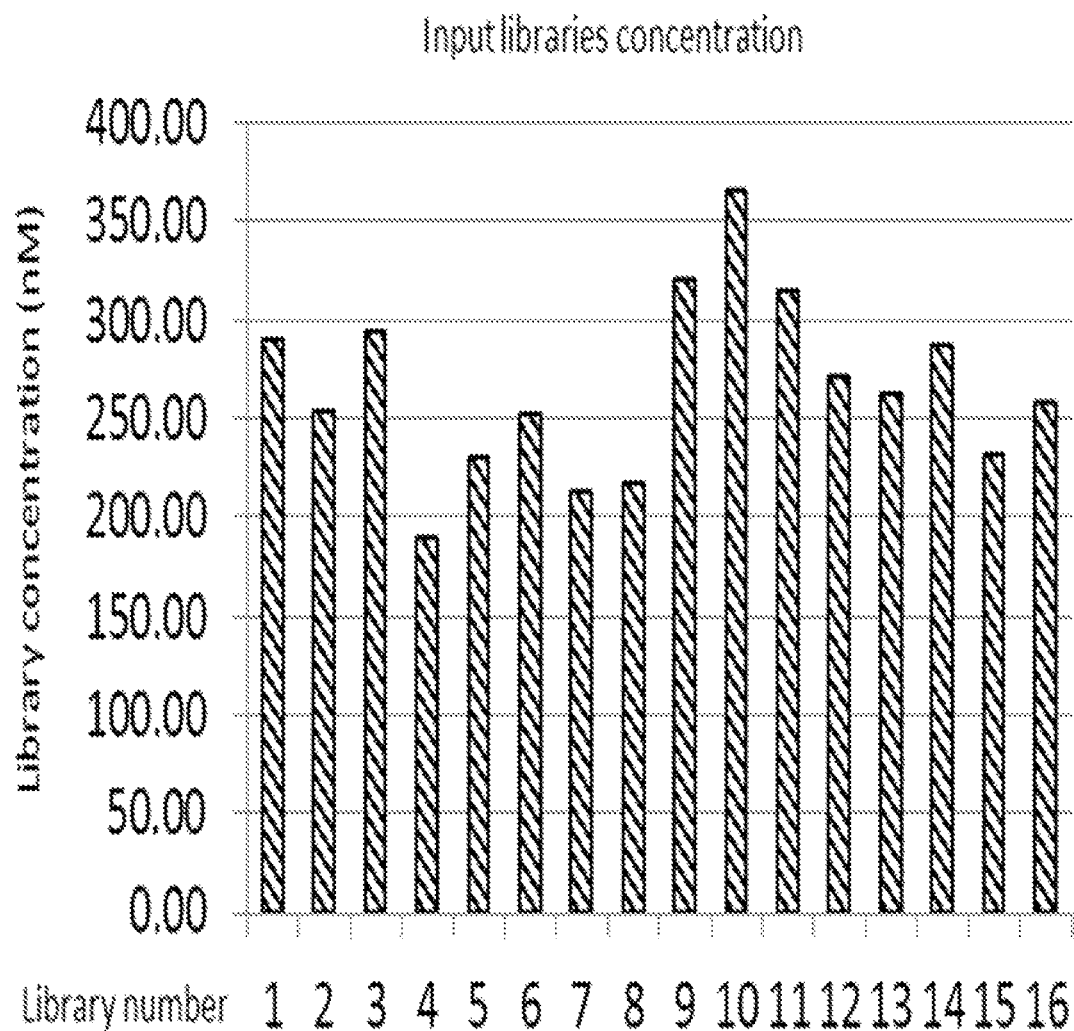
FIG. 40A depicts the library input concentration for libraries #1-16 in Example 11.
Figure 40B:
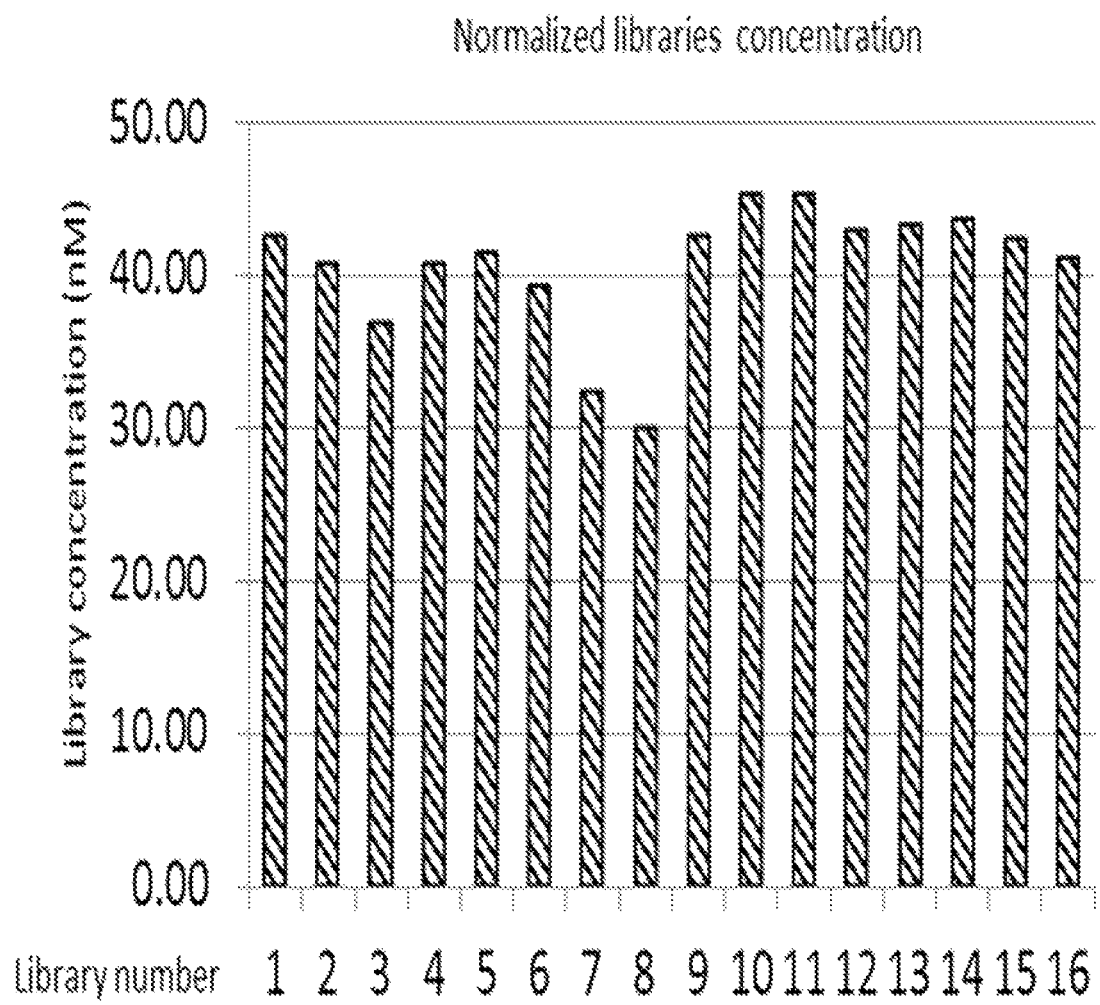
FIG. 40B depicts the normalized library concentration for libraries #1-16 in Example 11.
Figure 40C:
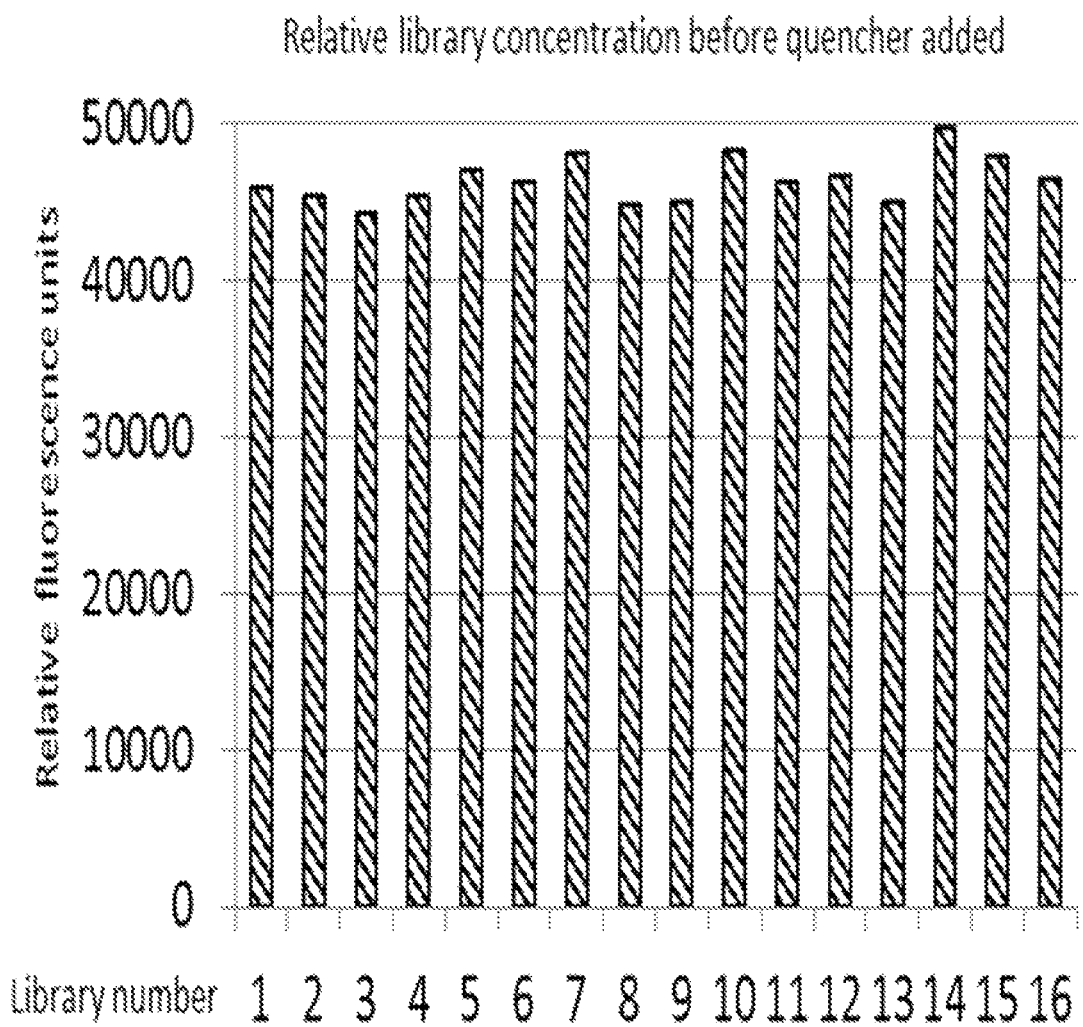
FIG. 40C depicts the relative library concentration before a quencher was added in Example 11.
Figure 40D:
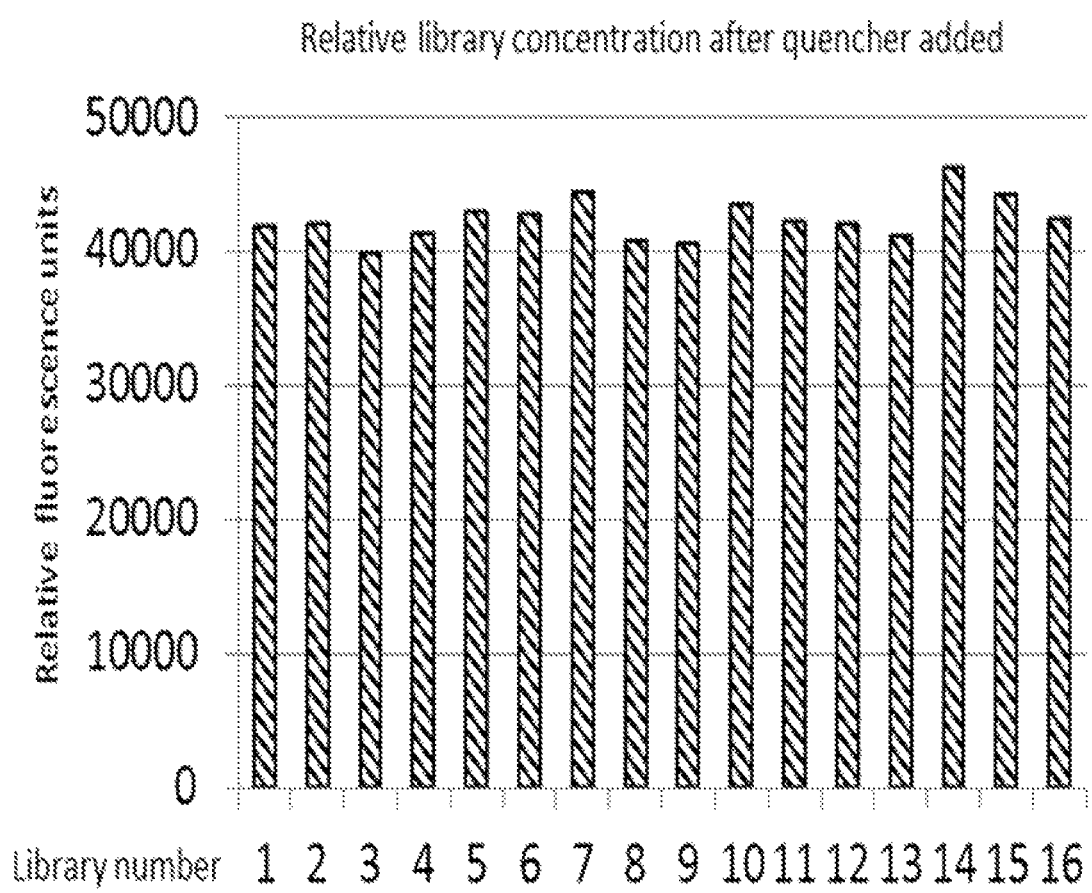
FIG. 40D depicts the relative library concentration after quencher was added in Example 11.

A sequencing library was constructed from 100 ng Coriell DNA NA12878 using Accel-NGS® 2S PCR-Free DNA Library Kit from Swift Biosciences. The library was eluted in 200 of low TE buffer and quantified using KAPA Library Quantification Kit and then a set of library dilutions of designated concentrations were prepared (FIGS. 38A-38B). To normalize the library dilutions to a 40 nM final concentration, libraries were subjected to normalization PCR reactions containing 150 of library dilutions, 250 of Q5® Hot Start High-Fidelity 2X Master Mix and 50 of each conventional or N-PCR primers (primer concentration at 40 nM). Libraries were amplified with the following cycling parameters: an initial enzyme activation at 98° C. for 45 sec and then 4 cycles consisting of 98° C. for 10 sec, 60° C. for 5 min, 72° C. for 1 min followed by 18 cycles consisting of 98° C. for 10 sec, 60° C. for 1 min, 72° C. for 1 min. Amplified libraries were quantified using KAPA Library Quantification Kit.

Results

Quantification results of the sequencing libraries before and after normalization are demonstrated on a FIGS. 38A-38D. The NGS DNA library was quantified and diluted with low TE buffer to create 150 aliquots of designated concentration between 1000 and 7.8 pM. Then each aliquot was subjected to the library normalization PCR as described above. All libraries amplified with N-PCR primers were successfully normalized to approximately the same concentration. In contrast, normalization amplification of the same samples with conventional primers demonstrates nearly 100% variation.

Conclusions

Normalization of 8 Accel-NGS 2S libraries using N-PCR Primers demonstrates ~10% relative deviation with 2S library inputs varying more than 100-fold. For the same samples, conventional primers showed almost 100% variation, demonstrating the advantage of using N-PCR primers over conventional primers for amplifying a specified quantity of PCR product when PCR primer concentration is limiting the PCR product yield in the reaction.

Example 10. Normalization of Accel-Amplicon Targeted NGS Libraries by PCR-Based Normalization (Using N-PCR Primers)

Materials
  400 nM N-PCR primer 1 (oligonucleotide 26)
  400 nM N-PCR primer 2 (oligonucleotide 27)
  HapMap DNA NA12878 (Coriell)
  Accel-Amplicon 56G Oncology Panel+Sample_ID (Swift Biosciences cat #AL-56248)
  Q5® Hot Start High-Fidelity 2X Master Mix (NEB, cat #M0494S)
  Low TE buffer (Teknova cat #TO227)
  KAPA Library Quantification Kit (Kapa Biosystems cat #KK4824)

Methods

An amplicon library was constructed from 10 ng Coriell DNA NA12878 using Accel-Amplicon 56G Oncology Panel Kit from Swift Biosciences according to manufacturer instructions. The library was eluted in 200 of low TE buffer and quantified using KAPA Library Quantification Kit and then a set of library dilutions of designated concentrations were prepared (FIG. 39). To normalize the library dilutions to a 40 nM final concentration, libraries were subjected to normalization PCR reactions containing 150 of library dilution, 250 of Q5® Hot Start High-Fidelity 2X Master Mix and 50 of each N-PCR primers (primer concentration at 40 nM). Libraries were amplified with the following cycling parameters: an initial enzyme activation at 98° C. for 45 sec and then 4 cycles consisting of 98° C. for 10 sec, 60° C. for 5 min, 72° C. for 1 min followed by 16 cycles consisting of 98° C. for 10 sec, 60° C. for 1 min, 72° C. for 1 min. Amplified libraries were quantified using KAPA Library Quantification Kit. Then libraries were diluted 10 fold, pooled together and sequenced on a MiSeq Sequencer (Illumina) at loading concentration 20 pM using MiSeq Reagent Nano Kit V2. The achievable % clusters formed on a flow cell for each library present in the pool was calculated using Illumina Sequencing Analysis Viewer software.

Results 56G amplicon libraries were constructed according to the kit protocol, quantified and diluted with low TE buffer by 180, 60, 30 and 18 fold. Then libraries were subjected to normalization PCR, quantification and sequencing as described above. As can be seen on FIGS. 39A-39C, all eight libraries were successfully normalized to the expected 40 nM concentration. Sequencing results also demonstrate predicted % of clusters formed on a flow cell for each library and equal to approximately 12.5%.

Conclusions

NGS library normalization that is PCR-based is a simple alternative to standard methods to streamline workflows in preparing libraries for loading a sequencer. The library yield that was achieved for each library was proportional to the N-PCR primer concentration, which generated a pool of libraries that demonstrated equal loading on an Illumina flowcell.

Example 11. Normalization of 16 Illumina Libraries Using N-PCR Primers Demonstrates Relative Quantification Accuracy Using qPCR Based and Fluorescent Based Quantification Methods Materials
- 400 nM fluorescently labeled N-PCR primer 1 (oligonucleotide 28)
- 400 nM N-PCR primer 2 (oligonucleotide 29)
- 200 nM quencher oligo (oligonucleotide 30)
- 16 Illumina libraries provided by collaborators
- Q5® Hot Start High-Fidelity 2X Master Mix (NEB, cat #M0494S)
- Low TE buffer (Teknova cat #TO227)
- KAPA Library Quantification Kit (Kapa Biosystems cat #KK4824)
- Synergy HTX multi-mode reader (BioTek)

Methods

Illumina libraries were quantified using KAPA Library Quantification Kit and diluted by 20 fold. To normalize the library dilutions to 40 nM final concentration libraries were subjected to normalization PCR reactions containing 20 of library dilutions, 250 of Q5® Hot Start High-Fidelity 2X Master Mix and 50 of each primer (final concentration 40 nM) and 130 of Low TE buffer. Libraries were amplified with the following cycling parameters: an initial enzyme activation at 98° C. for 45 sec and then 4 cycles consisting of 98° C. for 10 sec, 60° C. for 5 min, 72° C. for 1 min followed by 7 cycles consisting of 98° C. for 10 sec, 60° C. for 1 min, 72° C. for 1 min. Amplified libraries were quantified using KAPA Library Quantification Kit or Synergy HTX multi-mode reader.

Results

Quantification results of the normalized libraries by qPCR is demonstrated on the Example 11 results (FIGS. 40A-40D). As demonstrated at this figure all libraries amplified with N-PCR primers were successfully normalized to the approximately same concentration. More consistent relative quantification has been achieved by fluorometric assay with Synergy HTX multi-mode reader. Overall fluorescence levels dropped by approximately 10% when quenching oligonucleotide was added. This observation reflects the fact that not all of the normalization primers were utilized in normalization PCR reaction, where the 10% drop corresponds to about 10% unincorporated labeled primer.

Conclusions

The data demonstrated above shows that fluorometric assay utilizing fluorescently labeled primer in conjunction with quenching oligonucleotide can be a fast and reliable method for library quantification without the need to perform purification of the libraries from unutilized primers and without the needing information on library insert size to calculate molarity in case the library insert size is unknown or has a broad insert size distribution.

Example 12. Normalization of Illumina NGS Libraries by Synthesis that Involves Ligation of Normalization Adapter-Probe to a Library with a Truncated Adapter Sequence This example demonstrates the feasibility of NGS library normalization by synthesis method described in general terms on FIGS. 42E and 42G and shows that library normalization can be accomplished in a single enzymatic step by ligation of a specified molar amount of double-stranded or single-stranded normalization probe to a truncated NGS adapter at one end of a DNA library (T-library) to produce an equivalent amount of functional NGS library.

Materials
- Swift Biosciences Accel-NGS® 2S PCR-Free DNA Library Kit, cat #20024
- 6 μM primer P7 (oligonucleotide 31)
- 6 μM primer PT1 (oligonucleotide 32)
- 100 nM double stranded probe NT1 (formed by annealing of oligonucleotides 33 and 34)
- 6 μM primer PT2 (oligonucleotide 35)
- 100 nM single stranded probe NT2 (oligonucleotide 36)
- Q5® Hot Start High-Fidelity 2X Master Mix (NEB, cat #M0494S)
- T4 DNA ligase, 120,000 U/ml (Enzymatics cat #L6030-LC-L)
- 10× T4 DNA ligase buffer (Enzymatics cat #B6030L)
- Low TE buffer (Teknova cat #TO227)
- HapMap human DNA (Coriell Biorepository cat #NA12878)
- Invitrogen Qubit 2.0 Fluorimeter, cat #Q32866
- Qubit dsDNA BR Assay kit, cat #Q32853
- KAPA Library Quant Illumina kit, cat #KK4824
- SPRI select DNA size selection beads (BECKMAN COULTER cat #B23318)

Methods

An NGS library was prepared from human Coriell NA12878 DNA using Swift Biosciences Accel-NGS® 2S PCR-Free DNA Library Kit. The library was amplified by PCR using primer P7 and primer PT1 or primer PT2 as shown on FIGS. 43a and 43b. The PCR reaction was performed in 50 ul volume containing 25 ul of Q5 2× High-Fidelity master mix, 5 ul of oligonucleotide 31 (600 nM), 5 ul of oligonucleotide 32 (600 nM), 5 ul 2S NGS library diluted 1:500 and 10 ul of low TE (10 mM Tris, 0.1 mM EDTA). Amplification conditions were: 98° C.—45 sec, followed by 30 cycles at 98° C. for 10 sec and 66° C. for 1 min. After finishing the PCR reaction, the library was purified on SPRI beads using DNA: beads ratio 1.0, eluted in 500 of low TE DNA buffer and quantified using Invitrogen Qubit 2.0 Fluorimeter and Qubit dsDNA BR Assay complementary kit. Diluted truncated libraries (T-libraries) at 200 nM, 150 nM, 100 nM, 50 nM and 25 nM concentration were incubated with 120 units of T4 DNA ligase and 10 nM normalization N-probe in the T4 DNA ligase buffer for 1 h at 30° C. The T-libraries amplified with primer PT1 were incubated with double stranded normalization probe NT1, and the T-libraries amplified with primer PT2 were incubated with single stranded probe NT2. To measure the molarity of produced functional NGS libraries, the ligation products were quantified with KAPA qPCR-based Library Quant Illumina kit.

Results

Figure 43A:
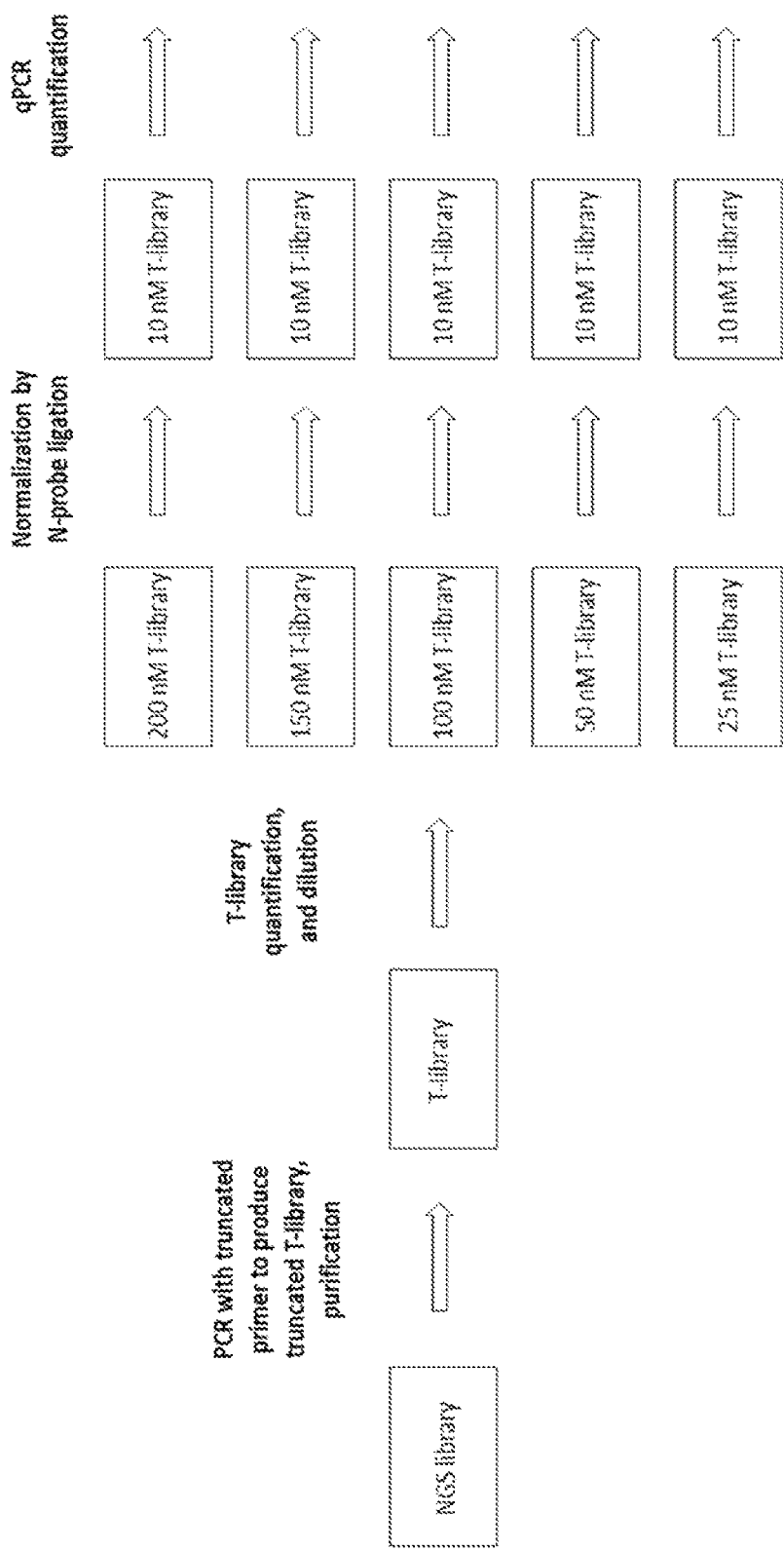
FIG. 43A depicts Example 12.
Figure 43B:
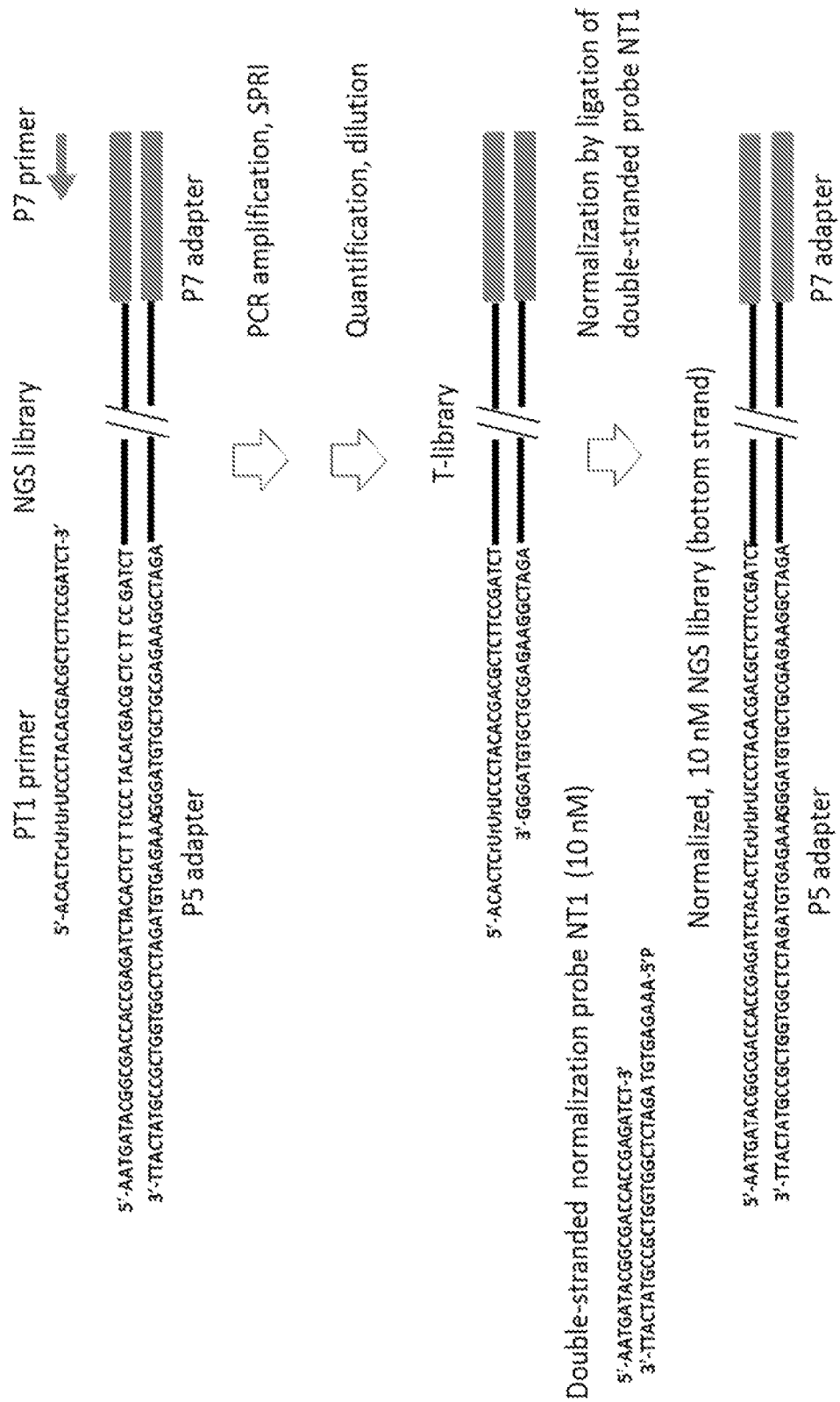
FIG. 43B depicts Example 12. Figure discloses SEQ ID NOS 32, 43, 102, 32, 103, 33, 34, 104, and 102, respectively, in order of appearance.
Figure 43C:
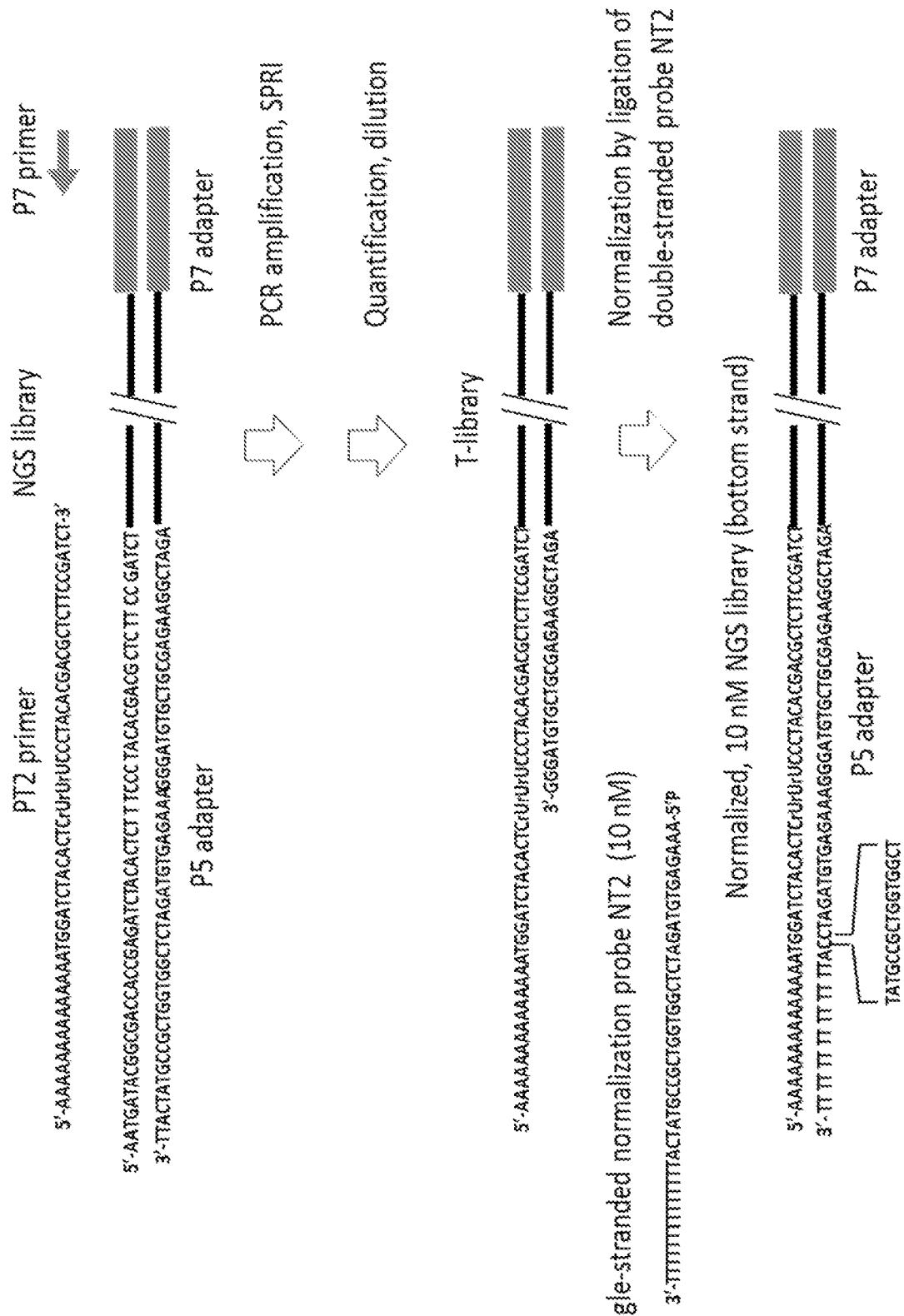
FIG. 43C depicts Example 12. Figure discloses SEQ ID NOS 105, 43, 102, 105, 103, 36, 105, 106, and 107, respectively, in order of appearance.
Figure 43D:
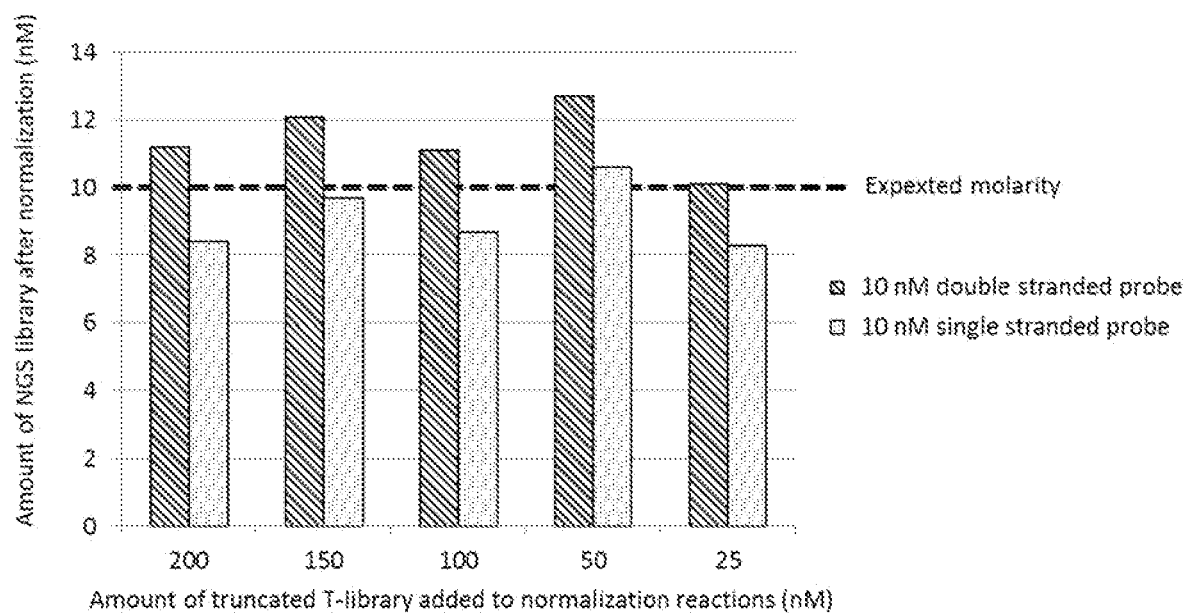
FIG. 43D depicts Example 12.

The experimental workflow is shown on FIG. 43a, while the normalization process and corresponding primer, adapter and probe sequences are presented on FIGS. 43b and 43c. Ligation of 10 nM double stranded normalization probe NT1 (FIG. 43b) or ligation of 10 nM single stranded probe NT2 (FIG. 43c) produces full size libraries where the truncated adapter (P5) becomes restored to its full length to become a functional NGS library. The completeness of library synthesis and normalization was assessed by qPCR quantification. As shown on FIG. 43d, the molar concentrations of produced libraries are at the expected 10 nM value within the accuracy of the quantification method used (~20%) despite the fact that the input amount of the T-library varied from 200 to 25 nM. Although the original library used in this study was a full size NGS library, it was diluted 500-fold and then amplified with the primer PT1 or PT2 to generate truncated T-library so the expected contribution of the original library to qPCR quantification is negligible.

Conclusions

The data presented provides evidence that NGS library normalization by controlled synthesis is simple and robust and can be used for library preparation prior to sequencing to replace time and labor consuming library quantification and concentration adjustment.

Example 13. Quantification of an NGS Library Normalized by Synthesis Using Fluorescent Dyes Specific to Double-Stranded DNA Fraction Library normalization method by synthesis presented in Example 12 and elsewhere in the current disclosure produces functional NGS library that is double-stranded and, in principle, can be stained with fluorescent dyes that are specific to double-stranded DNA. Unfortunately, the remaining non-functional library fraction is also double-stranded, can also be stained and, as a result, obscure quantification of the complete, functional library fraction.

Figure 44:
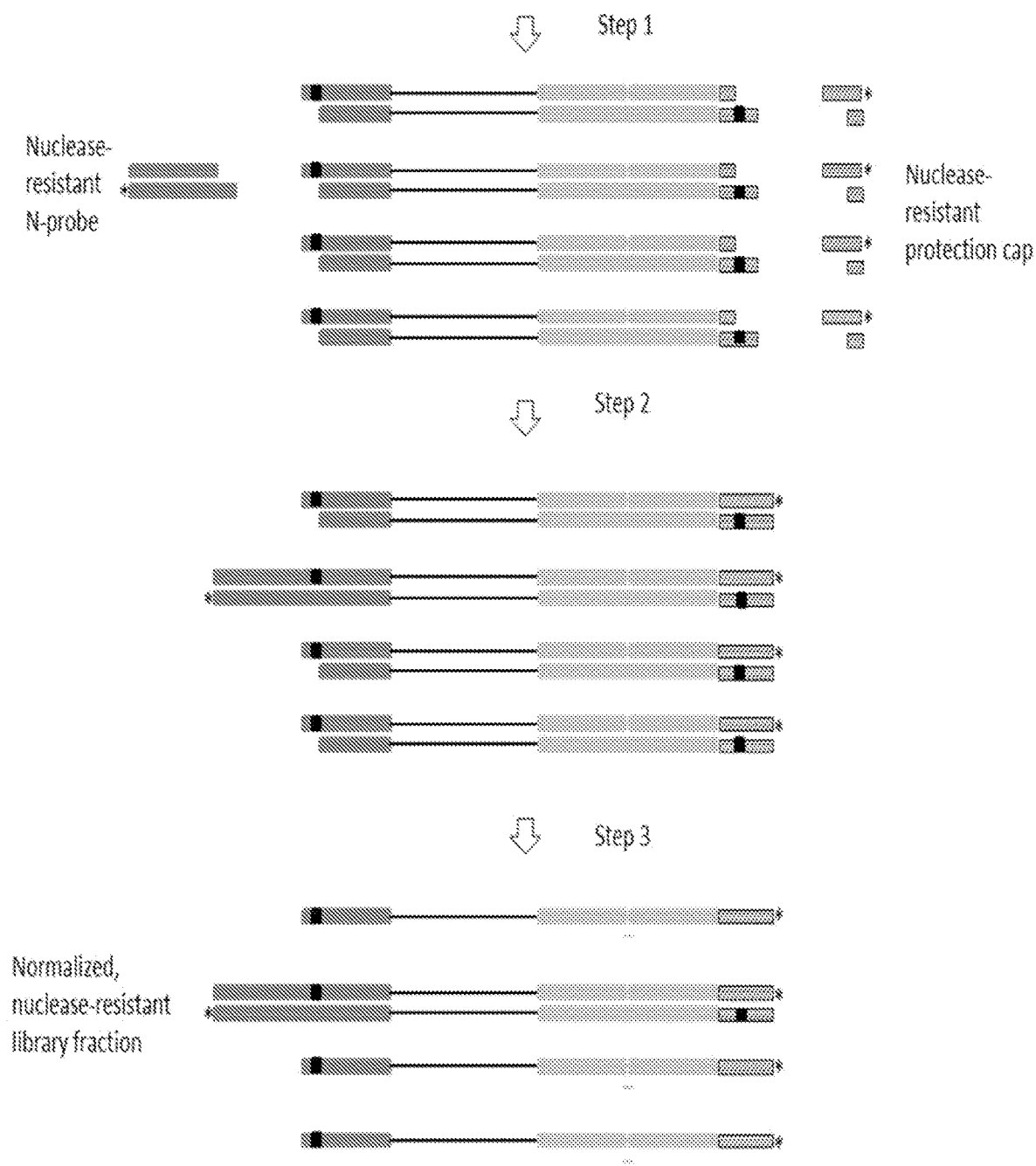
FIG. 44 depicts Example 13. Step 1: PCR amplification with primers both containing rU replication block. Step 2: Ligation of a specified amount of N-probe to recessed and excessive amount of protection cap to complete adapter end. Step 3: Incubation with exonuclease III to digest non-protected DNA strands.

This problem can be solved by library incubation with exonuclease III prior to quantification. Detailed description of this procedure is presented on FIG. 44. In the presented method, an NGS library that is truncated at one adapter end is amplified with PCR primers containing poly rU or poly rA replication blocks as described in other parts of the disclosure. In particular, one primer comprises the same truncated adapter sequence as in the PT1 primer from Example 12 while the P7 primer has an additional 5' tail with the poly(rU) or poly(rA) bases. PCR amplification with a high fidelity DNA polymerase such as Q5, PrimeSTAR GXL, or KAPA HiFi results in library molecules with a 5' overhang at both adapter ends. While the overhang sequence at the truncated P5 adapter end is dictated by the P5 adapter sequence, the overhang sequence at the full size P7 adapter end can be selected to have no complementarity for annealing to the normalization probe. In addition to the normalization probe which also has one or more nuclease-resistant bases at its 3' terminus (not involved in the ligation reaction), the normalization reaction mix also contains a protection cap molecule. The protection cap molecule is designed to have a 5' overhang complementary to the 5' overhang present at the P7 adapter end (created during PCR), be nuclease-resistant and present in a molar excess to provide protection against the exonuclease III to all P7 adapter ends. The cap is small and unlikely affects library performance during cluster formation and/or sequencing process on Illumina instruments.

The normalized library fraction containing nuclease-resistant bases at both 3' ends is resistant to exonuclease III treatment and remains double-stranded. On the other hand, all truncated library molecules that have nuclease-resistant bases at only one adapter end become converted into single-stranded form that is not detectable with double-strand-specific dyes like SYBR or Qubit. The presented protocol is not feasible in the absence of the protection cap molecule because all library molecules including the normalized fraction would be converted into the not-stainable, single-stranded form, in this case.

Example 14. Synthesis of Long Range Amplicon Libraries for Single-Molecule Sequencing Single-molecule sequencing is a very promising and quickly growing NGS sector that allows sequence analysis of very long DNA molecules. As in the case of Illumina and Ion Torrent sequencing platforms, single molecule sequencing also requires conversion of DNA fragments into a platform-specific NGS library carrying specialized adapter sequences at one or both ends. In the case of the Pacific Biosciences platform, the adapter is a single stem-loop at both ends, while in the case of the Oxford Nanopore platform it is a Y-shaped DNA structure with a covalently attached protein molecule. Frequently, the sequencing process involves multiplexed DNA samples and uses additional sample ID sequences (indices or barcodes) inserted between adapter and insert DNA sequences. Current methods of adapter and sample indexing are either time consuming and/or require several rounds of SPRI bead purification to remove non-attached adapter molecules. Here we propose a simple protocol that allows attachment of the stem-loop adapter sequence during PCR so only a nick-sealing or gap-filling reaction is necessary prior to sequencing (FIGS. 45-47). The gap-filling reaction can also be used to insert indexing sequences for multiplex applications. Stem-loop adapters can easily be converted into the Y-shaped adapters by cleaving the loop by modification-specific endonuclease.

Materials

6 µM primer (oligonucleotide 37)
6 µM primer (oligonucleotide 38)
10 µM linear universal primer (oligonucleotide 39)
10 µM stem-loop universal primer (oligonucleotide 40)
1 uM stem-loop adapter (oligonucleotide 41) 1 uM indexing linker (oligonucleotide 42)
E. Coli Migula genomic DNA (ATCC, cat #MG1655)
SPRI select DNA size selection beads (BECKMAN COULTER, cat #B23318)
T4 DNA ligase, 120,000 U/ml (Enzymatics, cat #L6030-LC-L)
10× T4 DNA ligase buffer (Enzymatics, cat #B6030L)
Low TE buffer (Teknova, cat #TO227)
Exonuclease III, 100,000 U/ml (Enzymatics, cat #X8020F)
Exonuclease VII, 10,000 U/ml (NEB cat #M0263S)
Q5® Hot Start High-Fidelity 2× Master Mix (NEB, cat #M0494S)
2100 BioAnalyzer (Agilent, cat #G2939BA)
High sensitivity DNA chip (Agilent, cat #5067-4626)

Methods

A primary E. coli amplicon was produced by PCR reaction using tailed primers (oligonucleotides 37 and 38 in 50 ul volume containing 25 ul of Q5 2× High-Fidelity master mix, 5 ul of oligo 37, 5 ul of oligo 38, 5 ul of E. coli DNA stock and 10 ul of low TE buffer. Amplification conditions were: 98° C.—45 sec, followed by 26 cycles at 98° C. for 10 sec and 66° C. for 1 min. After finishing the PCR reaction, the library was purified on SPRI beads using DNA: beads ratio 1.2 and eluted in 500 of low TE buffer.

The primary amplicon product was re-amplified with either universal linear primer (oligonucleotide 39) or universal stem-loop primer (oligonucleotide 40) at the following condition: 5 ul of the amplicon DNA from first PCR reaction diluted 100-fold, 25 ul of Q5 2× High-Fidelity master mix, 5 ul of universal primer and 15 ul of low TE buffer, with the final volume 50 ul. Amplification conditions were: 98° C.—45 sec, followed by 30 cycles at 98° C. for 10 sec and 66° C. for 1 min. PCR products were purified on SPRI beads using DNA: beads ratio 1.2 and eluted in 200 of low TE buffer.

The adapter attachment and gap-filling reactions (linear universal primer, FIG. 45a) or just gap-filling reaction (stem-loop universal primer, FIG. 45b) were performed by incubating the PCR product of linear universal primer with the stem-loop adapter (oligonucleotide 41) and indexing linker oligonucleotide (oligonucleotide 42), and the PCR product of stem-loop universal primer with the indexing linker oligonucleotide (oligonucleotide 42) with T4 DNA ligase at following conditions: 3 ul of PCR product, 5 ul of oligonucleotide 41, 10 ul of oligonucleotide 42, 4 ul of 10× T4 ligation buffer, 2 ul of T4 ligase and low TE buffer in total reaction volume 40 ul. Ligation reactions were performed at 30° C. for 30 min, and then half of the reaction was treated with Exonuclease III/Exonuclease VII mix for additional 15 min. After exonuclease treatment, reactions were purified on SPRI beads using library: beads ratio 1.2 and resolved on the Agilent 2100 Bioanalyzer using High Sensitivity DNA chip.

Results

Figure 45B:
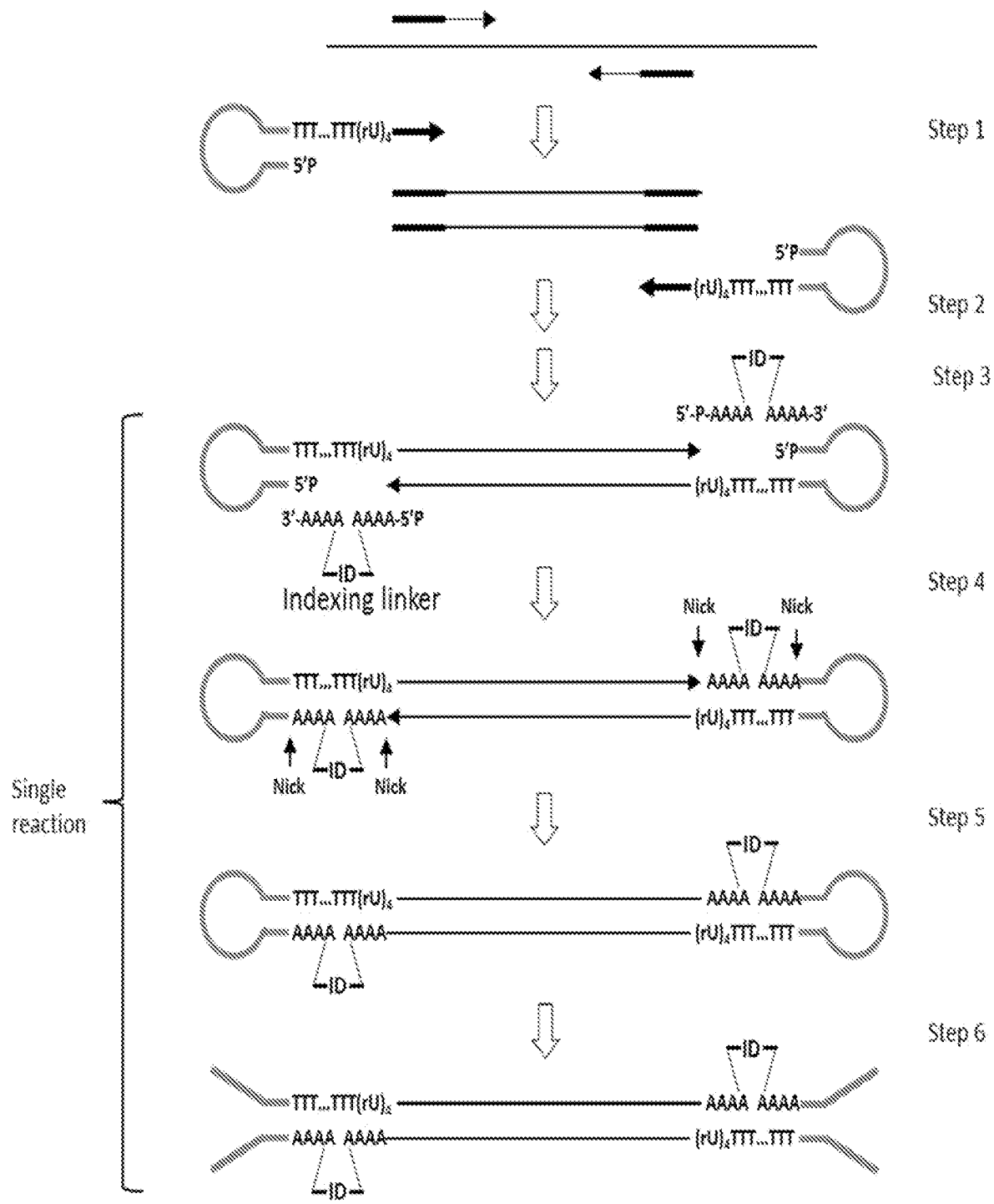
FIG. 45B depicts Example 14. Step 1: 1st PCR (multiplex). Step 2: 2nd PCR with a high fidelity DNA polymerase and universal stem-loop primer containing non-replicable poly (rU) linker creates a dumbbell DNA structure with single-stranded gap region. Step 3: SPRI removes non-incorporated primers. Step 4: Linker molecule containing indexing sequence ID and polyA tails at both ends anneals to the gap regions on both DNA strands. Step 5: T4 DNA ligase seal the nicks. Step 6: Endonuclease cleaves the loop (optional for use on Qxford Nanopore sequencing platform).

Use of linear (FIG. 45a) or stem-loop (FIG. 45b) universal primer containing (ribo U)$_4$ replication block during second PCR reaction creates DNA molecules with either the single-stranded 5' overhang containing sequence (GT)$_6$(T)$_{22}$(rU)$_4$ (SEQ ID NO: 61) (FIG. 45a) or the stem-loop overhang and single-stranded gap region containing sequence (T)$_{22}$(rU)$_4$ (SEQ ID NO: 62) (FIG. 45b). The single-stranded tail, in the first case, and single-stranded gap, in the second case, become the templates for annealing and ligation of the stem-loop adapter and indexing linker (first case) or just indexing linker (second case).

Figure 45C:
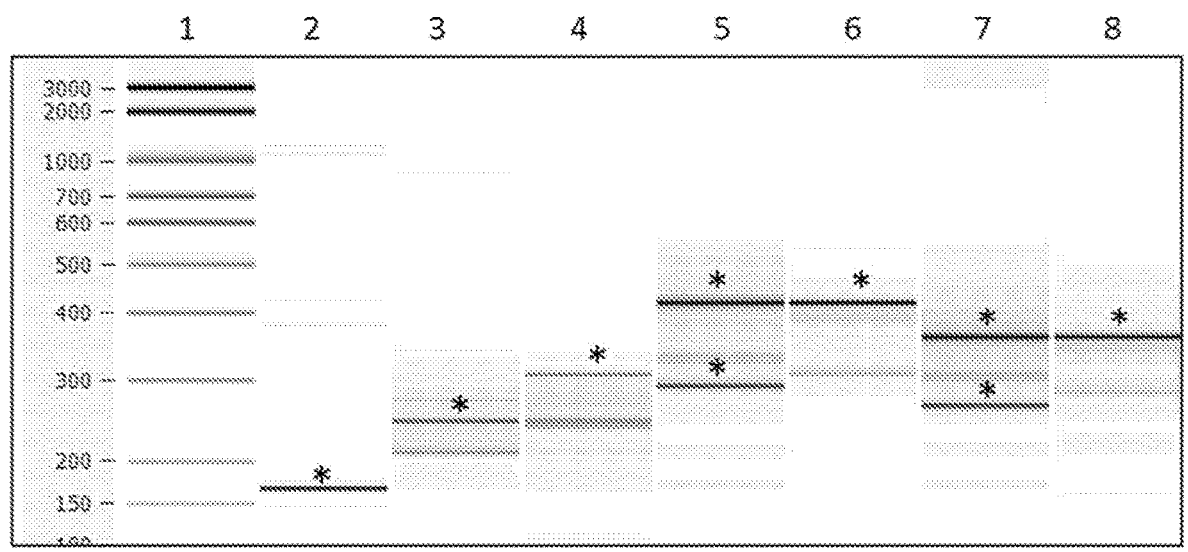
FIG. 45C depicts Example 14.

Bioanalyzer data is presented on FIG. 45c show that both the product of adapter/linker ligation after PCR with linear primer (lane 5) and the product of linker ligation after PCR with stem-loop primer (lane 7) have resistance to the combined exonuclease III/exonyclease VII treatment (lanes 6 and 8, correspondingly) that is indicative of the expected dumbbell structure at the library ends. The data show that more than 50% of PCR amplicons become converted into exonuclease-resistant molecules. Lanes 1, 2, 3 and 4 show DNA ladder, product of the first PCR reaction and the two products of the second PCR reactions described above, respectively.

Conclusions

The data presented describes a new highly efficient method for preparation of amplicon libraries with stem-loop adapters at both ends. The method also includes an efficient way of incorporation of sample ID sequences by including ID sequences into the linker oligonucleotide so it does not require synthesis of long barcoded adapter oligonucleotides. The stem-loop primer method can be applied without any limitations to generate amplicon libraries with Y-shaped adapters at the end by introducing a modified, cleavable base (such as dU, RNA, deoxyinosine, methylated cytosine, etc.) into the loop region of the PCR primer and cleaving the base by a modification-specific endonuclease (such as USER enzyme mix, RNase, endonuclease V, methylation-specific endonuclease, etc.). Such cleavage can be combined with an indexing/barcoding linker ligation step to limit the whole process to a single incubation reaction.

Figure 46A:
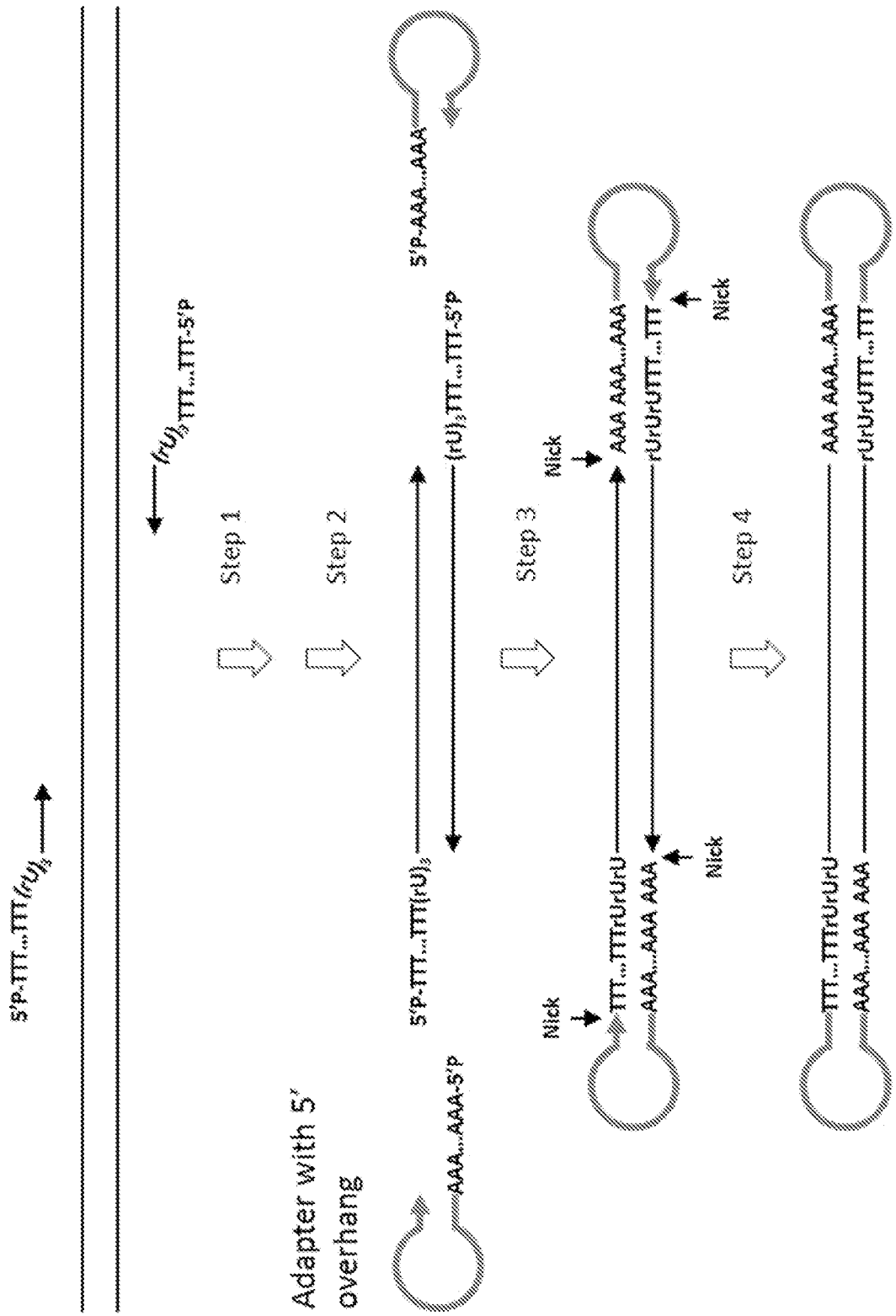
FIG. 46A depicts Example 14. Step 1: PCR with a high fidelity DNA polymerase and primers containing poly T 5' tail linked to the target specific portion through the non-replicable poly(rU) linker. Step 2: SPRI removes non-incorporated primers. Step 3: Stem-loop adapter anneals to the 5' end of DNA. Step 4: T4 DNA ligase seal the nicks.
Figure 46B:
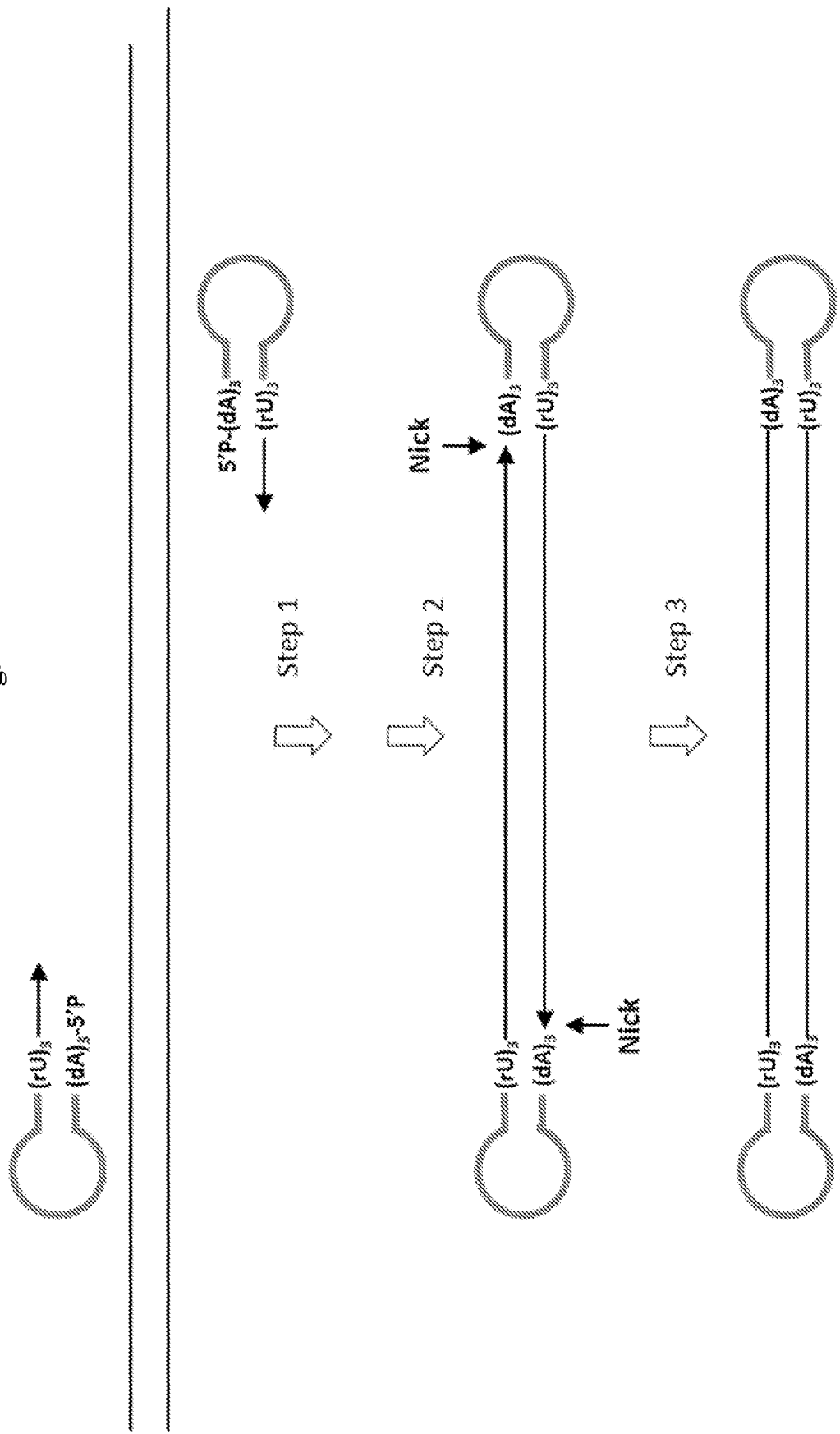
FIG. 46B depicts Example 14. Step 1: PCR with a high fidelity DNA polymerase and stem-loop primers containing non-replicable poly(rU) linker creates a dumbbell DNA structure with 2 nicks. Step 2: SPRI removes non-incorporated primers. Step 3: T4 DNA ligase seal the nicks.
Figure 47A:
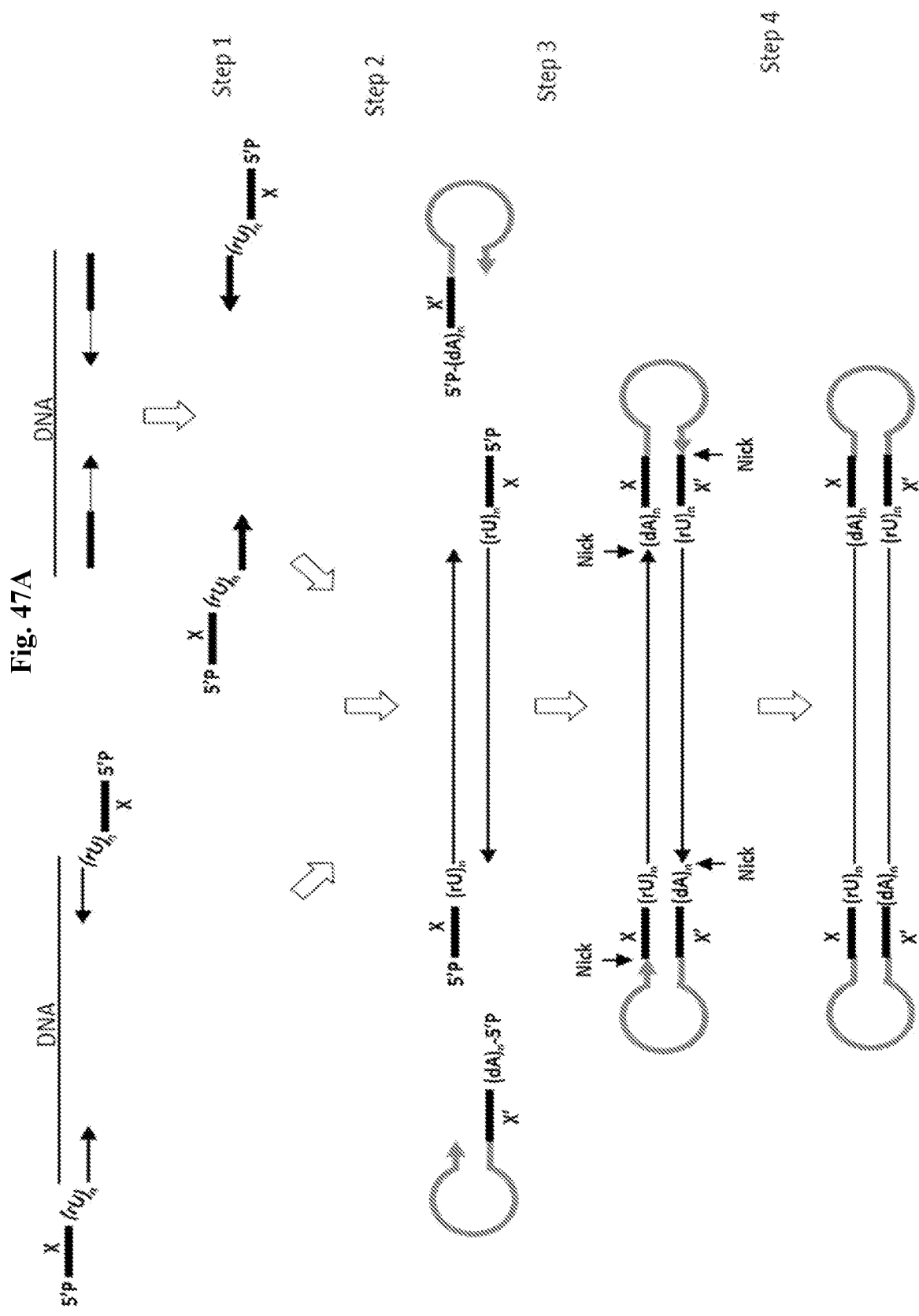
FIG. 47A depicts Example 14. Step 1: No PCR or 1st PCR with target specific tailed primers; 1st PCR with target-specific primers or 2nd PCR with universal primers containing 5' tail X linked to the target-specific or universal portion through non-replicable linker containing 3 or more rU bases. Step 2: SPRI removes non-incorporated primers. Step 3: Annealing of the stem-loop adapter with tail X' at the 5' end that is complementary to the primer tail X. Step 4: Ligation by T4 DNA ligase.

The method presented in example 14 is not limited to linker oligonucleotide ligation to make a covalently closed DNA structure, as shown on FIGS. 46a and 46b. The method prefers but is not limited to use of a homopolymer or/and dinucleotide repeat sequence at the 5' overhang to achieve stem-loop or Y-shaped adapter attachment as shown on FIG. 47a where the 5' overhang sequence X can be any DNA sequence. According to the data presented in this disclosure, rU and rA stretches of three or more bases provide best replication termination when used in combination with high fidelity DNA polymerases. On the other hand, three or more rG bases provide a termination of replication for Taq DNA polymerase.

Figure 47B:
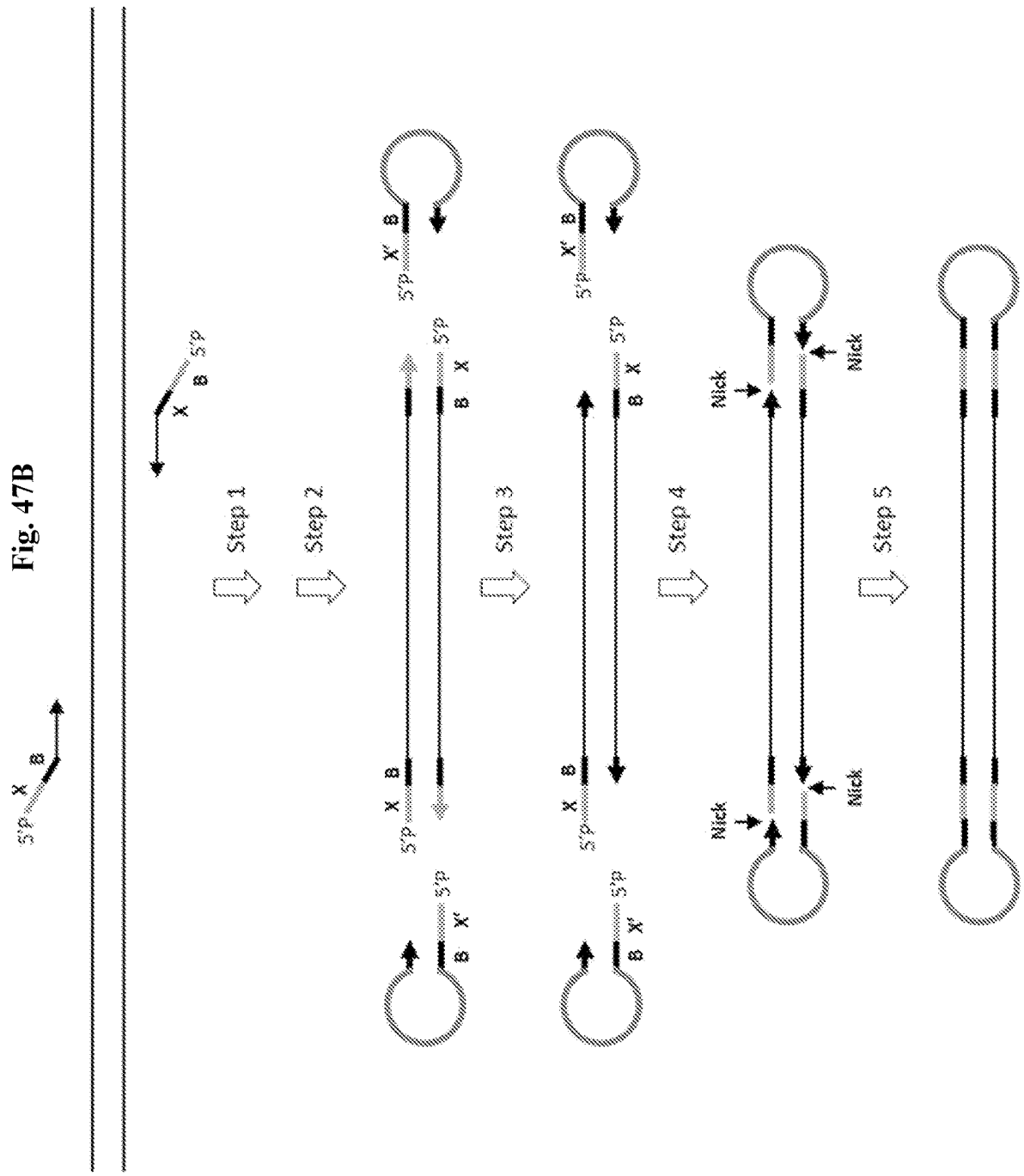
FIG. 47B depicts Example 14. Step 1: PCR with primers containing a reduced complexity tail sequence X with the adjacent buffer region B containing bases that are not present in the tail. Step 2: SPRI purification removes non-incorporated primers, nucleotides and polymerase. Step 3: Adapter, T4 DNA ligase, reaction buffer, and nucleotide triphosphates that are absent in the 3' amplicon tail sequence but present in the adjacent buffer sequence are added. T4 DNA polymerase in the presence of nucleotides present in the buffer region but absent in the tail region generates a 5' overhang X at the ends of the PCR amplicon. Step 4: Due to the presence of a similar buffer region B within the stem region the adapter integrity remains unaffected by T4 DNA polymerase. Adapter anneals by its single-stranded 5' end (sequence X') to the complementary overhang (sequence X) created at the ends of PCR amplicon by T4 DNA polymerase. Step 5: T4 DNA ligase seals the nicks.

Stem-loop adapter attachment can also utilize 5' overhangs created by T4 DNA polymerase as shown in FIG. 47b. In this case PCR primers produce amplicons and incorporate tails that contain two different DNA sequences: a reduced complexity sequence X and buffer sequence B that contains bases that are not present in the X region. For example, sequence X is a homopolymer AAA . . . AAA, and sequence B contains only G and C bases. In the presence of T4 DNA polymerase and restricted nucleotide mix containing buffer nucleotides (for example, dGTP and dCTP), but not bases complementary to region X (dTTP), the ends of PCR amplicon will be trimmed to produce X overhangs (polyA tails). A stem-loop adapter with sequence X' that is complementary to tail sequence X can be ligated after heat inactivation of the T4 DNA ligase. Alternatively, the ligation reaction can be combined with T4 DNA polymerase trimming reaction in the case when the stem-loop adapter has buffer sequence B with similar base composition but not necessarily the same sequence. The buffer region prevents the stem-loop adapter from T4 DNA polymerase-mediated exonuclease digestion the same way it works for the amplicon ends.

Example 15. Oligomerization of Long Range Amplicons for More Efficient Single-Molecule (Pacific Biosciences and Oxford Nanopore) Sequencing Methods developed for single molecule sequencing such as the Pacific Biosciences method that uses continuous detection of fluorescent bases incorporated into DNA during a primer extension reaction catalyzed by immobilized Phi29 DNA polymerase, or the Oxford Nanopore method that detects sequence-specific electric current fluctuations during DNA propagation through a nanopore, are able to sequence very long DNA sequences up to 50 (PacBio) or even 800 (ONT) kilobases. When substantially shorter DNA molecules are analyzed by such instruments, the efficiency of their utilization drops significantly. To overcome this problem, DNA molecules can be ligated into longer concatemer structures. DNA oligomerization can be also used to overcome size bias in chip loading that is prominent for PacBio instruments. Different loading efficiency for short and long DNA molecules makes expression analysis of cDNA molecules which size distribution varies from 1 to 10 kb (with a peak at about 2 kb) generates significant size bias if co-sequenced.

Figure 48A:
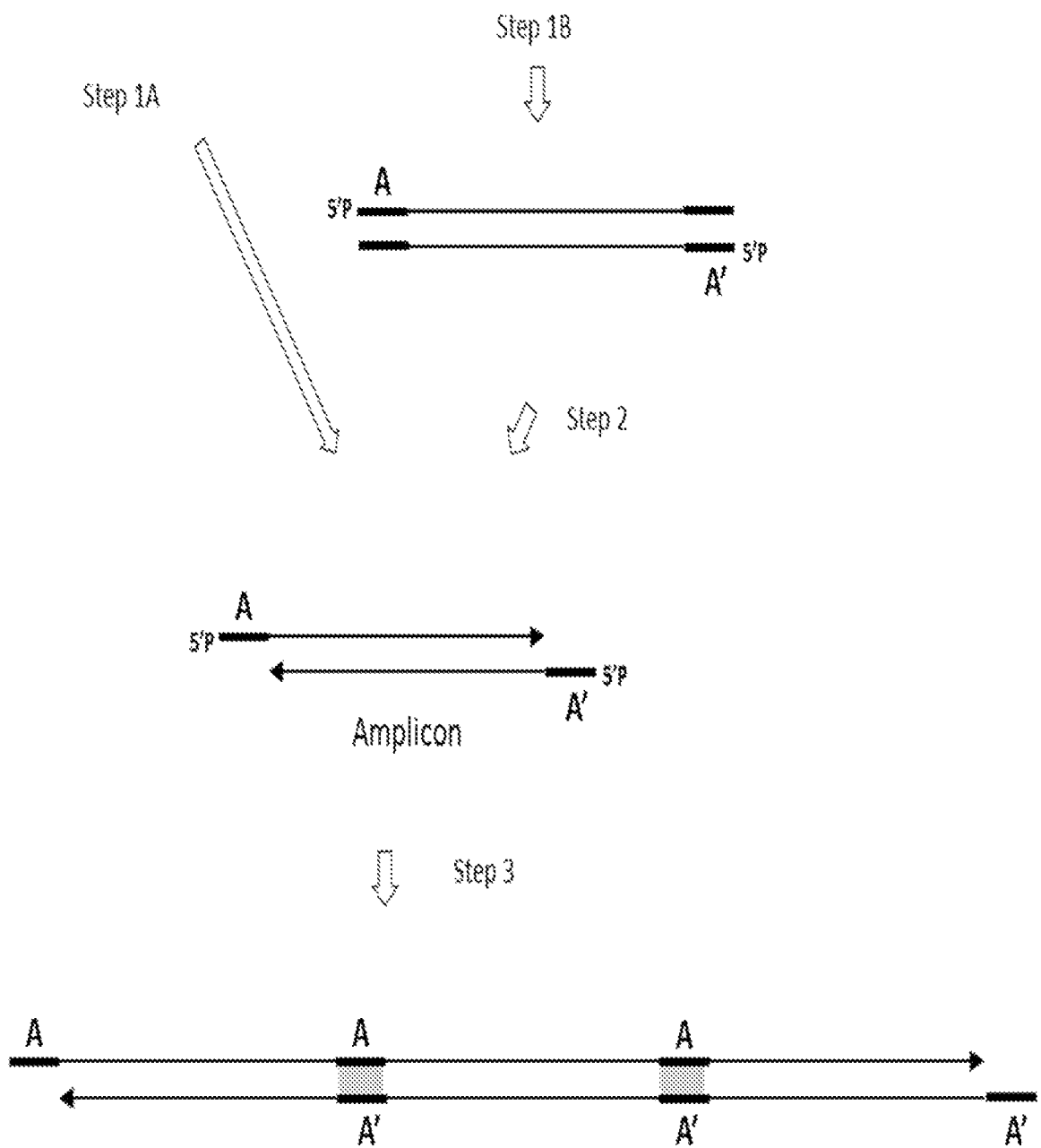
FIG. 48A depicts Example 15. Step 1A: PCR with primers containing tail sequences A and B with $(rU)_n$ and/or $(rA)_n$ replication block (not shown). Step 1B: PCR with primers containing a reduced complexity and complementary tail sequences A and A' with the adjacent buffer region containing bases that are not present in the tail (not shown). Step 2: Incubation with T4 DNA polymerase in the presence of nucleotides present in the buffer region but absent in the tail region. Step 3: Ligation reaction.
Figure 48C:
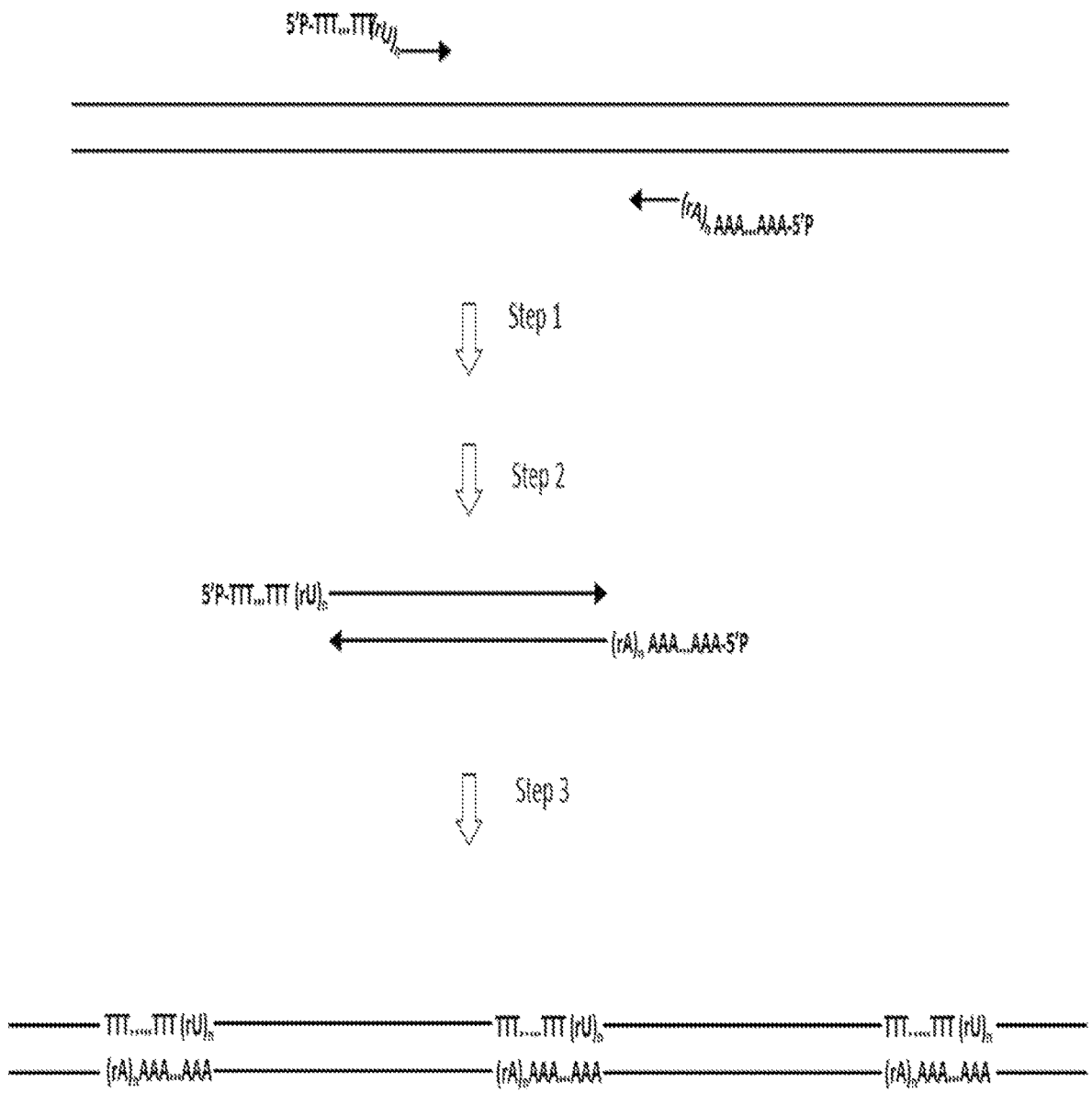
FIG. 48C depicts Example 15. Step 1: PCR with primers containing tail sequences $(T)_m$ and $(A)_m$ with the adjacent (ribo $U)_n$ and poly(ribo $A)_n$ replication blocks. Step 2: SPRI purification removes non-incorporated primers. Step 3: At high amplicon concentration amplicon ends anneals to each other and form oligomers that become covalently linked by a DNA ligase.
Figure 48D:
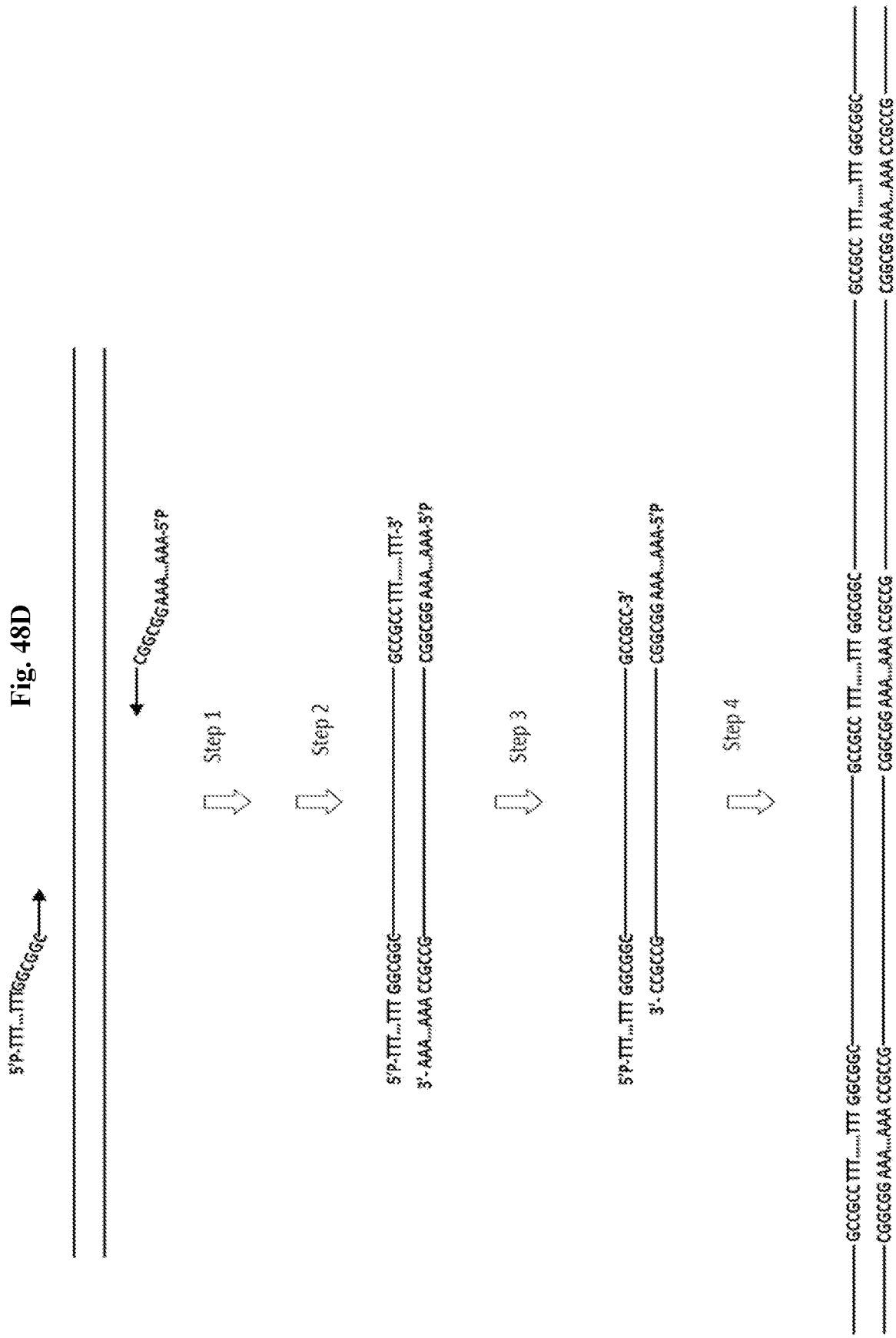
FIG. 48D depicts Example 15. Step 1: PCR with primers containing tail sequences $(T)_m$ and $(A)_m$ with the adjacent buffer region containing at least 6 G and C bases (no A and T). Step 2: SPRI purification removes non-incorporated primers. Step 3: T4 DNA polymerase in the presence of dGTP and dCTP nucleotides generates overhang $(T)_m$ at one and overhang $(T)_m$ on another end of PCR amplicon. Step 4: At high amplicon concentration amplicon ends anneals to each other and form oligomers that become covalently linked by a DNA ligase.
Figure 48E:
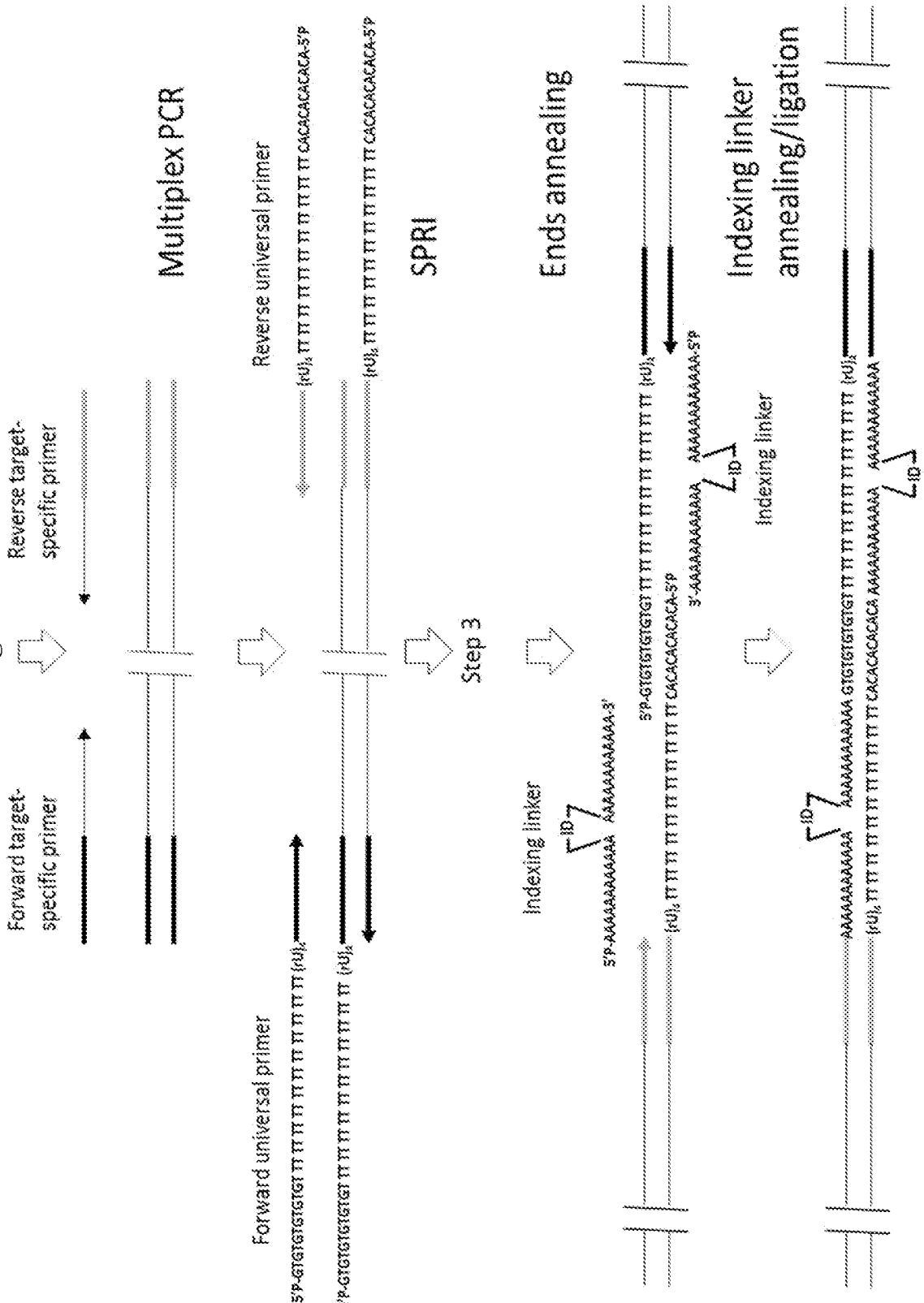
FIG. 48E depicts Example 15. Step 3: Concentrate DNA for intermolecular oligomerization, dilute DNA for intramolecular circularization. Figure discloses SEQ ID NOS: 61, 111, 61, 111, 109, 109, 61, 111, 110, 110, 109, 112, 113, and 109, respectively, in order of appearance.

Methods for efficient creation of 5' overhangs described in this application can be used to create concatamer amplicon molecules. We envision several strategies for amplicon oligomerization. In one strategy, shown on FIGS. 48a, 48c, and 48d, PCR alone (with riboU-containing primers, FIG. 48a, 48c) or PCR and subsequent incubation with T4 DNA polymerase (FIG. 48a, 48d) creates DNA molecules with complementary 5' overhangs A and A', similar to the creation of such overhangs for stem-loop adapter ligation described in Example 14. DNA molecules with complementary overhangs, in the presence of DNA ligase, will create long covalent concatamers similar to oligomerization of intact bacteriophage lambda DNA that has complementary 12 base overhangs at the ends. In another strategy, shown on FIG. 48b, either PCR alone (with riboU-containing primers) or PCR and subsequent incubation with T4 DNA polymerase creates DNA molecules with non-complementary 5' overhangs A and B. In this case DNA oligomerization is achieved by mixing amplicons with stoichiometrically equal molar amount of double-stranded linker DNA containing overhangs A' and B'. In yet another strategy, PCR amplification with riboU-containing primers creates amplicons with partially complementary overhangs as shown on FIG. 48e. In this case only the 5' portions of the two 5' overhangs are mutually complementary, and have GTGTGTGTGTGT (SEQ ID NO: 63) and ACACACACACAC (SEQ ID NO: 64) sequences. Annealing of amplicons create non-covalently associated oligomers with single-stranded gap regions containing homopolymer poly T sequences adjacent to rU bases. Addition and ligation of the linker oligonucleotide containing poly A homopolymer sequence results in formation of covalent oligomers. Linker oligonucleotides can be used not only to complete formation of the amplicon oligomers but also to integrate indexing sequence for sample multiplexing.

Example 16. Creation of Re-Amplifiable Single-Stranded Probes for Target Enrichment by Hybridization-Capture There is a high demand for preparation of single stranded molecules containing only a selected strand from PCR amplified DNA. Preparation of single-stranded DNA from double-stranded PCR products is an essential step in the identification of aptamers by Systematic Evolution of Ligands by EXponential enrichment (SELEX). It is also frequently used in genotyping and DNA-based diagnostics assays. Some methods utilize lambda 5' exonuclease to digest the DNA strand containing a 5' phosphate group while preserving the non-phosphorylated strand. Unfortunately, specificity of lambda exonuclease toward the phosphorylated DNA end is not absolute, resulting in non-specific degradation of the non-phosphorylated DNA strand. Other methods use immobilization of biotin-containing PCR product on streptavidin magnetic beads and where the strand of interest is selectively released from beads by NaOH treatment followed by acid neutralization. This approach is not suitable for preparation of biotinylated DNA or any large scale single-stranded DNA preparation.

Here we propose a novel method for a large scale generation of single stranded DNA molecules and, in particular, biotinylated single-stranded molecules from PCR products. The proposed method is highly efficient, has low production cost and scalable to large volumes and probe number and, as a result, ideally suitable for preparation of hybridization capture probes for targeted enrichment of DNA and RNA for NGS analysis. It can be also used for production of single-stranded DNA labeled with other ligands or chromophores. The method is strand-specific and allows preparation of probes for both DNA strands.

Figure 49A:
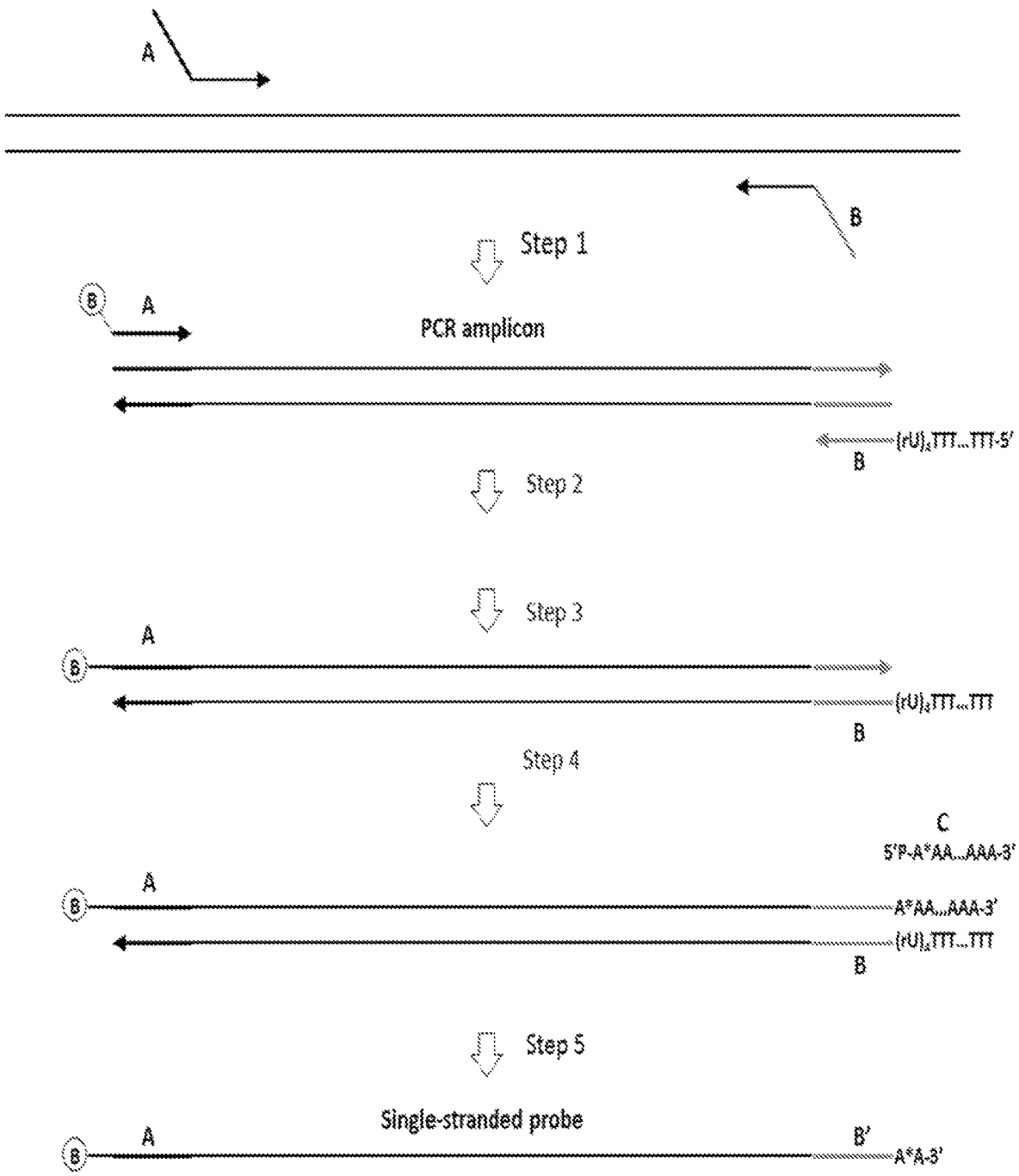
FIG. 49A depicts Example 16. Step 1: PCR with target-specific primers. Step 2: Dilution followed by second PCR with universal primers A and primer B containing biotin and $(rU)_4(dT)_{12}$ sequence at the 5' ends, respectively. Step 3: AMPure XP bead purification. Step 4: Annealing and ligation of nuclease-resistant poly A sequence C to the 3' end of PCR product. Step 5: Incubation with exonuclease III and generation of single-stranded probe with the biotin at the 5' end. Figure discloses "$(rU)_4(dT)_{12}$" as SEQ ID NO: 114.

The method involves several steps (FIG. 49a). First, amplification of a selected region from genomic or vector DNA with PCR using primers containing universal sequences A and B and a thermostable DNA polymerase. Second, dilution and re-amplification of PCR product with universal primers A and B, where primer A has a biotin group while primer B has $(rU)_4$ replication block followed by a stretch of 10-16 dT bases (SEQ ID NO: 65) at the 5' end, and a high fidelity DNA polymerase such as Q5, PrimeSTAR GXL, or Kapa HiFi. PCR produces double-stranded DNA molecules with a 5' overhang at one end. Production of target DNA molecules with a 5' overhang can also be accomplished in one PCR step using target-specific primers with a biotin and a $(rU)_4(dT)_{12-16}$ sequence (SEQ ID NO: 66) at their 5' ends. Choice of ribonucleotide bases for replication termination is not limited to only rU bases, it can be poly(rA) or any other ribonucleotide sequence that provides efficient polymerization arrest of the DNA polymerase selected for amplification and creates a 5' overhang sufficient for annealing and ligation of nuclease-resistant oligonucleotide. Third, annealing and ligation of the nuclease-resistant oligonucleotide containing 10-20 A bases (SEQ ID NO: 59), the 5' phosphate group and at least one phosphorothioate bond near the 5' end. Preferably, there are at least 4 phosphorothioate bonds for better protection against exonuclease. The 5' tail sequence of primer B and the complementary sequence of nuclease-resistant oligonucleotide C are not limited to poly T and poly A sequences and can be substituted by any other mutually complementary sequences. Choice of the poly T and poly A sequences is justified by their fast annealing and ligation time as was shown in Example 6. Fourth, purification with AMPure XP beads is performed to remove non-incorporated PCR primers and protection oligonucleotide. The amount of oligonucleotide C can be excessive to protect all DNA molecules produced by the PCR reaction, or limited and present at a specified molar concentration if the goal is to produce only a specified amount of single-stranded probe. Fifth, digestion with exonuclease III is performed to remove non-protected DNA strands. And, finally, exonuclease III heat inactivation or probe purification by spin-column or any other available method is performed.

Figure 49B:
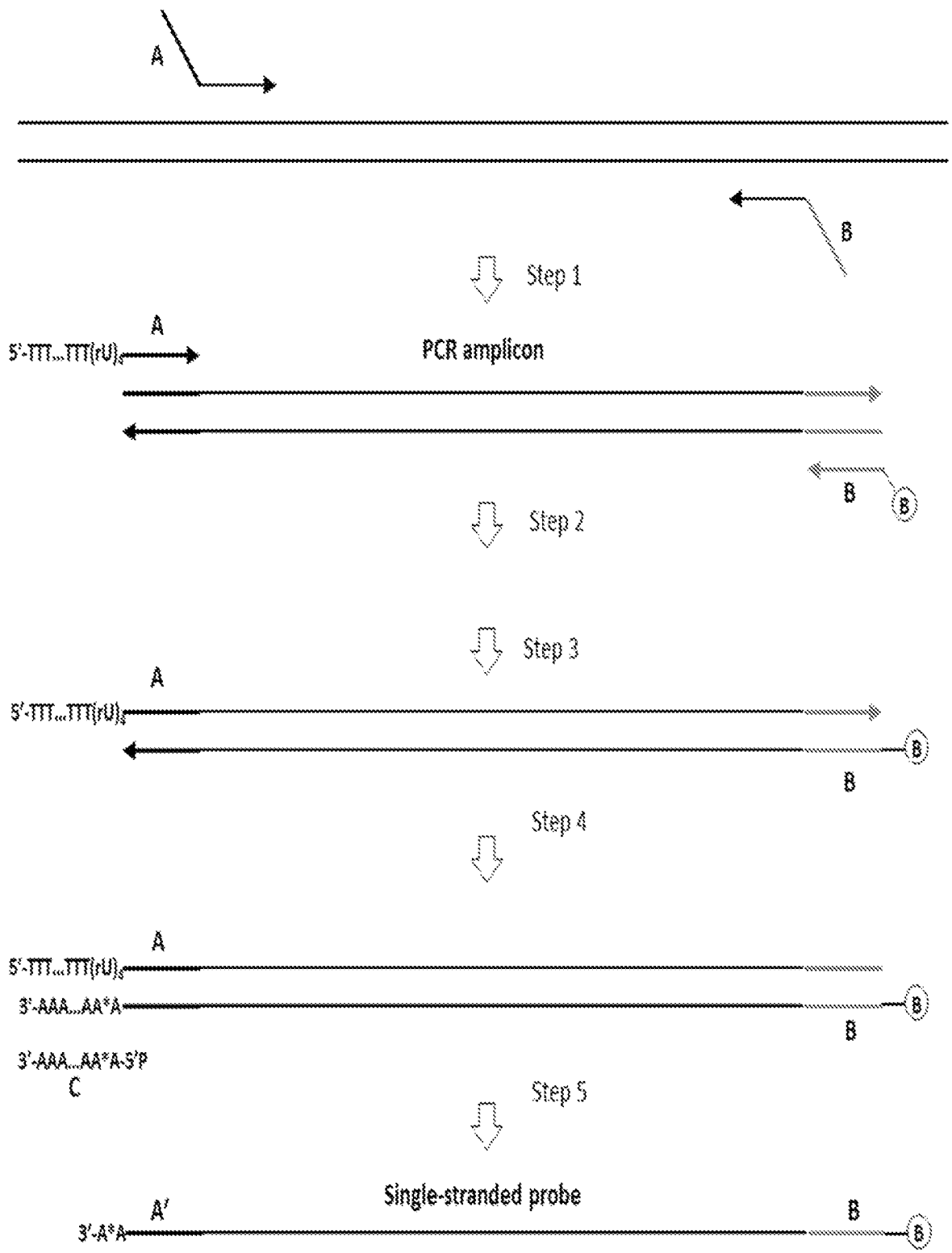
FIG. 49B depicts Example 16. Step 1: PCR with target-specific primers. Step 2: Dilution followed by second PCR with universal primers A and primer B containing $(rU)_4(dT)_{12}$ sequence and biotin at the 5' ends, respectively. Step 3: AMPure XP bead purification. Step 4: Annealing and ligation of nuclease-resistant poly A sequence C to the 3' end of PCR product. Step 5: Incubation with exonuclease III and generation of single-stranded probe with the biotin at the 5' end. Figure discloses "$(rU)_4(dT)_{12}$" as SEQ ID NO: 114.

The method described produces biotinylated, single-stranded DNA capture probes which strand specificity is dictated by the location of the biotin group and the $(rU)_4(dT)_{12-16}$ sequence (SEQ ID NO: 66) on the universal primers. By moving the biotin group to primer B, and correspondingly, the $(rU)_4(dT)_{12-16}$ sequence (SEQ ID NO: 66) to primer A, it is possible to create capture probes complementary to the second DNA strand (FIG. 49b).

Biotinylated, strand-specific probes can be pooled to form a panel for isolation of multiple target regions by hybridization to a denatured NGS library. To ensure that probes are present at equal concentrations, their amount should be quantified using standard methods and concentration adjusted by dilution. Pooling of multiple probes can be simplified if the amount of probe is normalized by controlled ligation of nuclease-resistant probe C. In this case, probe concentration measurement and adjustment prior to pooling can be skipped.

Figure 49C:
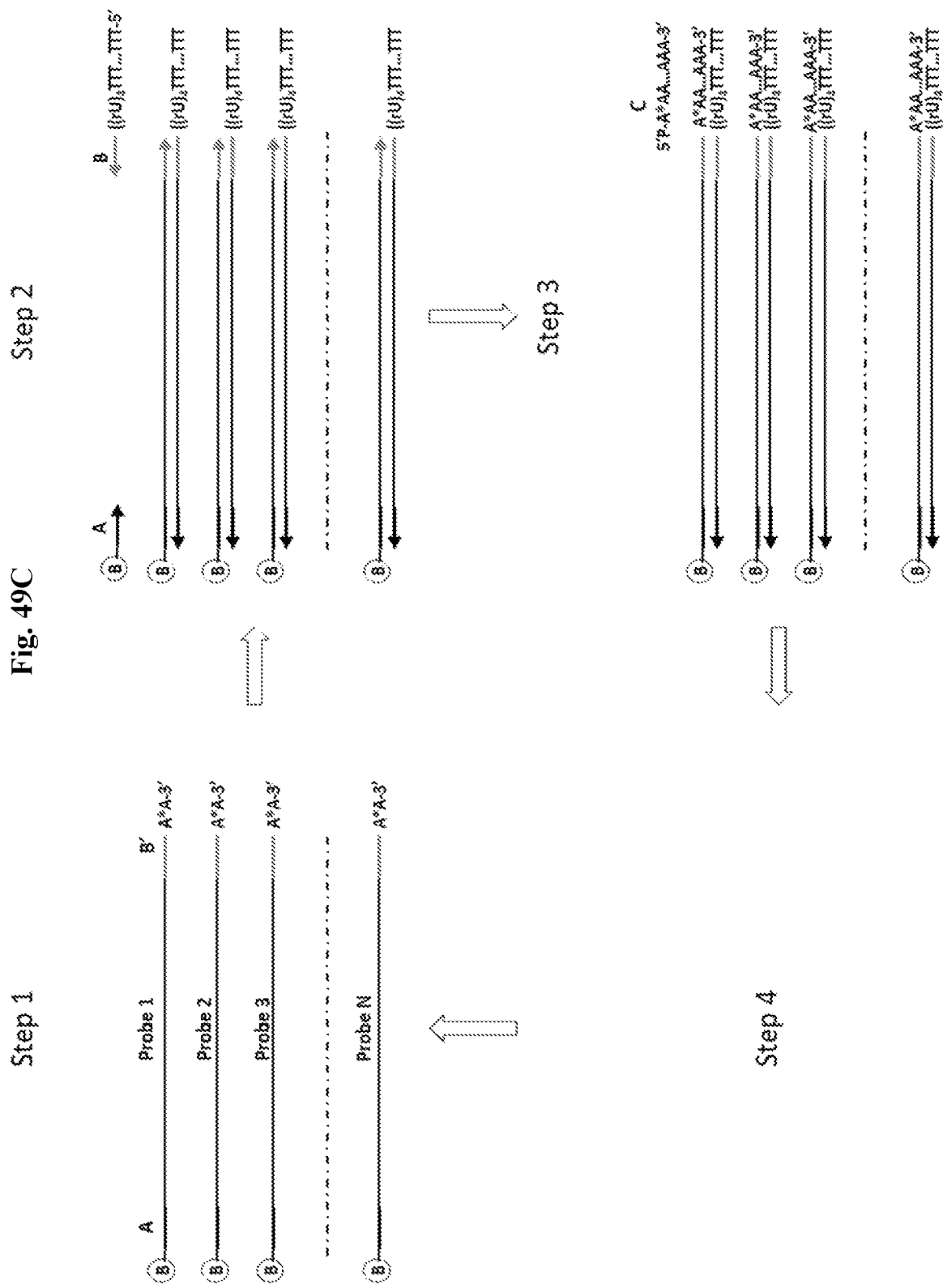
FIG. 49C. depicts Example 16. Step 1: Create a pool containing N probes. Step 2: Amplify pool by PCR using universal primers A and B. Step 3: Anneal and ligate nuclease-resistant oligo C containing 5' phosphate and phosphorothioated linkages near the 5' end, purify with AMPure XP beads. Step 4: Degrade non-biotin strand with exonuclease III, inhibit exo III by heating at 95° C. or purify.

The method described provides an unlimited resource for probe generation because as shown on FIG. 49c, pooled DNA probes can be repeatedly amplified by PCR with two universal primers, ligated to a nuclease-resistant oligonucleotide and digested with exonuclease III to create single-stranded, strand-specific, biotin-containing DNA capture probes.

Example 17 Buffer Region Requirement for T4 DNA Polymerase—Mediated Overhang Generation Data presented in this example show that a buffer DNA region composed from the most stable G and C bases should be at least 4 bases long to prevent T4 DNA polymerase from irreversible DNA end trimming.

Materials
  Oligonucleotide 48
  Oligonucleotide 49
  Oligonucleotide 50
  Oligonucleotide 51
  Oligonucleotide 52
  Oligonucleotide 53
  Oligonucleotide 54
  Oligonucleotide 55
  10× T4 DNA ligase buffer (Enzymatics, cat #B6030L)
  Low TE buffer (Teknova cat #TO227)
  T4 DNA polymerase (NEB, 30000 u/ml, cat #M0203L)
  dGTP, 100 mM (cat #55084)
  dCTP, 100 mM (cat #55084)
  15% TBE-Urea gel (Invitrogen, cat #EC68852BOX)
  SYBR Gold stain (Invitrogen, cat #S11494)

Methods

Double stranded oligonucleotide constructs a, b, c and d with 8 base long buffer GC region at one DNA end, variable length buffer GC region in the middle and polyT/polyA sequence at the other DNA end shown in FIG. 50 were prepared by annealing 5 ☐M oligo 48 with 5 ☐M oligo 49, 5 ☐M oligo 50 with 5 ☐M oligo 51, 5 ☐M oligo 52 with 5 ☐M oligo 53, and 5 ☐M oligo 54 with 5 ☐M oligo 55 in 50 mM NaCl at 25° C. for 30 min. Samples were boiled in formamide loading buffer and resolved on a 15% TBE-Urea Gel at 200 volts. The gel was stained with SYBR Gold stain, visualized on a Dark Reader light box (Clare Chemical Research) and photographed using a digital camera.

Results

Figure 50A:
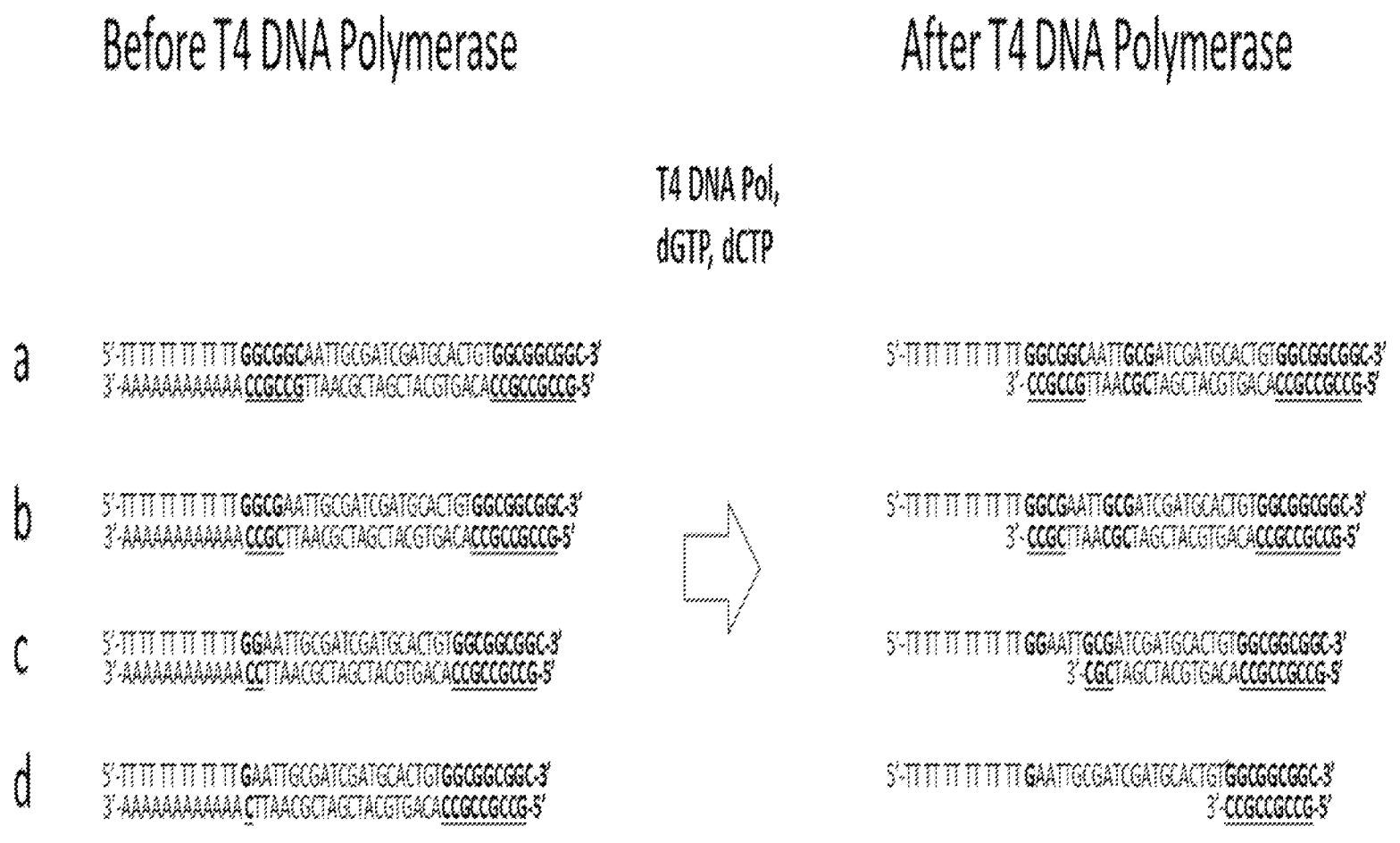
Figure 50B:
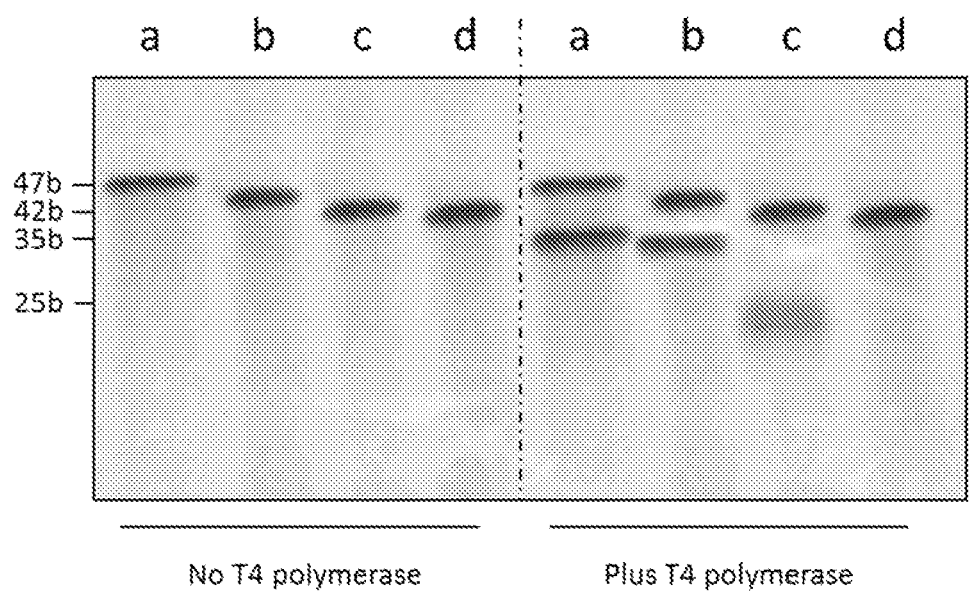
FIG. 50B depicts Example 17.

Oligonucleotide constructs and results of gel denaturing gel analysis before and after incubation with T4 DNA polymerase are shown on FIG. 50a-b. The first 4 lanes show the mobility of the oligonucleotides constituting the constructs a-b (oligonucleotides 48-55) prior to incubation with T4 DNA polymerase. Complementary oligonucleotides migrated as a single band because they had a similar size. After treatment with T4 DNA polymerase in the presence of dGTP and dCTP nucleotides, a new, faster migrating band appeared that corresponded to the polyA sequence trimmed by T4 DNA polymerase. The second strand remained intact due to the 9-base GGCGGCGGC buffer sequence on the opposite end of the construct. Constructs a and b, containing buffer regions GGCGGC and GGCG, respectively, produced sharp electrophoretic bands indicative of a prominent polymerase stop at the buffer regions. Construct c, containing a 2 base buffer region GG, did not stop T4 DNA polymerase at the expected position and produced a shorter diffuse electrophoretic band corresponding to the second, 3 base buffer sequence GCG located downstream of the GG site. Interestingly, construct d, containing a single G base as a buffer region, did not stop T4 DNA polymerase at the internal 3 base sequence GCG. This result suggests that the observed diffuse band of construct c represents a transient intermediate state detected after 15 min of incubation with T4 DNA polymerase due to the presence of the upstream trimming block provided by the GG dinucleotide.

Conclusions

The data presented in this Example indicate that 4 G/C bases represent the minimal size for a buffer region to prevent DNA polymerase from trimming through the buffer region. 3 G/C bases were not sufficient and provided only temporary block against 3' exonuclease activity of T4 DNA polymerase. This conclusion is valid for the G/C composition of the buffer and possibly would require a longer size if T and A bases are used as a buffer region. Trimming at higher temperature likely would require a longer buffer region due to higher exonuclease activity of T4 DNA polymerase. This requirement is substantially different from what was known in the art \ for ligation-independent cloning with T4 DNA polymerase where a single cytosine base is typically used to create 5' overhangs using T4 DNA polymerase and restricted nucleotide mix. Our data indicate that for applications where the precise 5' overhang length and sequence are required, it is advisable to use 5 or more buffer G/C bases and probably 6 or more A/T bases to ensure creation of predictable DNA overhang end structure.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated. Different features and disclosures of the various embodiments within the present disclosure may be combined within the scope of the present disclosure.

What is claimed is:

1. A kit comprising:
a first primer comprising a first portion, a second portion and a third portion, wherein the first portion is located at a 3' end of the first primer, wherein the second portion comprises 3 or more consecutive ribonucleotide bases and is located 5' to the first portion, and wherein the third portion is located 5' adjacent to the second portion and comprises a low complexity sequence selected from the group consisting of poly (A), poly(T), poly(G), poly(C), poly(AG), poly(AC), poly(GT), poly(CT), poly(AT), poly(GC), a trinucleotide, a tetranucleotide, and a pentanucleotide;
a second primer, wherein the second primer comprises a second primer first portion, a second primer second portion comprising 3 or more consecutive ribonucleotide bases located 5' adjacent to the second primer first portion and a second primer third portion located 5' adjacent to the second primer second portion and comprising a low complexity sequence selected from the group consisting of poly(A), poly(T), poly(G), poly(C), poly(AG), poly(AC), poly(GT), poly(CT), poly(AT), poly(GC), a trinucleotide, a tetranucleotide, and a pentanucleotide;
a ligase selected from the group consisting of T4 DNA ligase, T3 DNA ligase, T7 DNA ligase, and *E. coli* DNA ligase;
an enzyme with 3'-5' exonuclease activity; and
a probe, wherein the probe comprises a modification to provide resistance to digestion by the enzyme with 3'-5' exonuclease activity, and wherein at least a portion of the probe is complementary to at least a portion of the second and third portion of the first primer including the three or more consecutive ribonucleotide bases and at least a portion of the low complexity sequence.

2. The kit of claim 1, wherein the enzyme with 3'-5' exonuclease activity is exonuclease III.

3. The kit of claim 1, wherein the enzyme with 3'-5' exonuclease activity is T4 DNA Polymerase.

4. The kit of claim 1, wherein the ligase is T4 DNA ligase.

5. The kit of claim 1, wherein the low complexity sequence of the first primer is poly(T).

6. The kit of claim 5, wherein the low complexity sequence of the first primer is 10-20 bases.

7. The kit of claim 1, wherein the low complexity sequence of the first primer is 10-20 bases.

8. The kit of claim 1, wherein the enzyme with 3'-5' exonuclease activity is exonuclease III, wherein the ligase is T4 DNA ligase, and wherein the low complexity sequence of the first primer is 10-20 bases.

9. The kit of claim 8, wherein the low complexity sequence of the first primer is poly(T).

10. The kit of claim 8, wherein the modification to provide resistance to digestion by the enzyme with 3'-5' exonuclease activity comprises phosphorothioate linkages at the 5' end of the probe.

11. The kit of claim 1, wherein the low complexity sequence of the second primer is poly(T).

12. The kit of claim 11, wherein the low complexity sequence of the second primer is 10-20 bases.

13. The kit of claim 1, wherein the low complexity sequence of the second primer is 10-20 bases.

14. The kit of claim 1, wherein the enzyme with 3'-5' exonuclease activity is exonuclease III, wherein the ligase is T4 DNA ligase, and wherein the low complexity sequence of the second primer is 10-20 bases.

15. The kit of claim 14, wherein the low complexity sequence of the second primer is poly(T).

16. The kit of claim 14, wherein the modification to provide resistance to digestion by the enzyme with 3'-5' exonuclease activity comprises at least four consecutive phosphorothioate linkages at the 5' end of the probe.

17. The kit of claim 1, wherein the enzyme with 3'-5' exonuclease activity is exonuclease III, wherein the ligase is T4 DNA ligase, wherein the low complexity sequence of the first primer is 10-20 bases, wherein the low complexity sequence of the second primer is 10-20 bases, wherein the low complexity sequence of the first primer is poly(T), and wherein the low complexity sequence of the second primer is poly(T).

18. The kit of claim 17, wherein the modification to provide resistance to digestion by the enzyme with 3'-5' exonuclease activity comprises at least four consecutive phosphorothioate linkages at the 5' end of the probe.

19. The kit of claim 18, wherein the probe is single-stranded DNA.

20. The kit of claim 1, wherein the probe is single-stranded DNA and wherein the modification to provide resistance to digestion by the enzyme with 3'-5' exonuclease activity comprises phosphorothioate linkages at the 5' end of the probe, and wherein the enzyme with 3'-5' exonuclease activity is selected from the group consisting of T4 DNA Polymerase and exonuclease III.

* * * * *